(12) United States Patent
Lin et al.

(10) Patent No.: US 9,518,063 B2
(45) Date of Patent: Dec. 13, 2016

(54) ORGANIC ELECTROLUMINESCENT MATERIALS AND DEVICES

(71) Applicant: Universal Display Corporation, Ewing, NJ (US)

(72) Inventors: Chun Lin, Langhorne, PA (US); Bin Ma, West Windsor, NJ (US); Raymond Kwong, Plainsboro, NJ (US); Alexey Borisovich Dyatkin, Ambler, PA (US); Yonggang Wu, Ewing, NJ (US); Zeinab M. Elshenawy, Holland, PA (US)

(73) Assignee: Universal Display Corporation, Ewing, NJ (US)

( * ) Notice: Subject to any disclaimer, the term of this patent is extended or adjusted under 35 U.S.C. 154(b) by 15 days.

(21) Appl. No.: 14/735,589

(22) Filed: Jun. 10, 2015

(65) Prior Publication Data
US 2015/0274749 A1 Oct. 1, 2015

Related U.S. Application Data

(62) Division of application No. 12/647,927, filed on Dec. 28, 2009, now Pat. No. 9,067,947.

(60) Provisional application No. 61/145,370, filed on Jan. 16, 2009.

(51) Int. Cl.
| | |
|---|---|
| *C07D 491/04* | (2006.01) |
| *C07D 491/048* | (2006.01) |
| *C07D 495/04* | (2006.01) |
| *C07D 519/00* | (2006.01) |
| *H01L 51/00* | (2006.01) |
| *H01L 27/32* | (2006.01) |
| *H01L 51/50* | (2006.01) |
| *H05B 33/20* | (2006.01) |

(52) U.S. Cl.
CPC .......... *C07D 495/04* (2013.01); *C07D 491/04* (2013.01); *C07D 491/048* (2013.01); *C07D 519/00* (2013.01); *H01L 27/32* (2013.01); *H01L 27/3209* (2013.01); *H01L 51/0054* (2013.01); *H01L 51/0058* (2013.01); *H01L 51/0061* (2013.01); *H01L 51/0071* (2013.01); *H01L 51/0072* (2013.01); *H01L 51/506* (2013.01); *H01L 51/5012* (2013.01); *H01L 51/5056* (2013.01); *H01L 51/5064* (2013.01); *H01L 51/5068* (2013.01); *H01L 51/5088* (2013.01); *H01L 51/5092* (2013.01); *H01L 51/5096* (2013.01); *H05B 33/20* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Alicia L Otton
(74) *Attorney, Agent, or Firm* — Duane Morris LLP

(57) ABSTRACT

A new class of compounds containing aza-dibenzothiophene or aza-dibenzofuran are provided. The compounds may be used in organic light emitting devices giving improved stability, improved efficiency, long lifetime and low operational voltage. In particular, the compounds may be used as the host material of an emissive layer having a host and an emissive dopant, or as a material in an enhancement layer.

10 Claims, 4 Drawing Sheets

(56) References Cited

U.S. PATENT DOCUMENTS

| | | |
|---|---|---|
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2006/0288577 A1 | 12/2006 | Bormuth |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0153034 A1 | 6/2009 | Lin et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2011/0215309 A1 | 9/2011 | D'Andrade et al. |
| 2014/0217335 A1 | 8/2014 | Tanabe et al. |
| 2015/0274749 A1 | 10/2015 | Lin et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2008021687 | 10/2008 |
| JP | 2008545729 | 12/2008 |
| JP | 2012502485 | 1/2012 |
| JP | 2012515216 | 7/2012 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006/130598 | 12/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008075517 A1 | 6/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato)beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).

Huang, Wei-Sheng et al., "Highly Phosphorescent Bis-Cyclometalated Iridium Complexes Containing Benzoimidazole-Based Ligands," Chem. Mater, 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

(56) References Cited

OTHER PUBLICATIONS

Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater, 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
STN Registry database entries for CAS RN 244-91-7; CAS RN 318-69-4; and CAS RN 244-93-9 (Published in STN Registry Nov. 16, 1984); Accessed Sep. 23, 2013.
Database Beilstein [Online] Beilstein Institute for Organic Chemistry, Frankfurt-Main, DE; vol. 78, Jan. 1, 1958 (Jan. 1, 1958), pp. 943-945.
Kauffman JM et al: "Synthesis and photophysical properties of fluorescent dibenzofurans, a dibenzothiophene and carbazoles substituted with benzoxazole and hydroxyl groups to produce excited state intramolecular proton-transfer" Journal of Heterocyclic Chemistry, vol. 32, Jan. 1, 1995 (Jan. 1, 1995), pp. 1541-1555.
Partial International Search Report in PCT/US2010/021111 application.
U.S. Appl. No. 61/145,370, filed Jan. 16, 2009.
U.S. Appl. No. 12/209,928, filed Sep. 12, 2008.
U.S. Appl. No. 11/443,586, filed May 31, 2006.
Search Report issued for corresponding Taiwan Patent Application No. 104131505.
Notice of Reasons for Rejection issued Apr. 25, 2016 for corresponding JP Application No. 2014-188613.

ORGANIC ELECTROLUMINESCENT MATERIALS AND DEVICES

CROSS-REFERENCE TO RELATED APPLICATIONS

This application is a divisional application of U.S. patent application Ser. No. 12/647,927, filed Dec. 28, 2009, which claims priority to U.S. Provisional Application No. 61/145,370, filed Jan. 16, 2009, the disclosures of which are herein expressly incorporated by reference in their entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic complexes containing aza-dibenzothiophene or aza-dibenzofuran. The materials may be useful in organic light emitting devices (OLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the structure:

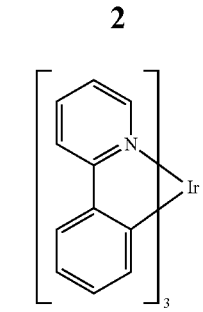

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A process is provided for making aza-dibenzothiophene compounds or aza-dibenzofuran compounds. The process, comprising treating an acetic acid solution of an amino-arylthio pyridine intermediate having the formula

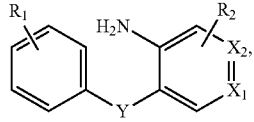

wherein one of $X_1$ and $X_2$ is nitrogen and the other of $X_1$ and $X_2$ is carbon and wherein Y is S or O, with $^t$BuONO to produce an aza complex having the formula

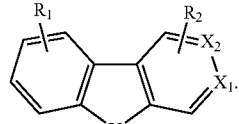

$R_1$ and $R_2$ may represent mono, di, tri or tetra substitutions. $R_1$ is selected from the group consisting of hydrogen, alkyl, aryl, heteroaryl and halide. Preferably, $R_1$ is halide. $R_2$ is selected from the group consisting of hydrogen, alkyl, aryl and halide. Preferably, one of $X_1$ and $X_2$ may be carbon and the other may be nitrogen. More preferably, $X_1$ is nitrogen and $X_2$ is carbon or $X_1$ is carbon and $X_2$ is nitrogen. Preferably, Y is S. Alternatively, Y may preferably be O. $R_2$ may include at least one halide, and $R_2$ may include only halide substituents. The process may be used to make compounds where $R_2$ is not halide and the amino-arylthio pyridine intermediate is treated with $H_2SO_4$ prior to treatment with $^t$BuONO. The yield of

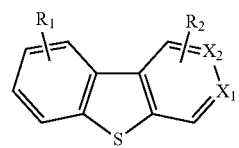

may be greater than 50%.

A novel class of aza-dibenzothiophene and aza-dibenzofuran compounds are provided. The compounds have the formula:

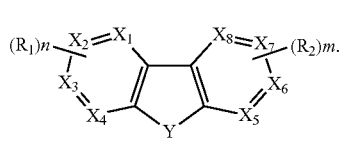

FORMULA I $X_1$, $X_2$, $X_3$, $X_4$, $X_5$, $X_6$, $X_7$, and $X_8$ are independently selected from the group consisting of a carbon atom and a nitrogen atom, and at least one of $X_1$, $X_2$, $X_3$, $X_4$, $X_5$, $X_6$, $X_7$, and $X_8$ is a nitrogen atom. Y is S or O. $R_1$ and $R_2$ may represent mono, di, tri, or tetra substitutions. $R_1$ and $R_2$ are independently selected from the group consisting of hydrogen, alkyl, aryl and halide, and at least one of $R_1$ and $R_2$ is selected from the group consisting of:

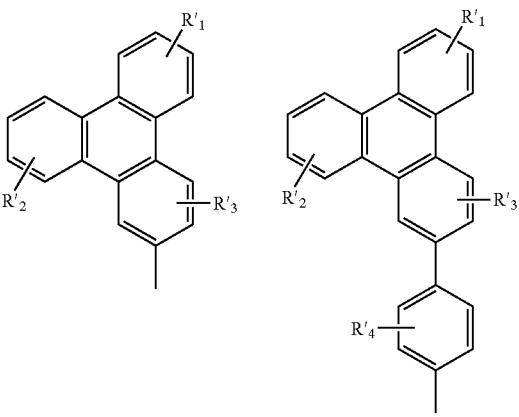

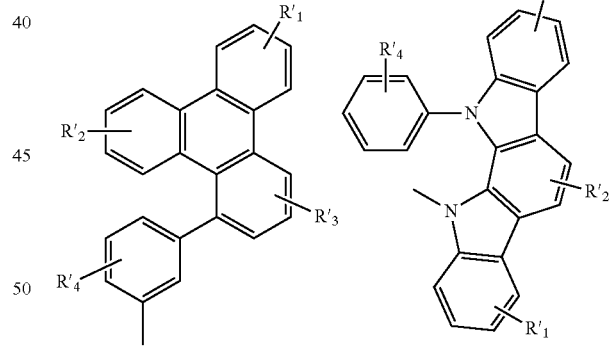

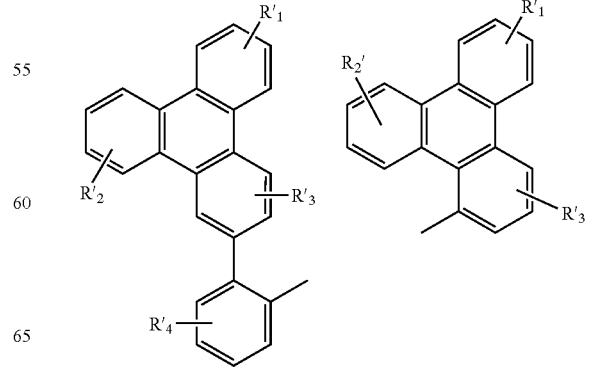

-continued

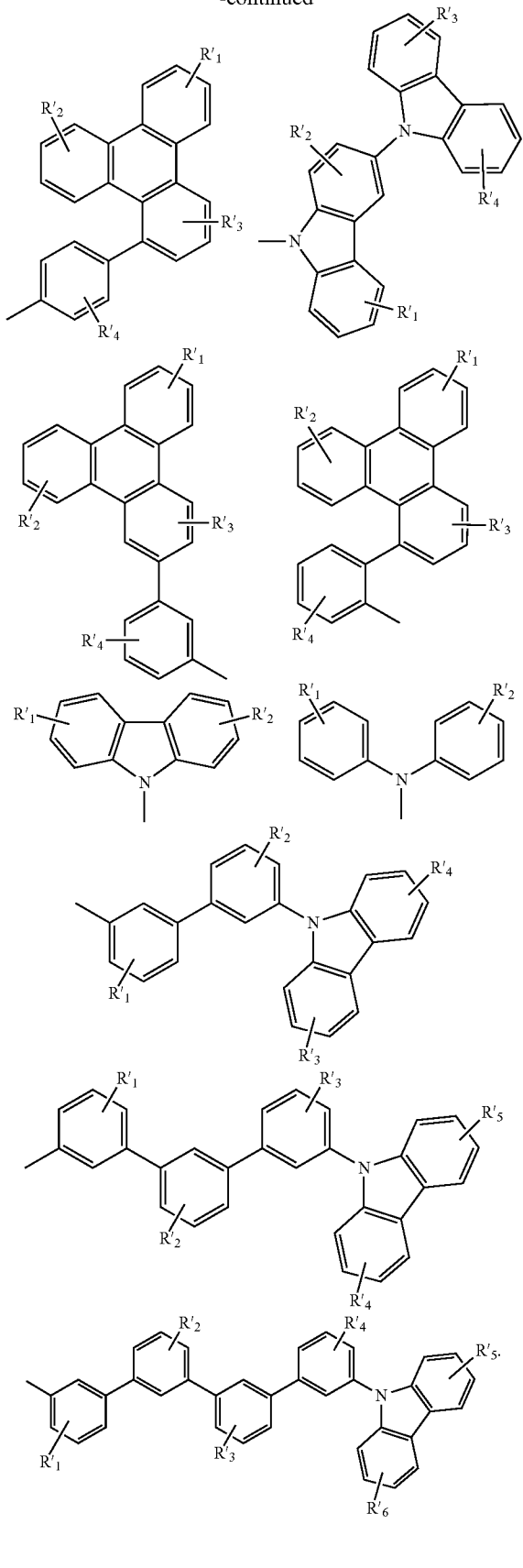

R'₁, R'₂, R'₃, and R'₄ may represent mono, di, tri, tetra or penta substitutions, and R'₁, R'₂, R'₃, and R'₄ are independently selected from the group consisting of hydrogen, alkyl, heteroalkyl, aryl and heteroaryl. Preferably, m and n are 0, 1, 2, 3, or 4; and wherein m+n is equal to or greater than 2 and m+n is equal to or less than 6. Preferably, R'₁, R'₂, R'₃, and R'₄ are each independently hydrogen or methyl.

Additionally, a novel class of aza-dibenzothiophene and aza-dibenzofuran compounds are provided. The compounds have the formula:

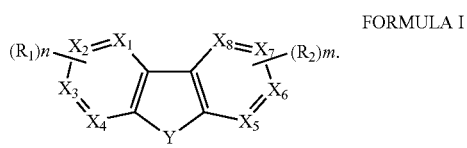

FORMULA I $X_1$, $X_2$, $X_3$, $X_4$, $X_5$, $X_6$, $X_7$, and $X_8$ are independently selected from the group consisting of a carbon atom and a nitrogen atom, and at least one of $X_1$, $X_2$, $X_3$, $X_4$, $X_5$, $X_6$, $X_7$, and $X_8$ is a nitrogen atom. Y is S or O. $R_1$ and $R_2$ may represent mono, di, tri, or tetra substitutions. $R_1$ and $R_2$ are independently selected from the group consisting of hydrogen, alkyl, aryl and halide, and at least one of $R_1$ and $R_2$ is selected from the group consisting of:

-continued

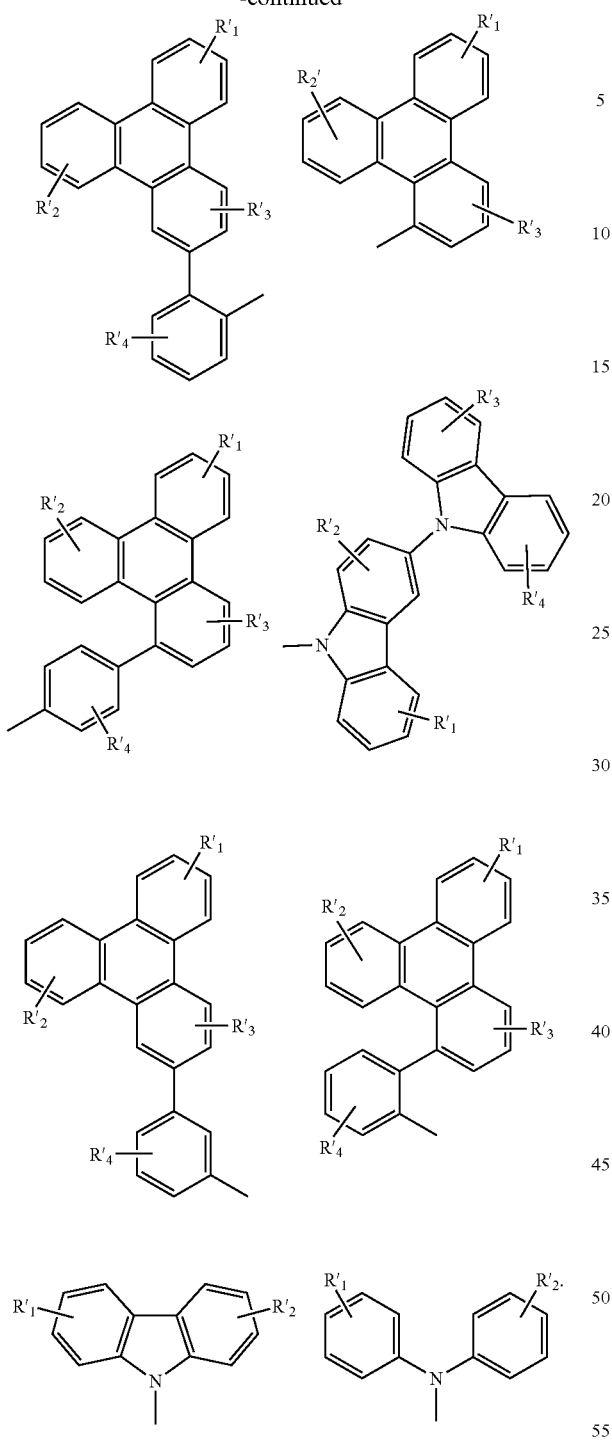
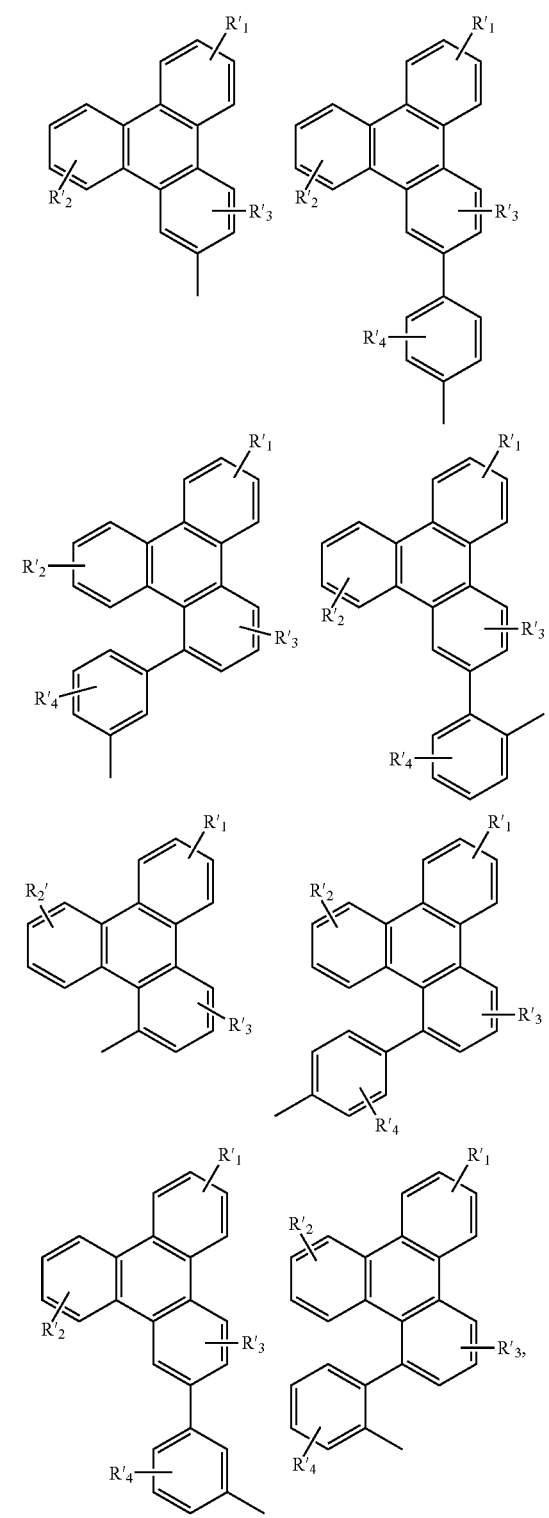

R'$_1$, R'$_2$, R'$_3$, and R'$_4$ may represent mono, di, tri, tetra or penta substitutions, and R'$_1$, R'$_2$, R'$_3$, and R'$_4$ are independently selected from the group consisting of hydrogen, alkyl, heteroalkyl, aryl and heteroaryl. Preferably, m and n are 0, 1, 2, 3, or 4; and wherein m+n is equal to or greater than 2 and m+n is equal to or less than 6. Preferably, R'$_1$, R'$_2$, R'$_3$, and R'$_4$ are each independently hydrogen or methyl.

Compounds are also provided where one of R$_1$ and R$_2$ is hydrogen and the other of R$_1$ and R$_2$ is selected from the groups consisting of

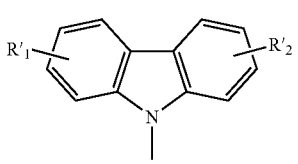

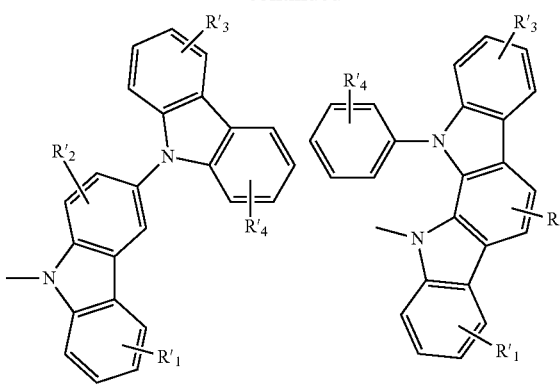
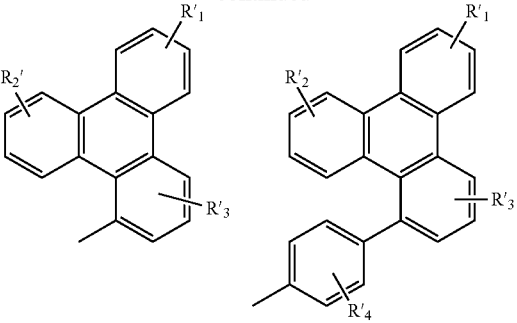
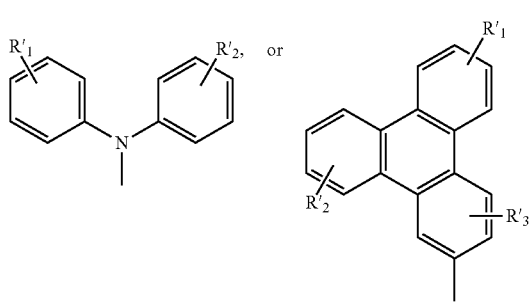
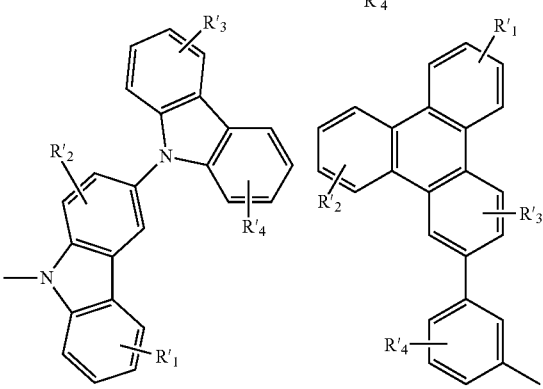
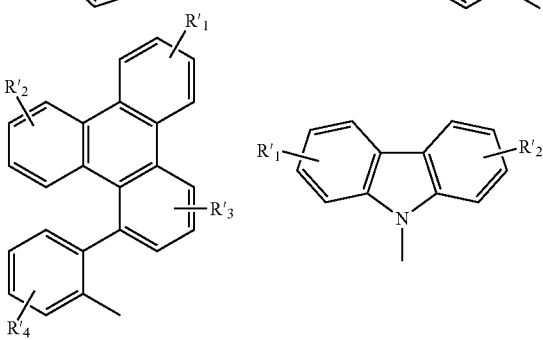
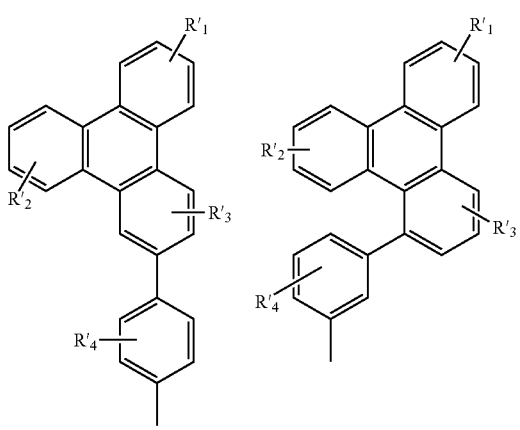
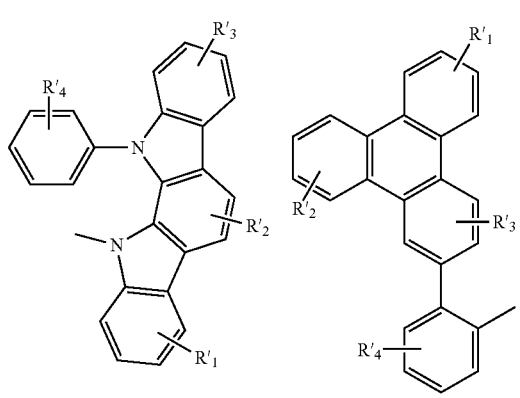

In addition, compounds are provided wherein both $R_1$ and $R_2$ are selected from the groups provided herein. Moreover, compounds are provided wherein $R_1$ is selected from the groups provided herein.

Specific examples of the aza-dibenzothiophene compounds and aza-dibenzofuran compounds are provided including Compounds 1-93.

Specific examples of the aza-dibenzothiophene compounds and aza-dibenzofuran compounds are provided including Compounds 1-79.

A first device comprising an organic light emitting device is provided. The device further comprises an anode, a cathode, and an organic layer disposed between the anode and the cathode. The organic layer comprises a compound having FORMULA I. In particular, the organic layer of the device may comprise a compound selected from Compounds 1-93.

In one aspect, the first device is a consumer product.

An organic light emitting device is also provided. The device comprises an anode, a cathode, and an organic layer disposed between the anode and the cathode. The organic layer comprises a compound having FORMULA I. In particular, the organic layer of the device may comprise a compound selected from Compound 1-79. Preferably, the organic layer is an emissive layer and the compound having FORMULA I is a host. The emissive layer may further comprise an emissive dopant. Preferably, the emissive dopant has the formula

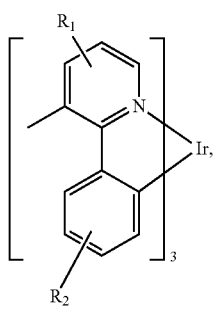

P1 where $R_1$ and $R_2$ are each independently selected from the group consisting of hydrogen, alkyl, and aryl.

Additionally, a consumer product is also provided. The product contains a device that has an anode, a cathode, and an organic layer disposed between the anode and the cathode, where the organic layer comprises a compounds having FORMULA I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75. No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
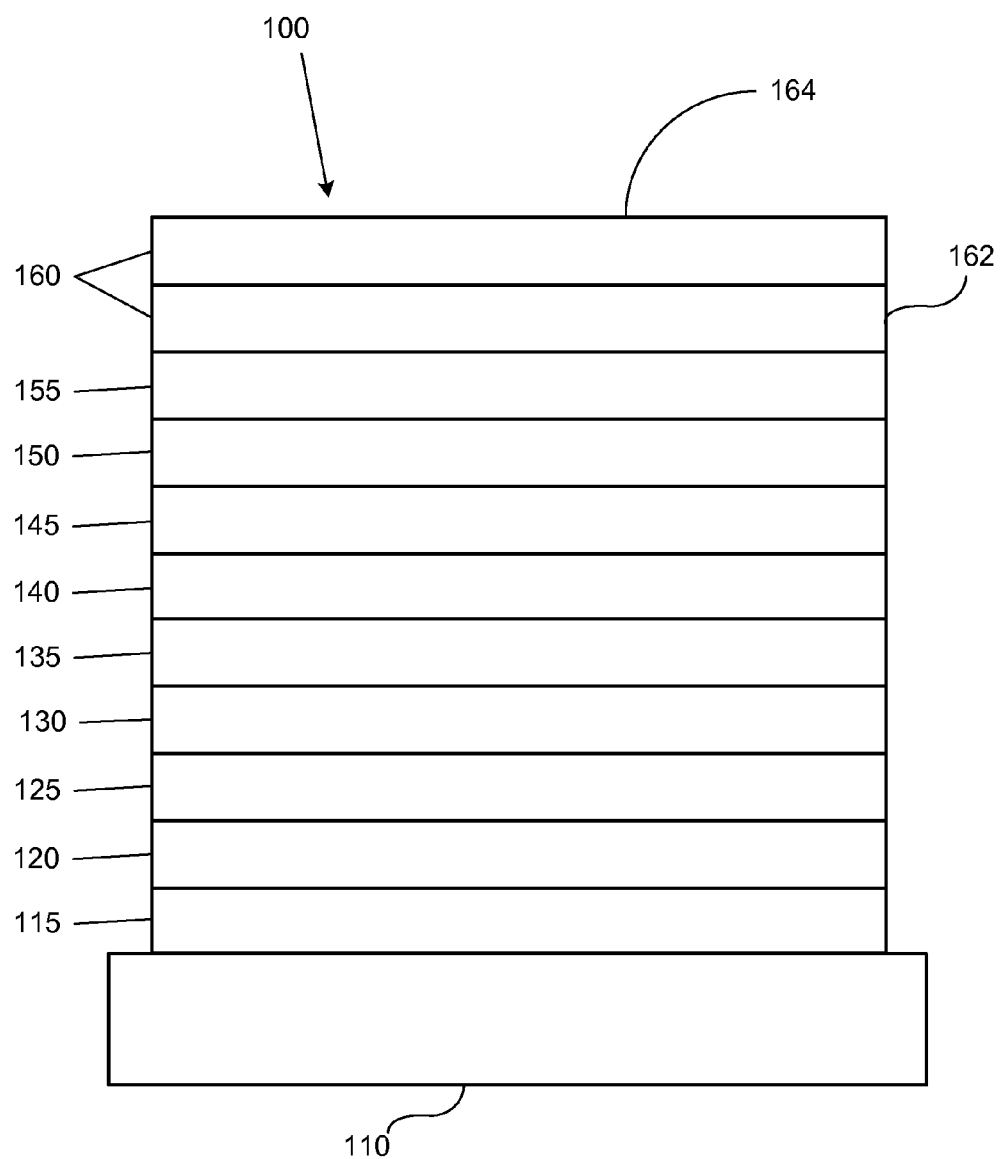
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
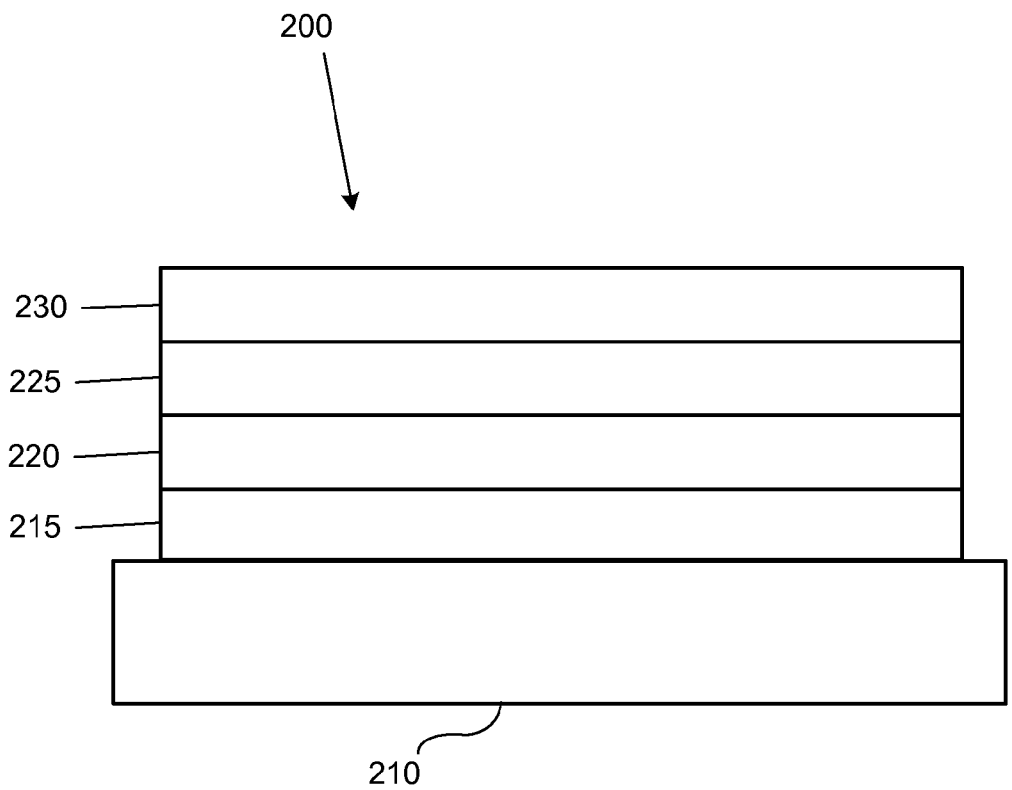
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used.

Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
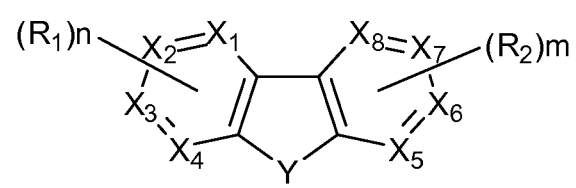
FIG. 3 shows aza-dibenzothiophene compounds and aza-dibenzofuran compounds.

A new class of compounds containing an aza-dibenzothiophene or aza-dibenzofuran core are provided (illustrated in FIG. 3). In particular, aza-dibenzothiophene compounds or aza-dibenzofuran compounds further substituted with triphenylene and/or nitrogen-containing substituents are provided. These compounds may be advantageously used in phosphorescent organic light emitting devices. Preferably, these compounds may be used as a host material in an emissive layer or as a material in an enhancement layer.

While there are existing syntheses for aza-dibenzothiophene compounds and aza-dibenzofuran compounds, these synthetic routes may have limited practicality. For example, substrates of aza-dibenzothiophene and aza-dibenzofuran were first synthesized by the well-known Pschorr Cyclization method which involves the formation of diazonium salt followed by cyclization in an aqueous medium with or without catalysts, such as Cu, CuCl. However, the general yield of the Pschorr Cyclization method is not consistent and can be less than 10%. Therefore, it is highly desirable to provide a process for making aza-dibenzothiophene compounds and aza-dibenzofuran compounds in improved yields. A new process for making aza-dibenzothiophene compounds is provided herein (illustrated in FIG. 4). The processes described in this invention differ from the existing synthesis at least by using acetic acid, not aqueous medium, and do not employ any metal catalyst. Preferably, the acetic acid is pure (or glacial) acetic acid. The process provided herein may provide yields higher than 50% or yields higher than 70%.

Dibenzothiophene-containing and dibenzofuran-containing materials are typically hole transporting materials that have a relatively high triplet energy. Given the beneficial properties of dibenzothiophene and dibenzofuran, these compounds have been used in the OLED area and some of these compounds have achieved good device performance. See Lin et al., *Dibenzothiophene-containing Materials in Phosphorescent Light Emitting Diodes*, 2008, U.S. application Ser. No. 12/208,907 and Ma et al., *Benzo-fused Thiophene/Triphenylene Hybrid Materials*, 2008, PCT/US2008/072499. Without being bound by theory, it is thought that anion injection and anion stability may play an important role in device stability. In order to have high anion stability and a lower energy barrier for anion injection to the emissive layer, compounds with a lower LUMO level are desired. In particular, dibenzothiophene and dibenzofuran containing compounds having a lower LUMO value (i.e., compounds that are more easily reduced) may be beneficial.

The compounds provided herein contain an aza-dibenzothiophene or aza-dibenzofuran core further substituted with particular chemical groups having desirable properties. Specifically, these aza-type compounds are substituted with triphenylene groups and/or nitrogen-containing groups (e.g., carbazole) to maintain high triplet energy and provide improved charge transport properties. Therefore, these substituted aza-dibenzothiophene compounds and aza-dibenzofuran compounds may provide devices having improved stability, improved efficiency, and a longer lifetime. In addition, these aza-type compounds have been demonstrated to be more easily reduced than their dibenzothiophene or dibenzofuran counterparts, and thus may provide devices having low operating voltage.

Triphenylene is a polyaromatic hydrocarbon with high triplet energy, yet high n-conjugation and a relatively small energy difference between the first singlet and first triplet levels. This would indicate that triphenylene has relatively easily accessible HOMO and LUMO levels compared to other aromatic compounds with similar triplet energy (e.g., biphenyl). These characteristics of triphenylene make it a good molecular building block in OLED hosts to stabilize charges (hole or electron). One advantage of using triphenylene and its derivatives as hosts is that it can accommodate red, green and even blue phosphorescent dopants to give high efficiency without energy quenching. Triphenylene hosts may be used to provide high efficiency and stability PHOLEDs. See Kwong and Alleyene, *Triphenylene Hosts in Phosphorescent Light Emitting Diodes*, 2006, 60 pp, U.S. 2006/0280965 A1. A compound containing an aza-dibenzothiophene or aza-dibenzofuran core and a triphenylene moiety may be beneficial as a host in PHOLEDs. More specifically, the triplet energy of both portions of the compound are relatively high thereby maintaining an overall high triplet energy. In addition, the combination of these two groups in one compound may also offer improved charge balance thus improving device efficiency and lifetime. Non-limiting examples triphenylene groups that may be the triphenylene moiety of such compounds may include

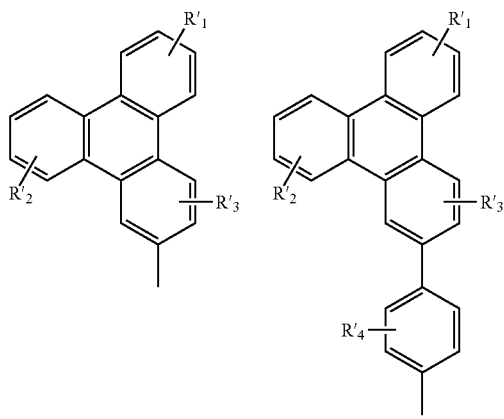

-continued

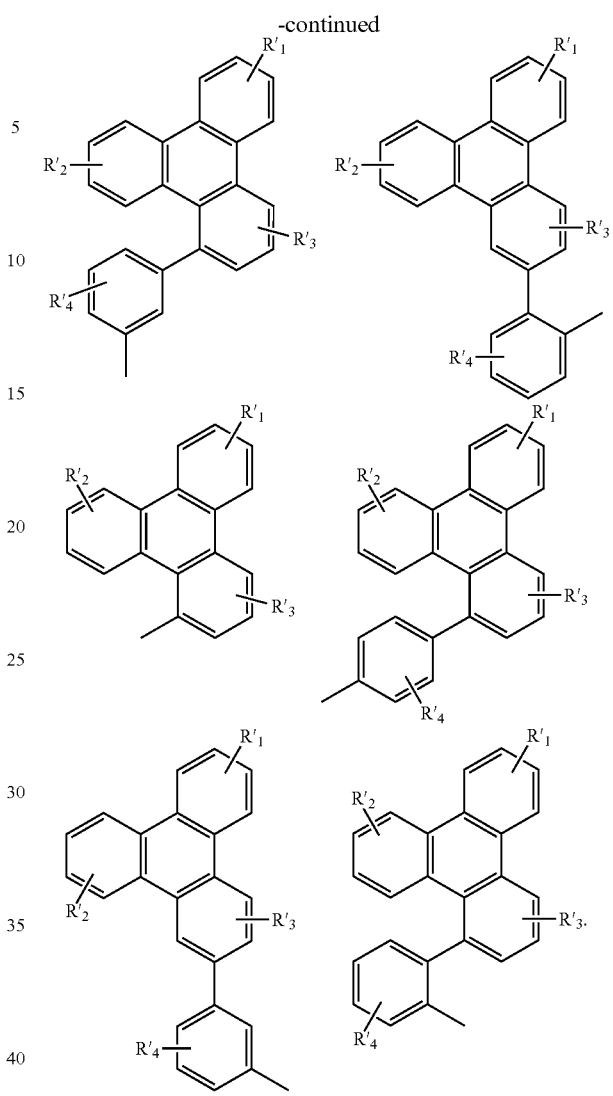

Nitrogen containing groups may also be used as substituents of the aza-dibenzothiophene compounds and aza-dibenzofuran compounds. Such nitrogen containing groups may include carbazole, oligocarbazole, indolocarbazole, and diphenylamine. Carbazole is a nitrogen containing heteroaromatic, having high triplet energy, and has hole transporting and electron transporting properties. One advantage to using carbazole-containing compounds (i.e., carbazole, oligocarbazole and indolocarbazole) as host materials is that they simultaneously possess sufficiently large triplet energies and carrier transport properties. For example, the indolocarbazole and 3-(9-carbazolyl)carbazole have a relatively low electrochemical oxidation potential. As such, these compounds are easier to oxidize and to reverse the oxidation, which improves overall host stability. Another advantage is that these carbazole building blocks can serve as donors, while coupling with aza-dibenzothiophenes or aza-dibenzofurans which are acceptors here, to form a donor-acceptor type molecule. It is believed that these molecules having a donor-acceptor molecular arrangement contribute, at least in part, to the low voltage character in the device.

The compounds provided herein may be used as host materials in blue, green and red PHOLEDs. In particular, aza-dibenzothiophene or aza-dibenzofuran compounds substituted with triphenylene may be used in blue, green and red devices as these compounds can accommodate blue, green and red emissive dopants. Preferably, these compounds may be used in blue devices. The aza-type compounds provided herein may also be substituted with both triphenylene and nitrogen-containing substituents. These compounds substituted with both triphenylene and nitrogen-containing groups may be used in green and red devices as these compounds can accommodate green and red emissive dopants. Preferably, these compounds may be used in green devices.

The heteroaromatic compounds (i.e., aza-dibenzothiophene and aza-dibenzofuran) described herein may be more easily reduced than their dibenzothiophene or dibenzofuran counterparts, in particular by 0.2 V to 0.5 V. As a result, these aza-type compounds may provide devices having low operational voltage and long lifetimes. Without being bound by theory, it is thought that the more easily reduced compounds may provide better anion stability and easier anion injection from the electron transport layer (ETL) to the emissive layer (EML) in the device.

The compounds described herein have the formula:

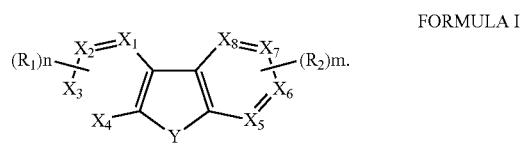

FORMULA I $X_1$, $X_2$, $X_3$, $X_4$, $X_5$, $X_6$, $X_7$, and $X_8$ are independently selected from the group consisting of a carbon atom and a nitrogen atom, and at least one of $X_1$, $X_2$, $X_3$, $X_4$, $X_4$, $X_6$, $X_7$, and $X_8$ is a nitrogen atom. Y is S or O. $R_1$ and $R_2$ may represent mono, di, tri, or tetra substitutions. $R_1$ and $R_2$ are independently selected from the group consisting of hydrogen, alkyl, aryl and halide. At least one of $R_1$ and $R_2$ is selected from the group consisting of:

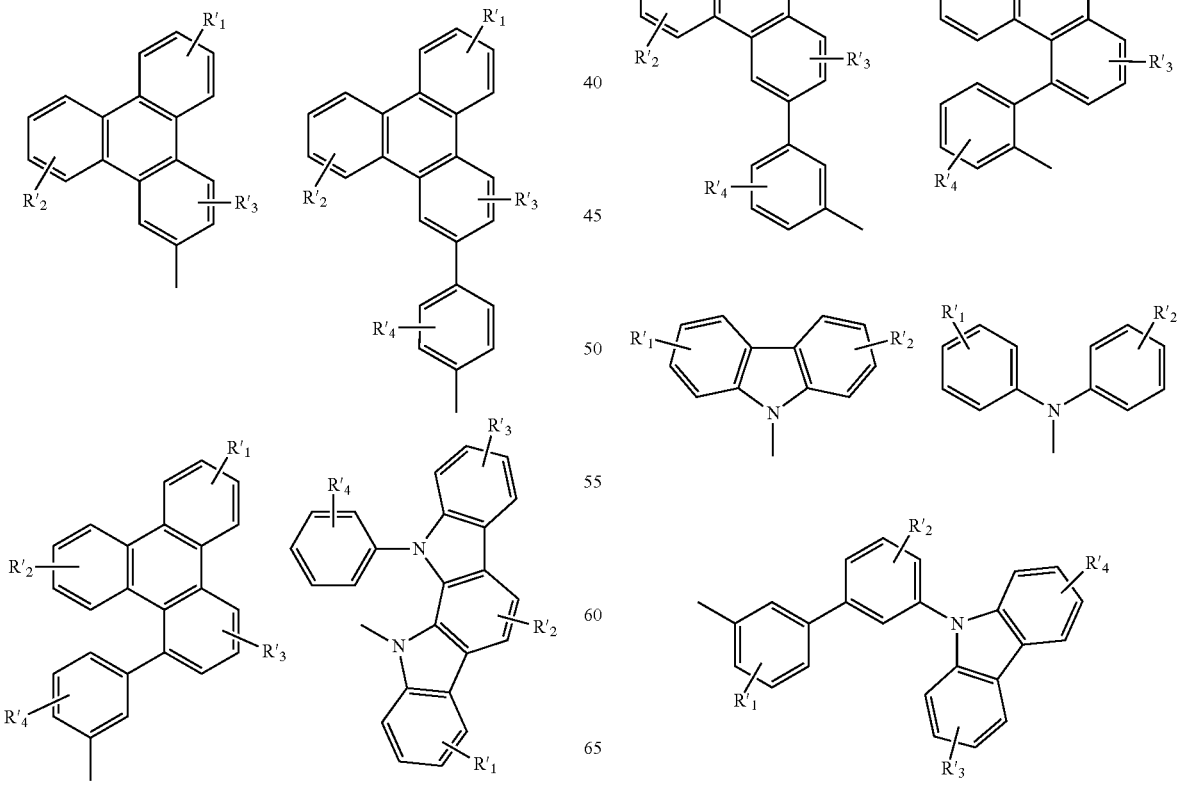

-continued

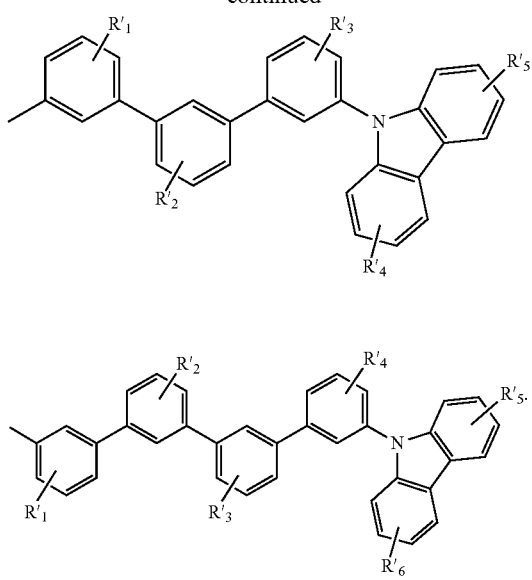

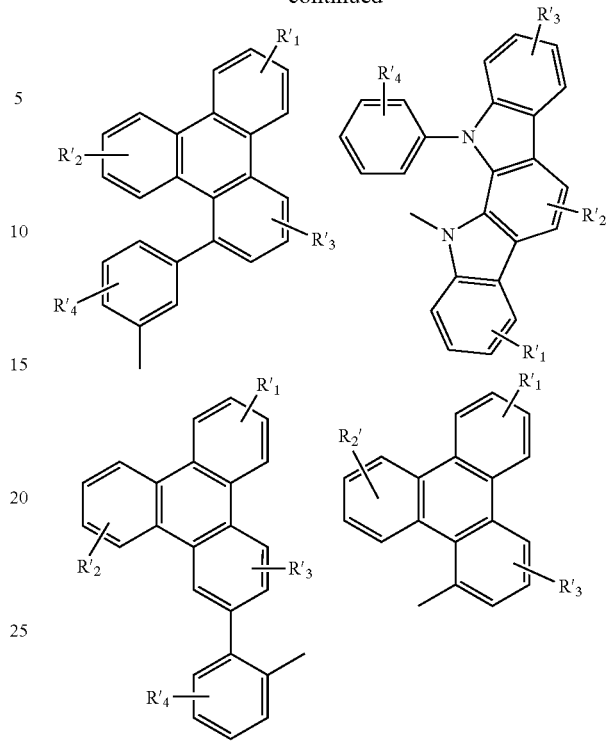

R'₁, R'₂, R'₃, and R'₄ may represent mono, di, tri, or tetra or penta substitutions; and R'₁, R'₂, R'₃, and R'₄ are independently selected from the group consisting of hydrogen, alkyl, heteroalkyl, aryl and heteroaryl. Preferably, R'₁, R'₂, R'₃, and R'₄ are each independently hydrogen or methyl.

The compounds described herein have the formula:

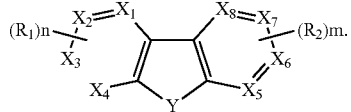

FORMULA I

Where $X_1$, $X_2$, $X_3$, $X_4$, $X_5$, $X_6$, $X_7$, and $X_8$ are independently selected from the group consisting of a carbon atom and a nitrogen atom, and at least one of $X_1$, $X_2$, $X_3$, $X_4$, $X_5$, $X_6$, $X_7$, and $X_8$ is a nitrogen atom. Y is S or O; wherein $R_1$ and $R_2$ may represent mono, di, tri, or tetra substitutions. $R_1$ and $R_2$ are independently selected from the group consisting of hydrogen, alkyl, aryl and halide and at least one of $R_1$ and $R_2$ is selected from the group consisting of:

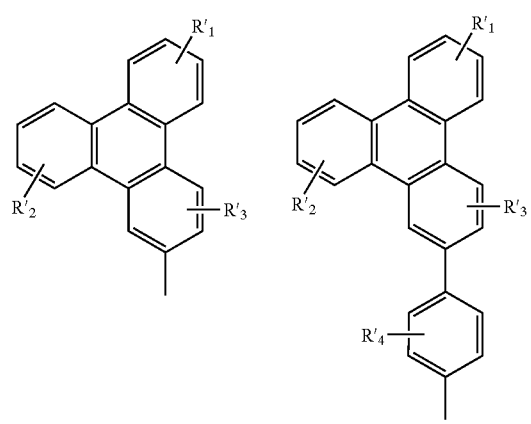

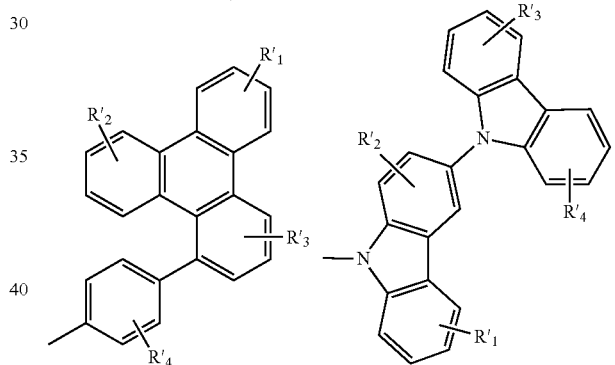

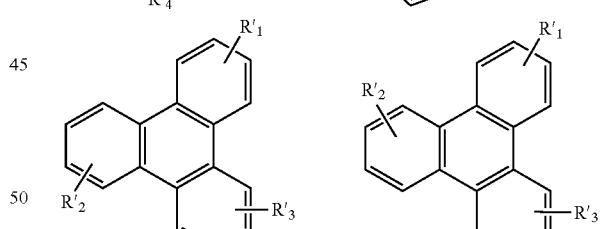

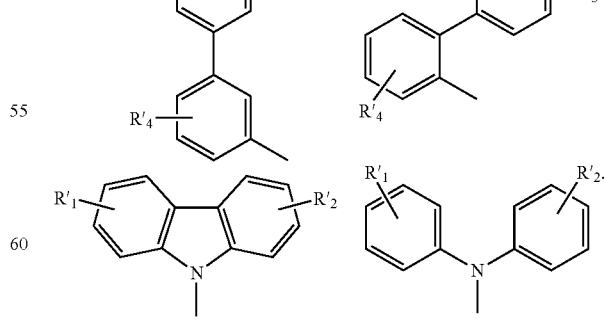

R'₁, R'₂, R'₃, and R'₄ may represent mono, di, tri, or tetra or penta substitutions; and R'₁, R'₂, R'₃, and R'₄ are independently selected from the group consisting of hydrogen, alkyl, heteroalkyl, aryl and heteroaryl. Preferably, $R'_1$, $R'_2$, $R'_3$, and $R'_4$ are each independently hydrogen or methyl.

Preferably, m and n are 0, 1, 2, 3, or 4, and m+n is equal to or greater than 2 and m+n is equal to or less than 6. Without being bound by theory, it is thought that at least 2 provides better electron transport properties by providing a preferred amount of electron transport moieties. Moreover, it is thought that greater than 6 may result in an increase in sublimation temperature so that the manufacturing of devices with such compounds is not as practical.

In one aspect, at least one of $R_1$ and $R_2$ is selected from the group consisting of:

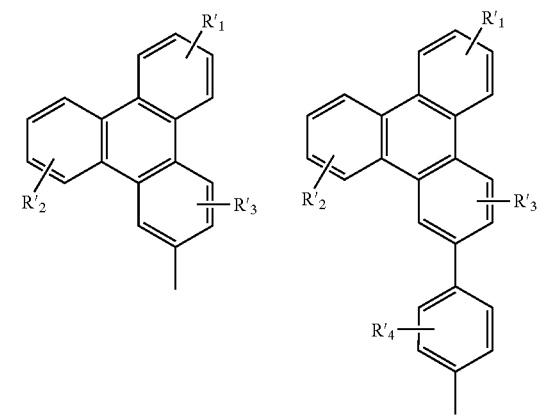

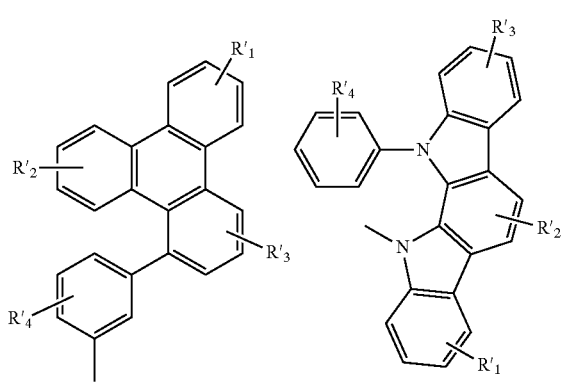

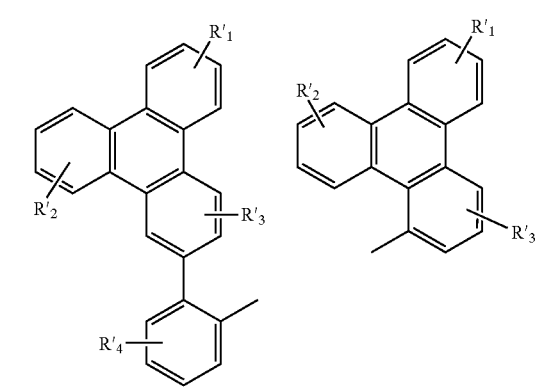

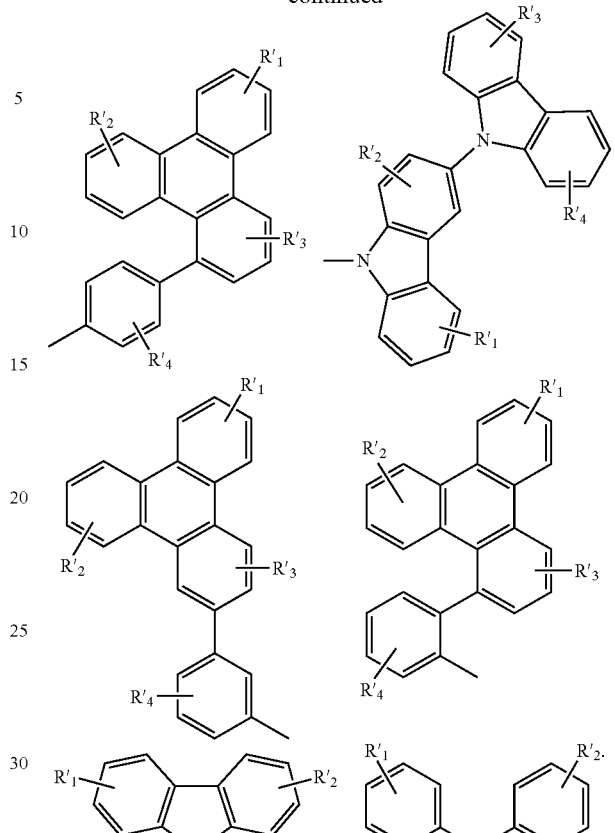

-continued $R'_1$, $R'_2$, $R'_3$, and $R'_4$ are independently selected from the group consisting of hydrogen, alkyl, heteroalkyl, aryl and heteroaryl. Preferably, $R'_1$, $R'_2$, $R'_3$, and $R'_4$ are each independently hydrogen or methyl.

Specific examples of the compounds are provided, and include compounds selected from the group consisting of:

Compound 1

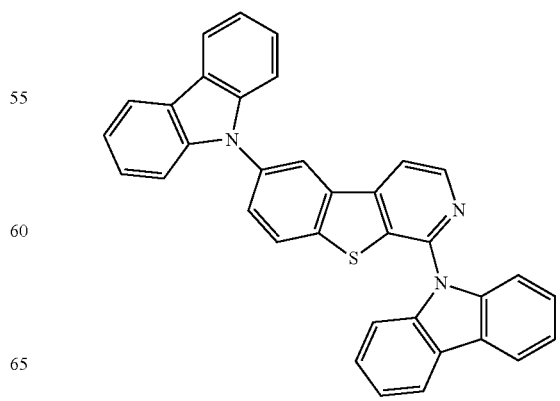

Compound 2
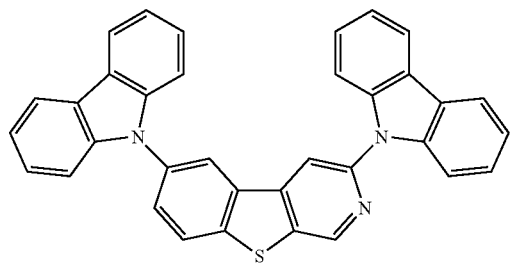
Compound 3
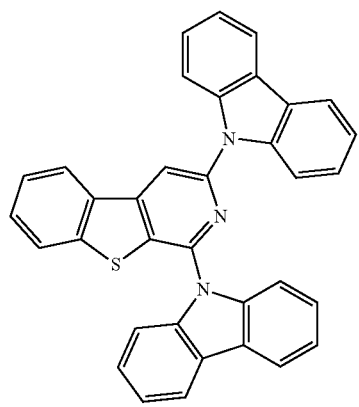
Compound 4
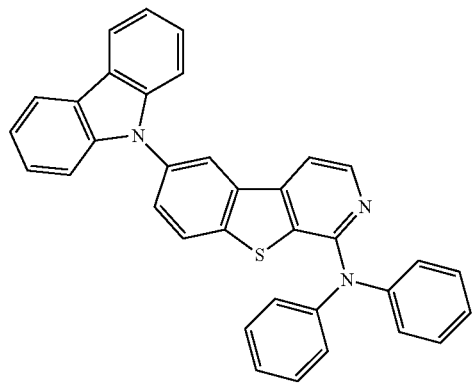
Compound 5
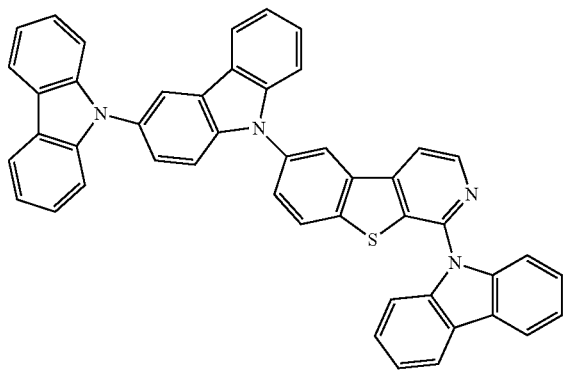
Compound 6
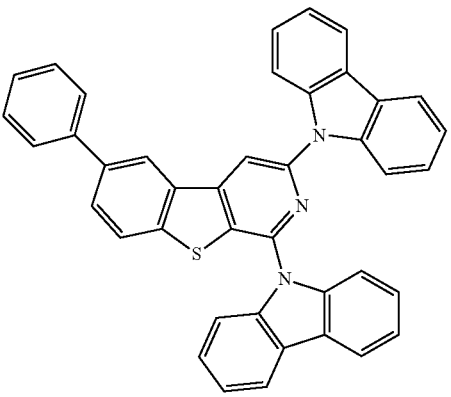
Compound 7
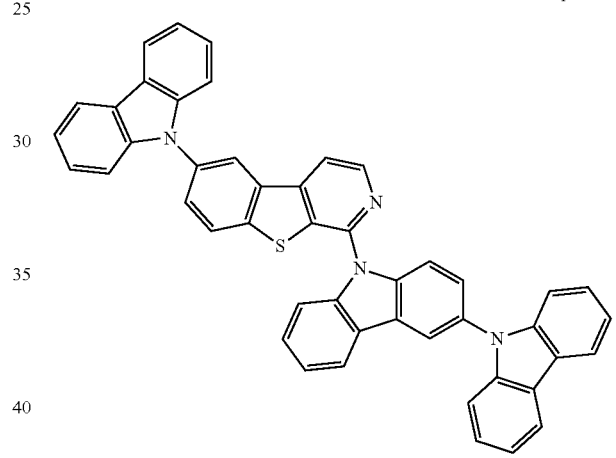
Compound 8
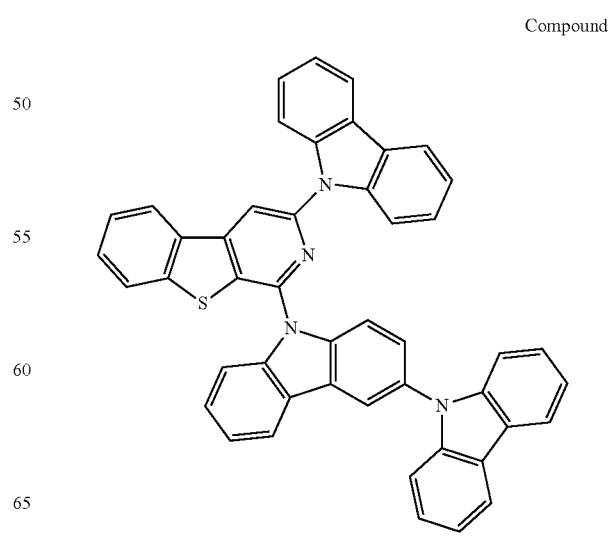

Compound 9
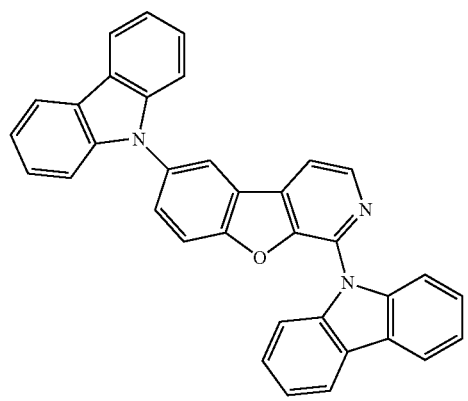
Compound 10
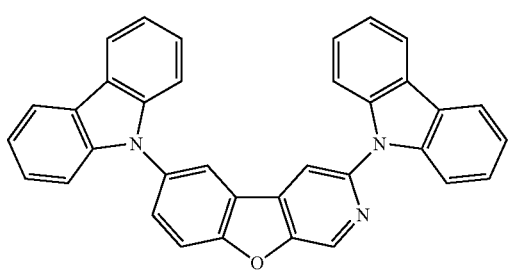
Compound 11
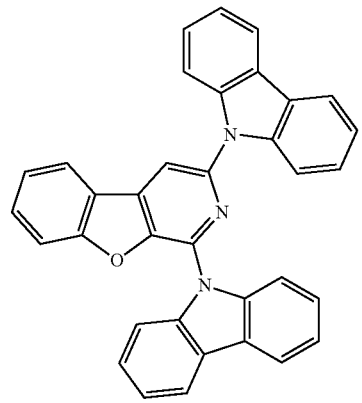
Compound 12
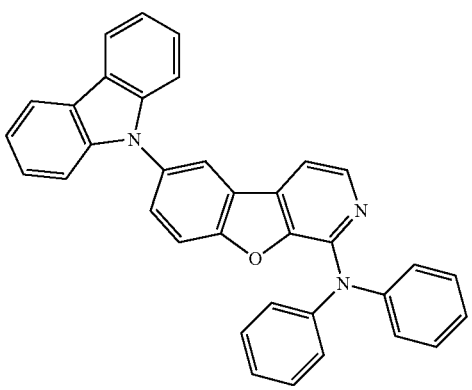
Compound 13
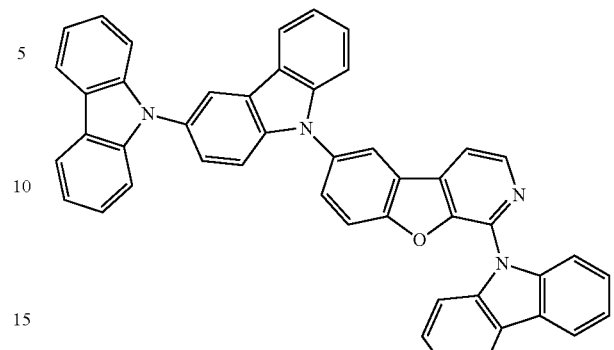
Compound 14
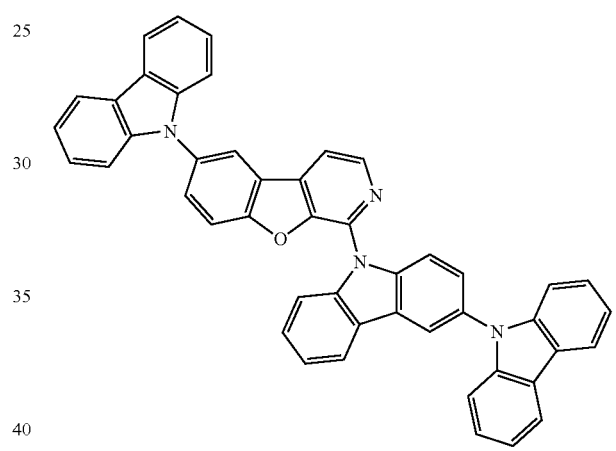
Compound 15
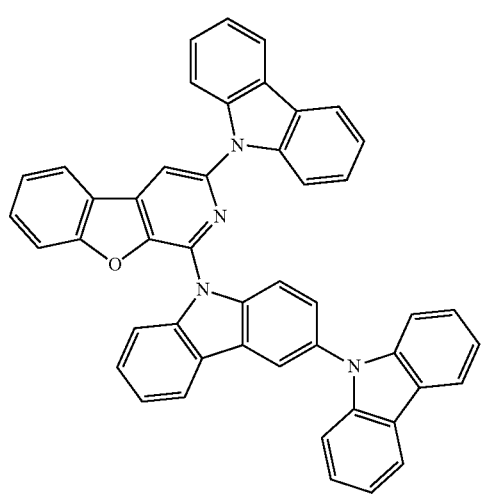

Compound 16
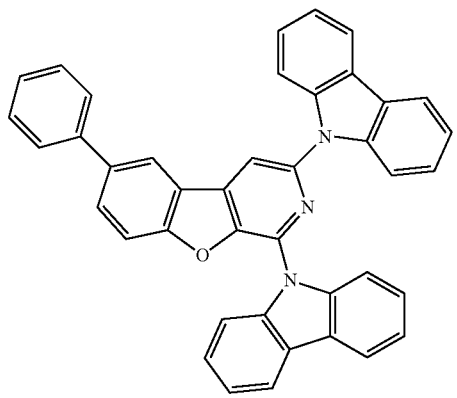
Compound 17
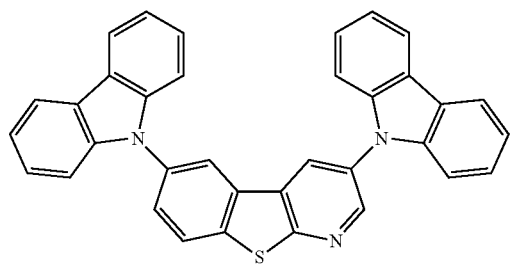
Compound 18
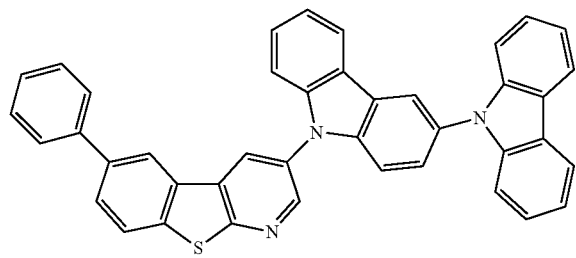
Compound 19
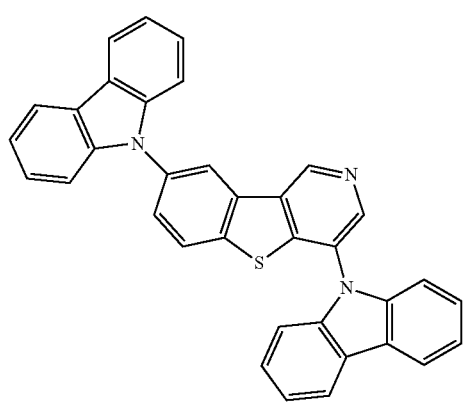
Compound 20
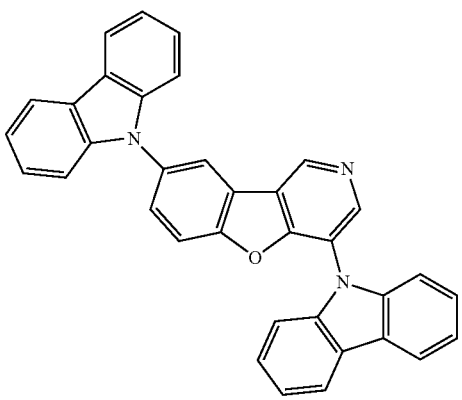
Compound 21
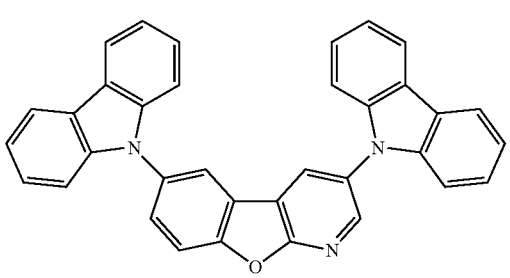
Compound 22
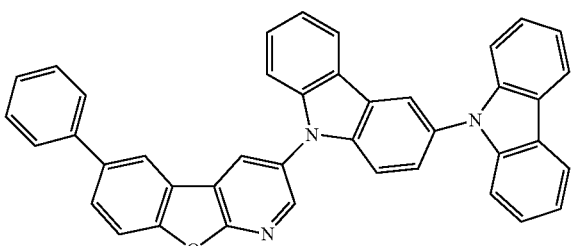
Compound 23
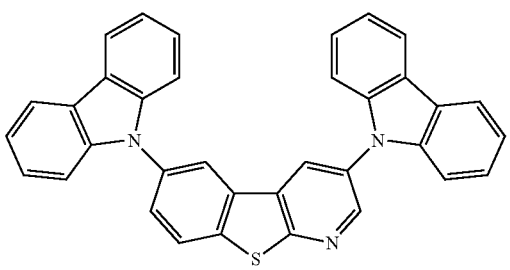
Compound 24
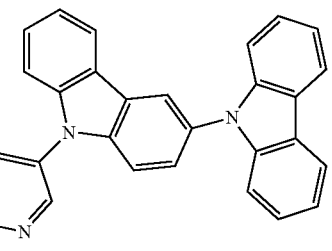

Compound 25
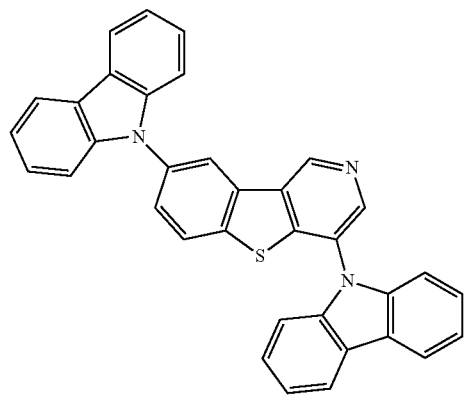
Compound 26
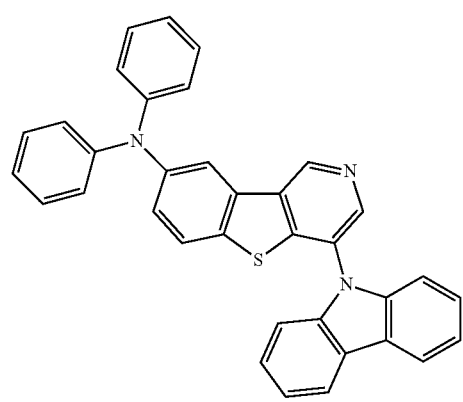
Compound 27
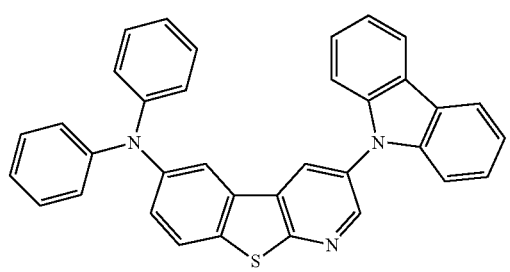
Compound 28
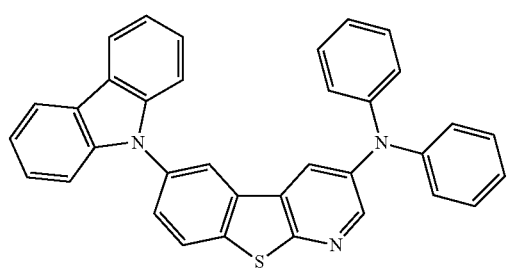
Compound 29
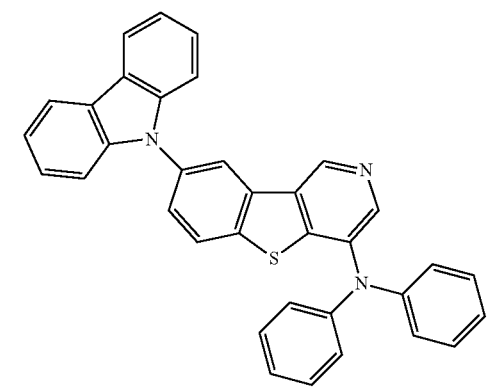
Compound 30
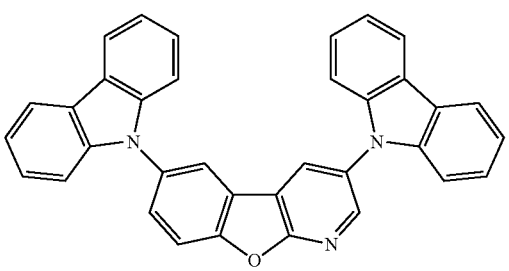
Compound 31
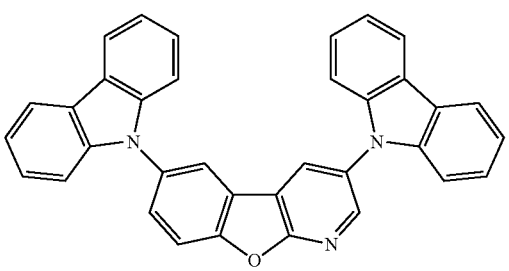
Compound 32
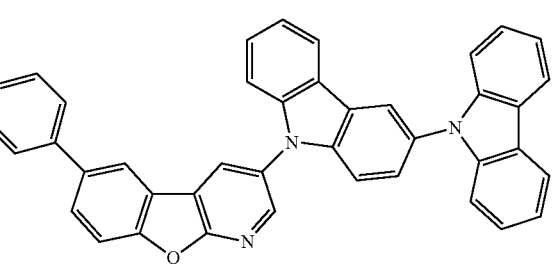

-continued
Compound 33
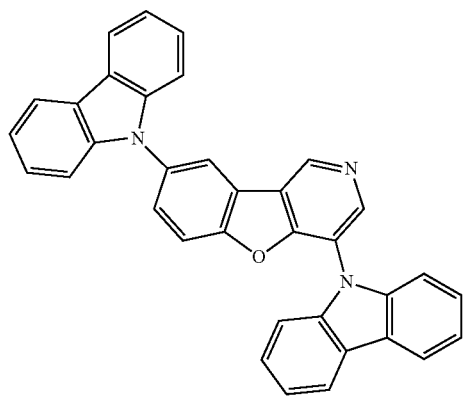
Compound 34
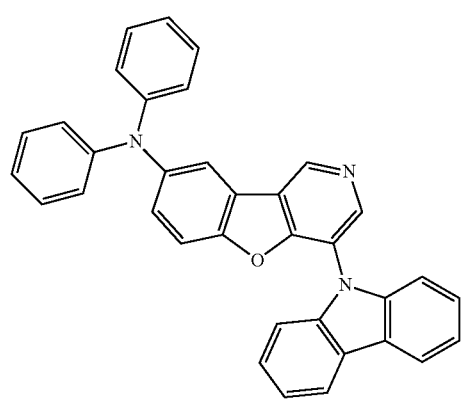
Compound 35
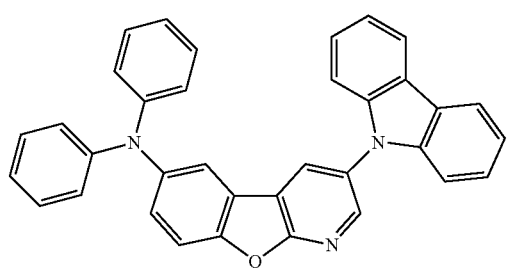
Compound 36
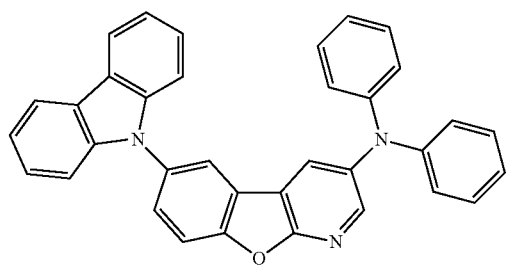
-continued
Compound 37
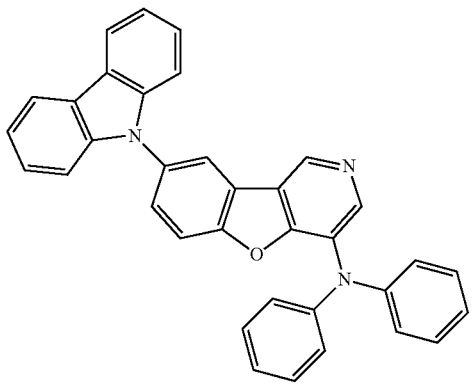
Compound 38
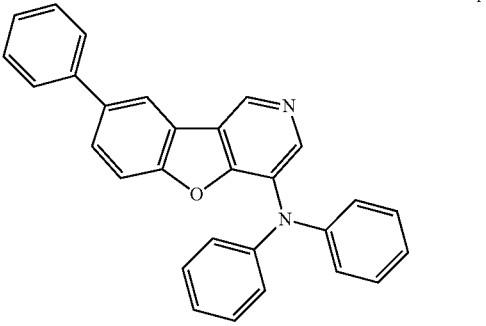
Compound 39
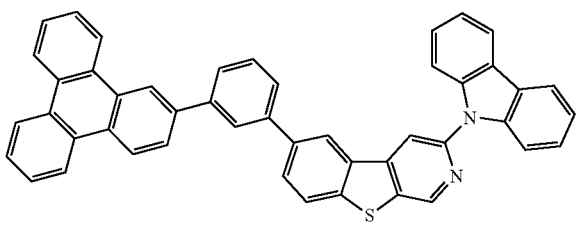
Compound 40
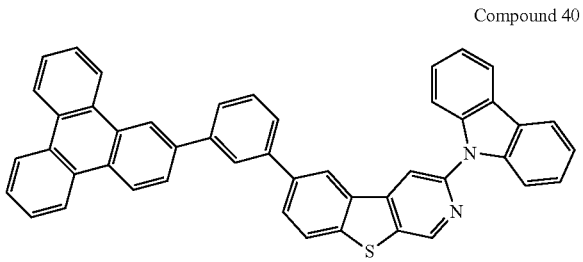
Compound 41
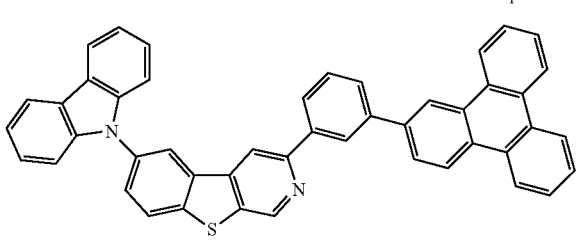

-continued
Compound 42
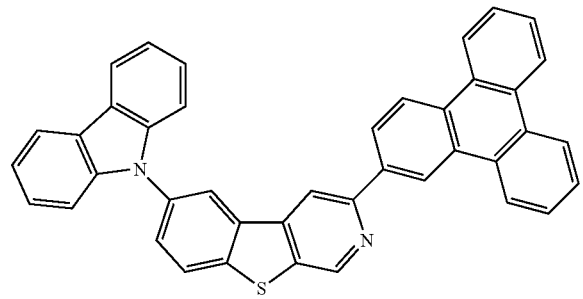
Compound 43
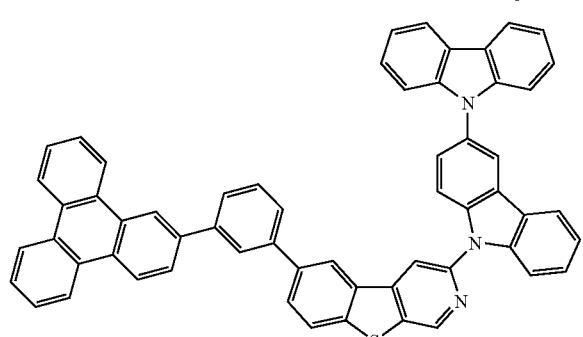
Compound 44
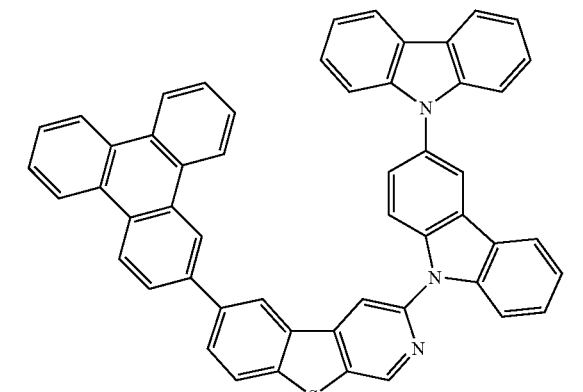
Compound 45
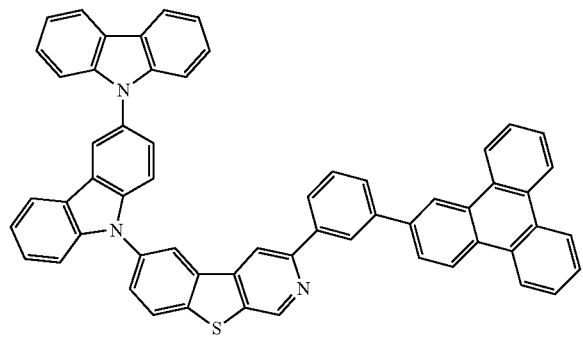
-continued
Compound 46
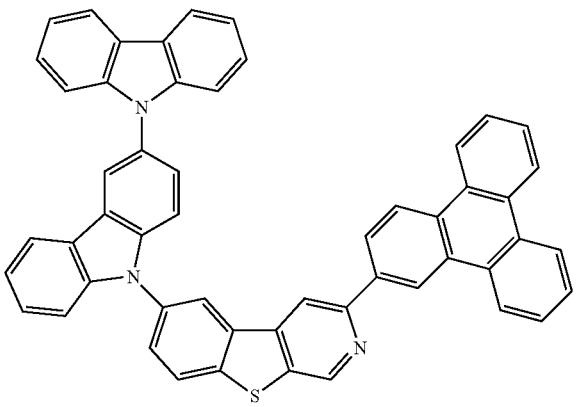
Compound 47
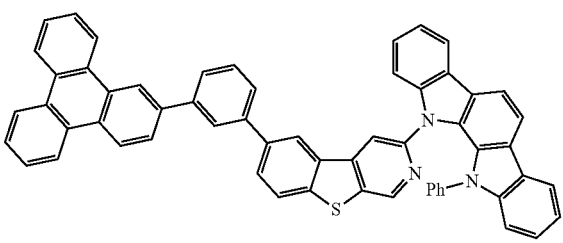
Compound 48
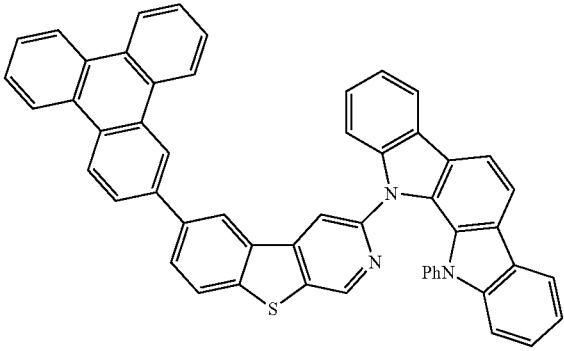
Compound 49
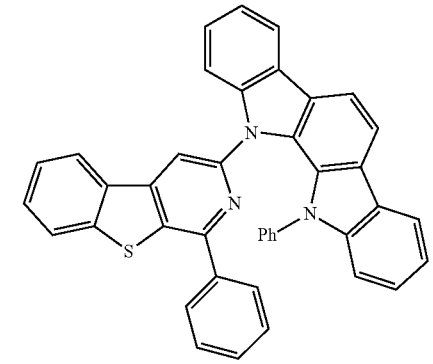

-continued
Compound 50
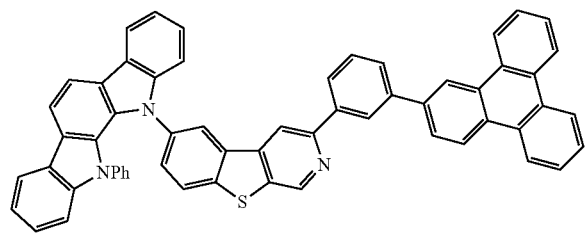
Compound 51
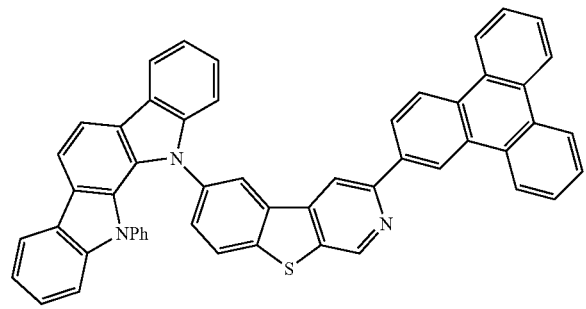
Compound 52
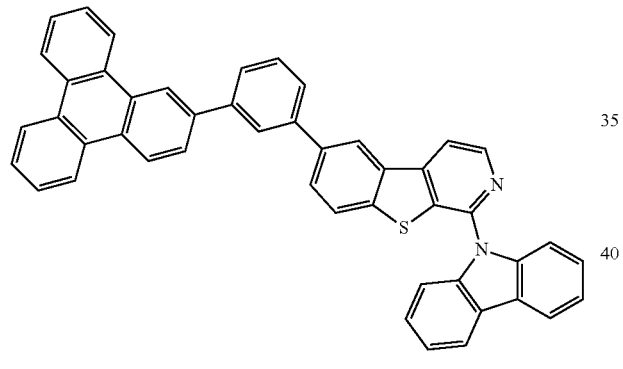
Compound 53
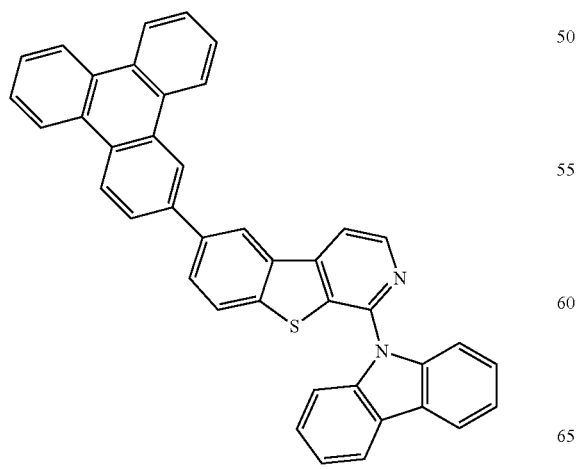
-continued
Compound 54
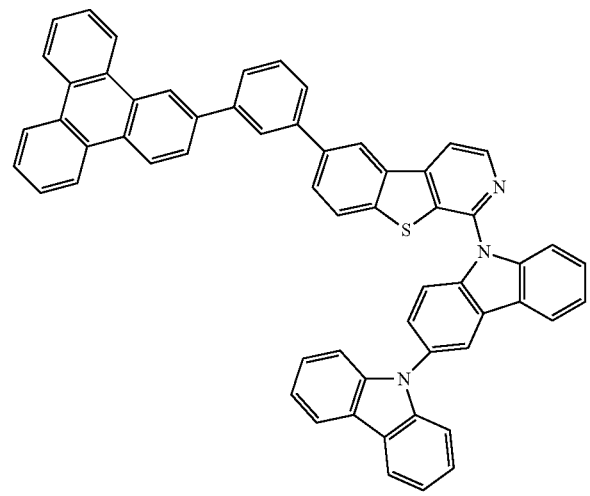
Compound 55
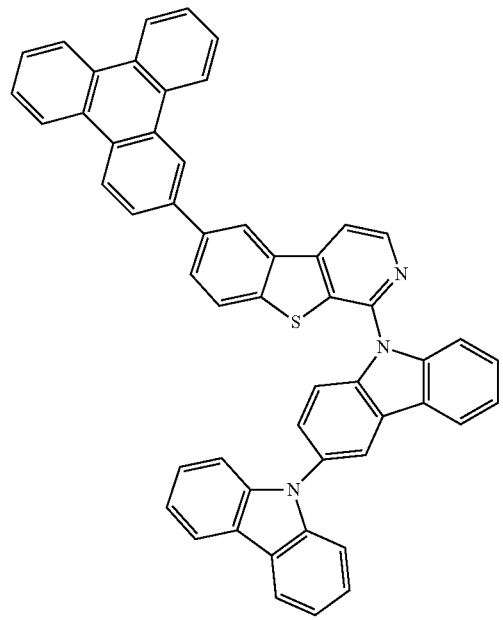
Compound 56
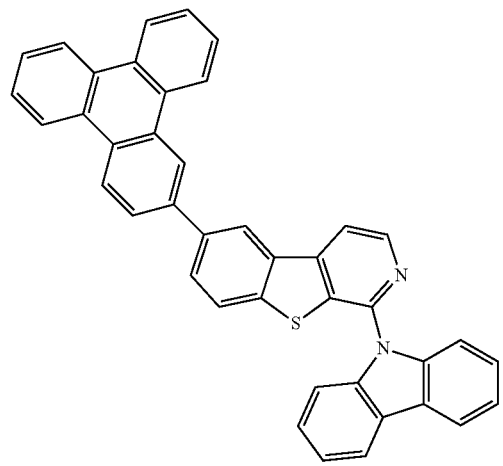

Compound 57
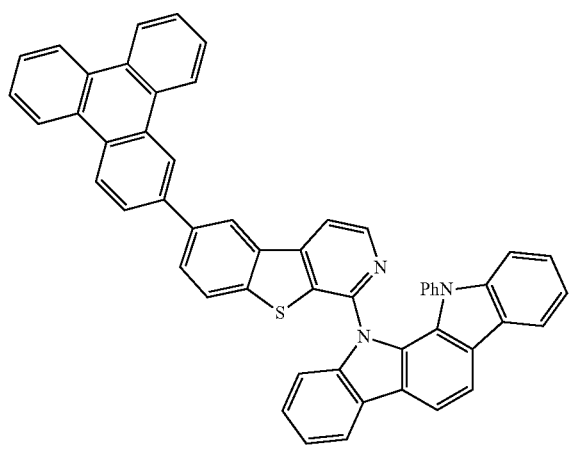
Compound 58
Compound 59
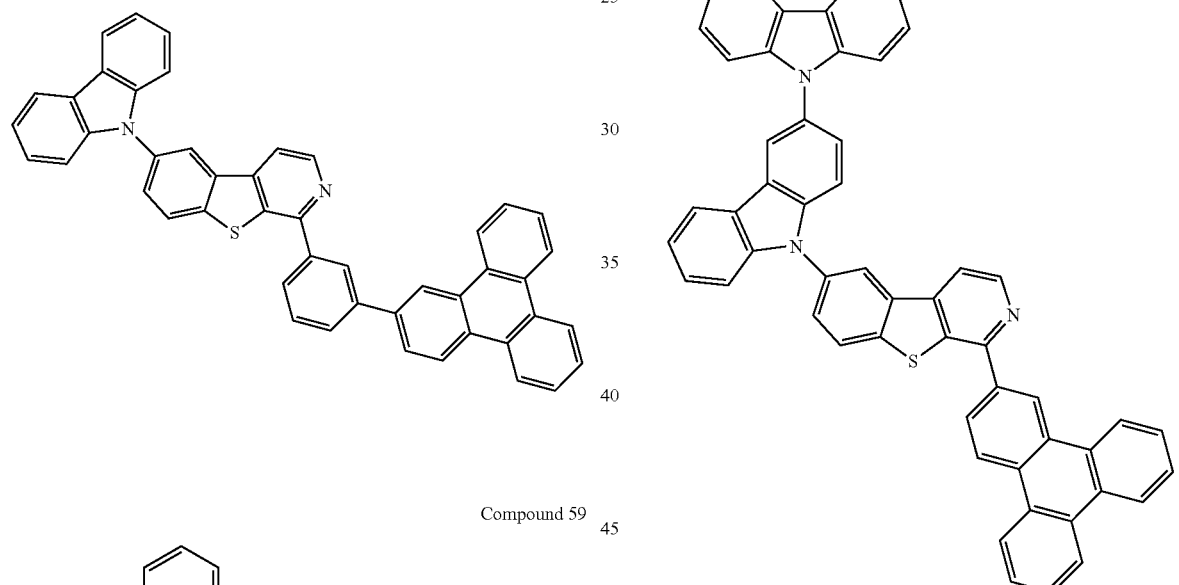
Compound 60
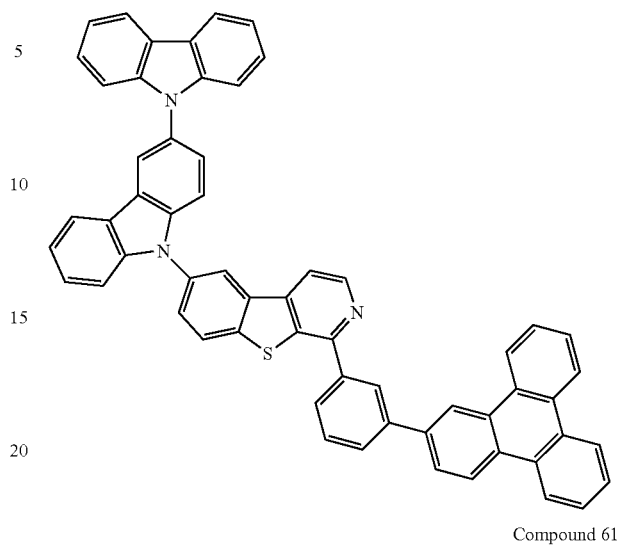
Compound 61
Compound 62
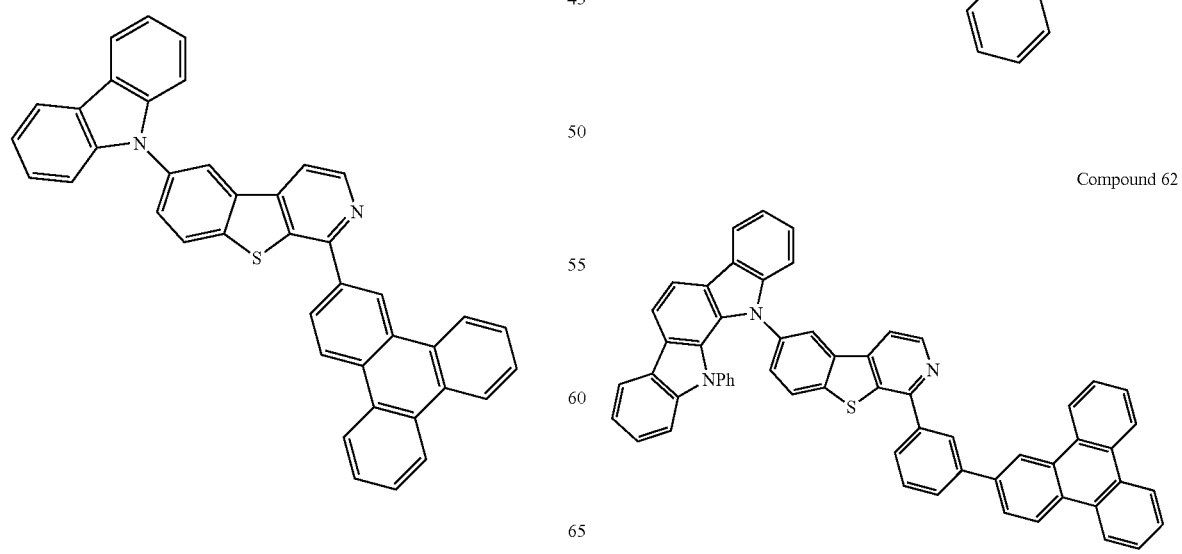

Compound 63
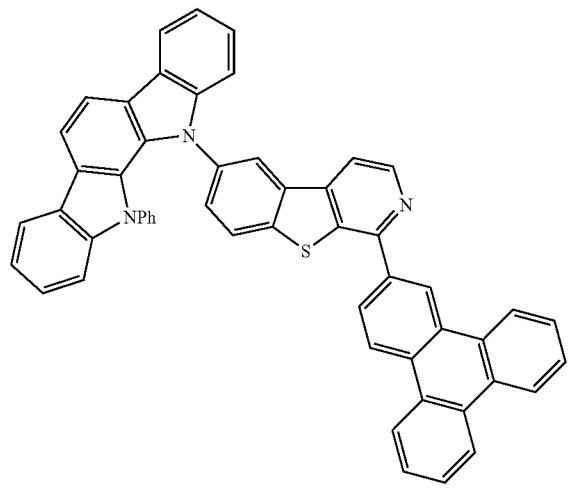
Compound 64
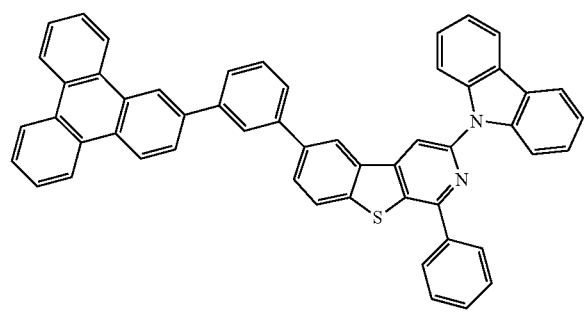
Compound 65
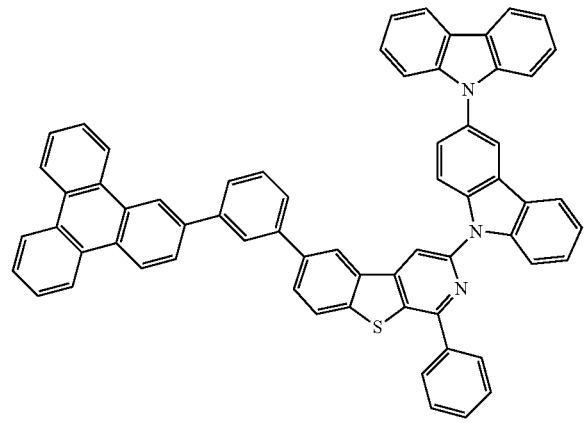
Compound 66
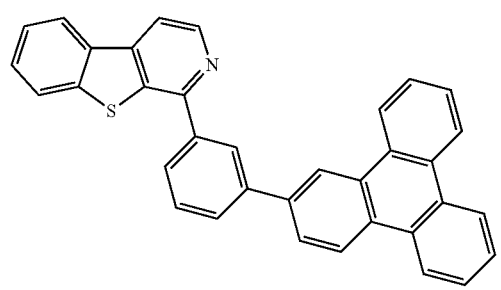
Compound 67
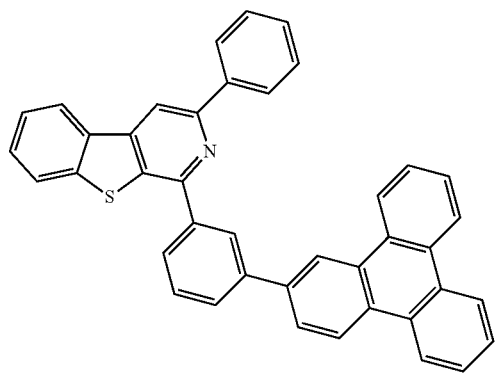
Compound 68
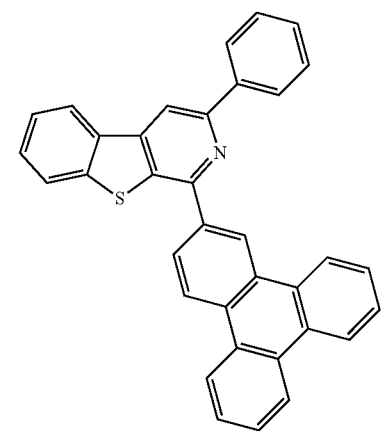
Compound 69
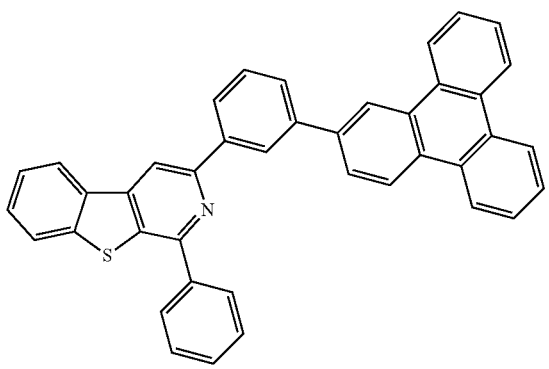
Compound 70
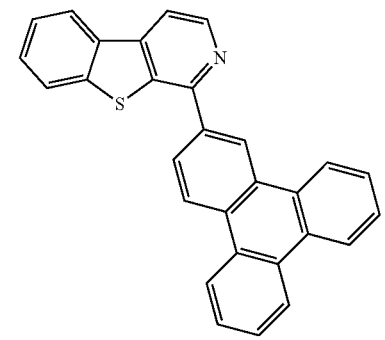

Compound 71
Compound 72
Compound 73
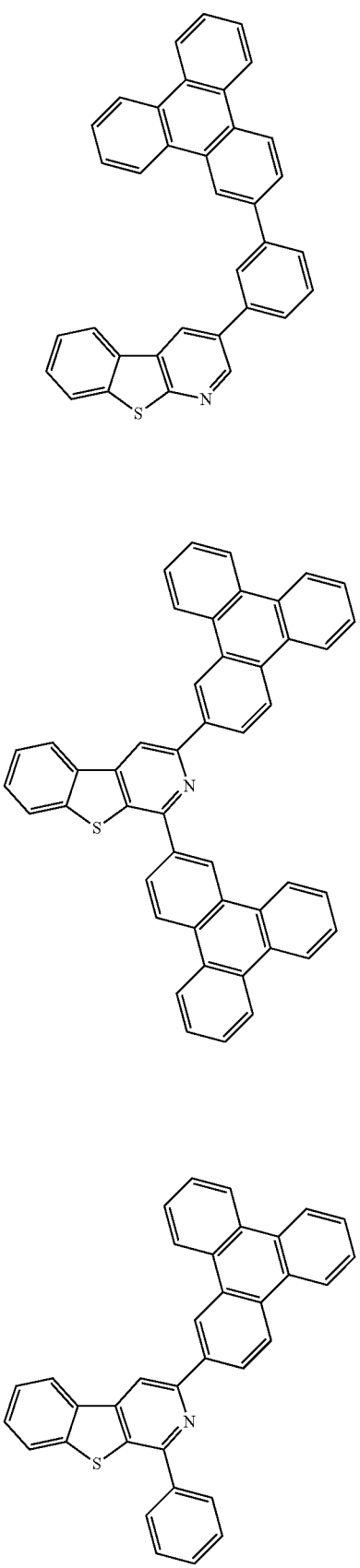
Compound 74
Compound 75
Compound 76
Compound 77
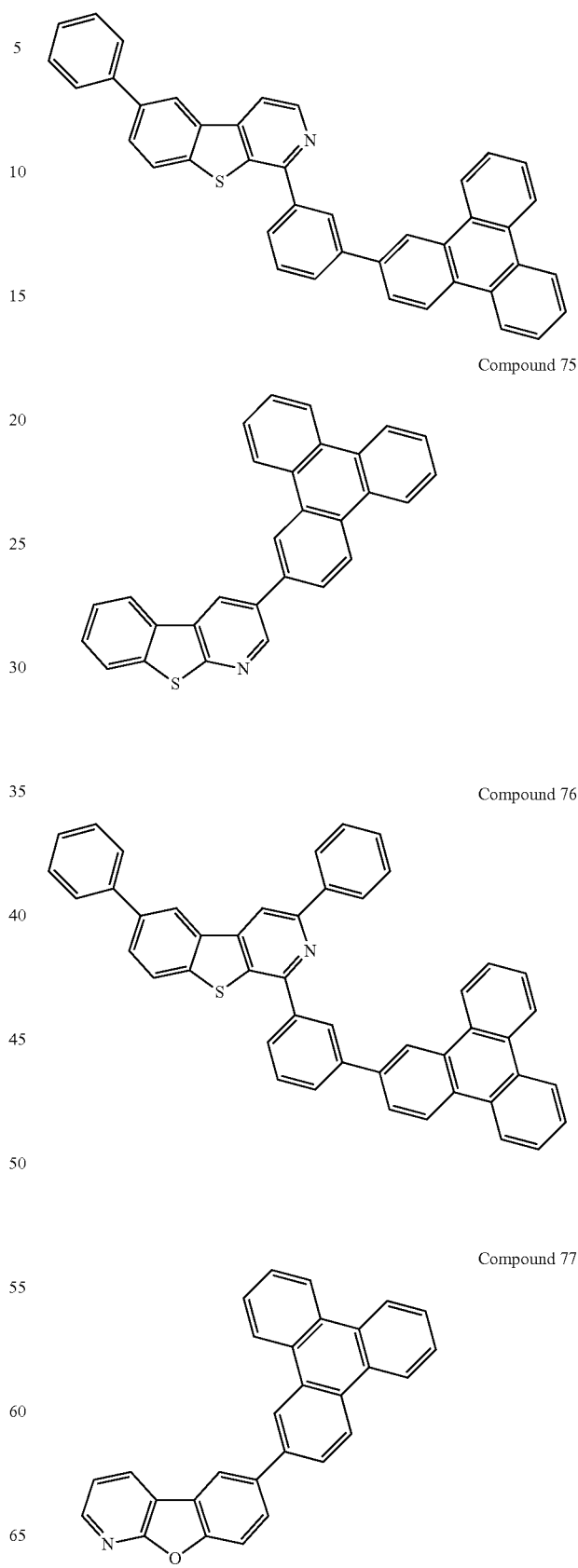

Compound 78
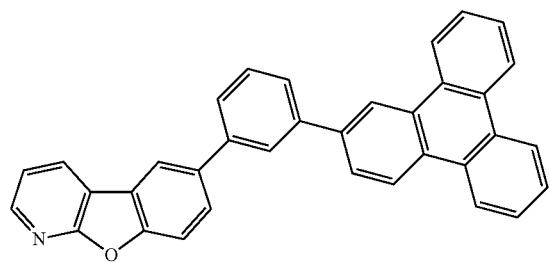
Compound 79
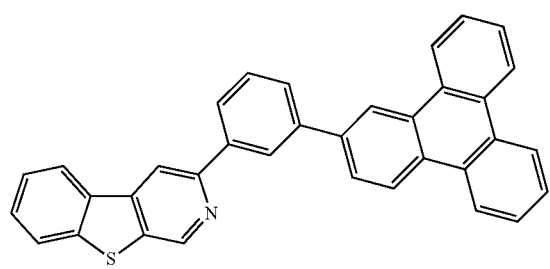
Compound 80
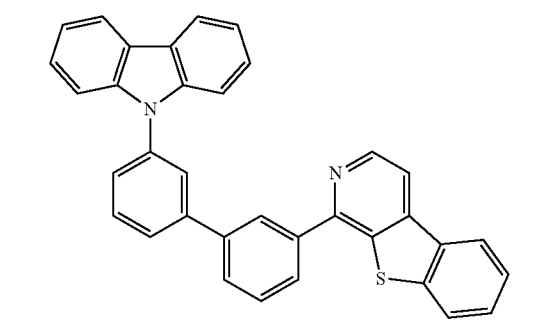
Compound 81
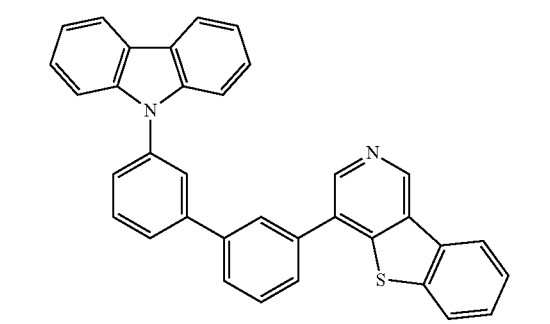
Compound 82
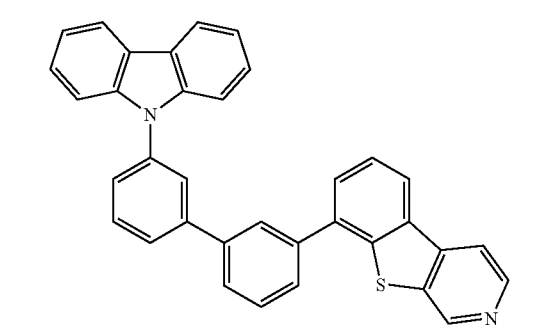
Compound 83
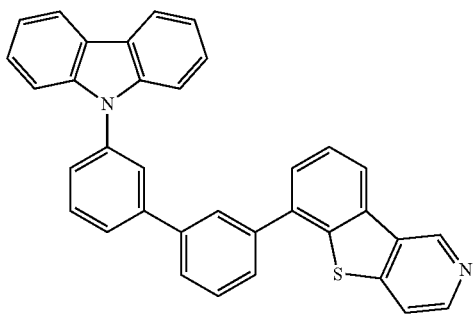
Compound 84
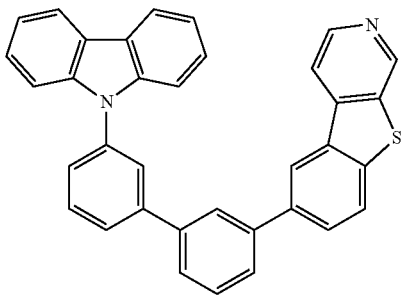
Compound 85
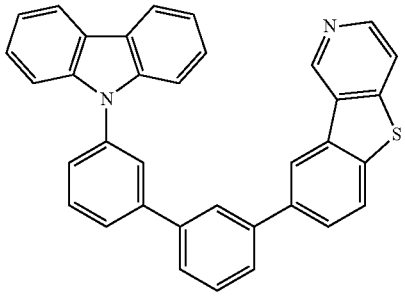
Compound 86
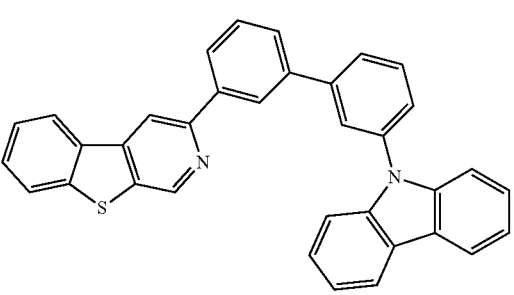

Compound 87
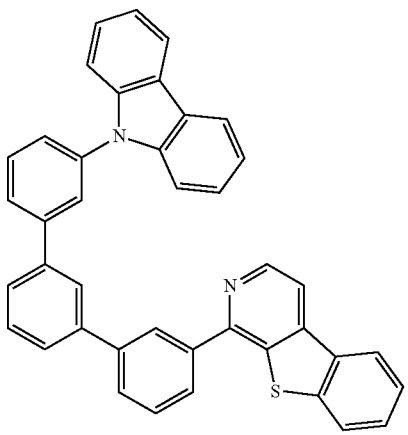
Compound 88
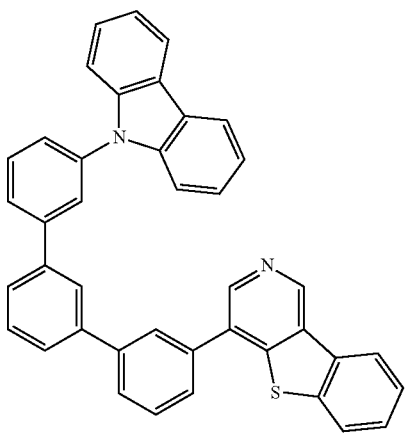
Compound 89
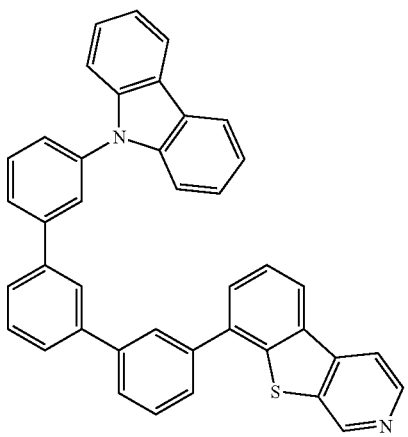
Compound 90
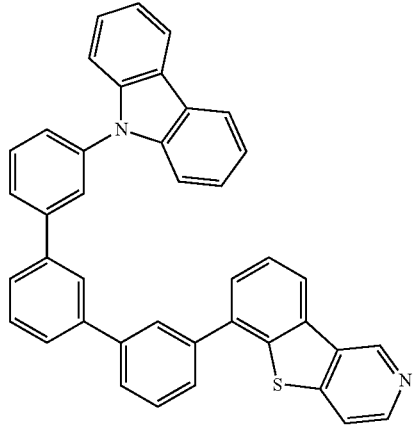
Compound 91
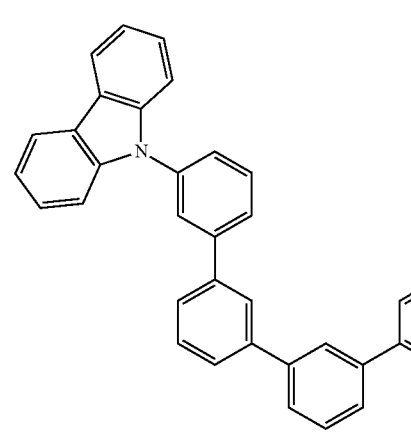
Compound 92
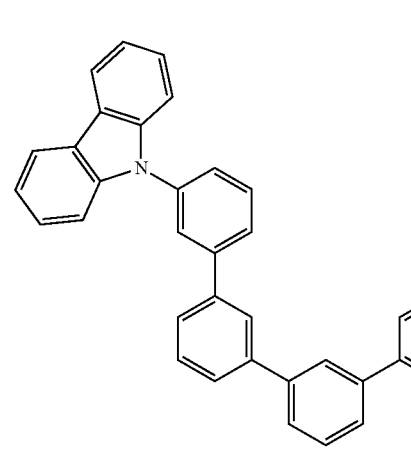

Compound 93
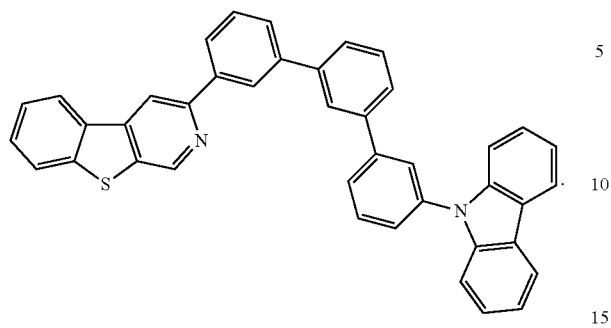
Specific examples of such compounds are provided, and include compounds selected from the group consisting of:
Compound 1
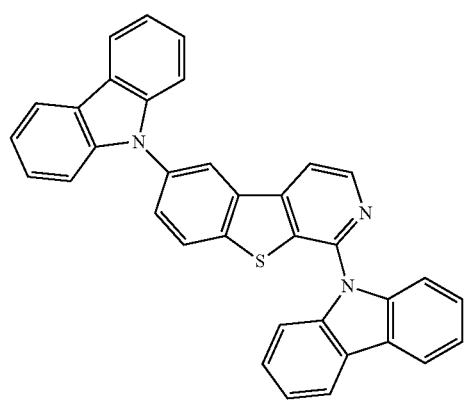
Compound 2
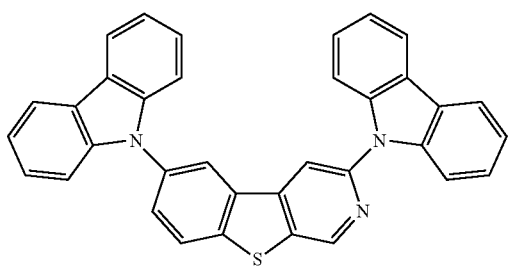
Compound 3
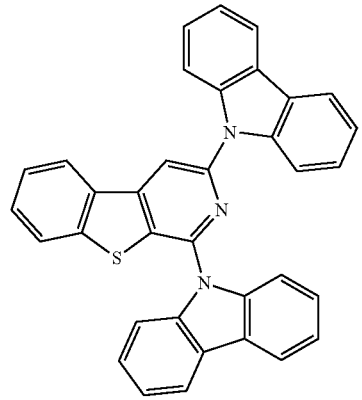
Compound 4
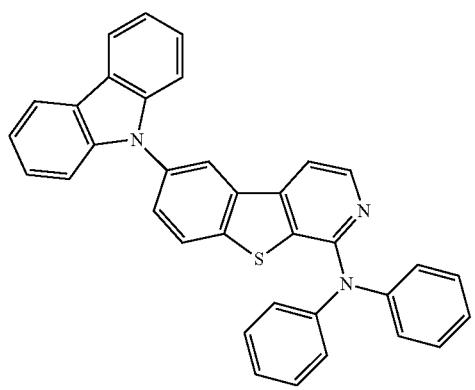
Compound 5
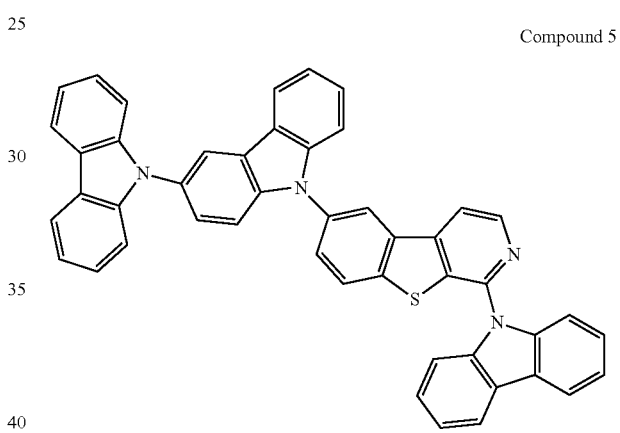
Compound 6
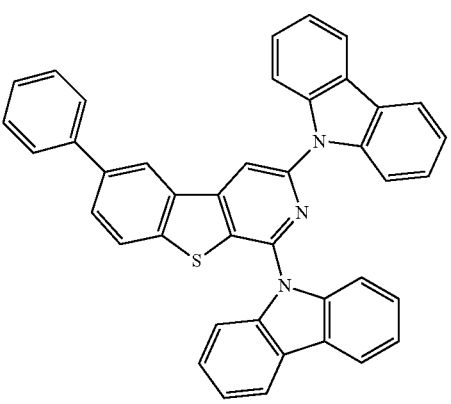

Compound 7
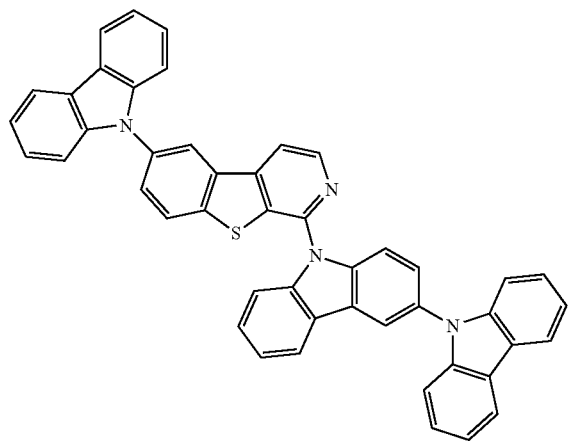
Compound 8
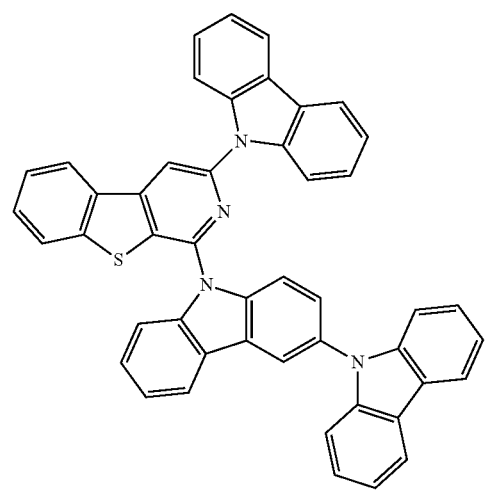
Compound 9
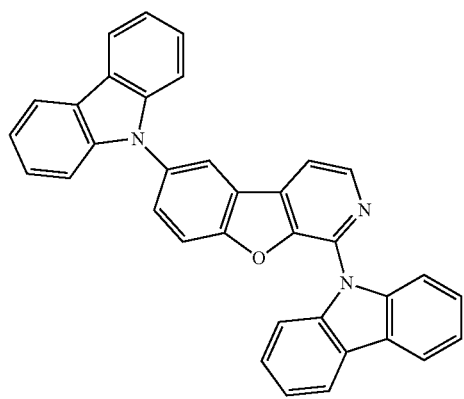
Compound 10
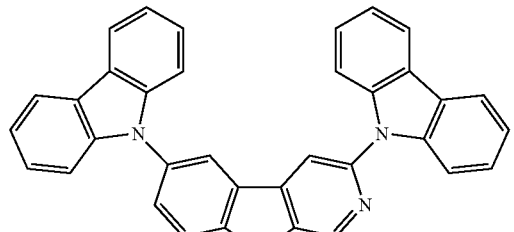
Compound 11
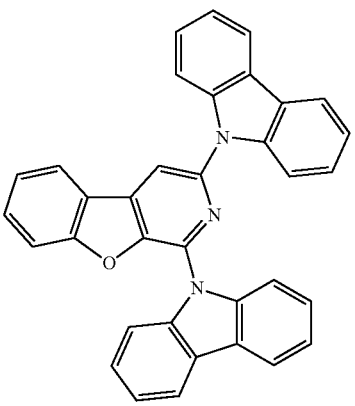
Compound 12
Compound 13
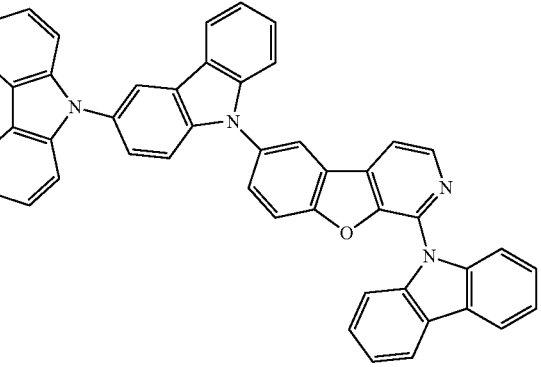

Compound 14
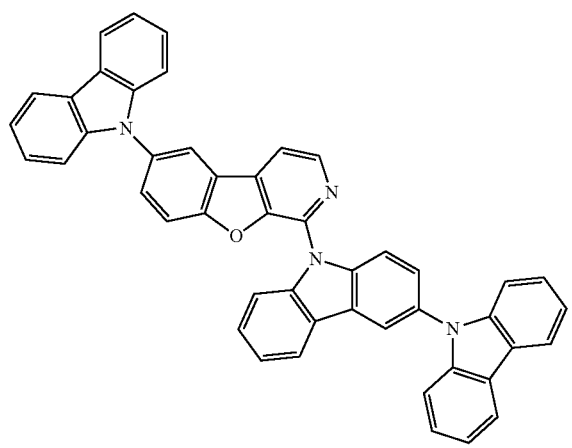
Compound 15
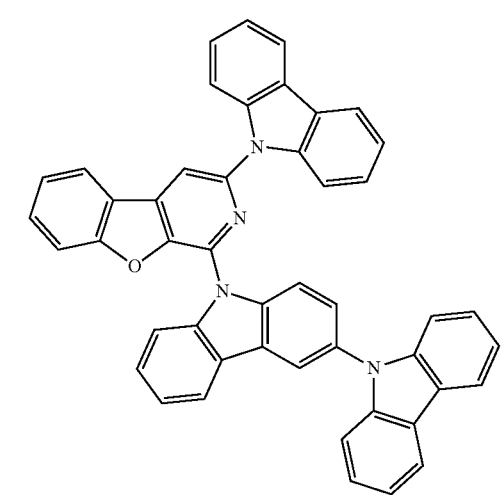
Compound 16
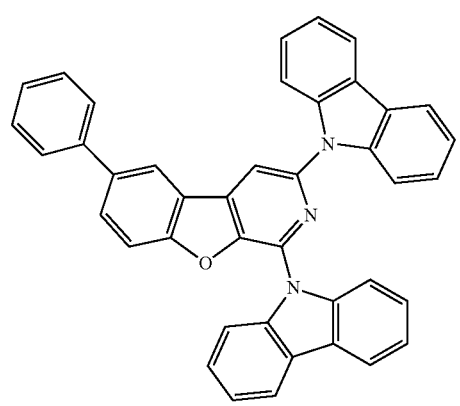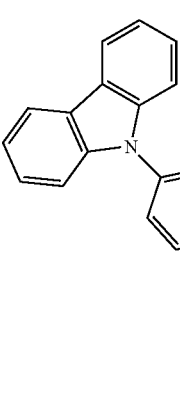
Compound 17
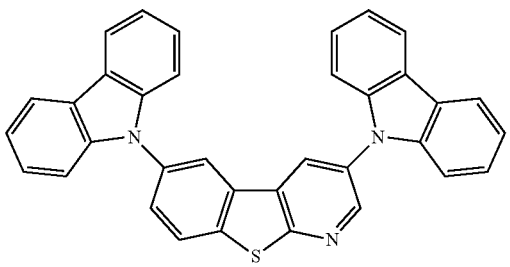
Compound 18
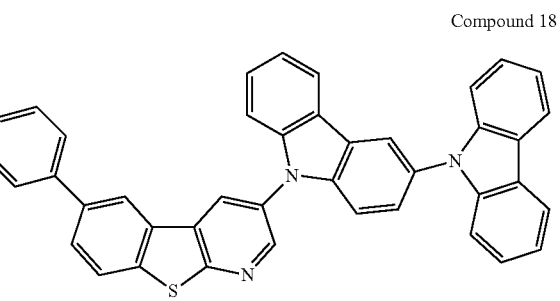
Compound 19
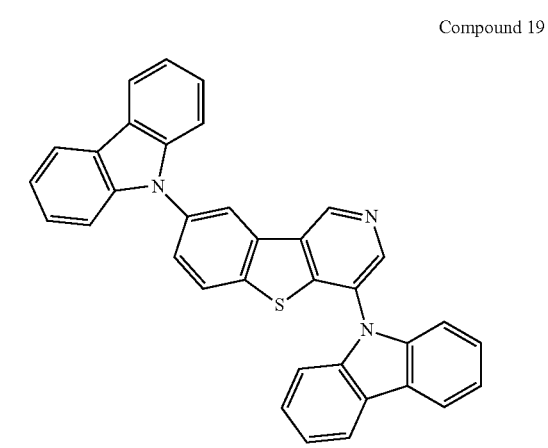
Compound 20

Compound 21
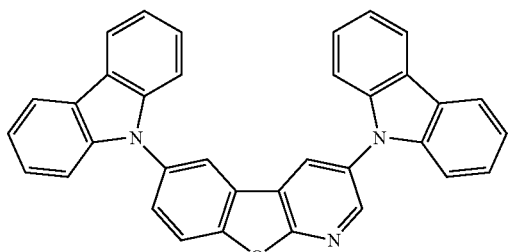
Compound 22
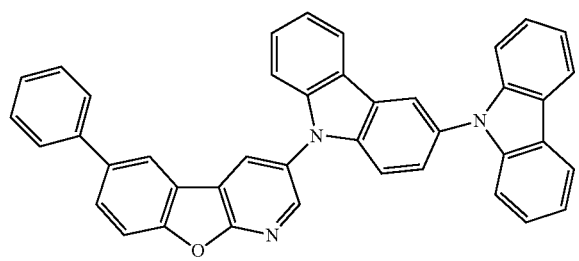
Compound 23
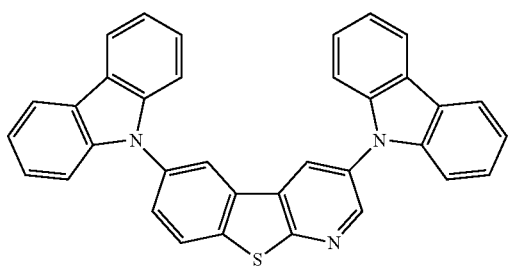
Compound 24
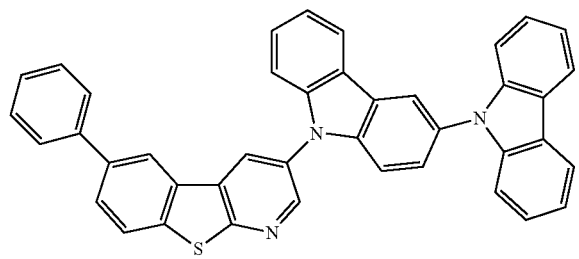
Compound 25
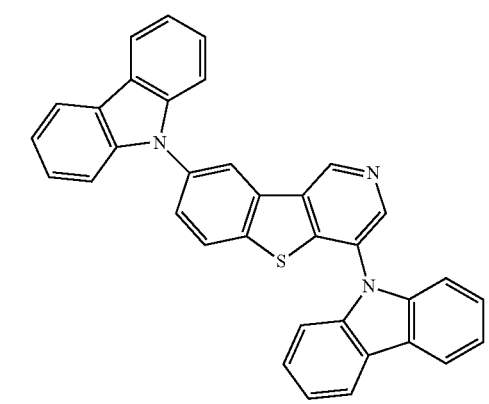
Compound 26
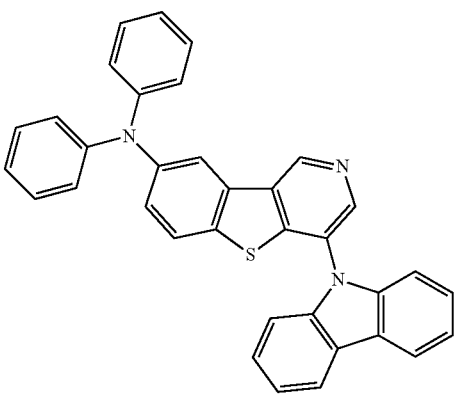
Compound 27
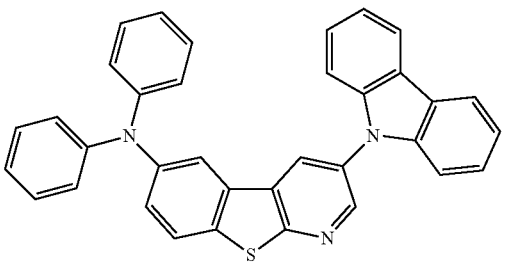
Compound 28
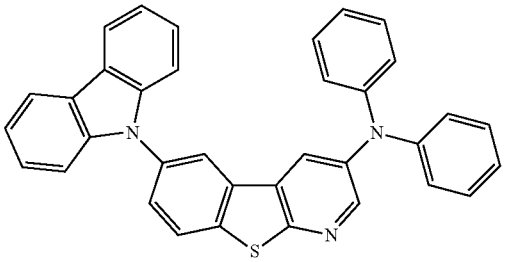
Compound 29
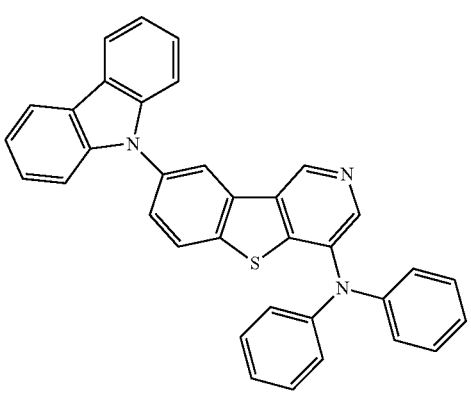

-continued
Compound 30
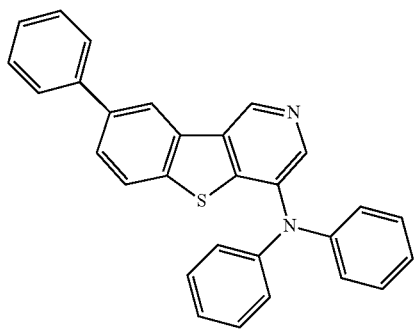
Compound 31
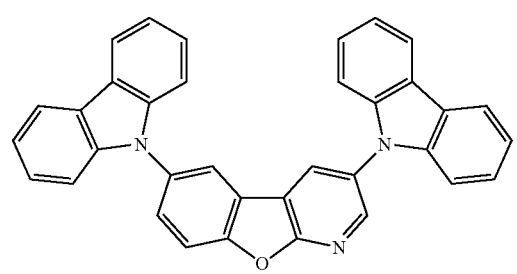
Compound 32
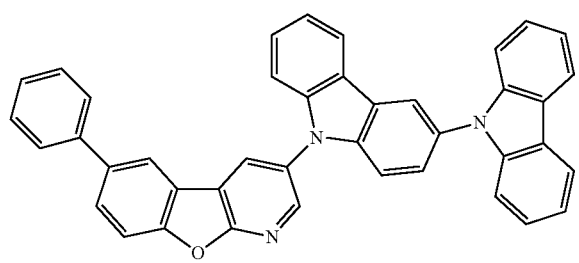
Compound 33
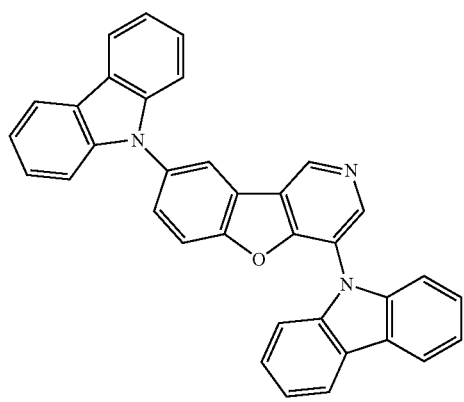
Compound 34
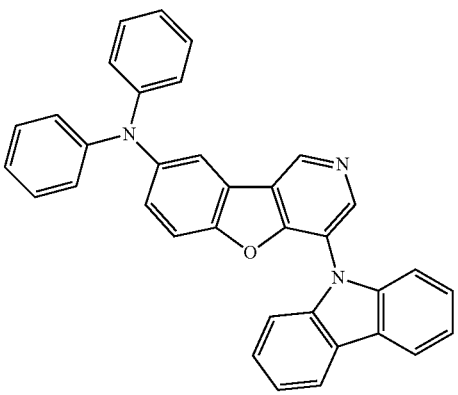
Compound 35
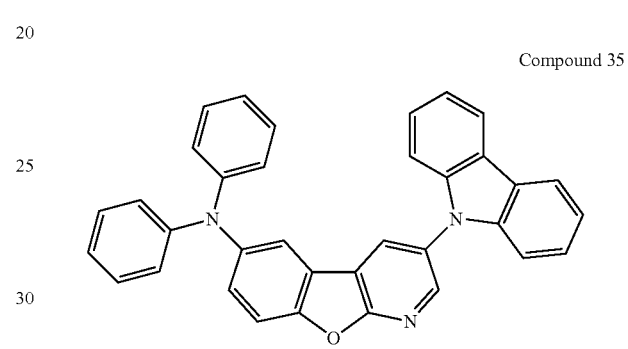
Compound 36
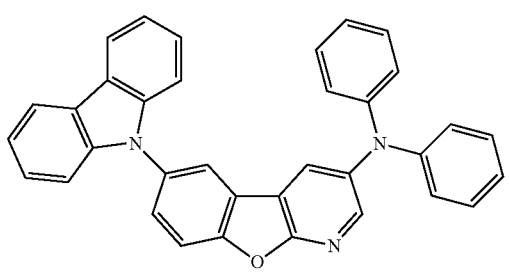
Compound 37
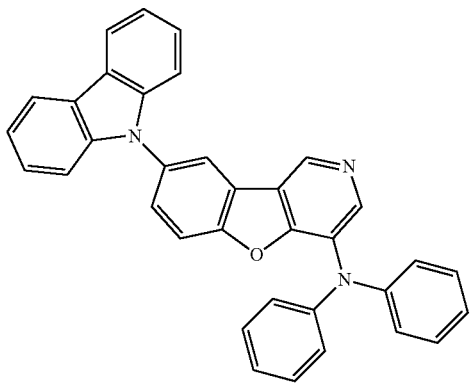

Compound 38
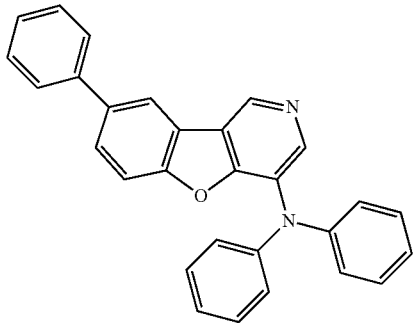
Compound 39
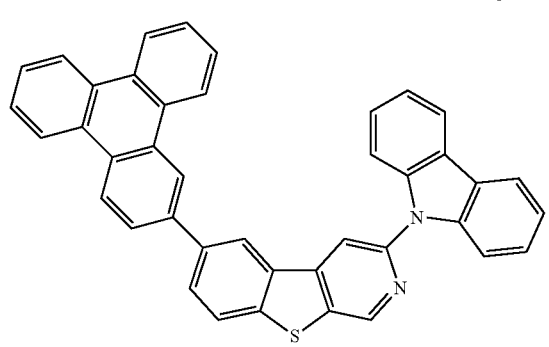
Compound 40
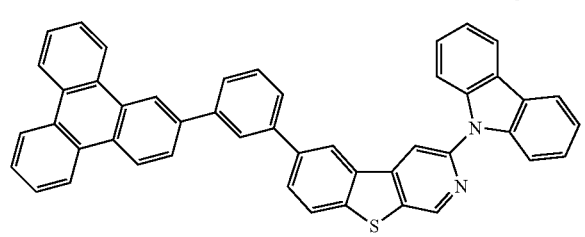
Compound 41
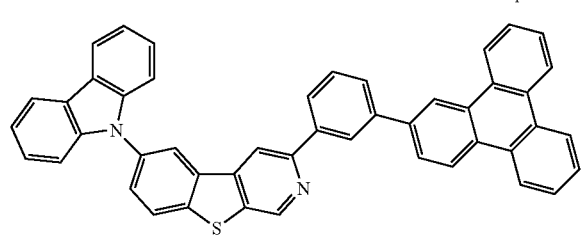
Compound 42
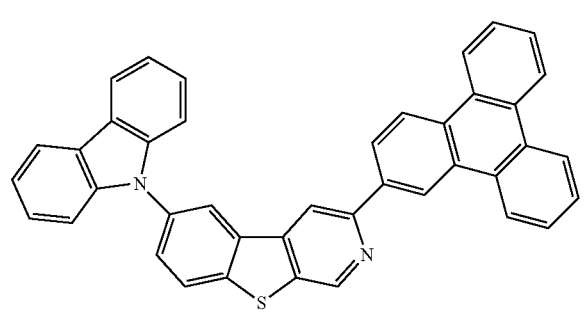
Compound 43
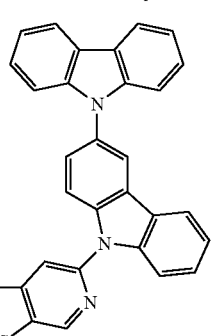
Compound 44
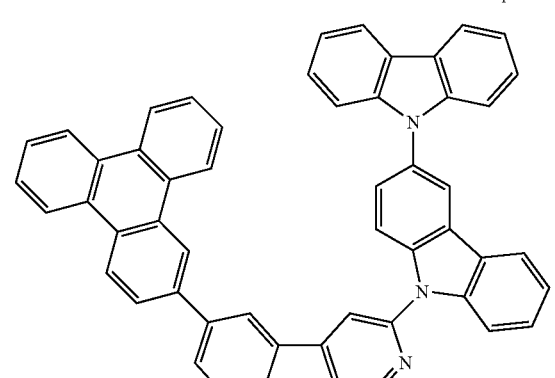
Compound 45
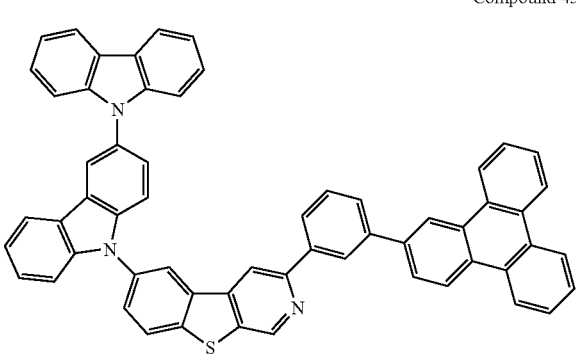
Compound 46
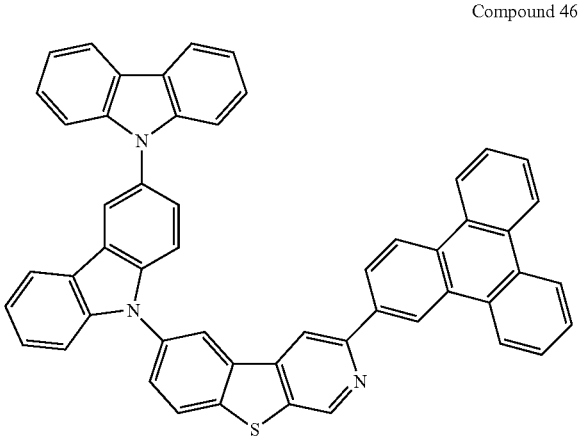

Compound 47
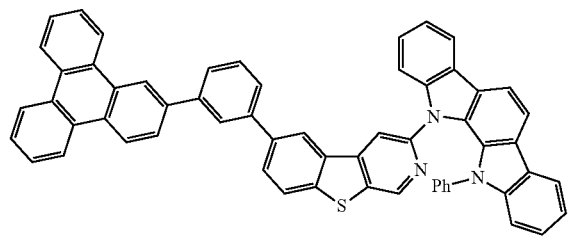
Compound 52
Compound 48
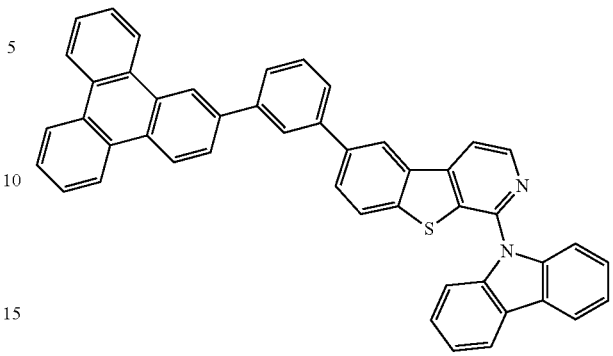
Compound 49
Compound 53
Compound 50
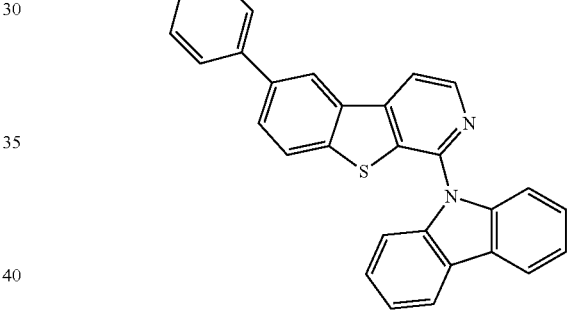
Compound 54
Compound 51
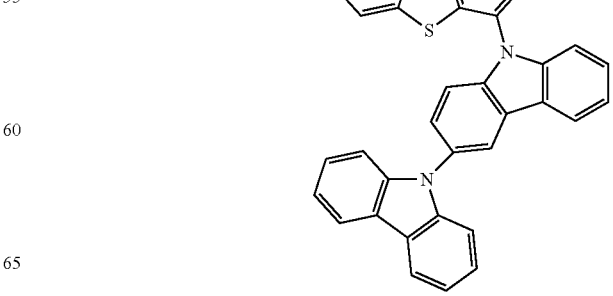

Compound 55
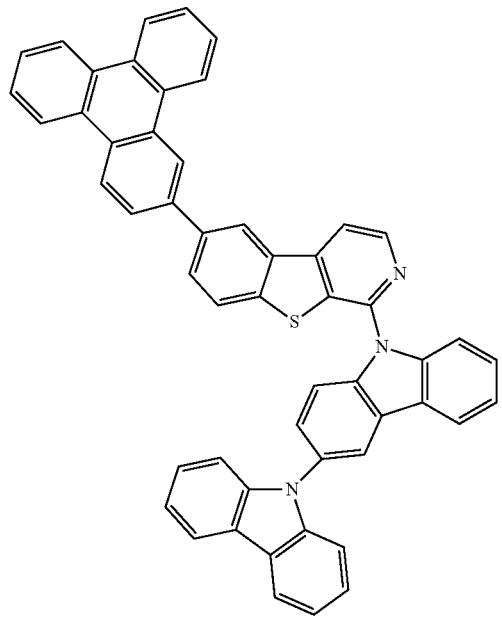
Compound 58
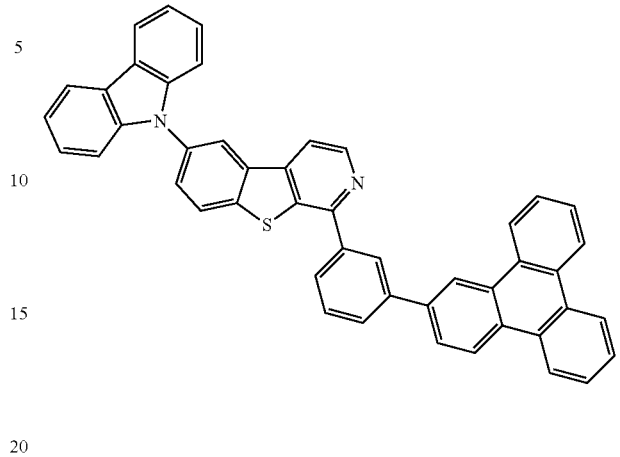
Compound 56
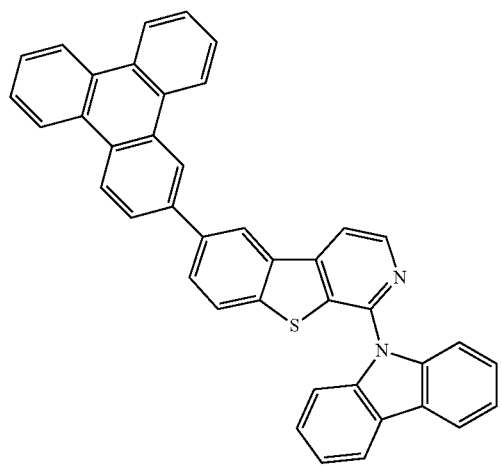
Compound 59
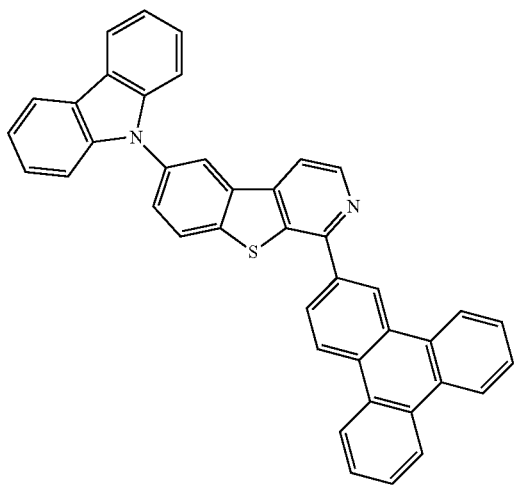
Compound 57
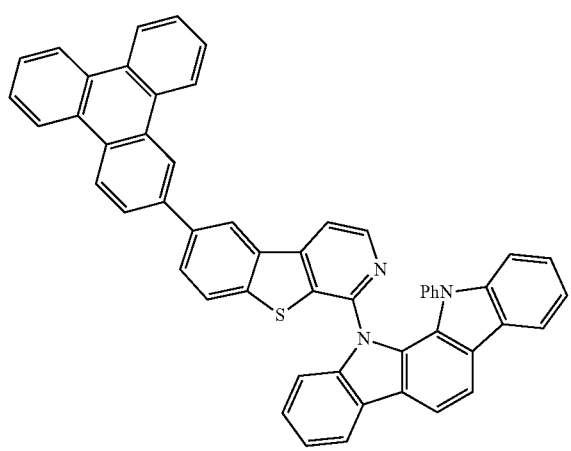
Compound 60
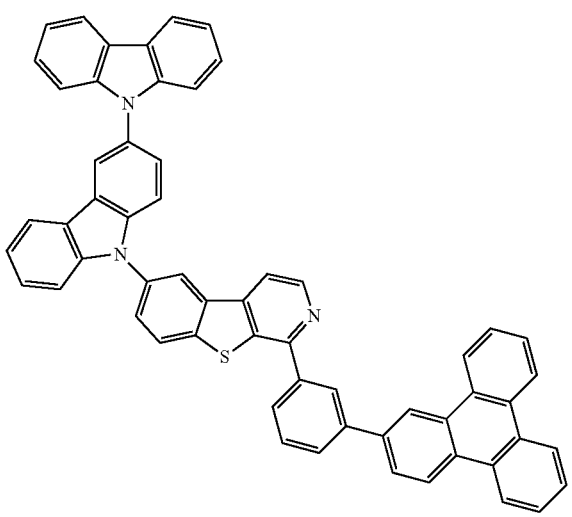

Compound 61
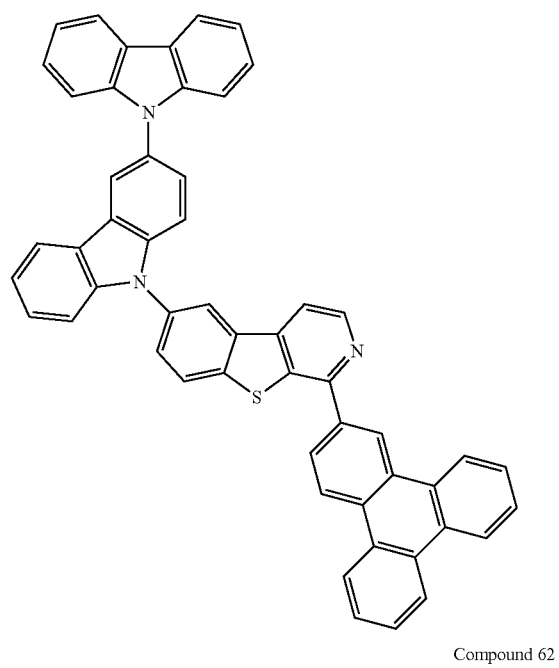
Compound 62
Compound 63
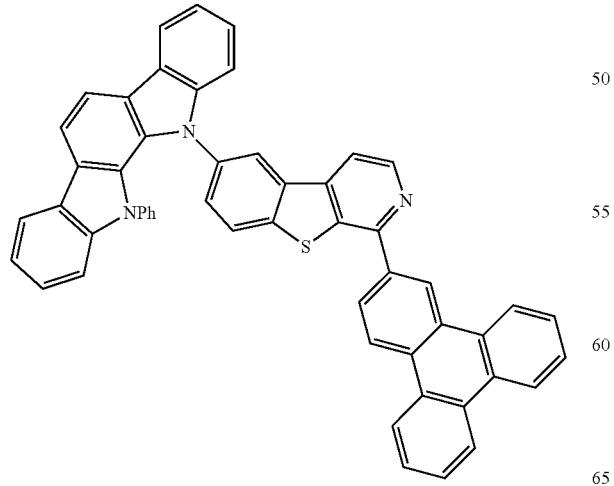
Compound 64
Compound 65
Compound 66
Compound 67
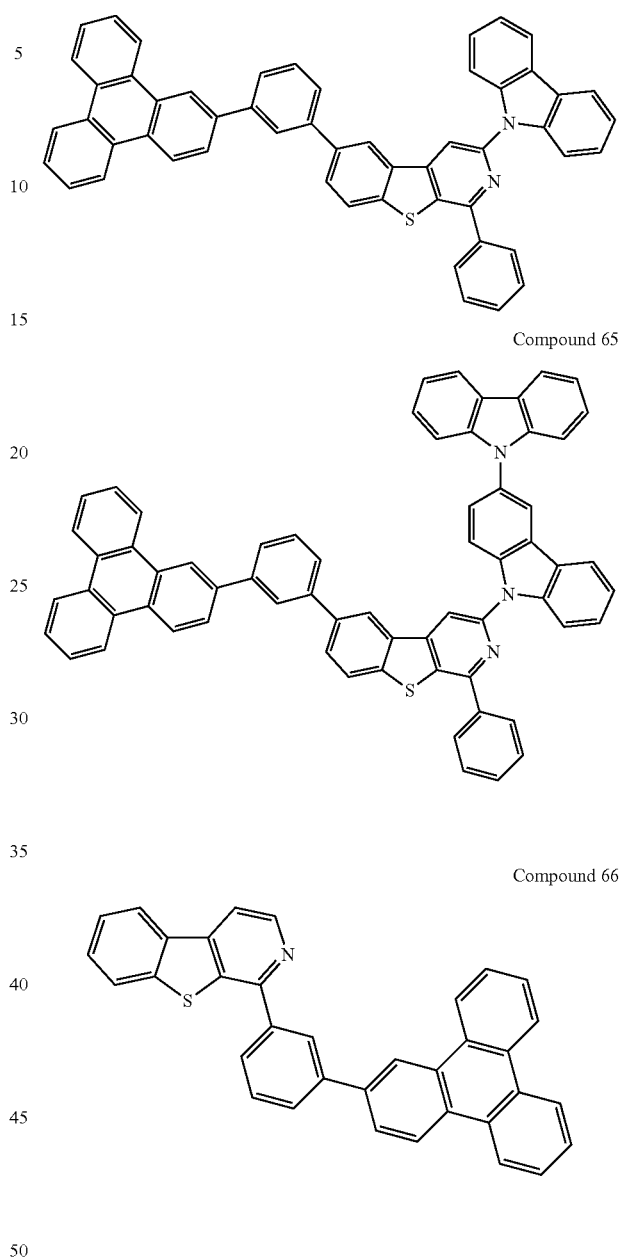

-continued
Compound 68
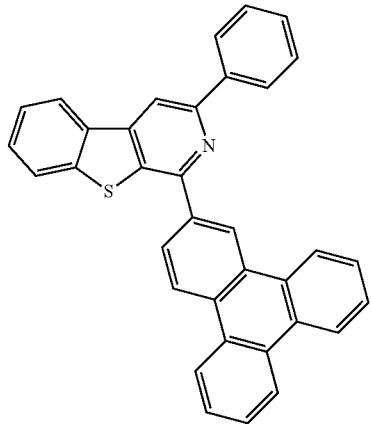
Compound 69
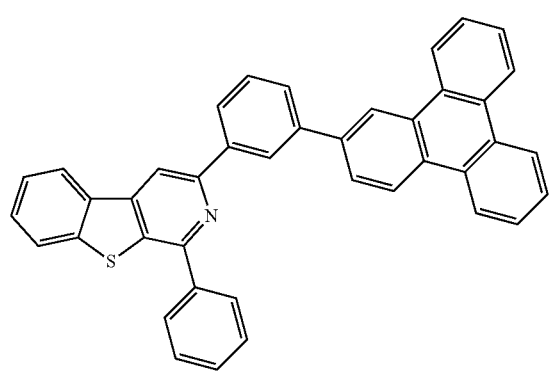
Compound 70
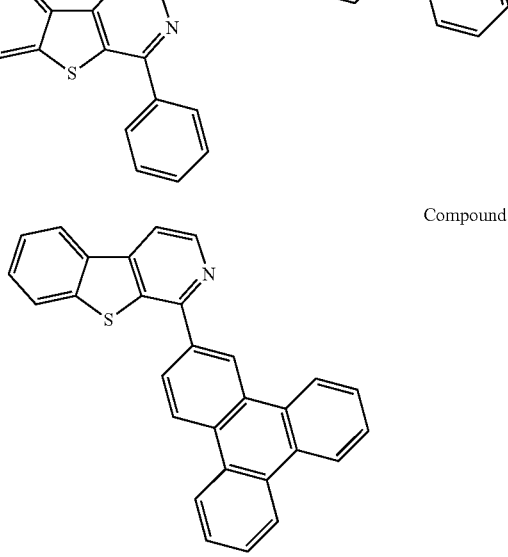
Compound 71
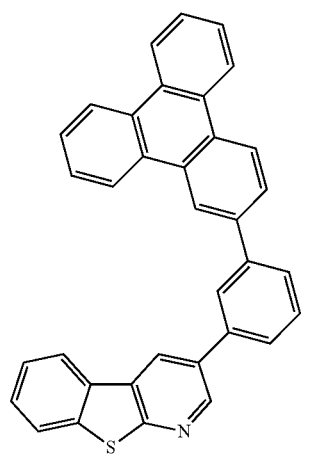
Compound 72
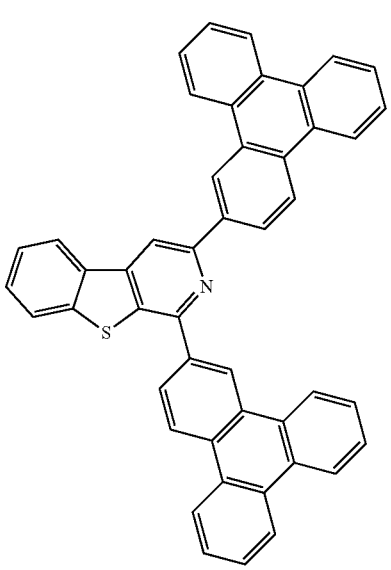
Compound 73
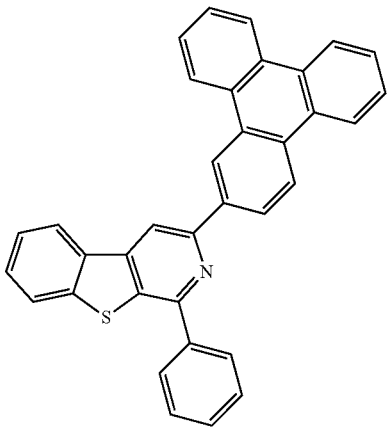
Compound 74
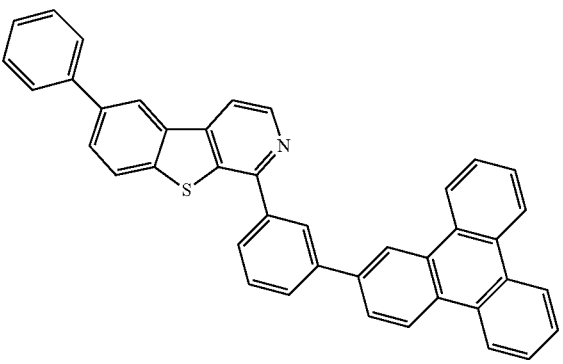

-continued
Compound 75
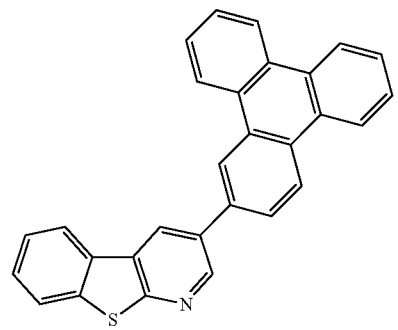
Compound 76
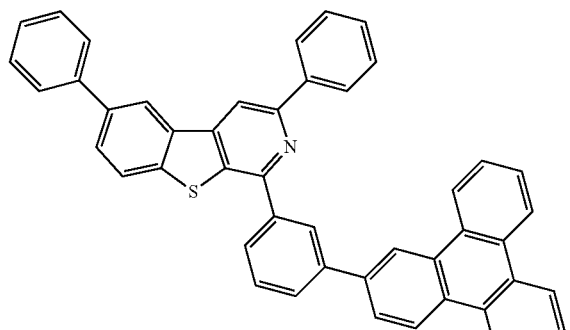
Compound 77
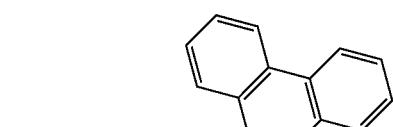
Compound 78
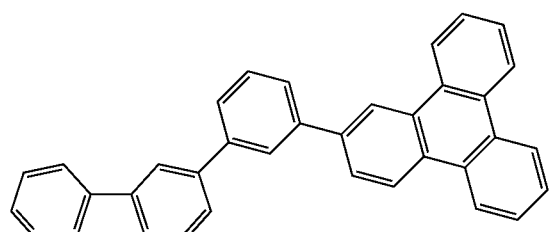
Compound 79
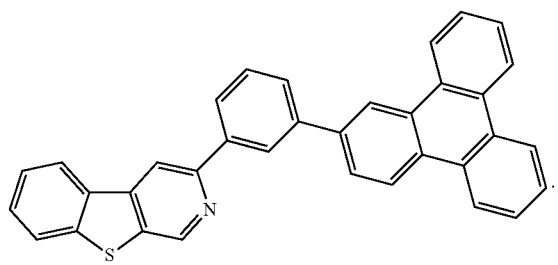
In another aspect, at least one of $R_1$ and $R_2$ is selected from the group consisting of:
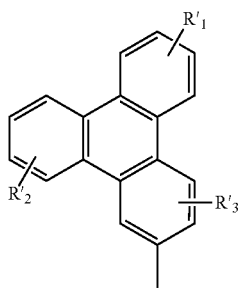
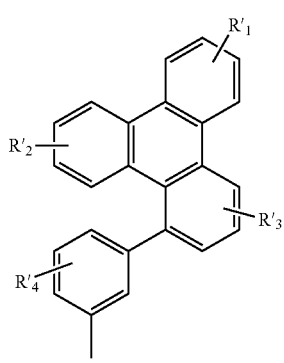
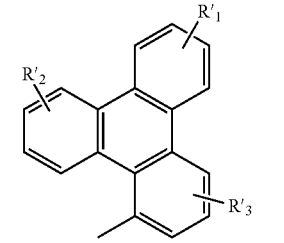
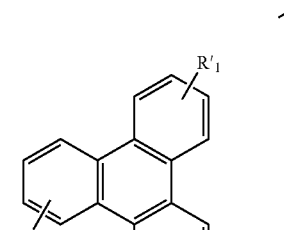
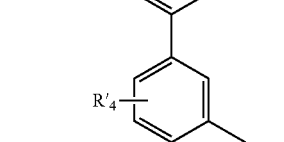
$R'_1$, $R'_2$, $R'_3$, and $R'_4$ are independently selected from the group consisting of hydrogen, alkyl, heteroalkyl, aryl and heteroaryl. Preferably, $R'_1$, $R'_2$, $R'_3$, and $R'_4$ are each independently hydrogen or methyl.

Specific examples of such compounds include compounds selected from the group consisting of:
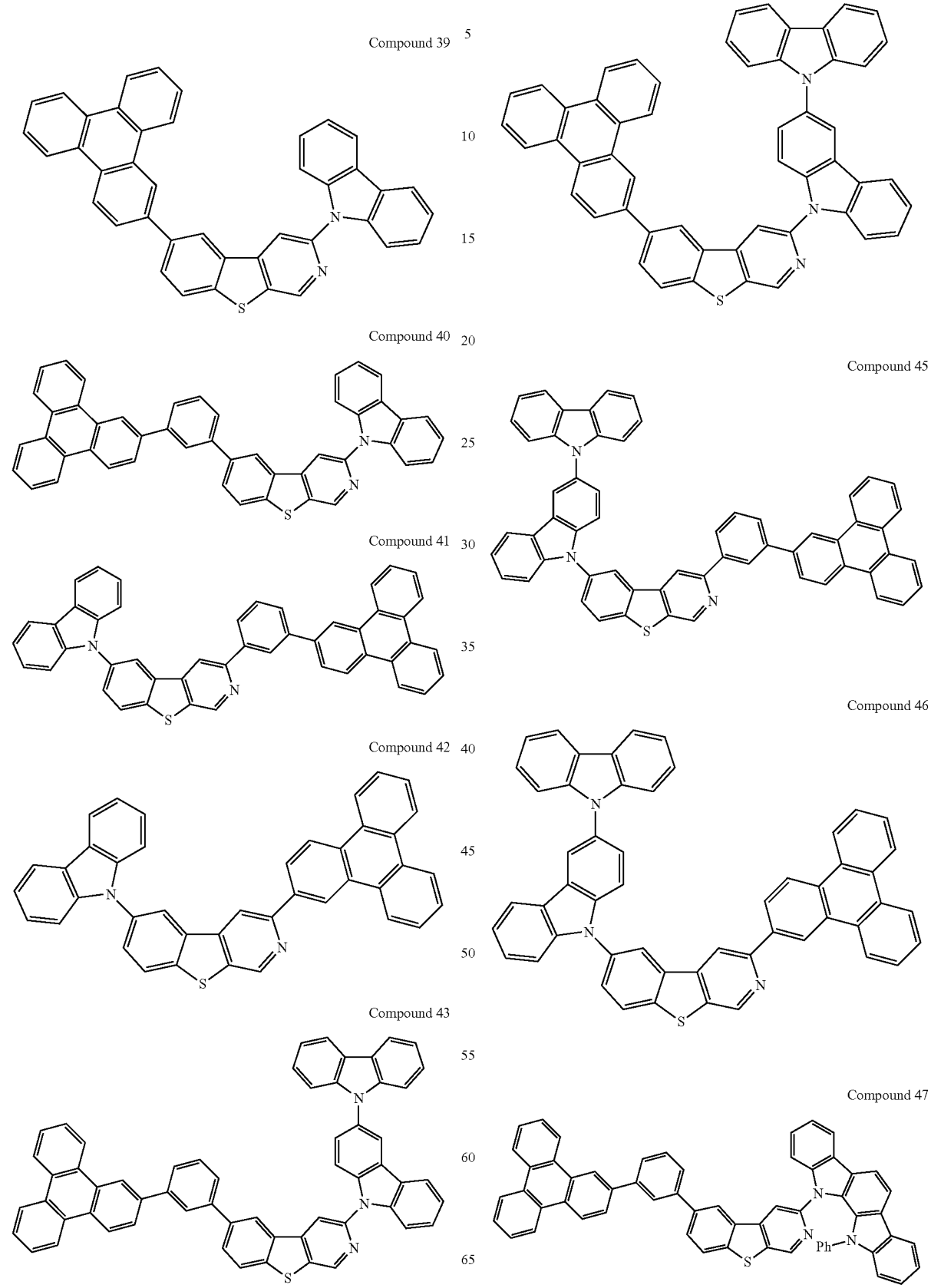

Compound 48
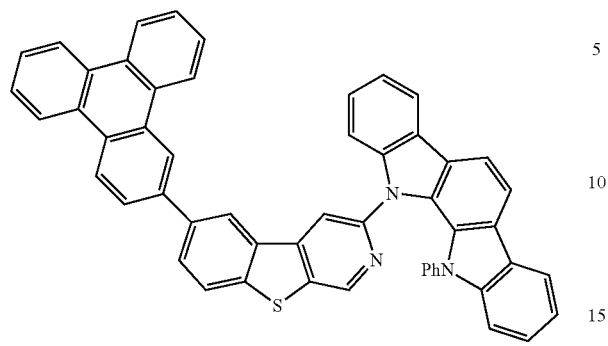
Compound 50
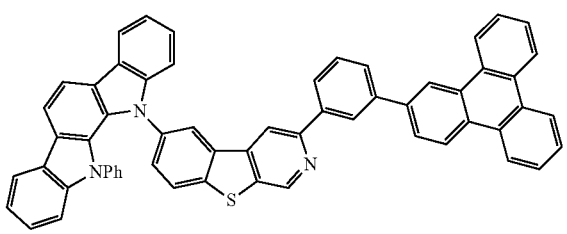
Compound 51
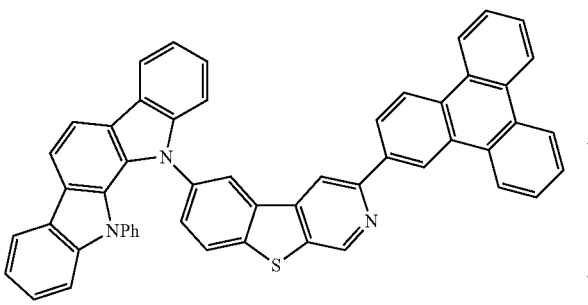
Compound 52
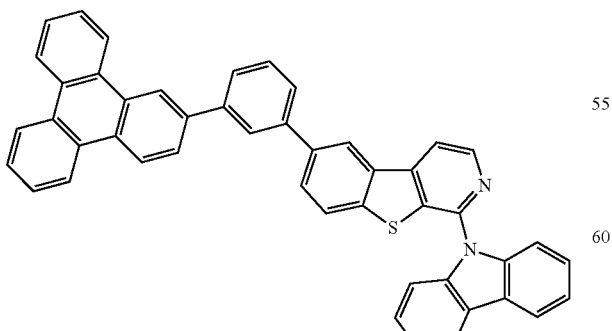
Compound 53
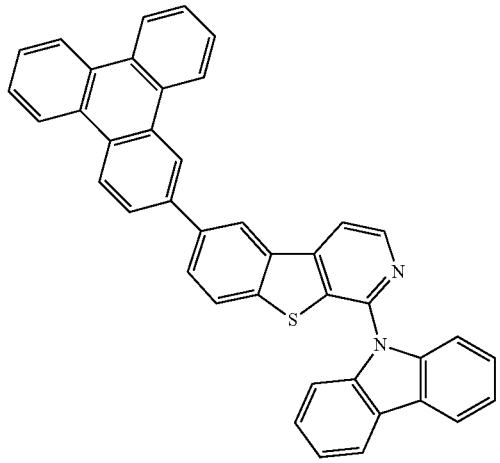
Compound 54
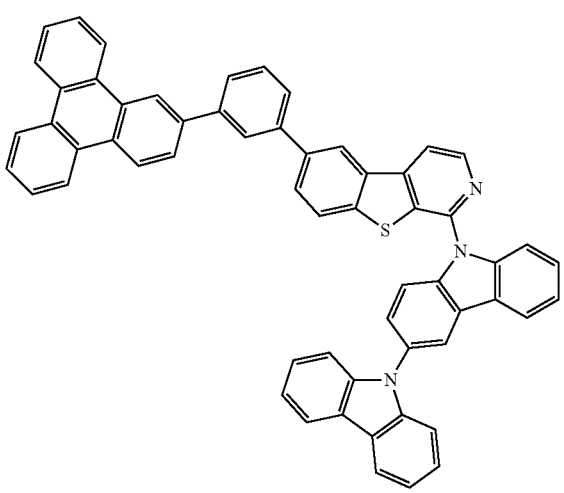
Compound 55
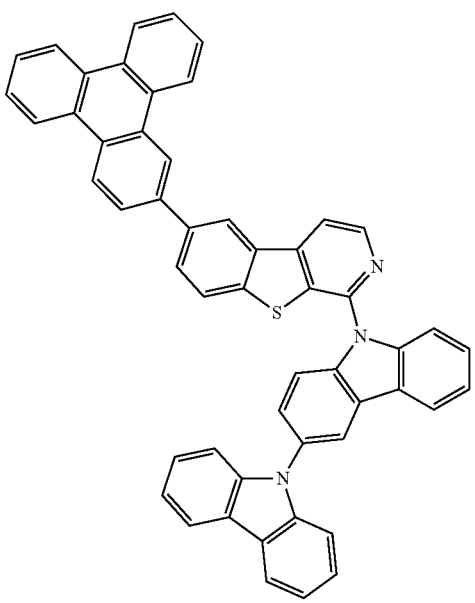

Compound 56
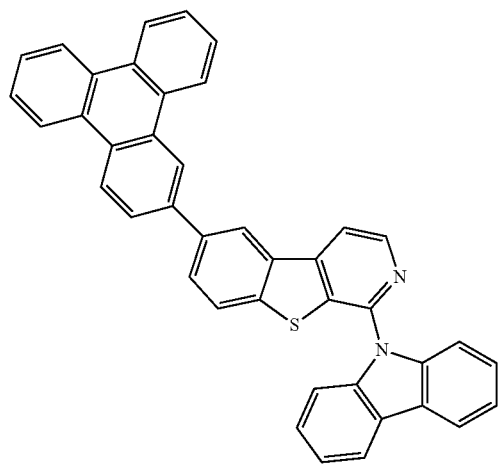
Compound 57
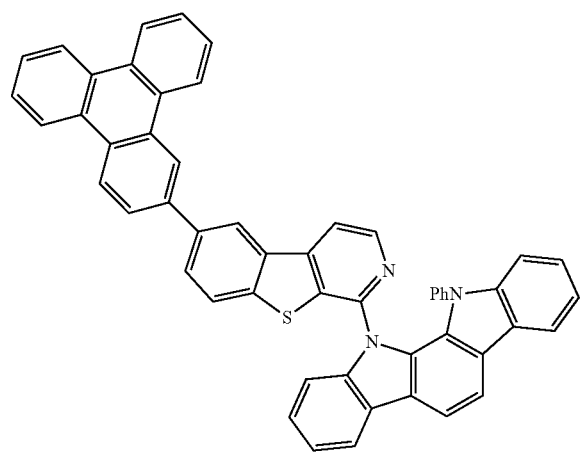
Compound 58
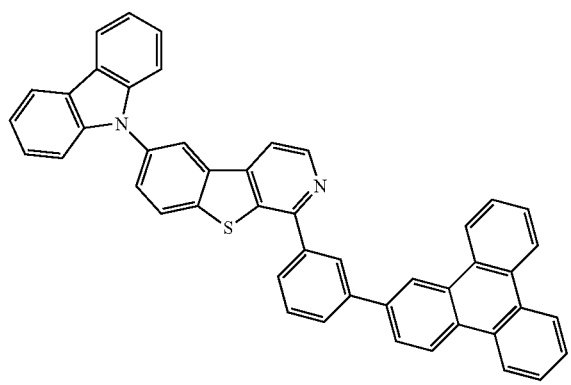
Compound 59
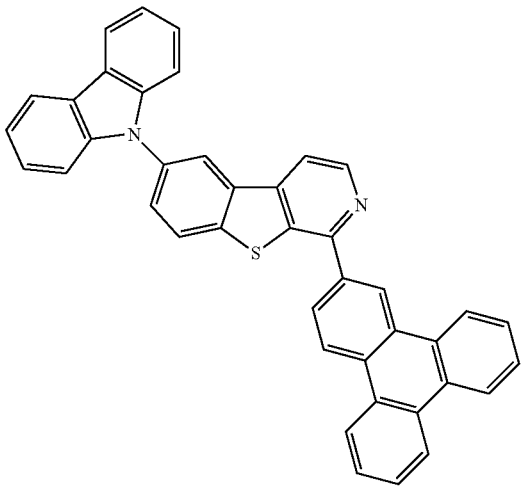
Compound 60
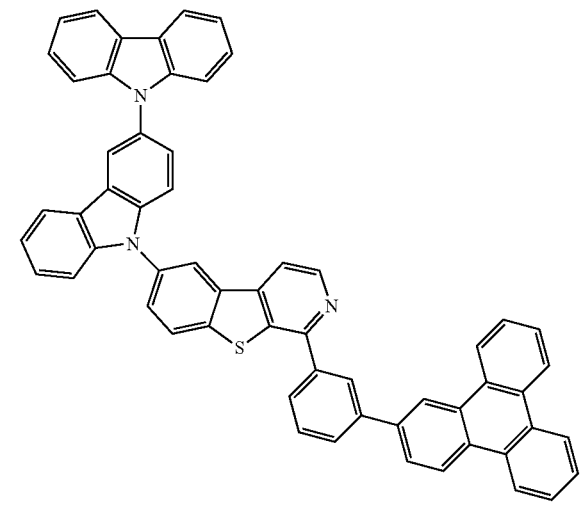
Compound 61
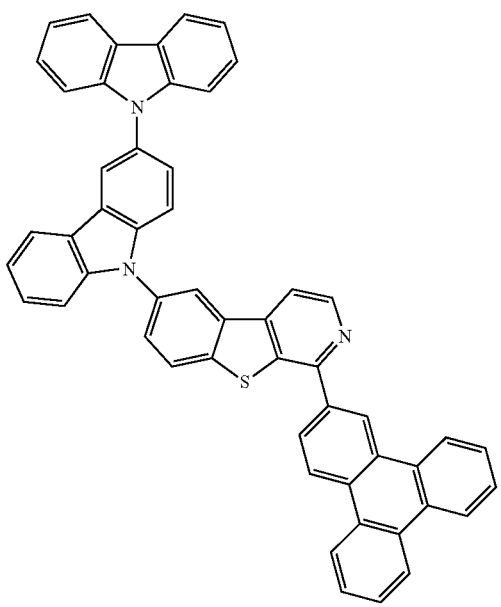

Compound 62
Compound 63
Compound 64
Compound 65
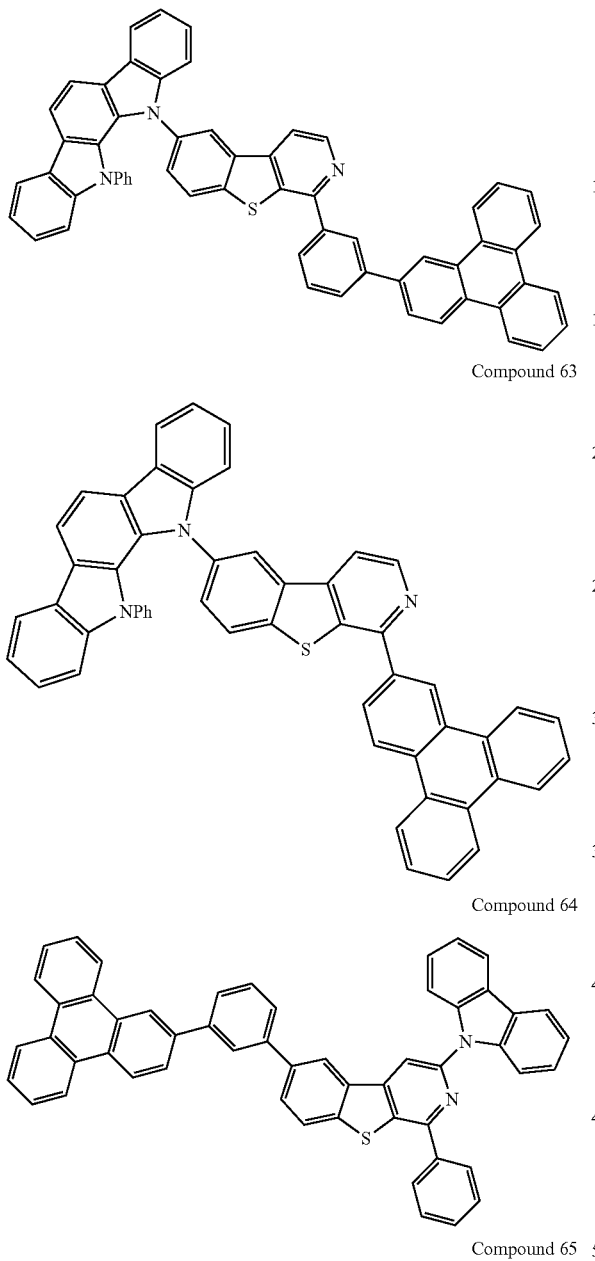
Compound 66
Compound 67
Compound 68
Compound 69
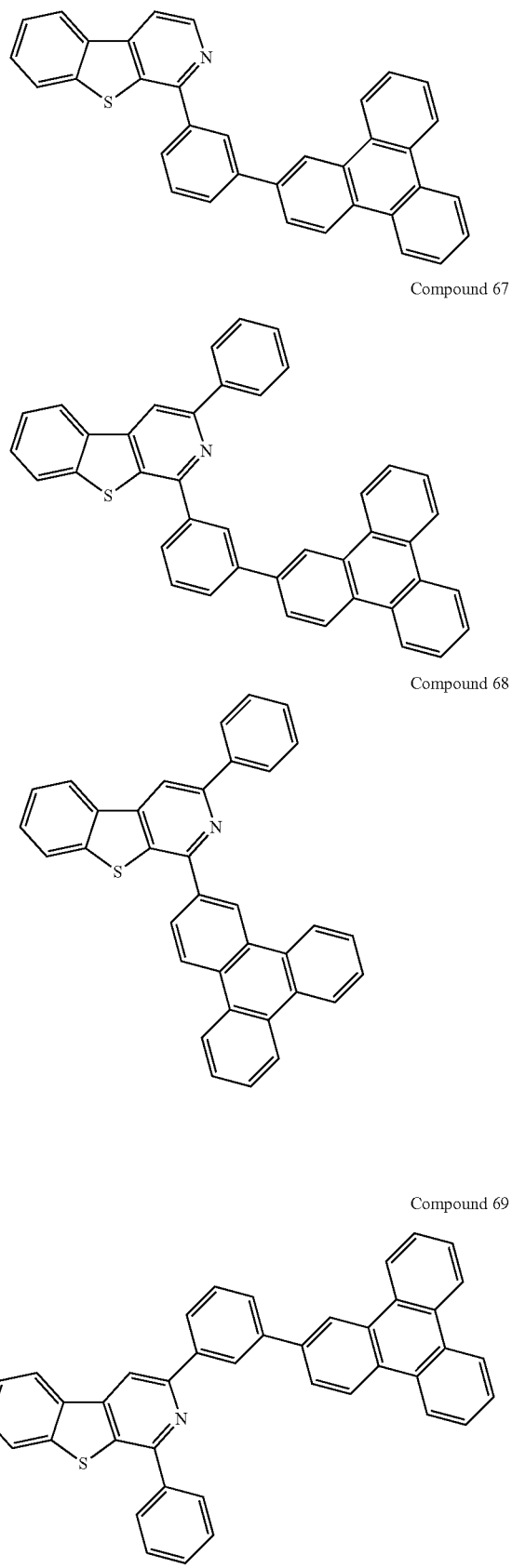

Compound 70
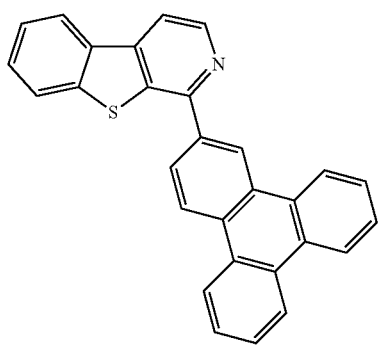
Compound 71
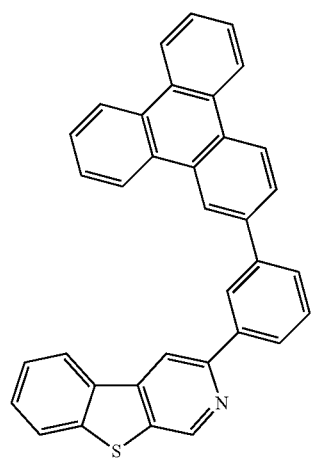
Compound 72
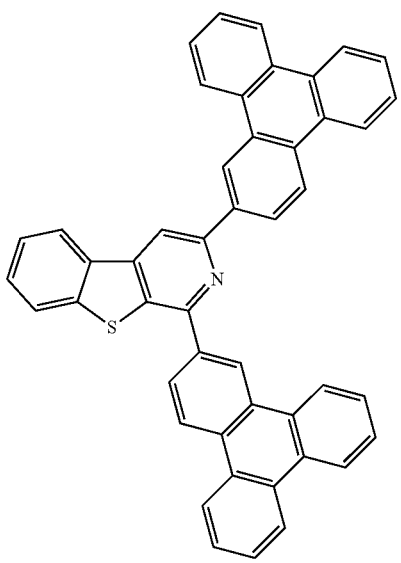
Compound 73
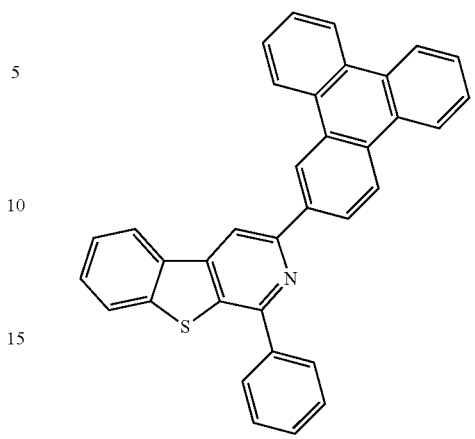
Compound 74
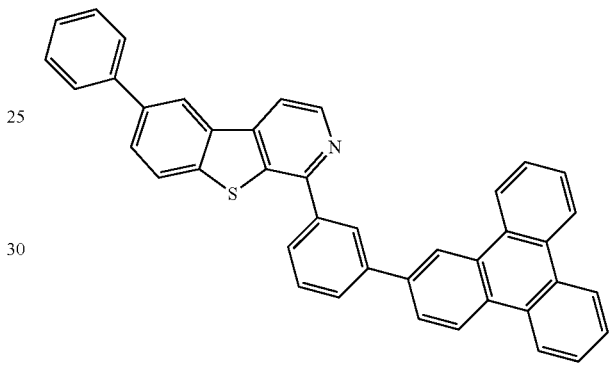
Compound 75
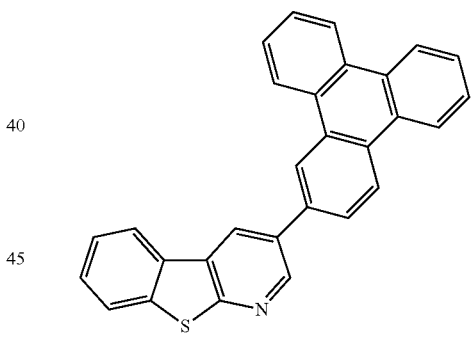
Compound 76
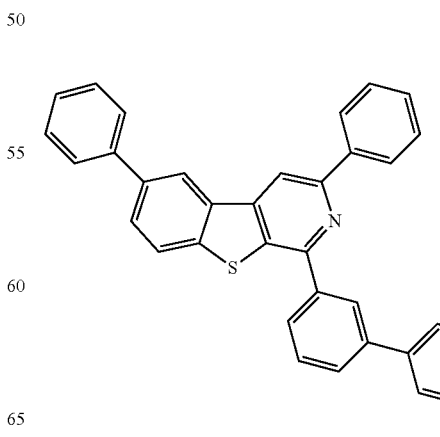

-continued

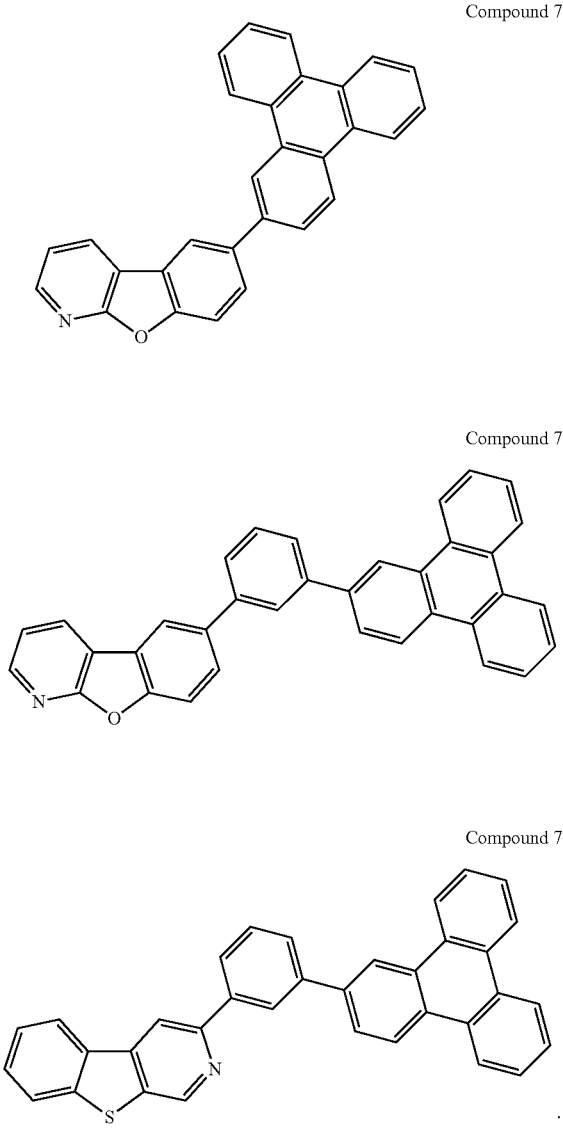

In another aspect, R$_1$ and R$_2$ are each independently selected from the group consisting of hydrogen and

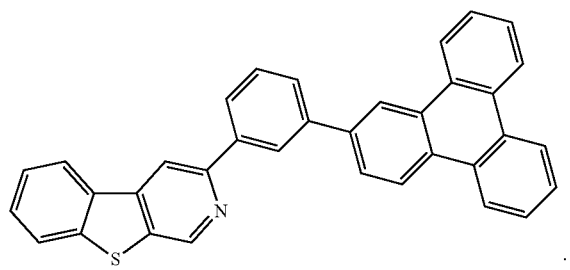

-continued

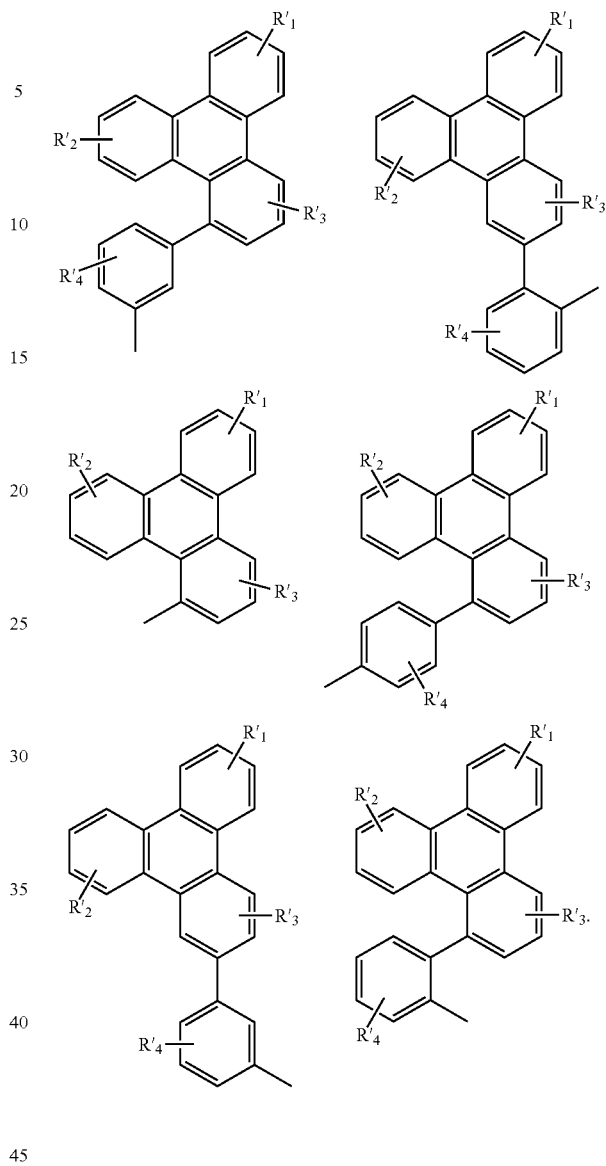

R'$_1$, R'$_2$, R'$_3$, and R'$_4$ are independently selected from the group consisting of hydrogen, alkyl, heteroalkyl, aryl and heteroaryl. Preferably, R'$_1$, R'$_2$, R'$_3$, and R'$_4$ are each independently hydrogen or methyl.

Specific examples of such compounds include compounds selected from the group consisting of:

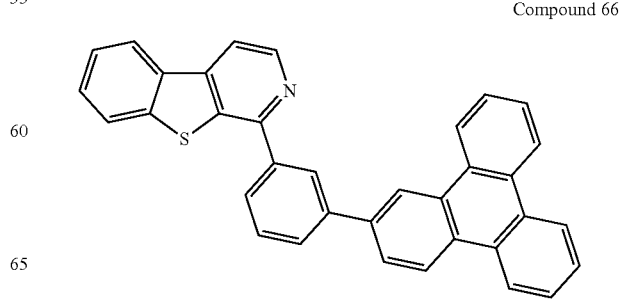

-continued
Compound 70
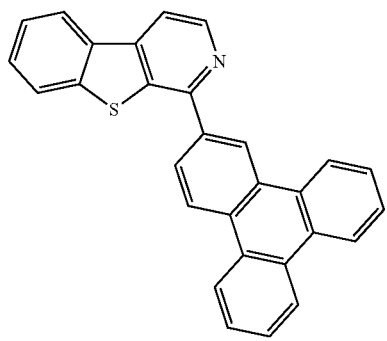
Compound 71
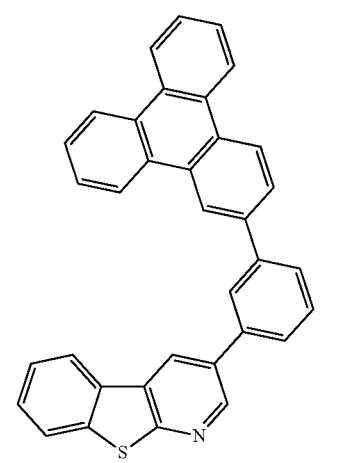
Compound 72
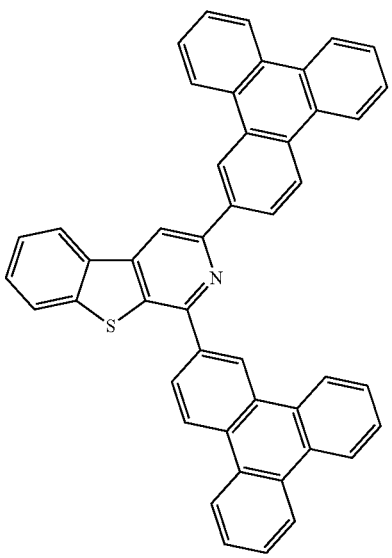
-continued
Compound 75
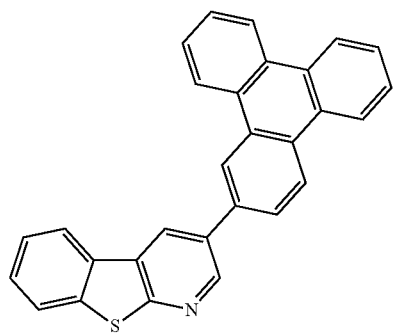
Compound 77
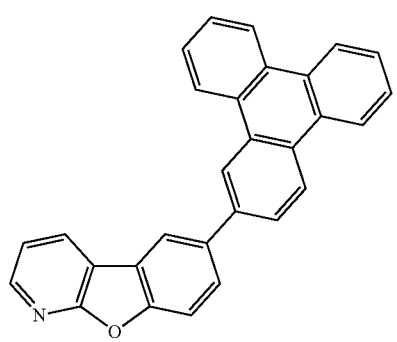
Compound 78
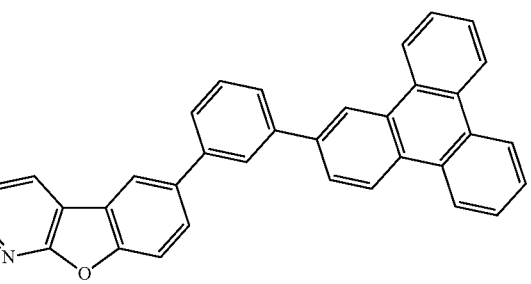
Compound 79
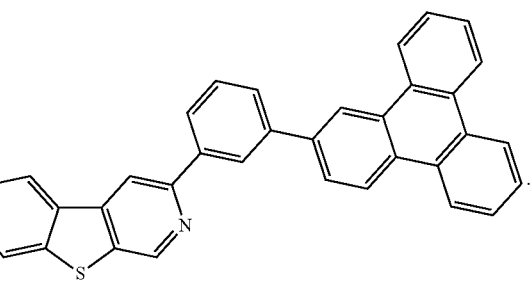
In one aspect, at least one of $R_1$ and $R_2$ is selected from the group consisting of:
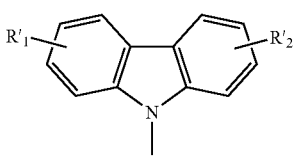

-continued
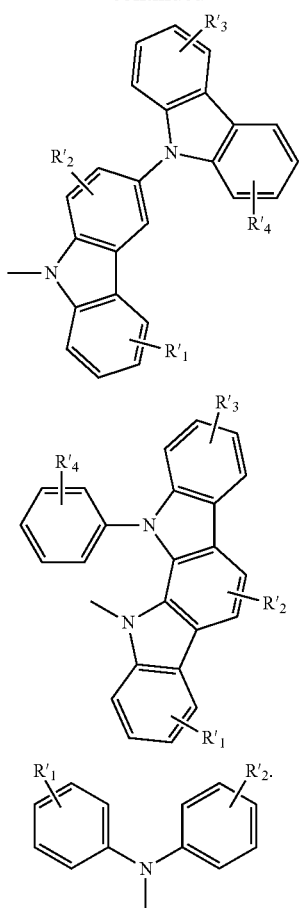
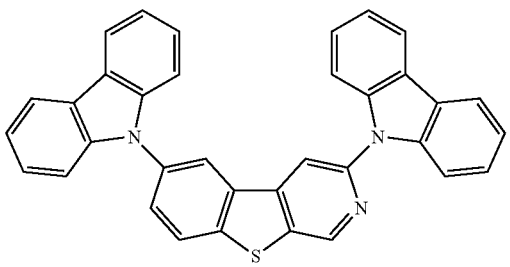
Compound 2
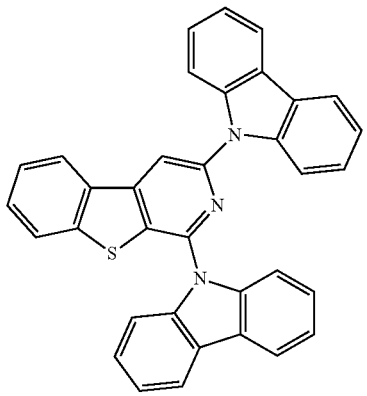
Compound 3
R'₁, R'₂, R'₃, and R'₄ are independently selected from the group consisting of hydrogen, alkyl, heteroalkyl, aryl and heteroaryl. Preferably, R'₁, R'₂, R'₃, and R'₄ are each independently hydrogen or methyl.
Specific examples of such compounds include compounds selected from the group consisting of:
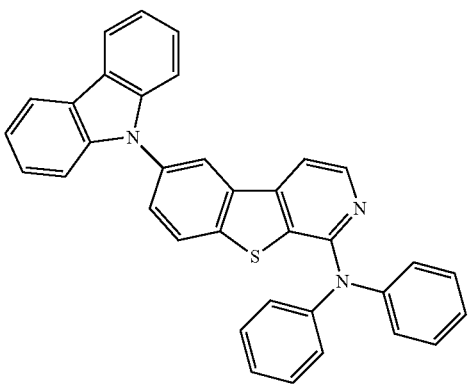
Compound 4
Compound 1
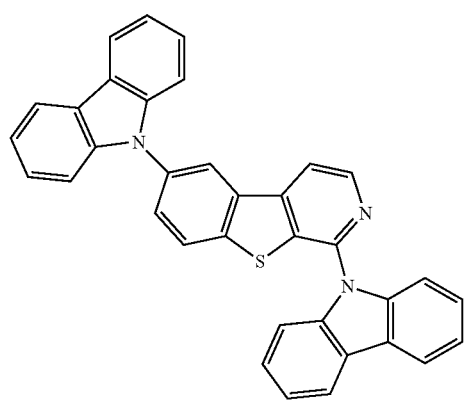
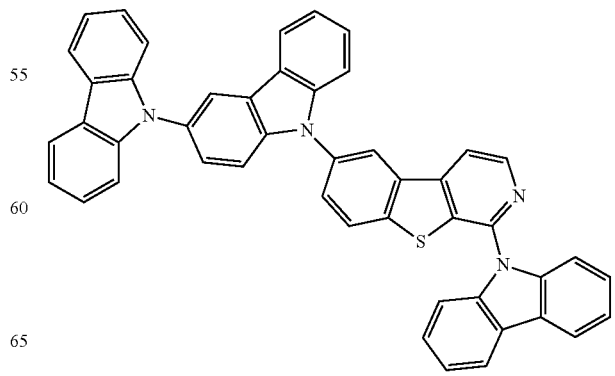
Compound 5

-continued
Compound 6
Compound 7
Compound 8
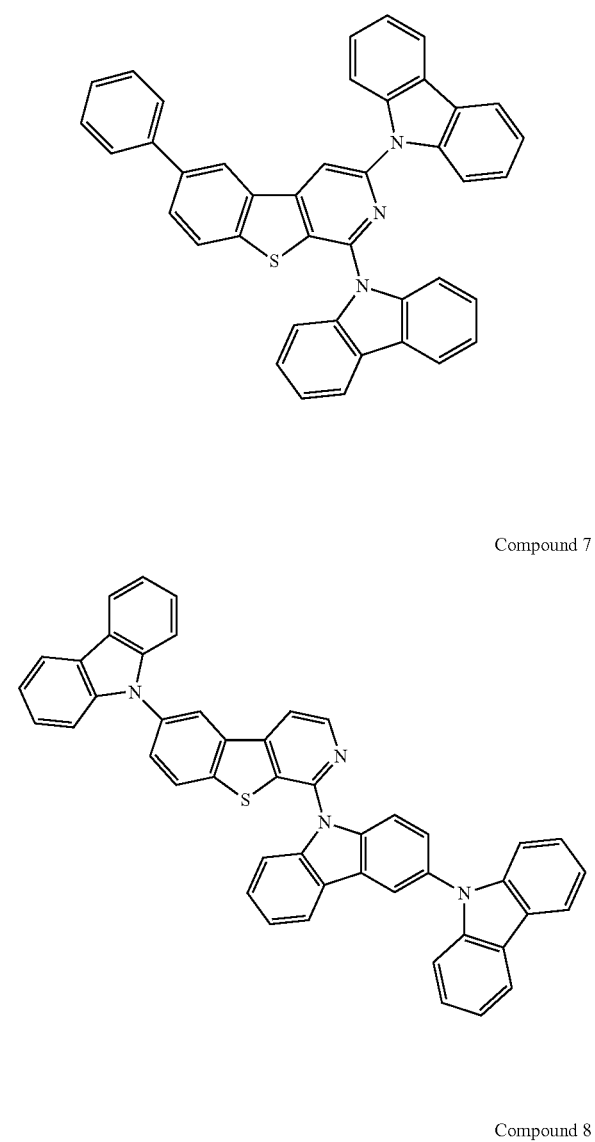
Compound 9
Compound 10
Compound 11
Compound 12
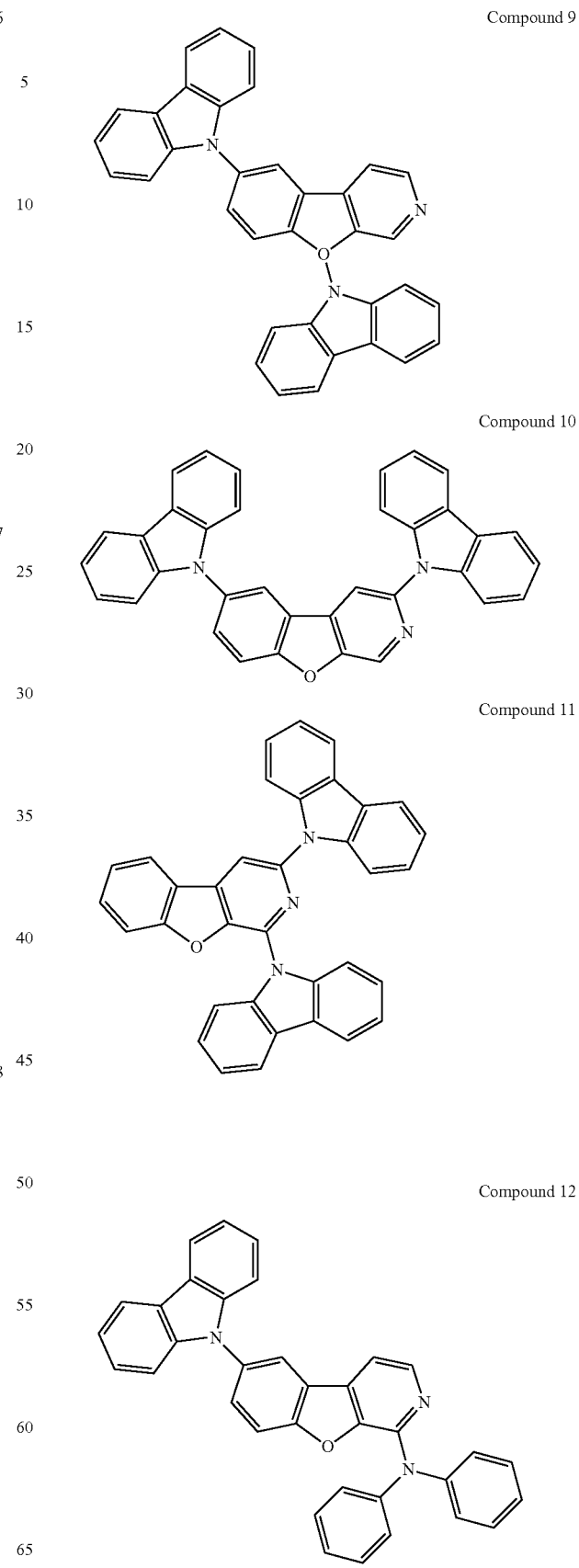

Compound 13
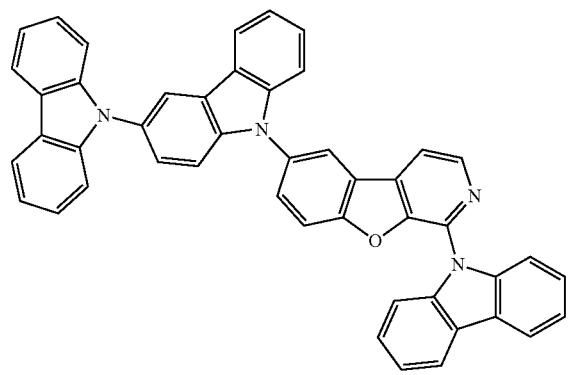
Compound 14
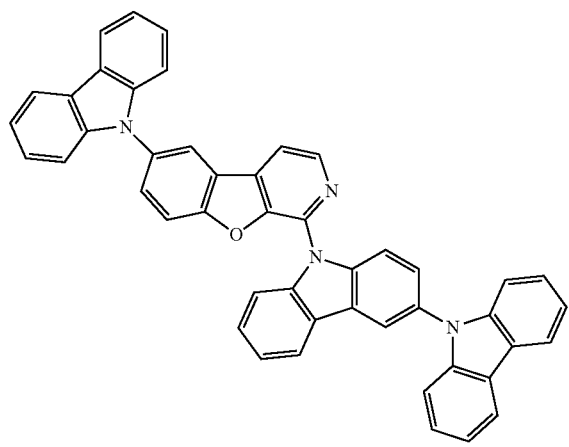
Compound 15
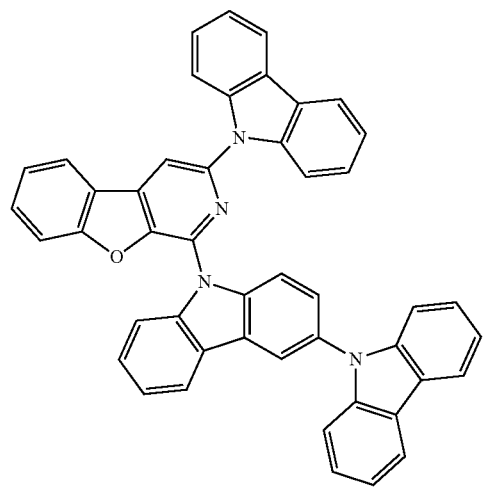
Compound 16
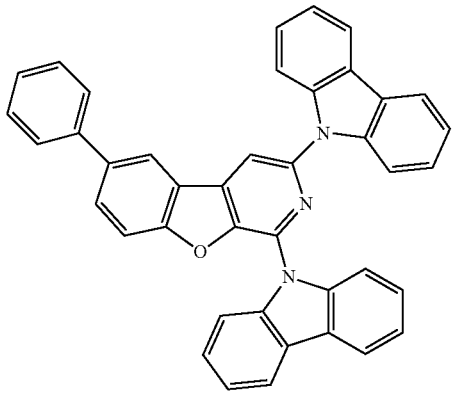
Compound 17
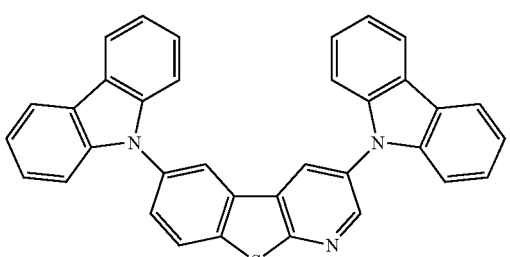
Compound 18
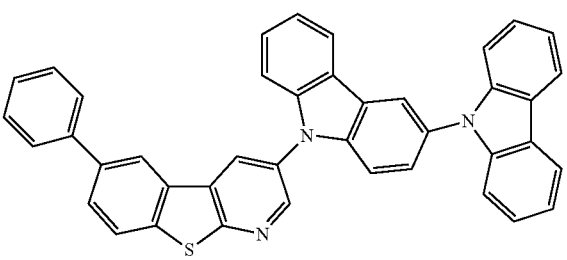
Compound 19

-continued
Compound 20
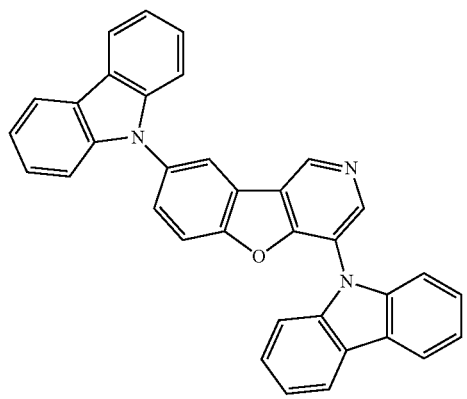
Compound 21
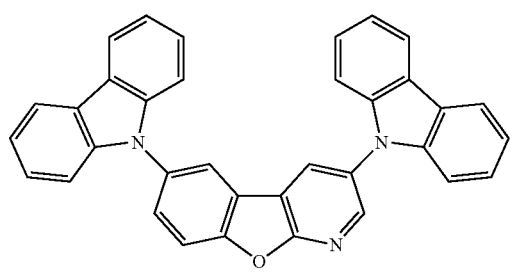
Compound 22
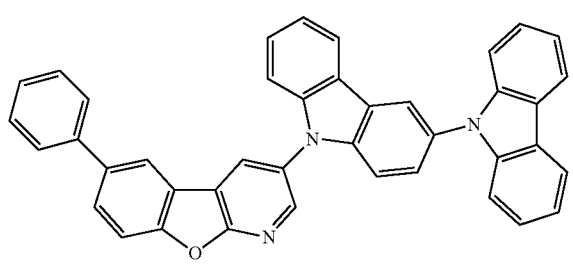
Compound 23
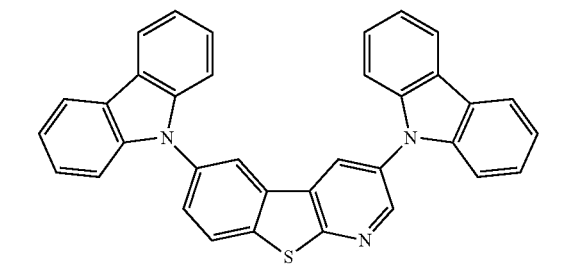
Compound 24
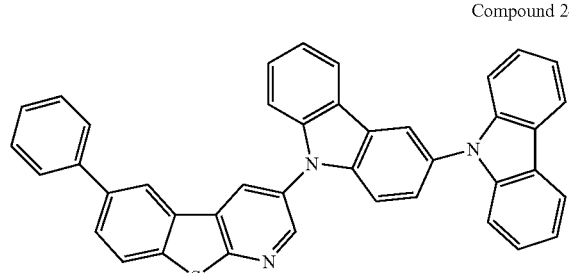
-continued
Compound 25
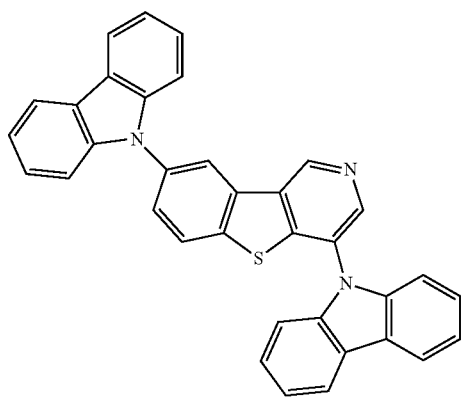
Compound 26
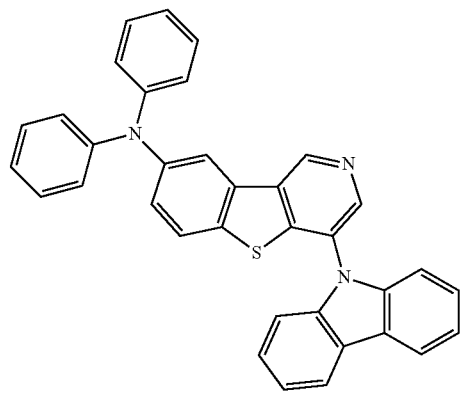
Compound 27
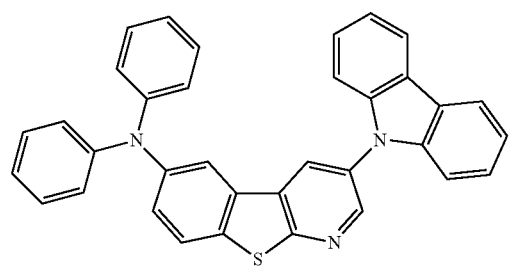
Compound 28
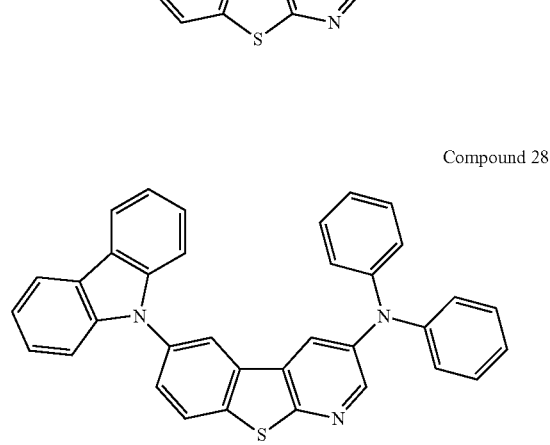

Compound 29
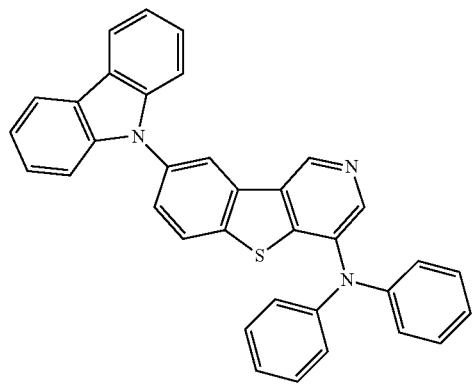
Compound 30
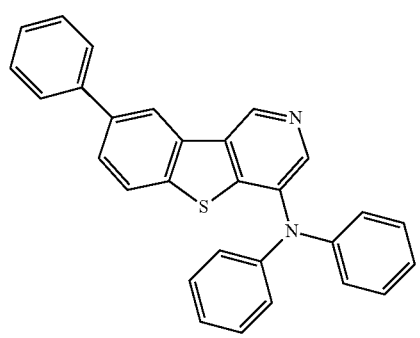
Compound 31
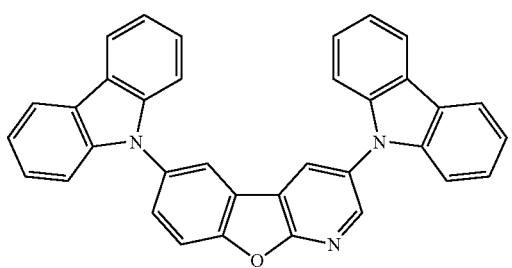
Compound 32
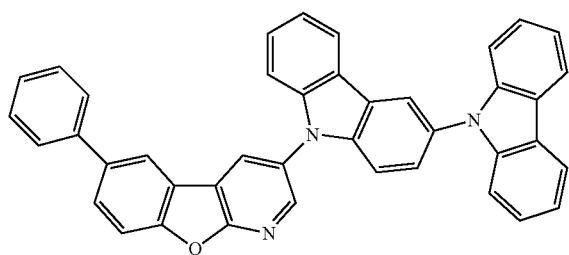
Compound 33
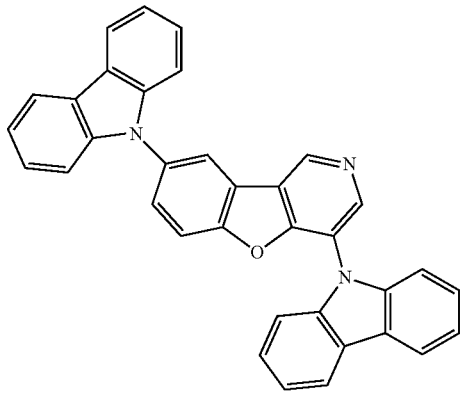
Compound 34
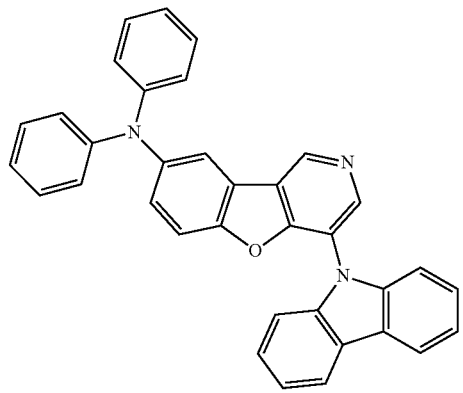
Compound 35
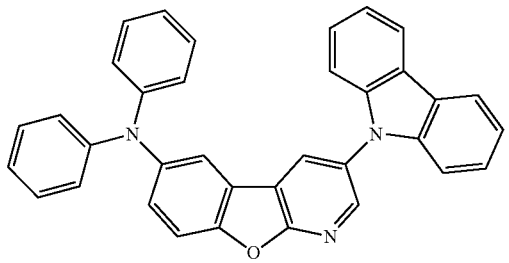
Compound 36
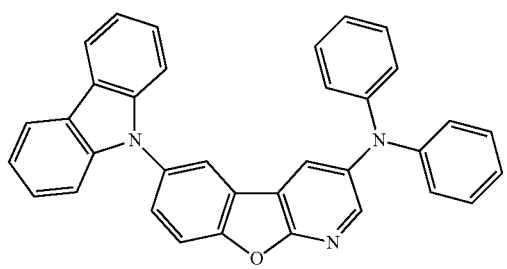

Compound 37
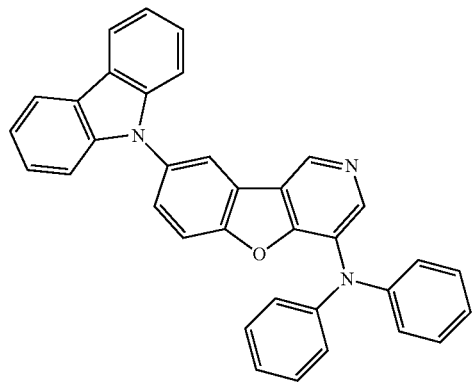
Compound 38
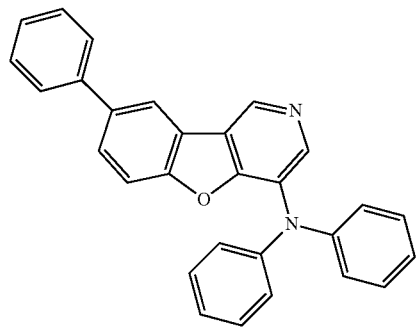
Compound 39
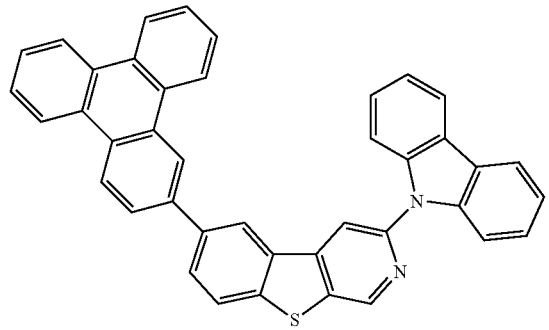
Compound 40
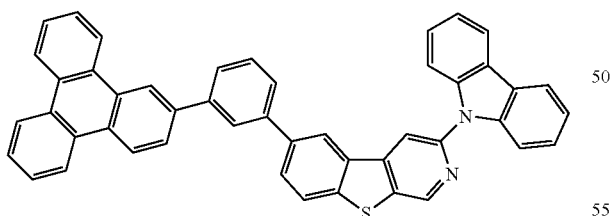
Compound 41
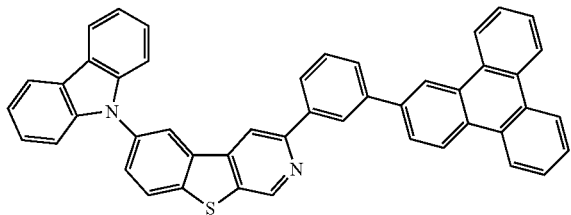
Compound 42
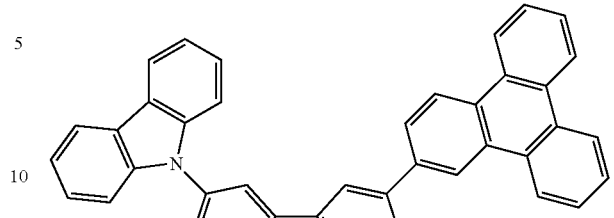
Compound 43
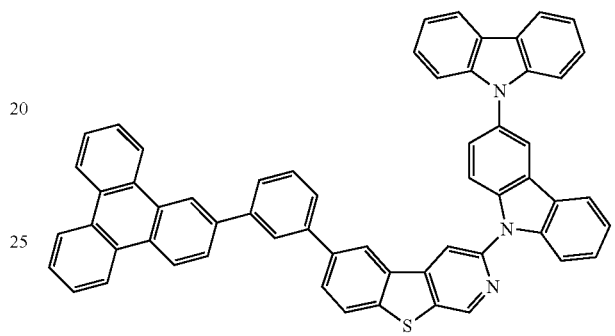
Compound 44
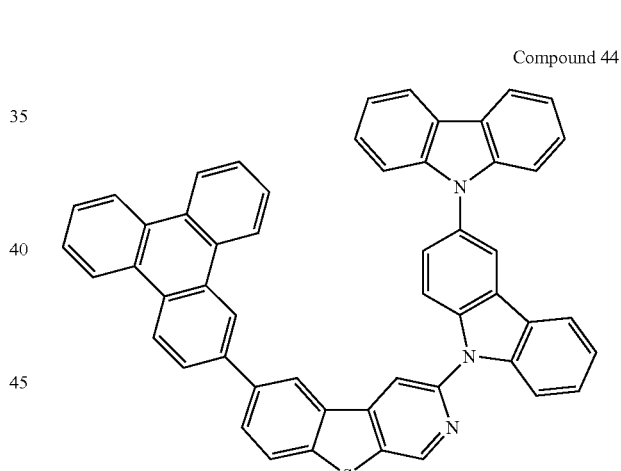
Compound 45
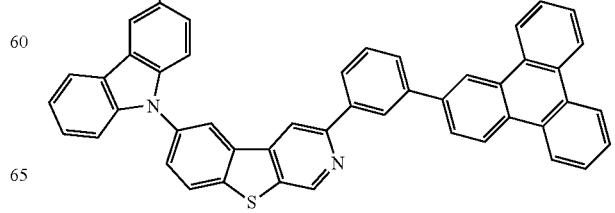

Compound 46
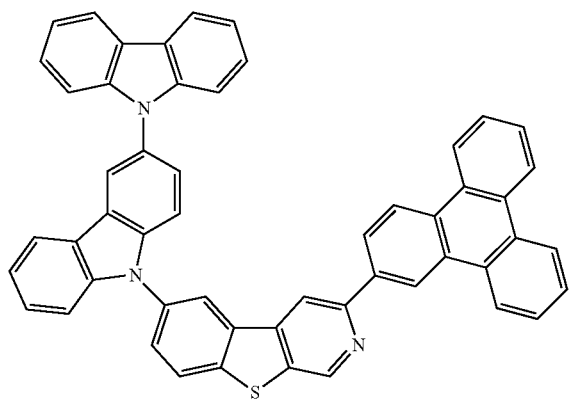
Compound 47
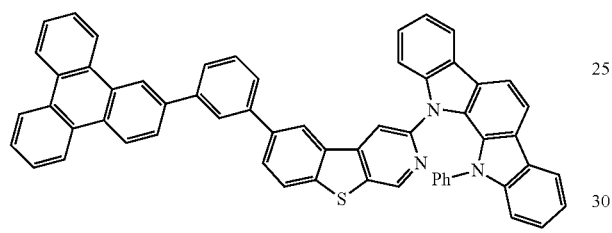
Compound 48
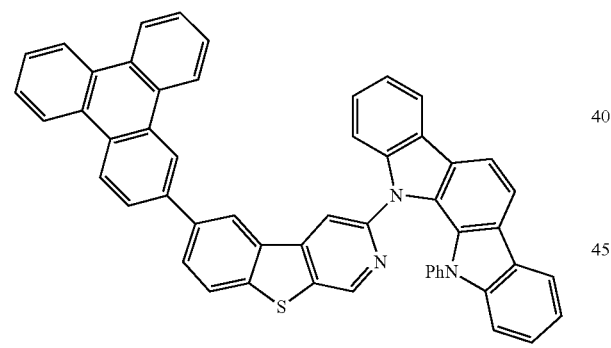
Compound 49
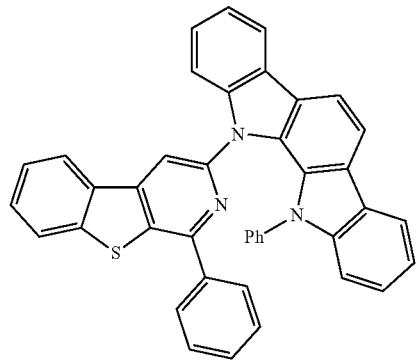
Compound 50
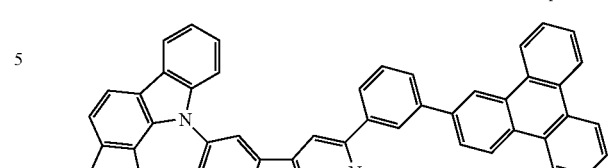
Compound 51
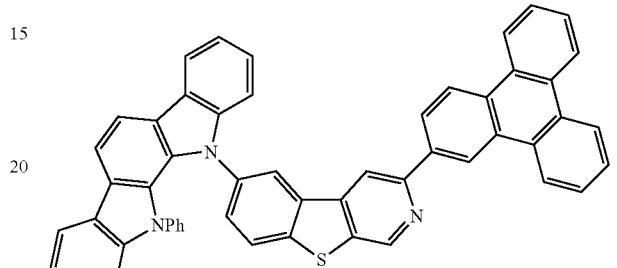
Compound 52
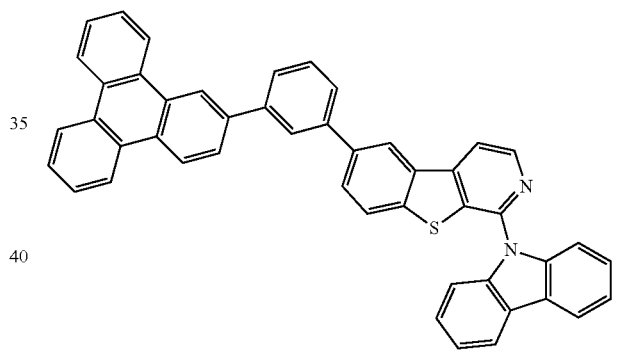
Compound 53
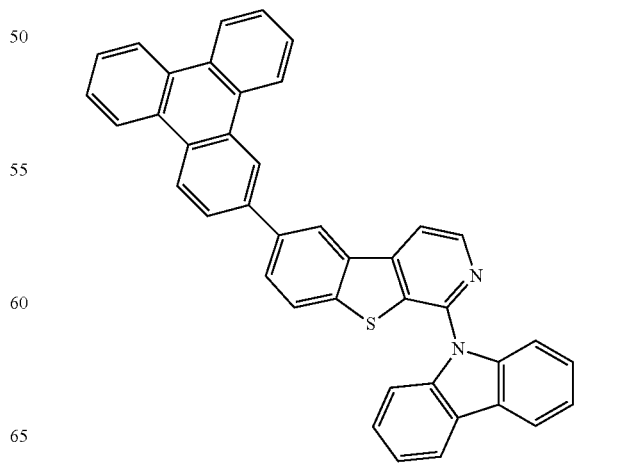

-continued
Compound 54
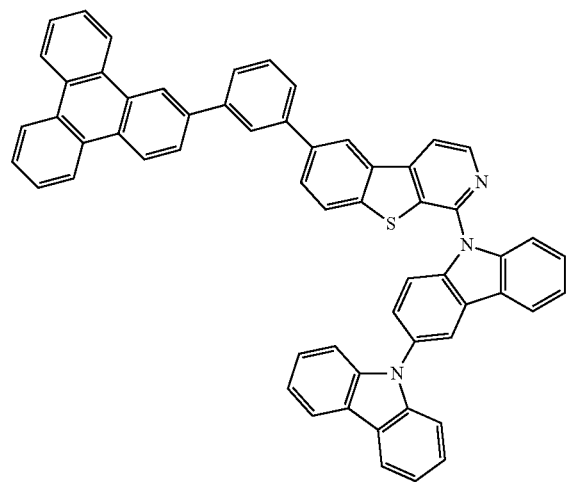
Compound 55
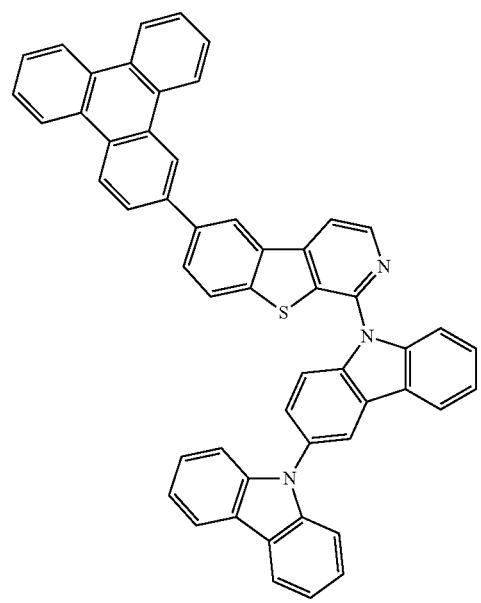
Compound 56
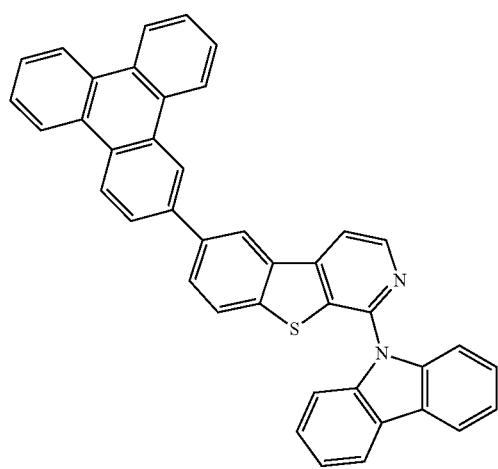
-continued
Compound 57
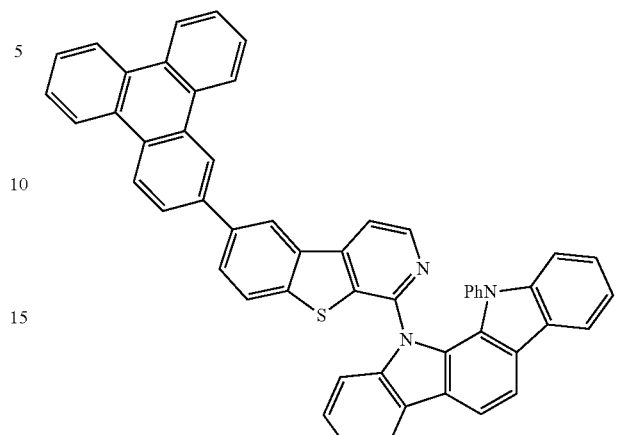
Compound 58
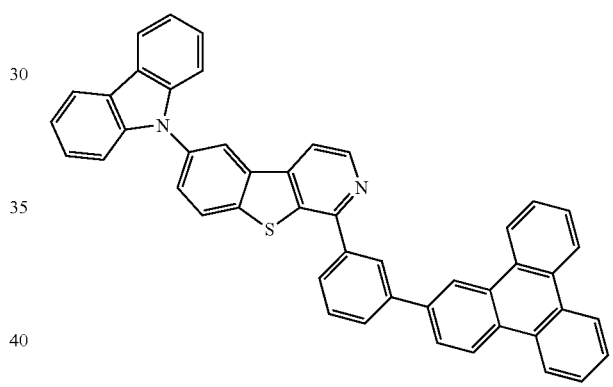
Compound 59
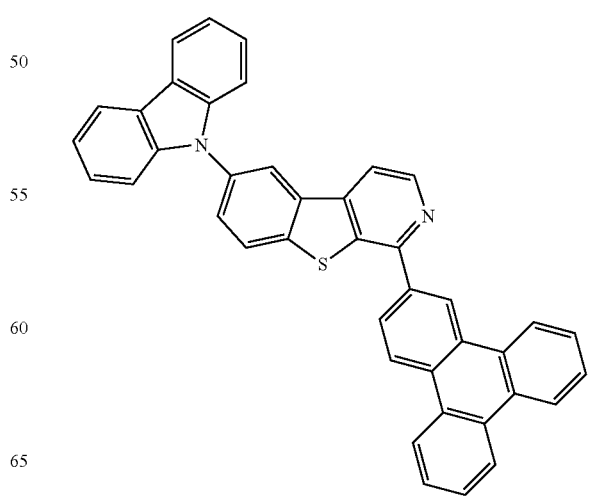

Compound 60
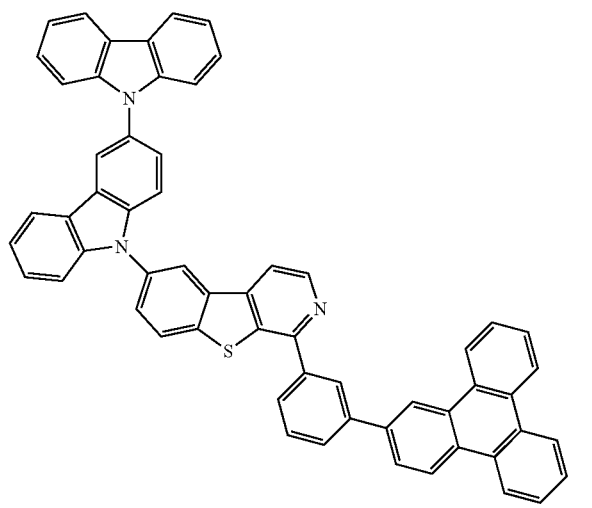
Compound 61
Compound 62
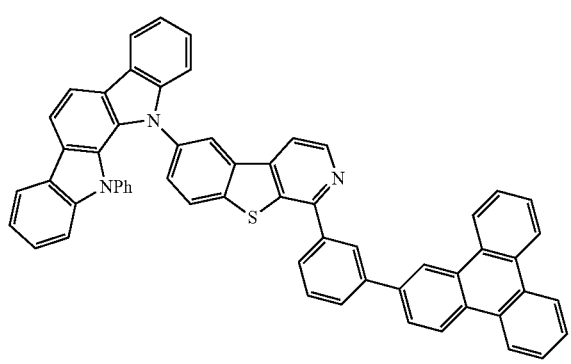
Compound 63
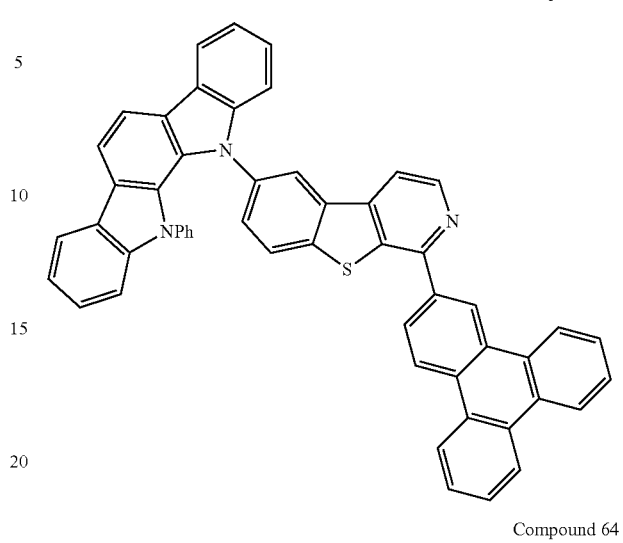
Compound 64
Compound 65
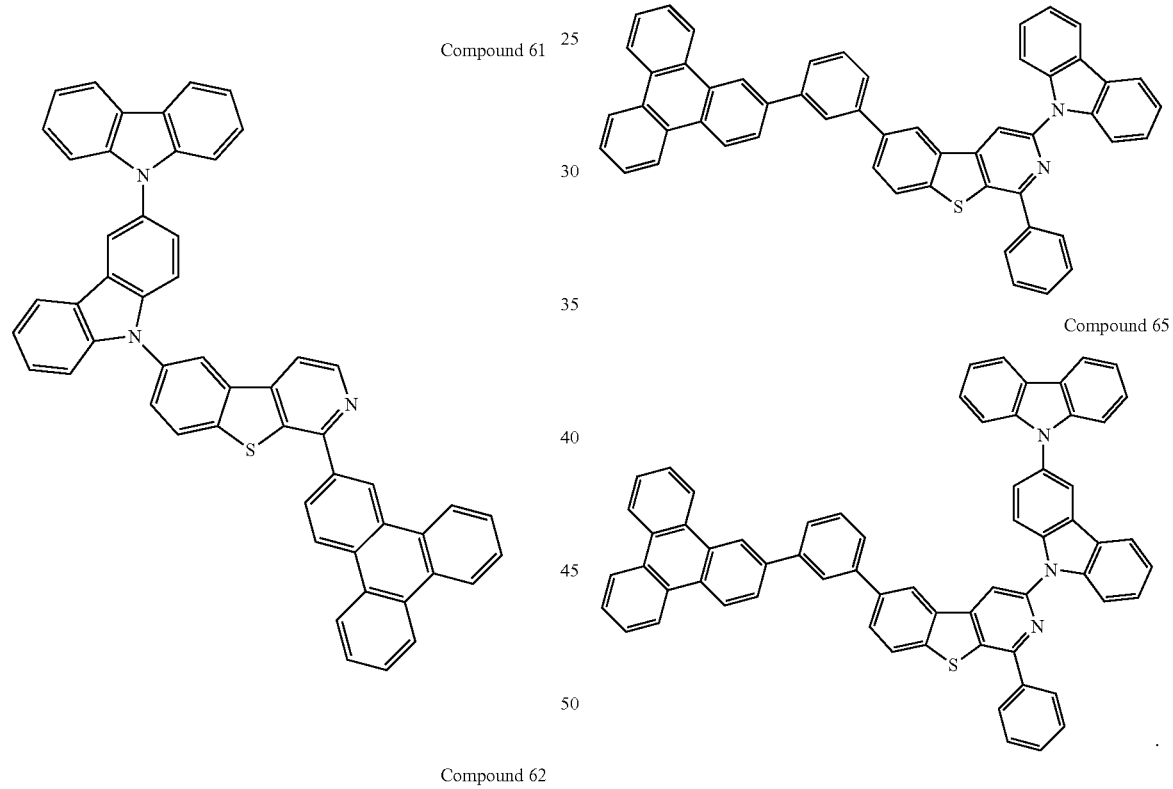
In another aspect, $R_1$ and $R_2$ are each independently selected from the group consisting of hydrogen and
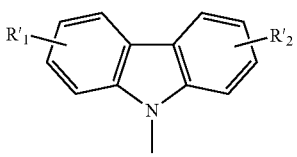

-continued

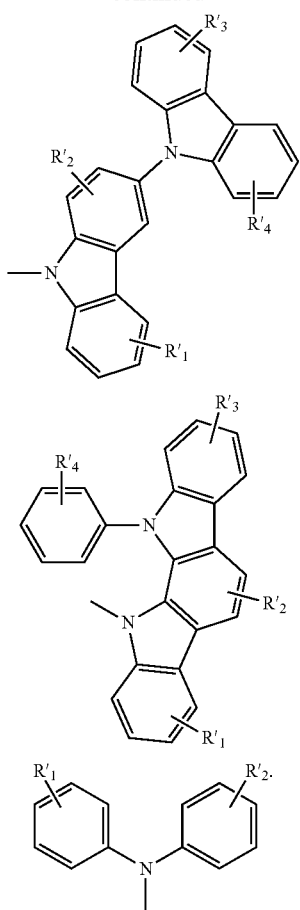

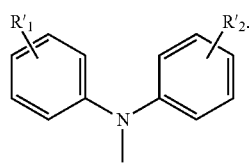

R′₁, R′₂, R′₃, and R′₄ are independently selected from the group consisting of hydrogen, alkyl, heteroalkyl, aryl and heteroaryl. Preferably, R′₁, R′₂, R′₃, and R′₄ are each independently hydrogen or methyl.

Specific examples of such compounds include compounds selected from the group consisting of:

Compound 1

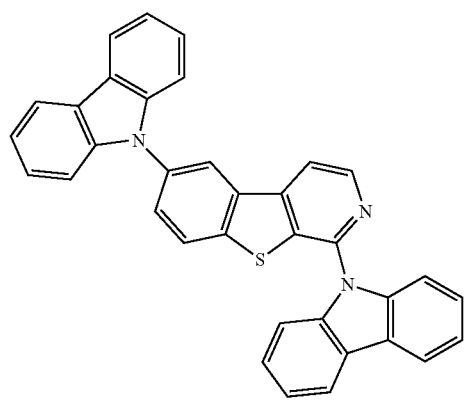

-continued

Compound 2

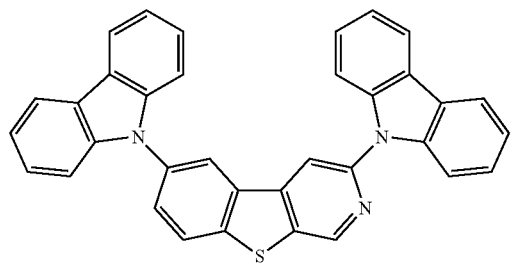

Compound 3

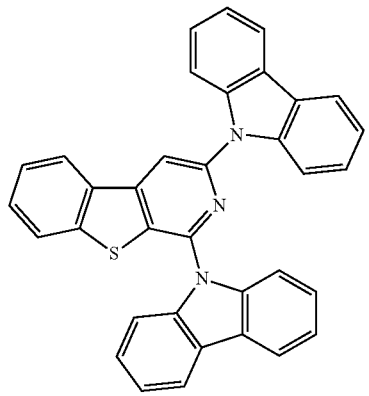

Compound 4

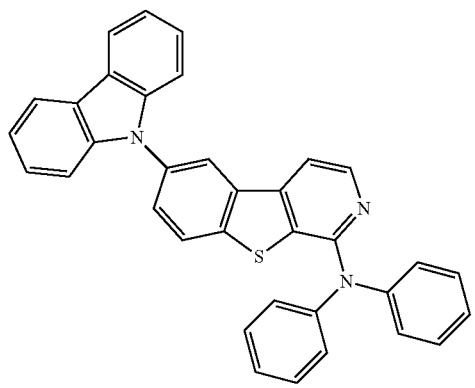

Compound 5

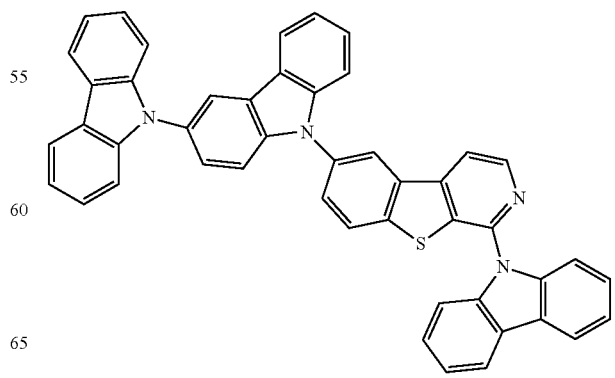

Compound 7
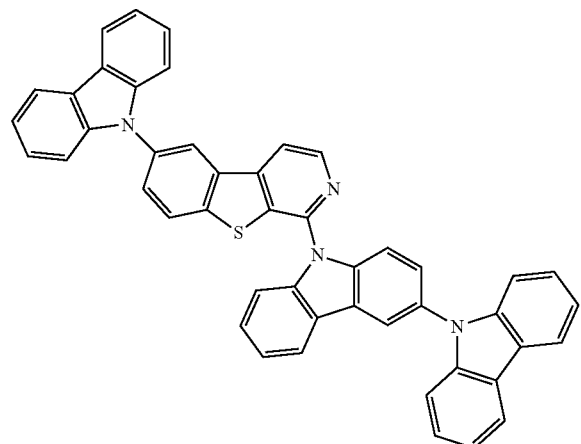
Compound 8
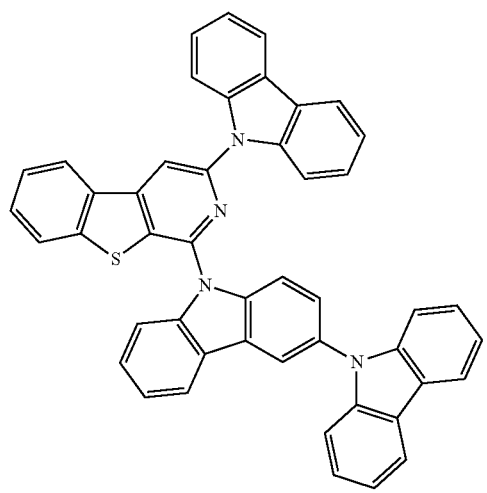
Compound 9
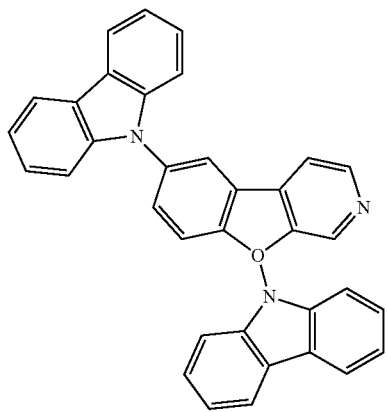
Compound 10
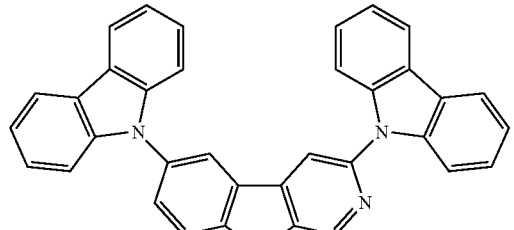
Compound 11
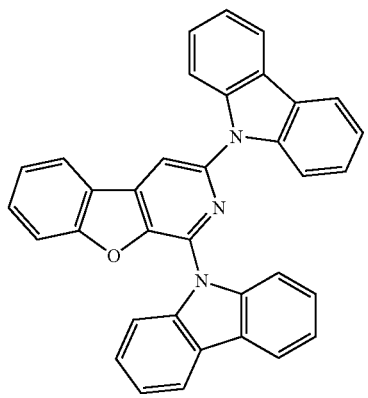
Compound 12
Compound 13
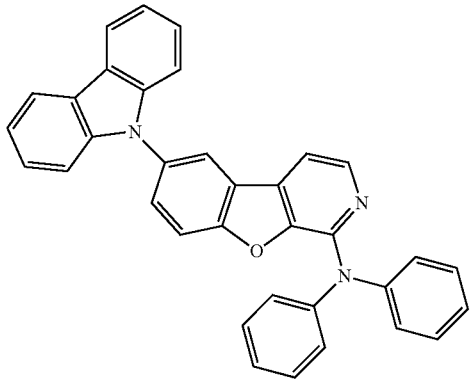

Compound 14
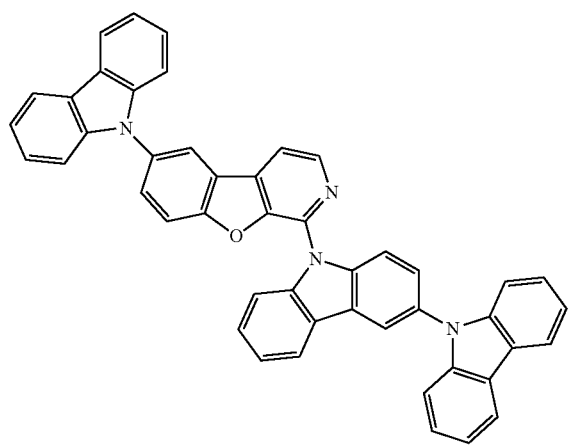
Compound 15
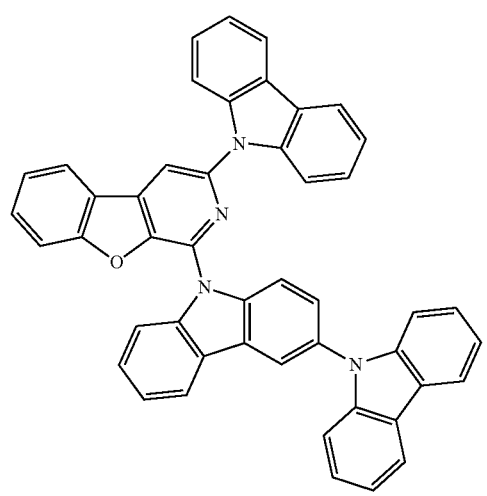
Compound 17
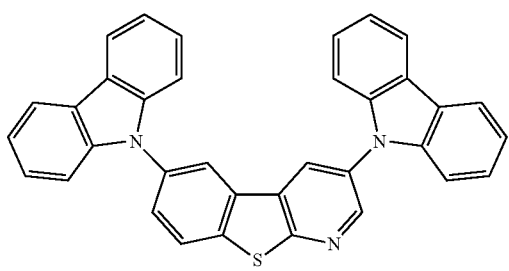
Compound 19
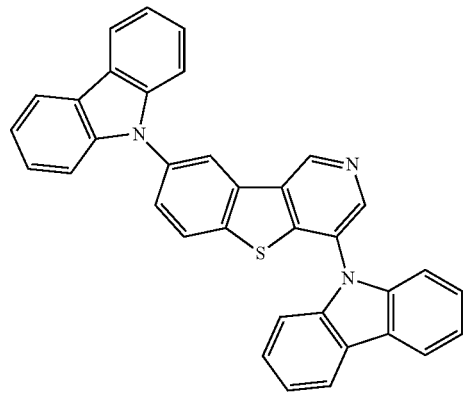
Compound 20
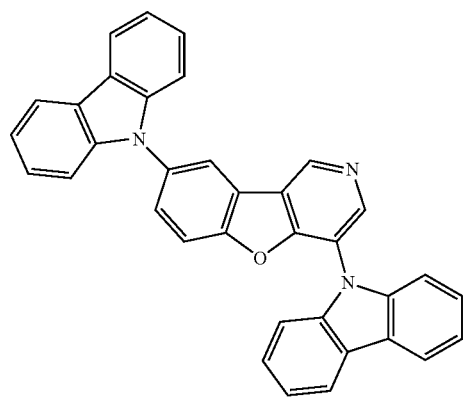
Compound 21
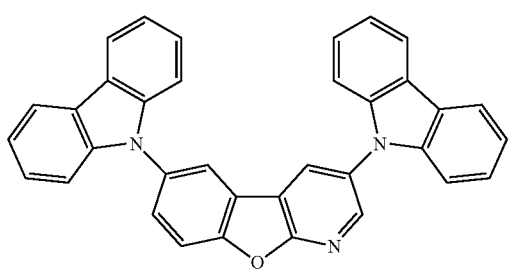
Compound 23
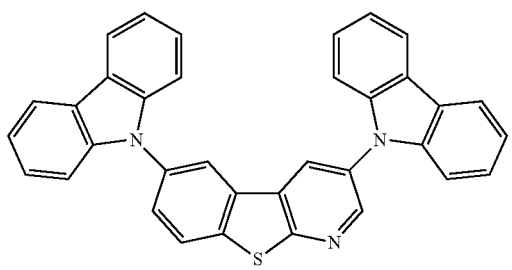

Compound 25
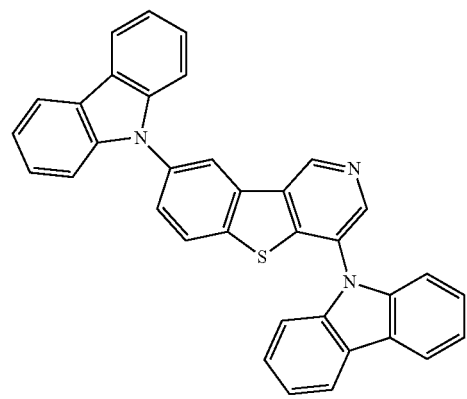
Compound 26
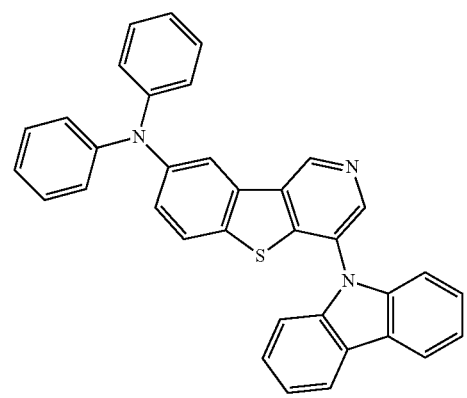
Compound 27
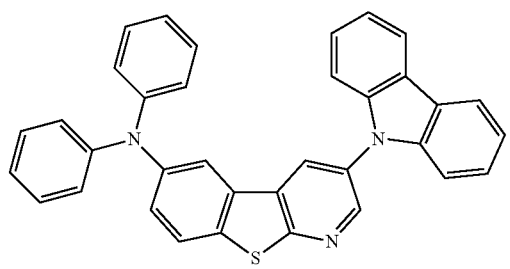
Compound 28
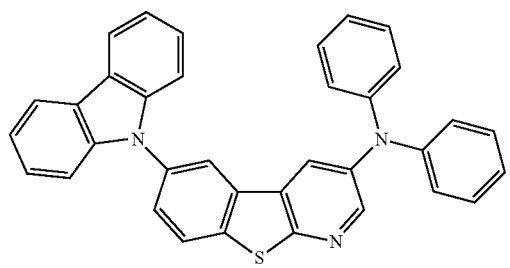
Compound 29
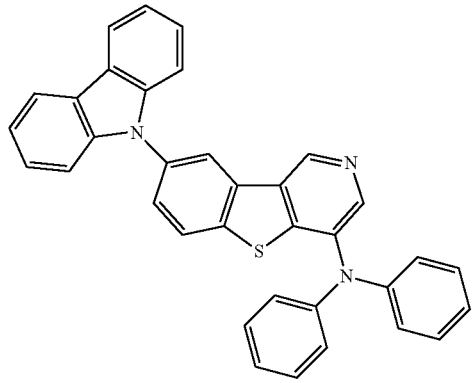
Compound 31
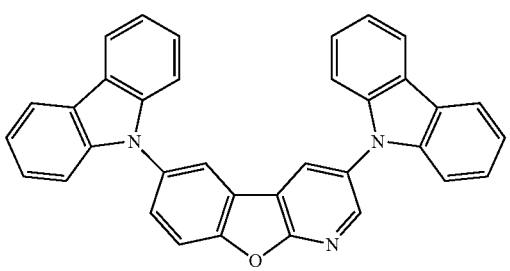
Compound 33
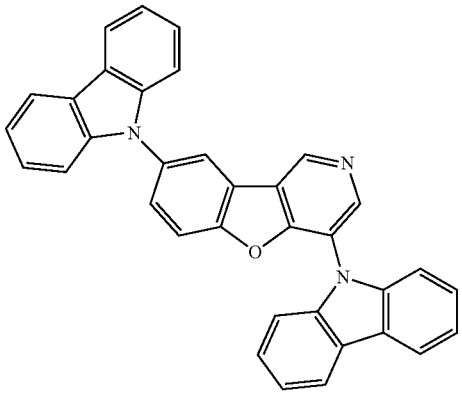
Compound 34
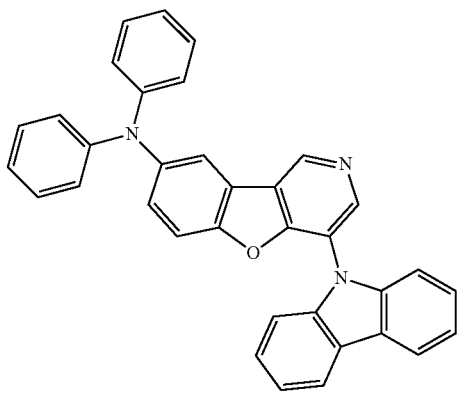

Compound 35
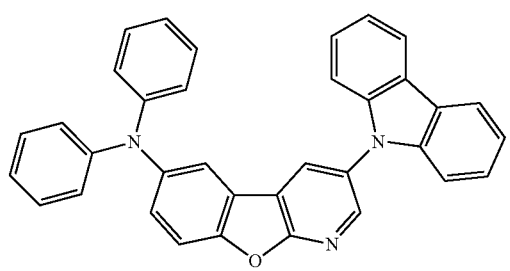
Compound 36
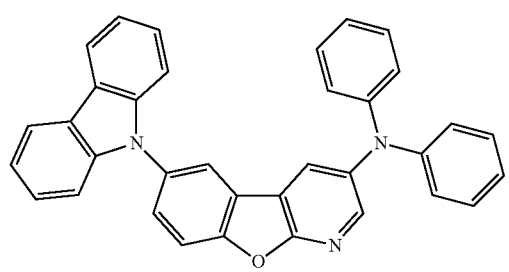
Compound 37
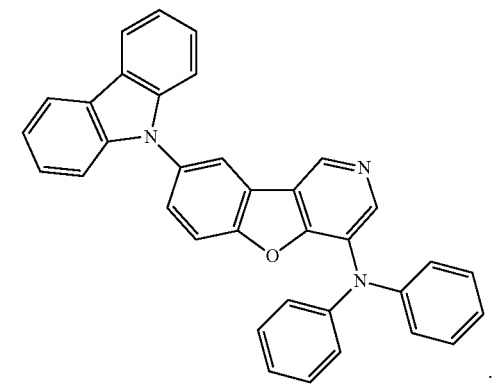
In one aspect, R₁ and R₂ are each independently selected from the group consisting of hydrogen and
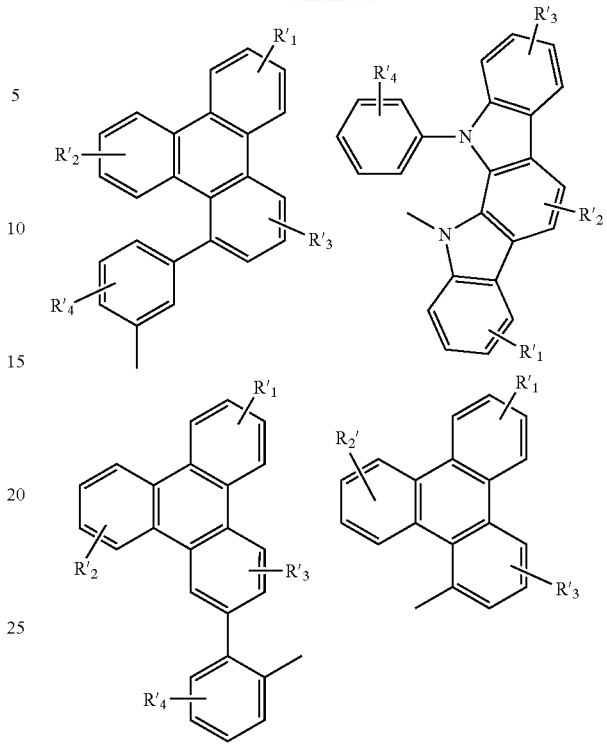
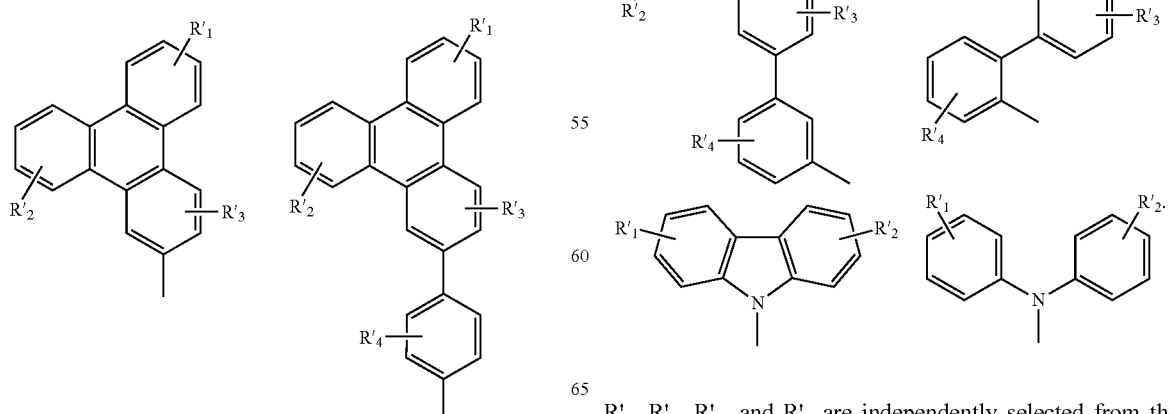
R'₁, R'₂, R'₃, and R'₄ are independently selected from the group consisting of hydrogen, alkyl, heteroalkyl, aryl and heteroaryl. Preferably, $R'_1$, $R'_2$, $R'_3$, and $R'_4$ are each independently hydrogen or methyl.
Specific examples of such compounds include compounds selected from the group consisting of:
Compound 1
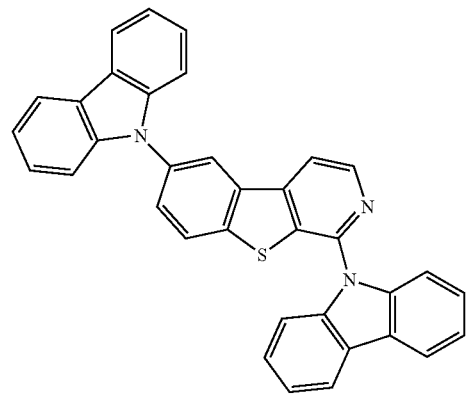
Compound 2
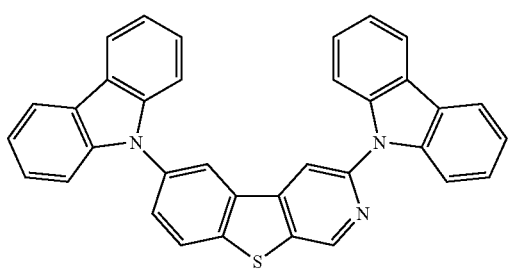
Compound 3
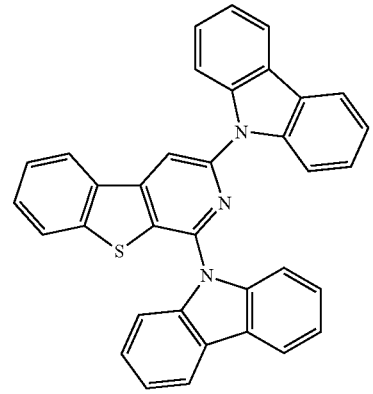
Compound 4
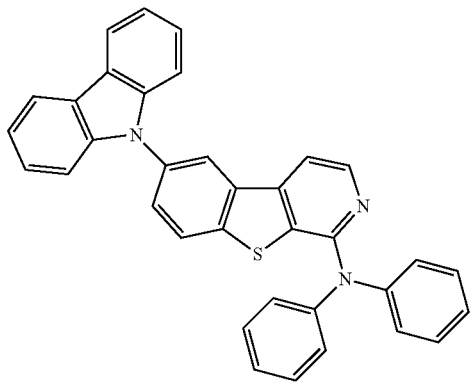
Compound 5
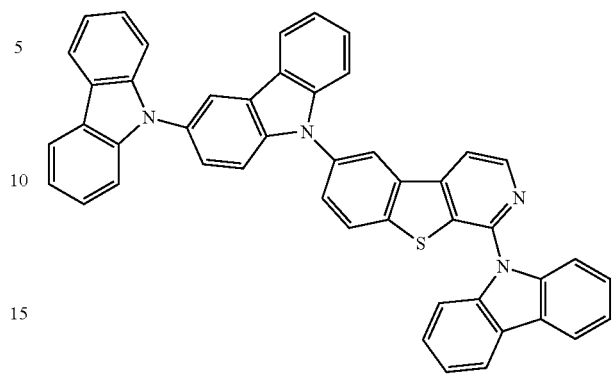
Compound 7
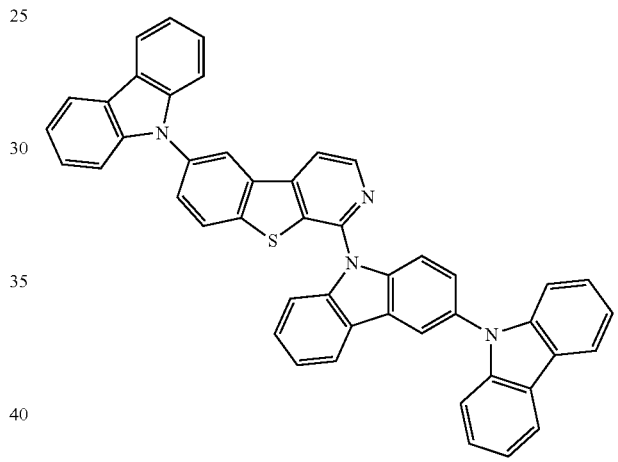
Compound 8
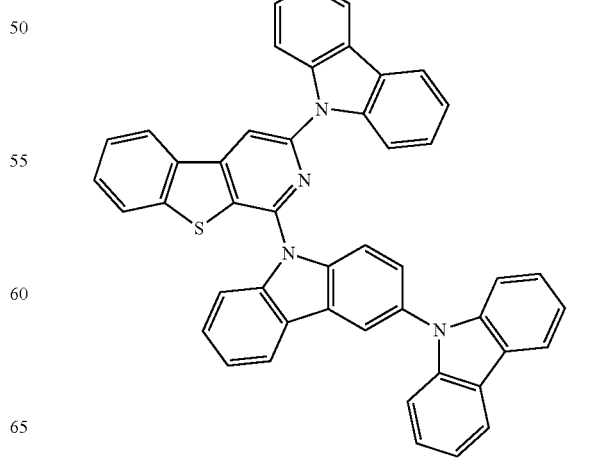

-continued
Compound 9
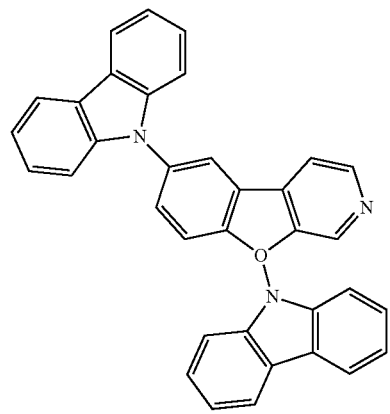
Compound 10
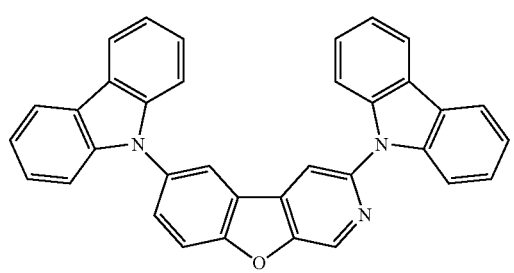
Compound 11
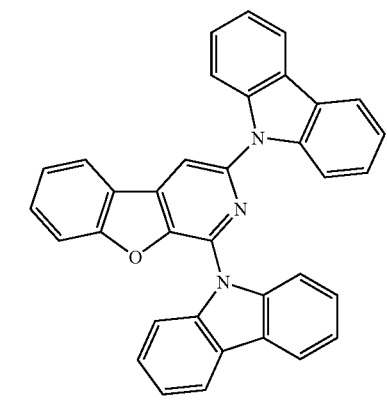
Compound 12
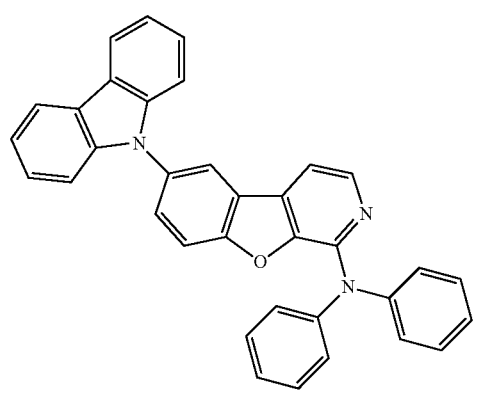
-continued
Compound 13
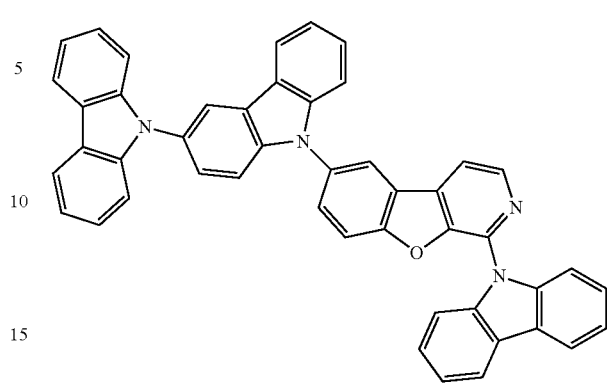
Compound 14
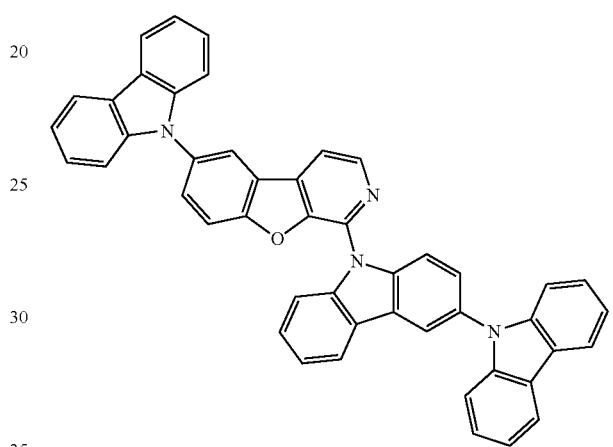
Compound 15
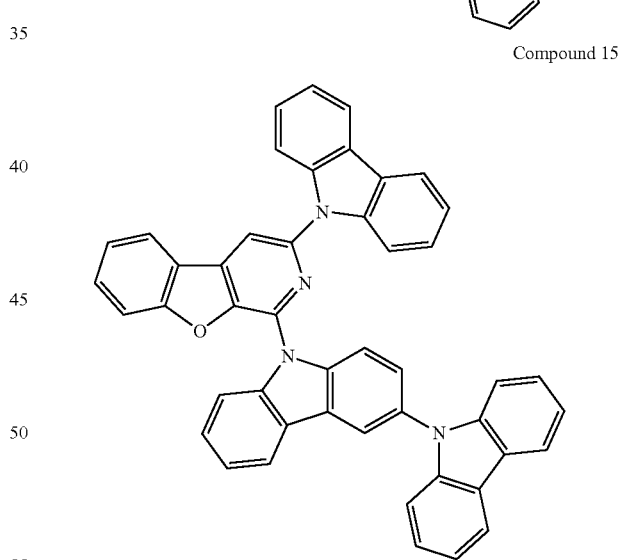
Compound 17
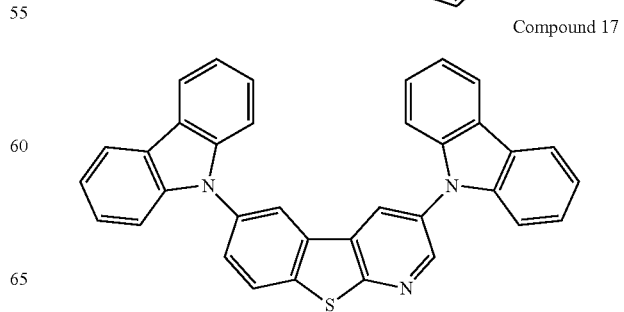

Compound 19
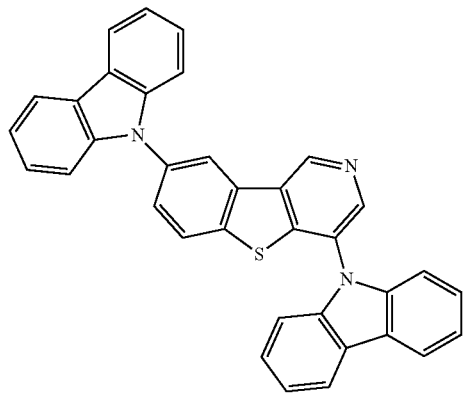
Compound 25
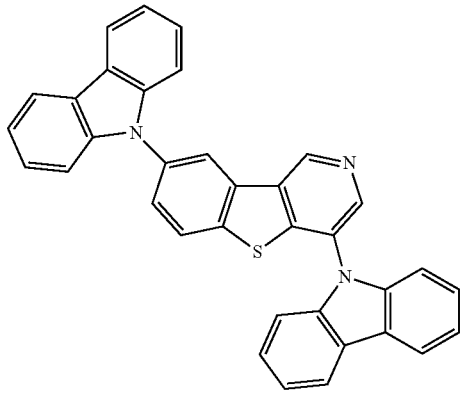
Compound 20
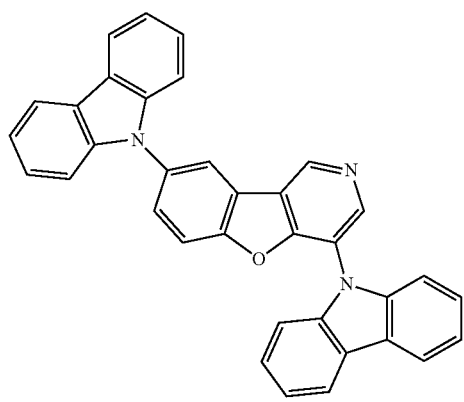
Compound 26
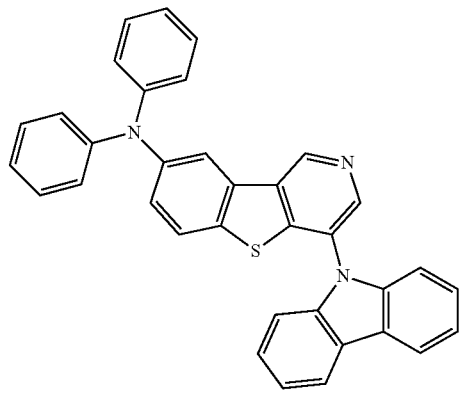
Compound 21
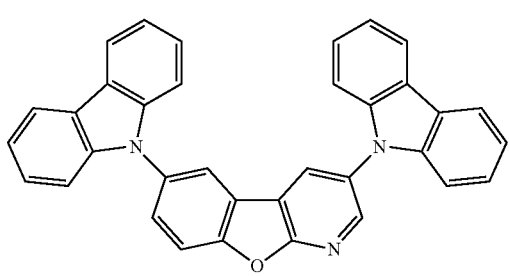
Compound 27
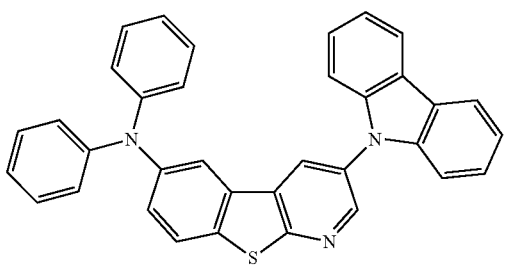
Compound 23
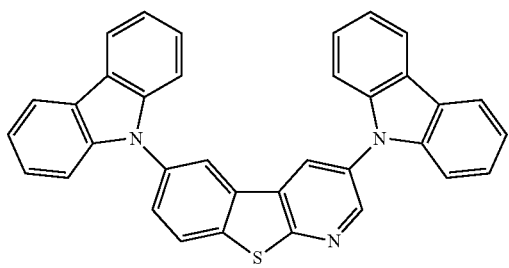
Compound 28
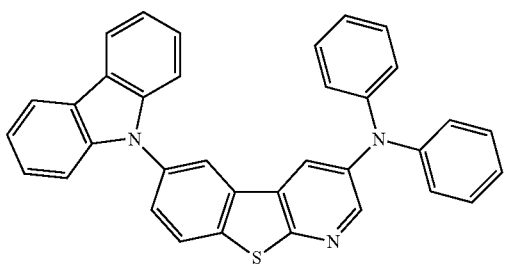

Compound 29
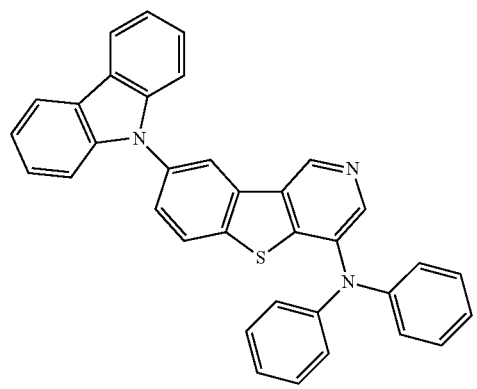
Compound 31
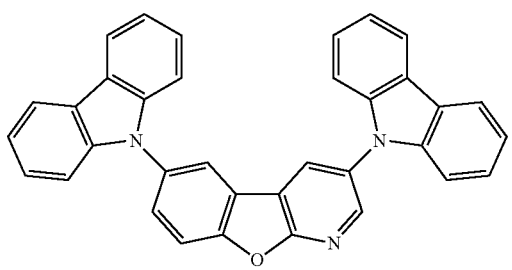
Compound 33
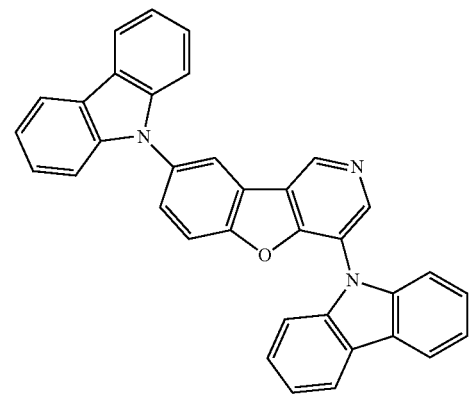
Compound 34
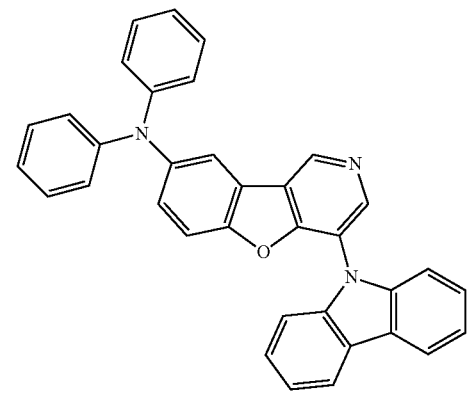
Compound 35
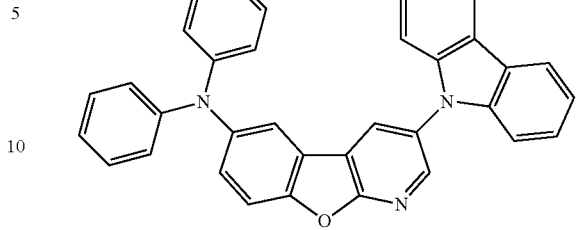
Compound 36
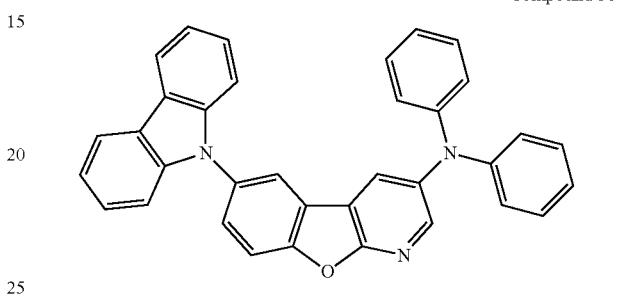
Compound 37
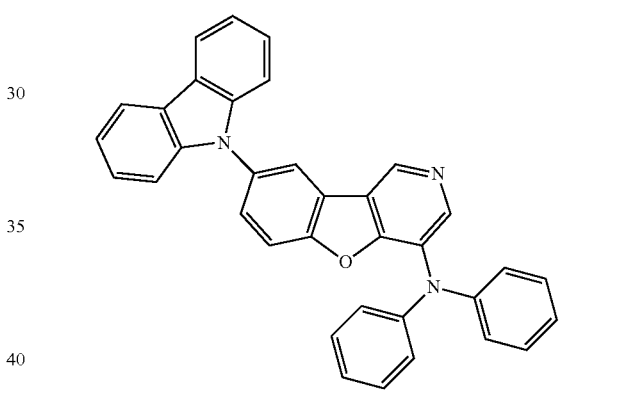
Compound 39
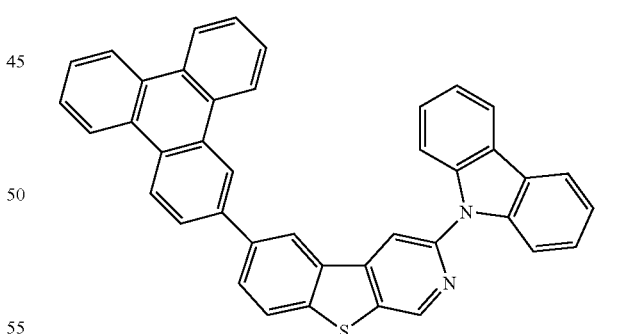
Compound 40
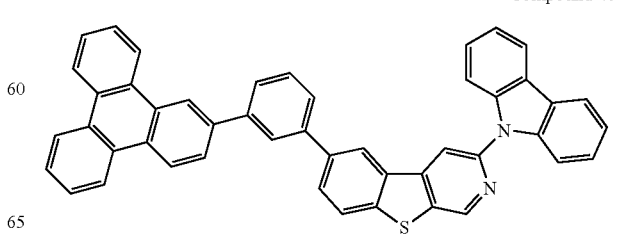

Compound 41
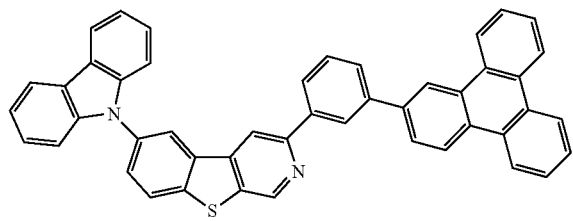
Compound 42
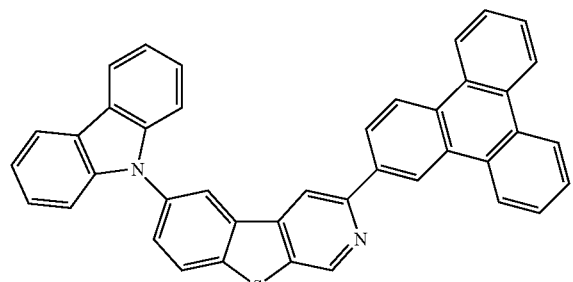
Compound 43
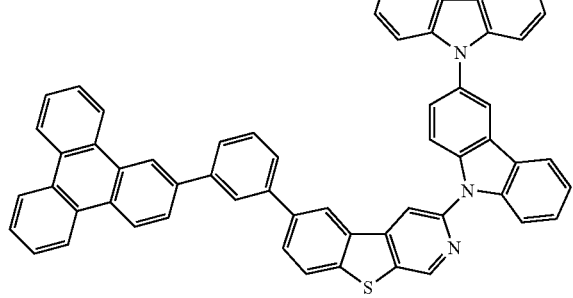
Compound 44
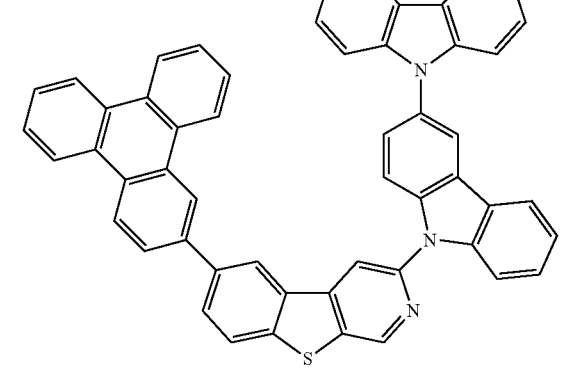
Compound 45
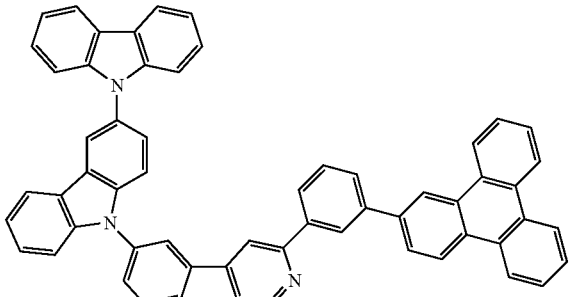
Compound 46
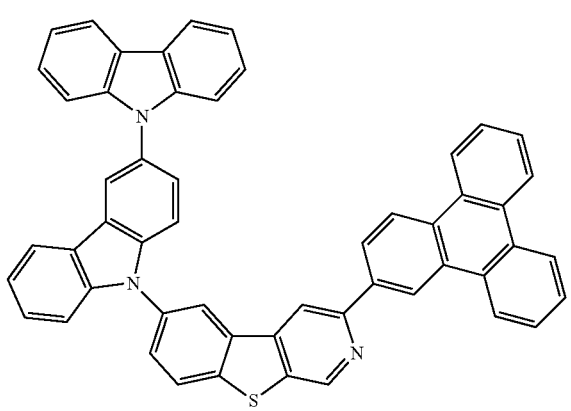
Compound 47
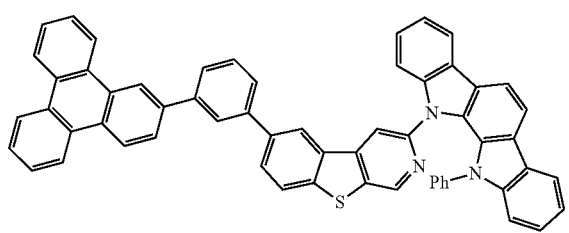
Compound 48
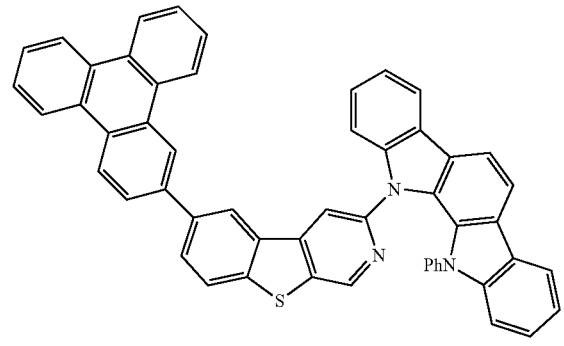
Compound 50
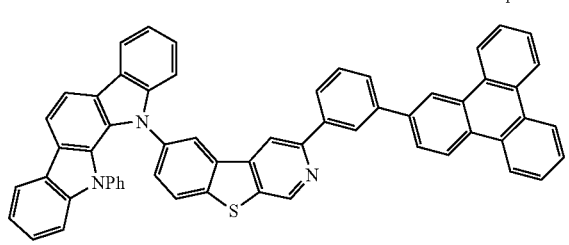

Compound 51
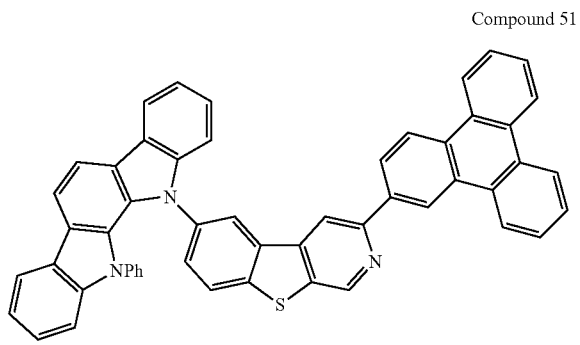
Compound 52
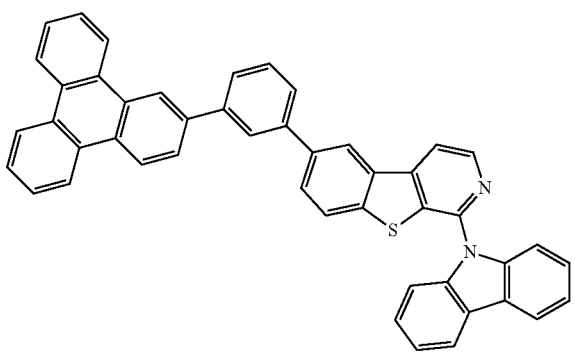
Compound 53
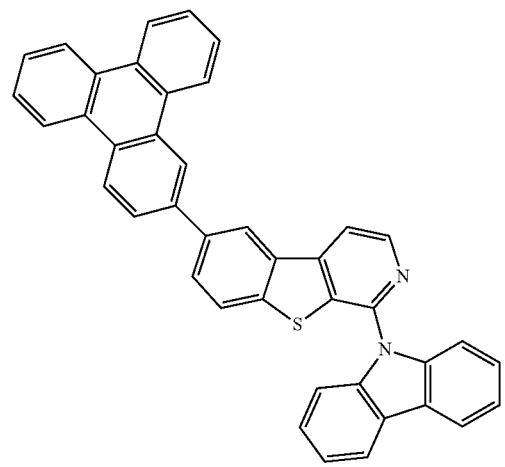
Compound 54
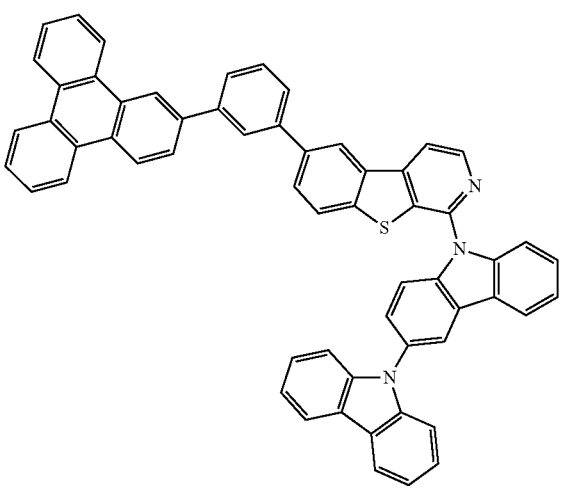
Compound 55
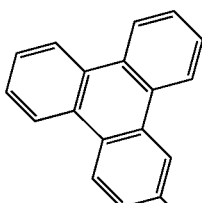
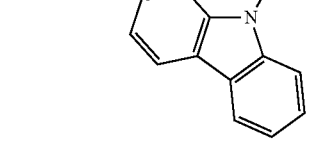
Compound 56
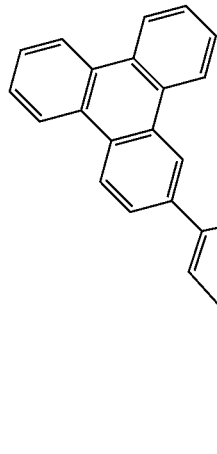

Compound 57
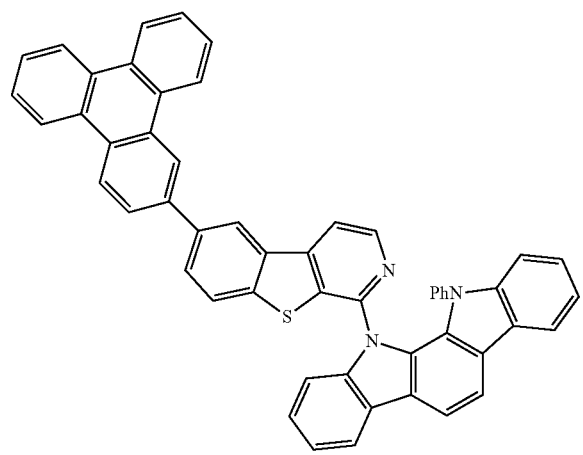
Compound 58
Compound 59
Compound 60
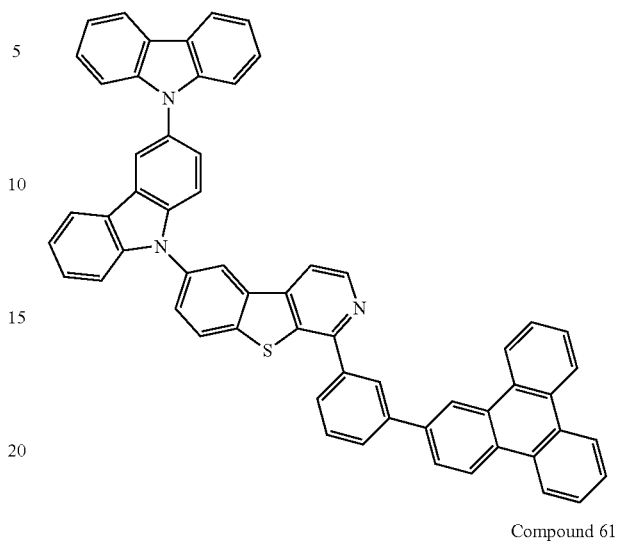
Compound 61
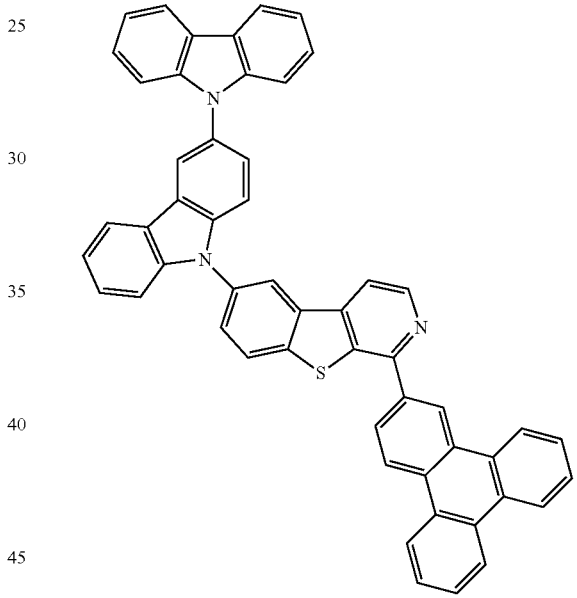
Compound 62
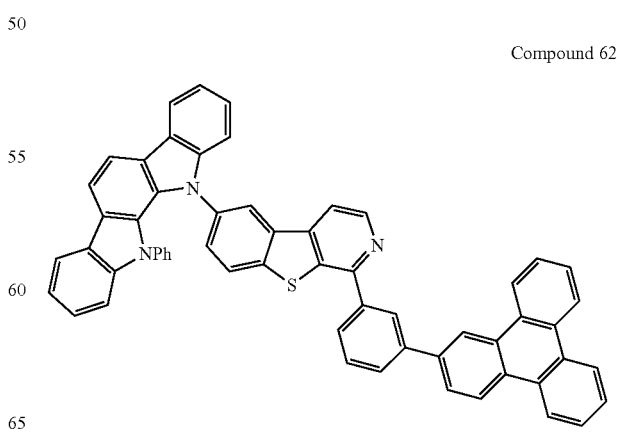

-continued
Compound 63
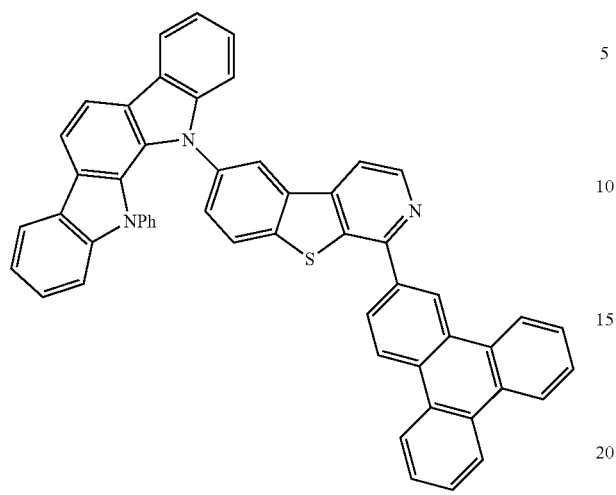
Compound 64
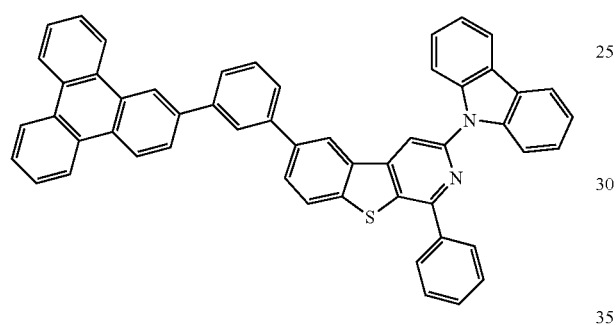
Compound 65
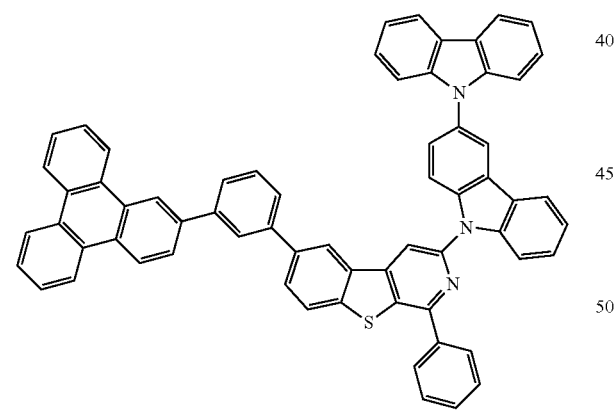
Compound 66
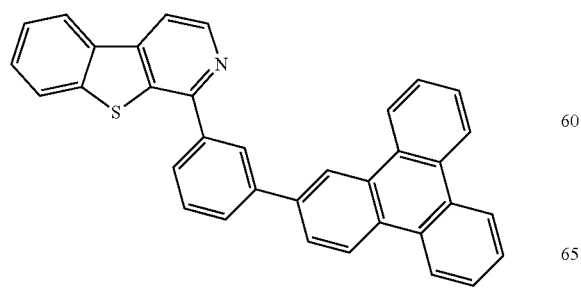
-continued
Compound 70
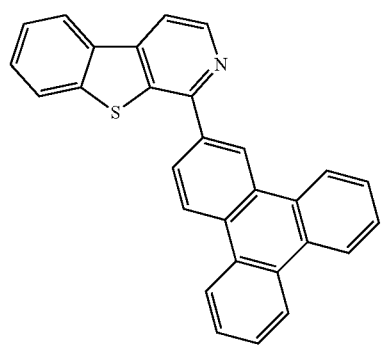
Compound 71
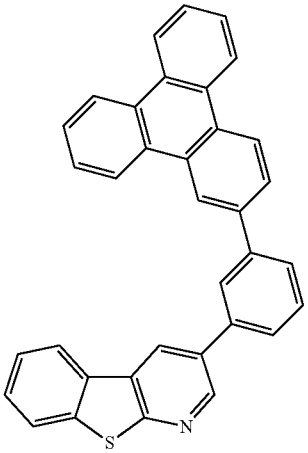
Compound 72
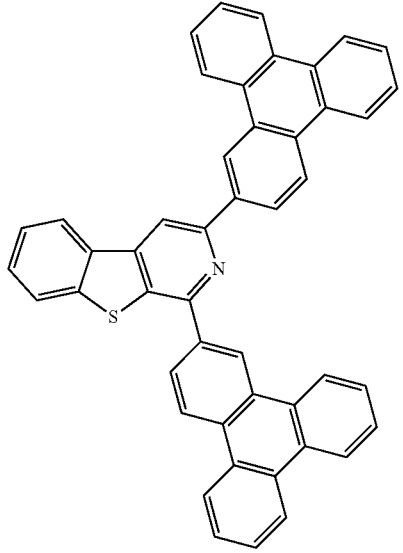

-continued
Compound 75
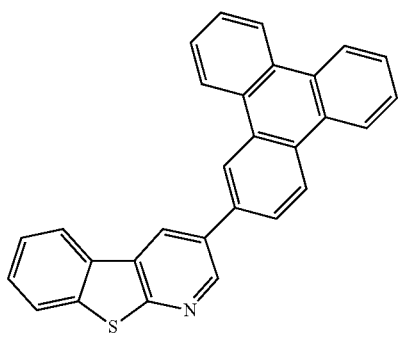
Compound 78
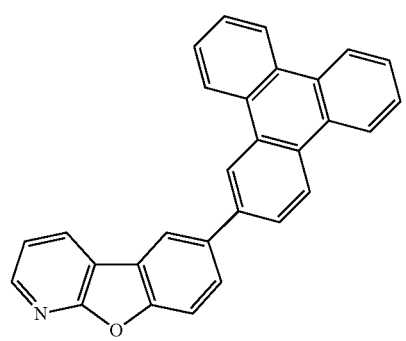
Compound 79
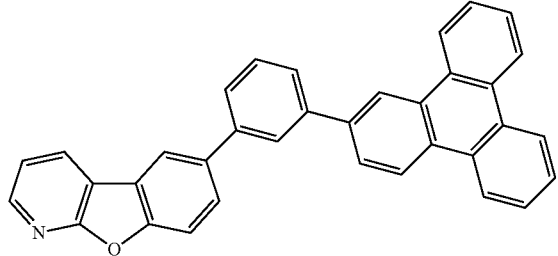
In another aspect, $R_1$ is selected from the group consisting of:
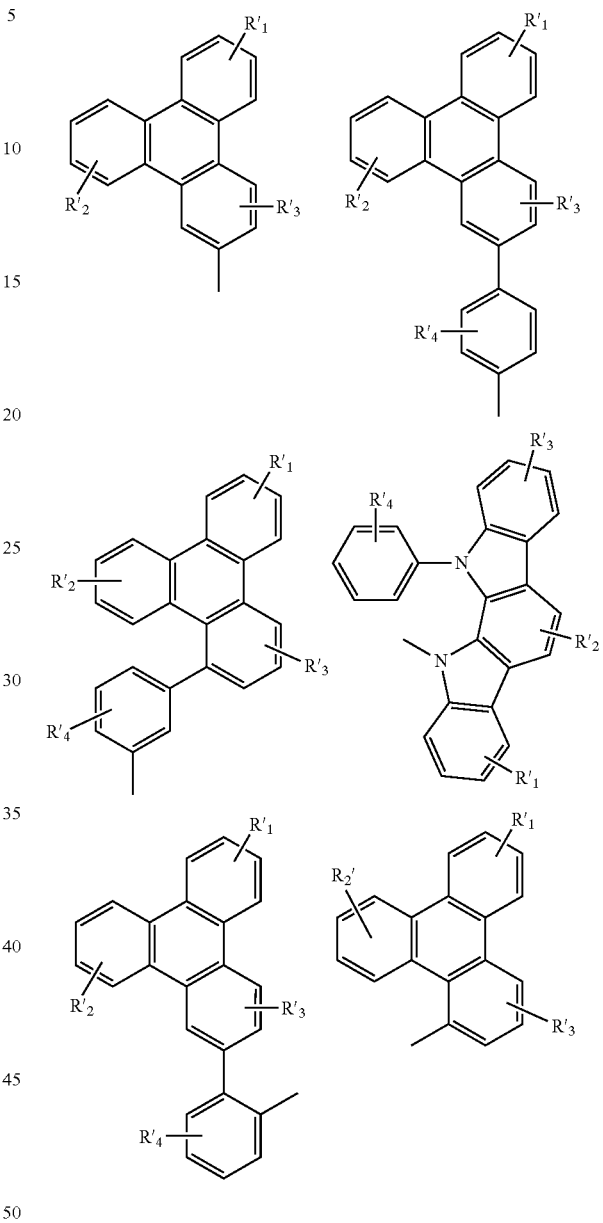
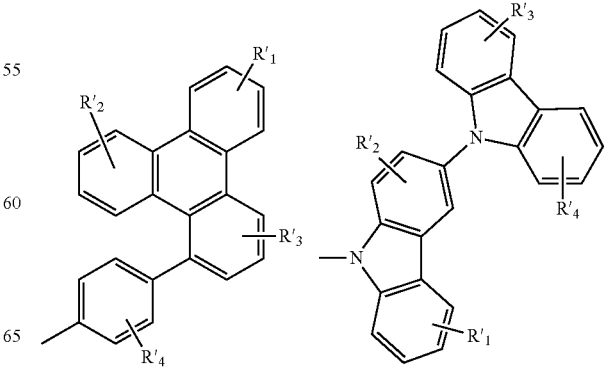

-continued

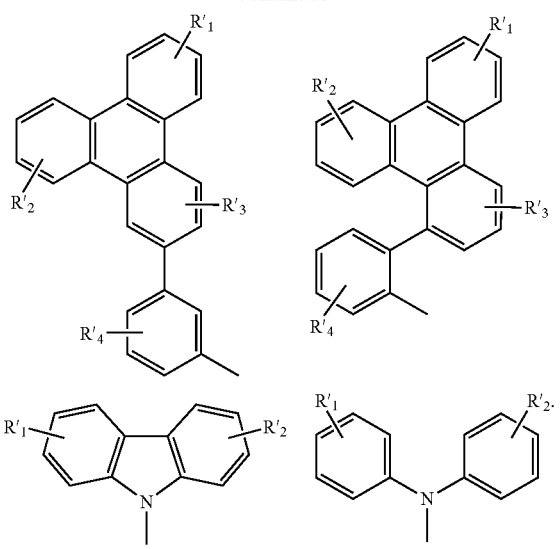

R'$_1$, R'$_2$, R'$_3$, and R'$_4$ are independently selected from the group consisting of hydrogen, alkyl, heteroalkyl, aryl and heteroaryl. R$_2$ is hydrogen. Preferably, R'$_1$, R'$_2$, R'$_3$, and R'$_4$ are each independently hydrogen or methyl.

Specific examples of such compounds include compounds selected from the group consisting of:

Compound 1

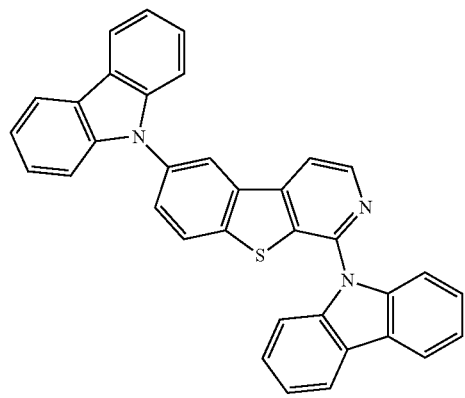

Compound 2

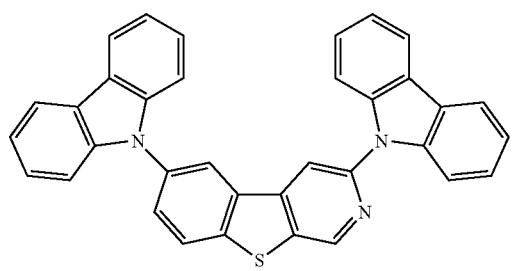

-continued

Compound 3

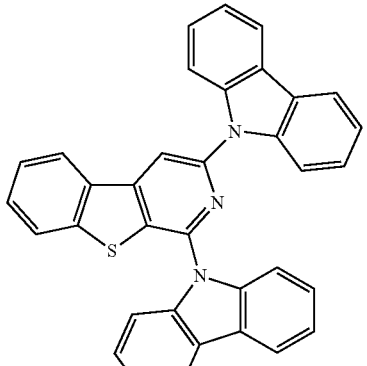

Compound 4

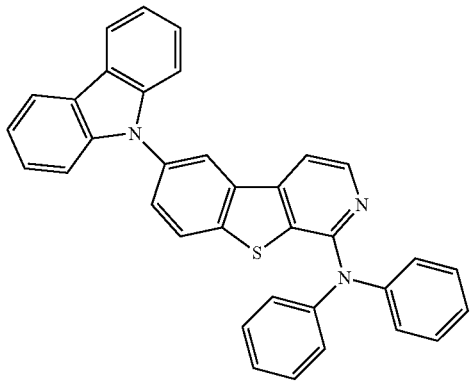

Compound 5

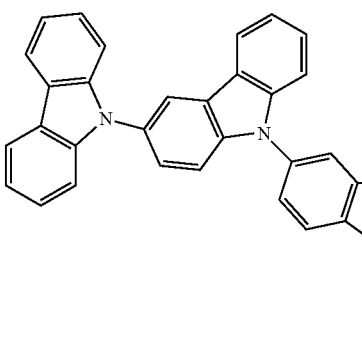

Compound 6

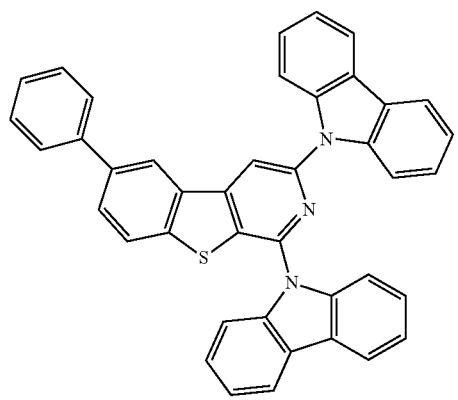

Compound 7
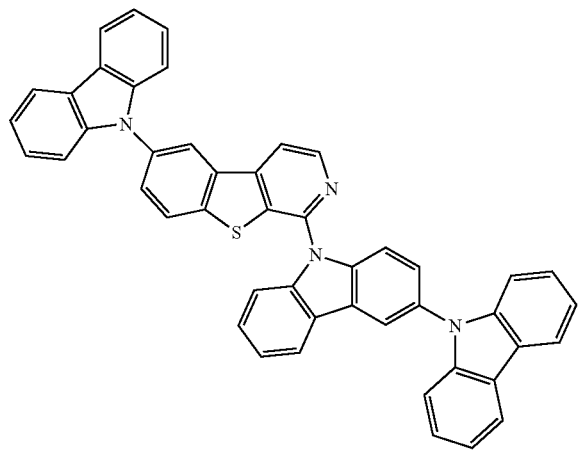
Compound 8
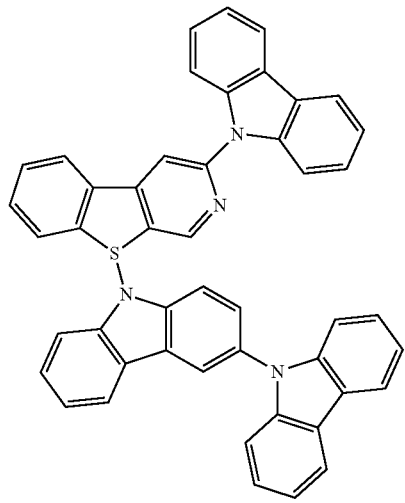
Compound 9
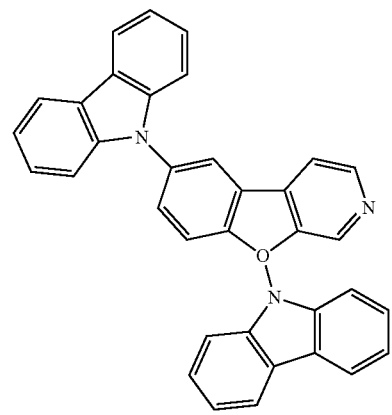
Compound 10
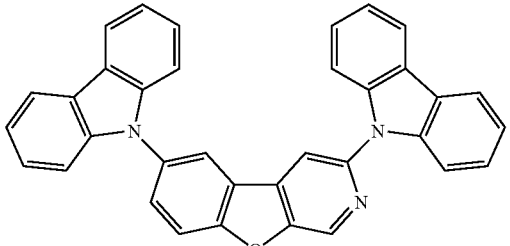
Compound 11
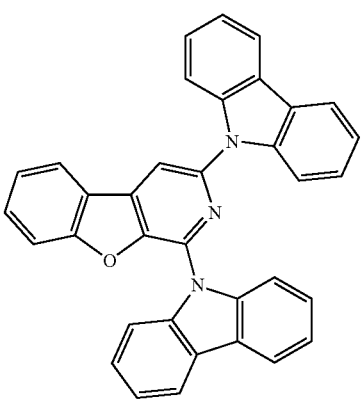
Compound 12
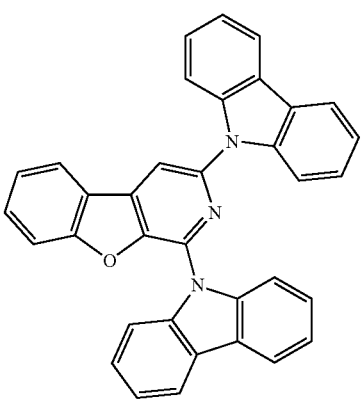
Compound 13
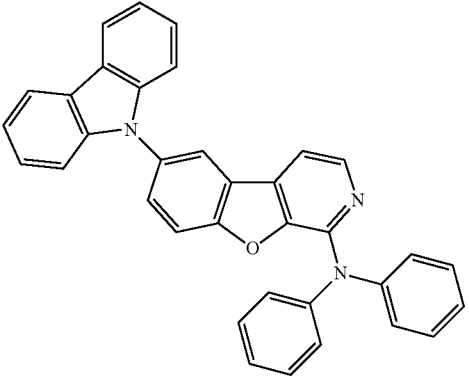

Compound 14
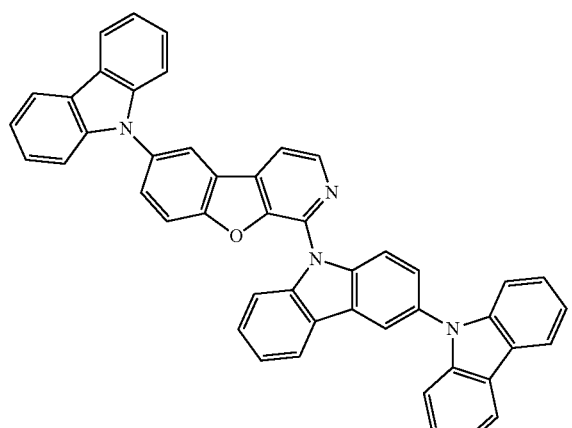
Compound 15
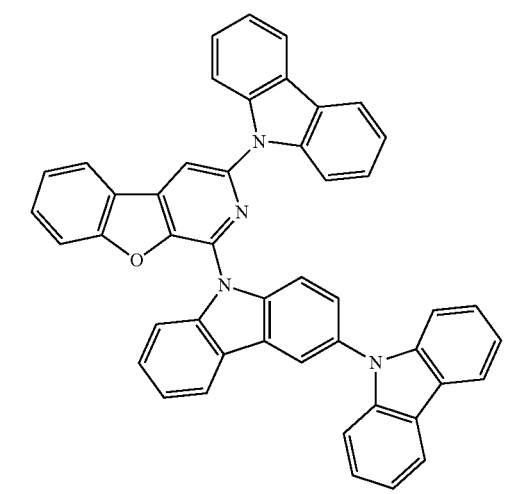
Compound 16
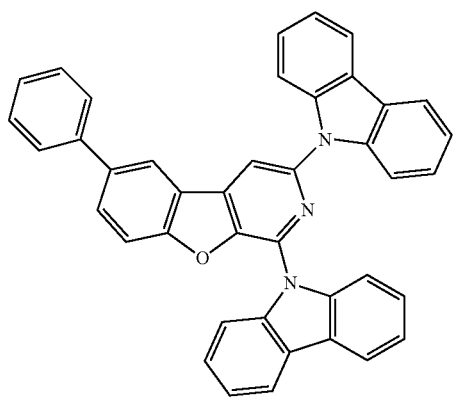
Compound 17
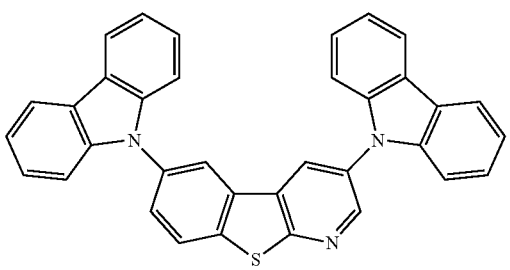
Compound 18
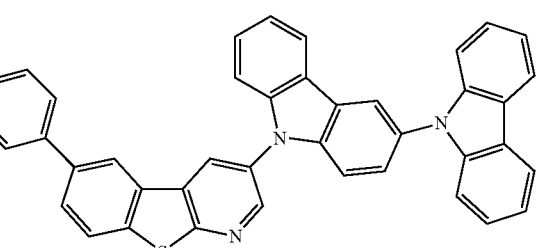
Compound 19
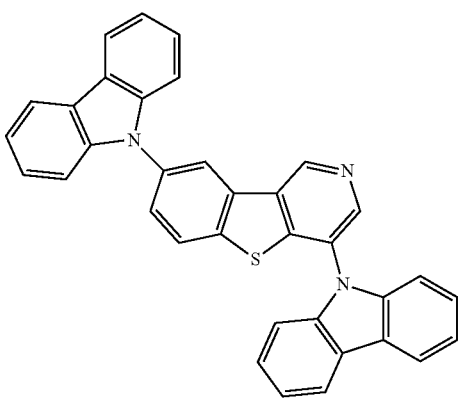
Compound 20
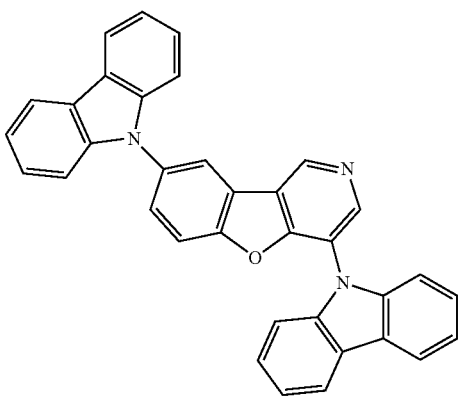

Compound 21
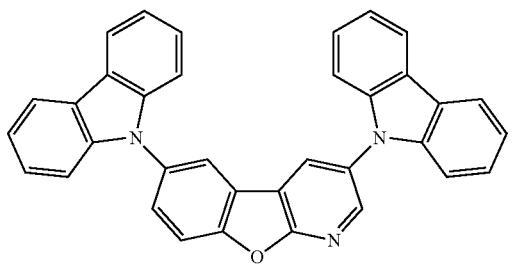
Compound 22
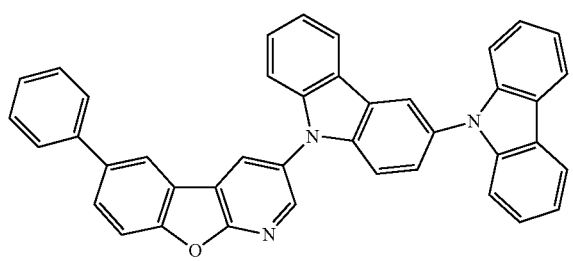
Compound 23
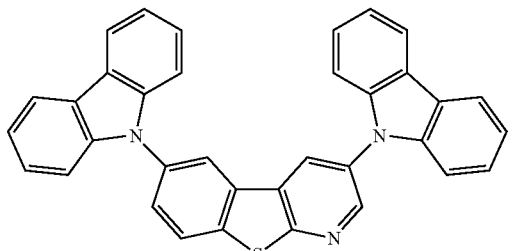
Compound 24
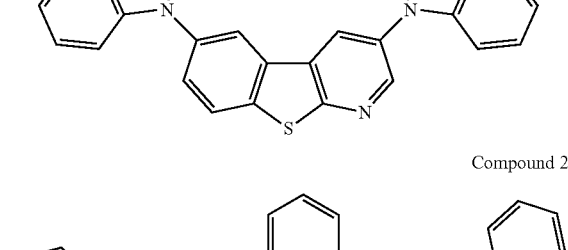
Compound 25
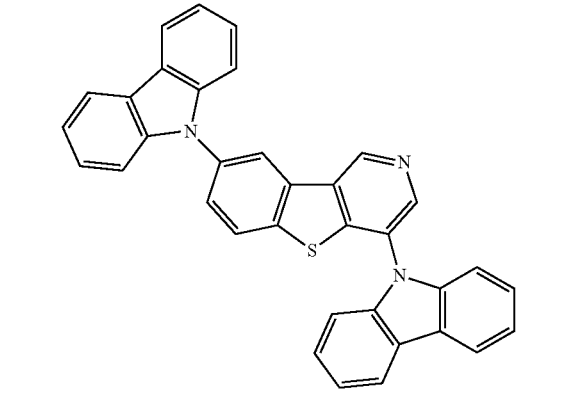
Compound 26
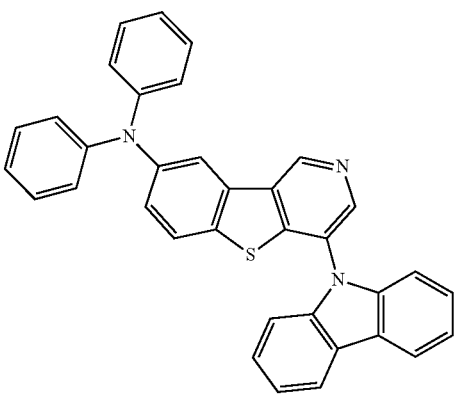
Compound 27
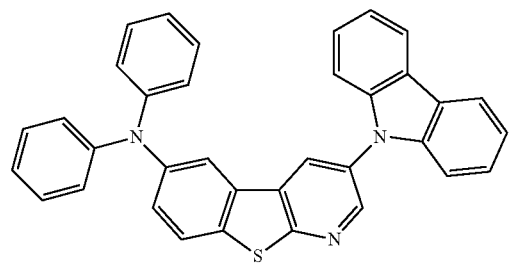
Compound 28
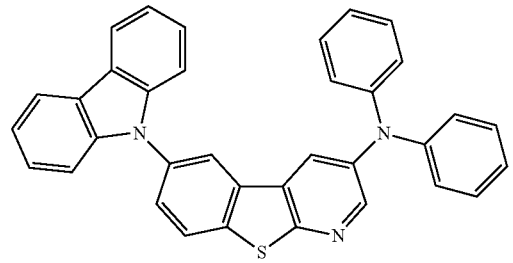
Compound 29
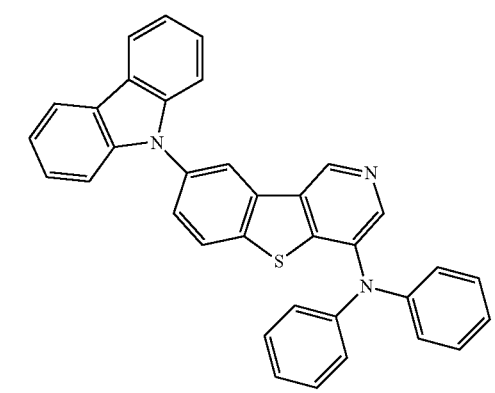

Compound 30
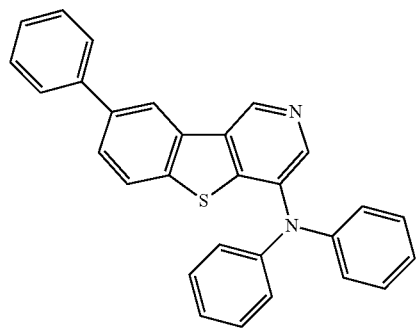
Compound 31
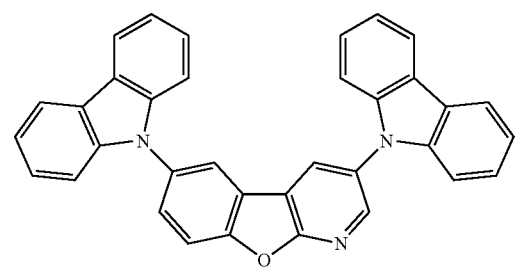
Compound 32
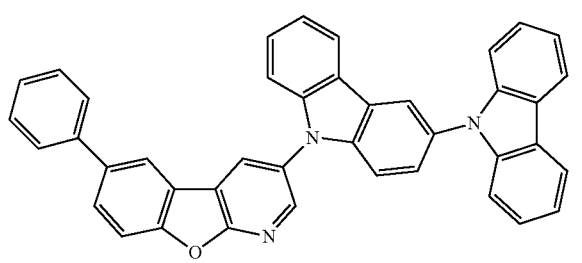
Compound 33
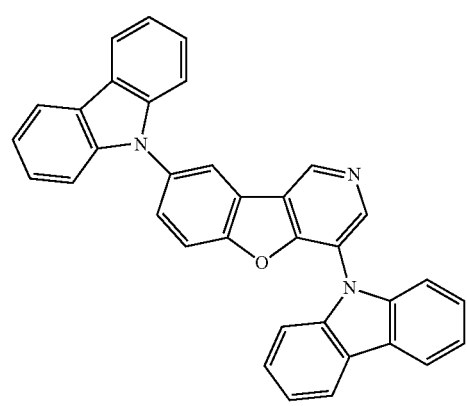
Compound 34
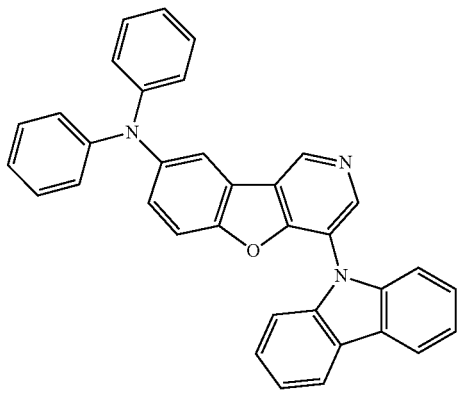
Compound 35
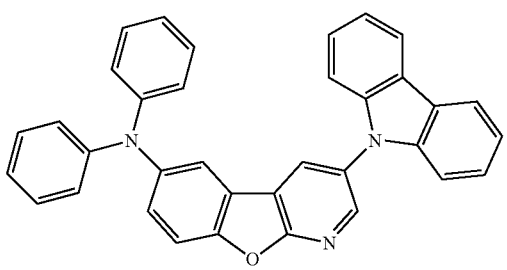
Compound 36
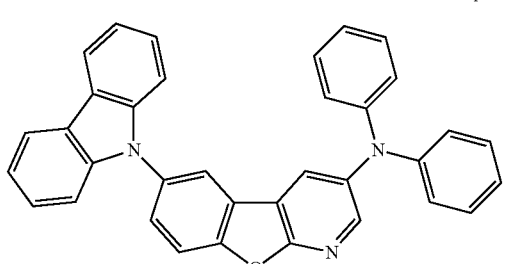
Compound 37
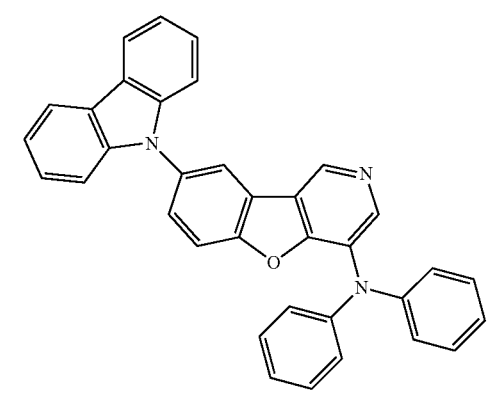

Compound 38
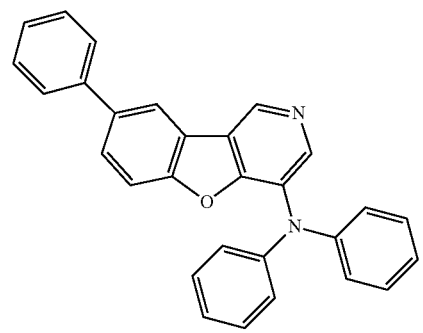
Compound 39
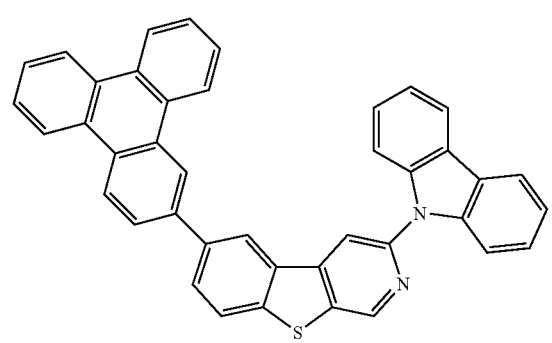
Compound 40
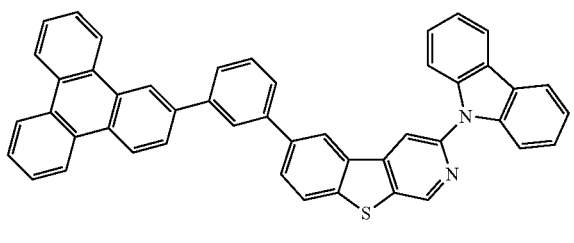
Compound 41
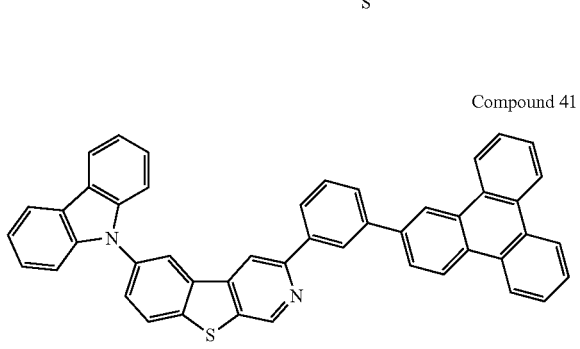
Compound 42
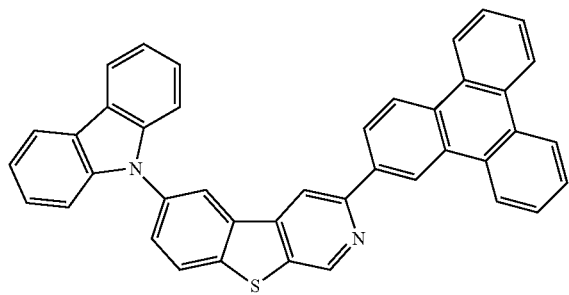
Compound 43
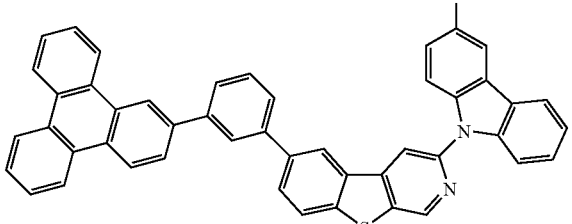
Compound 44
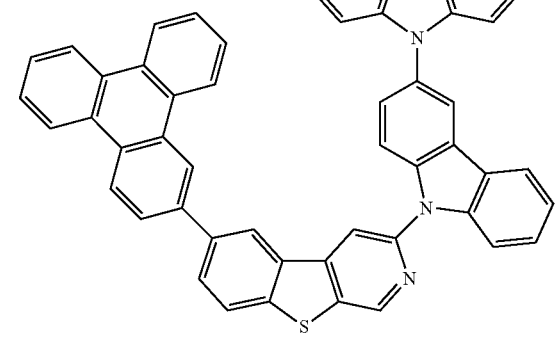
Compound 45
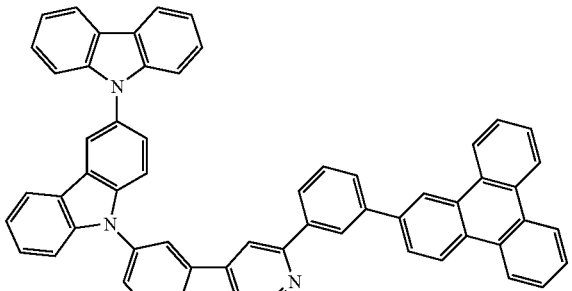
Compound 46

Compound 47
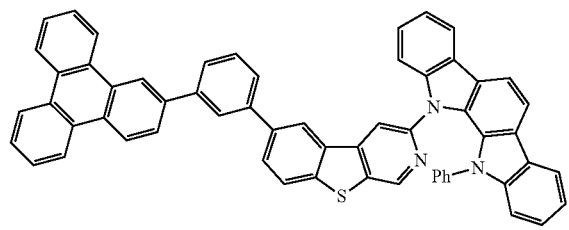
Compound 48
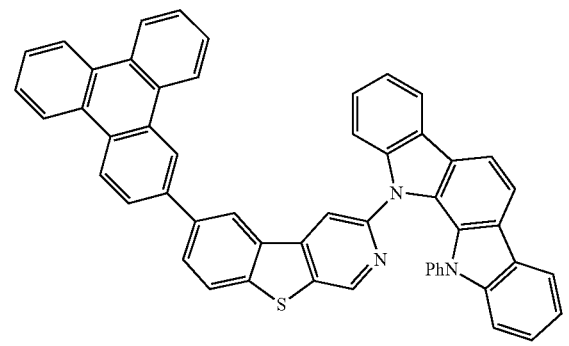
Compound 49
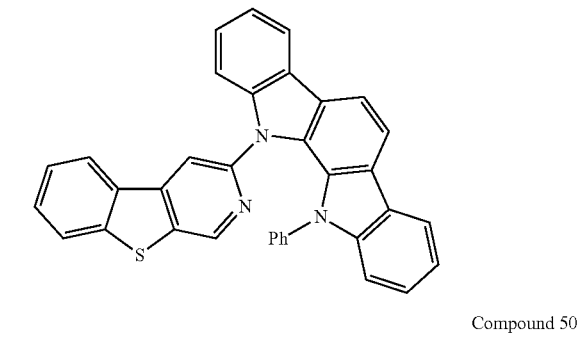
Compound 50
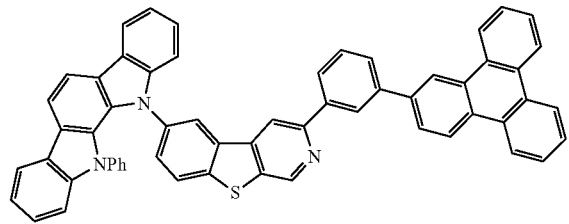
Compound 51
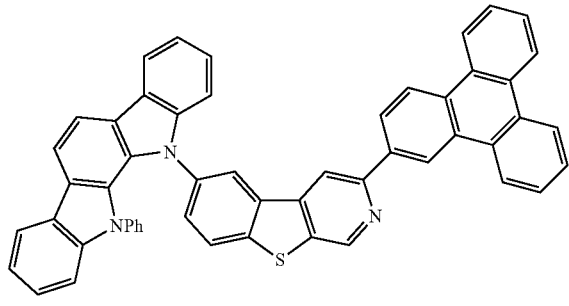
Compound 52
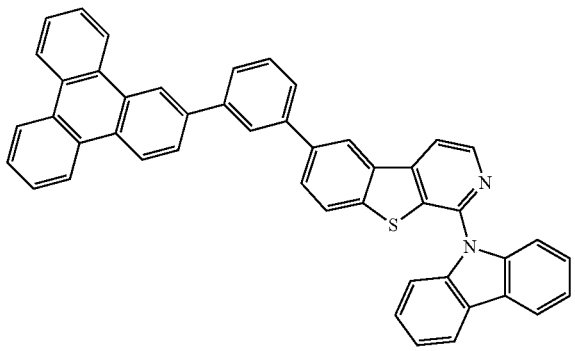
Compound 53
Compound 54
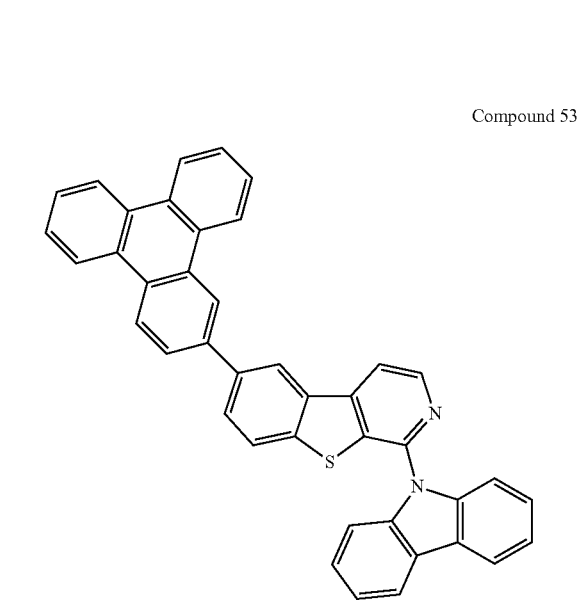

Compound 55
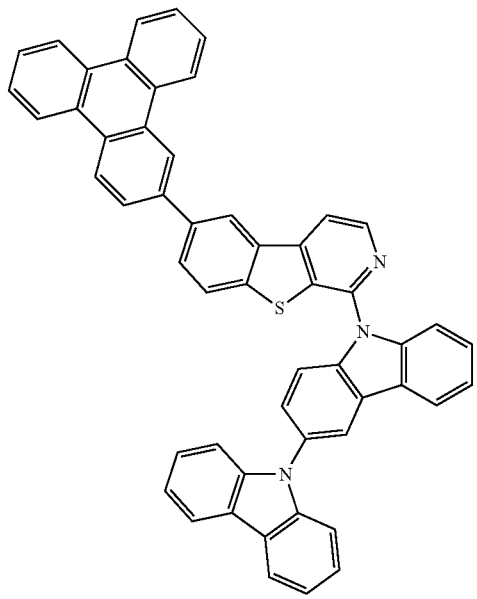
Compound 56
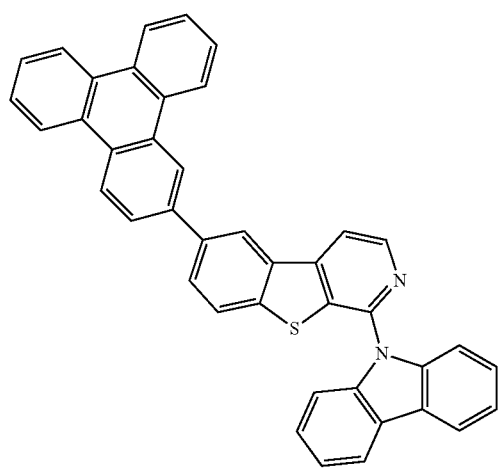
Compound 57
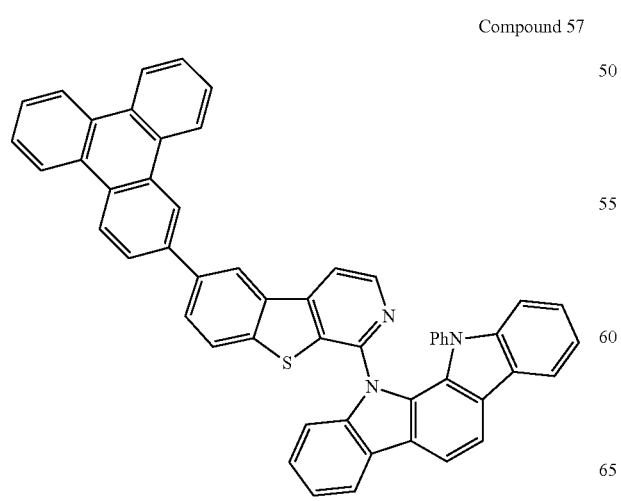
Compound 58
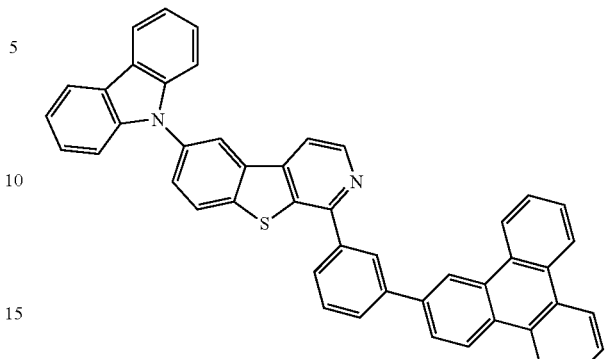
Compound 59
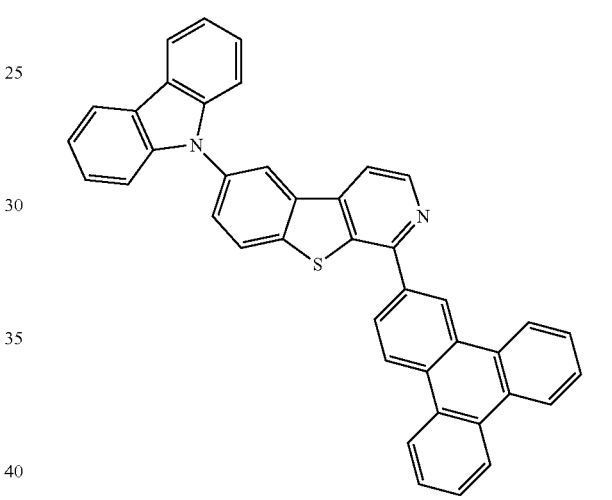
Compound 60
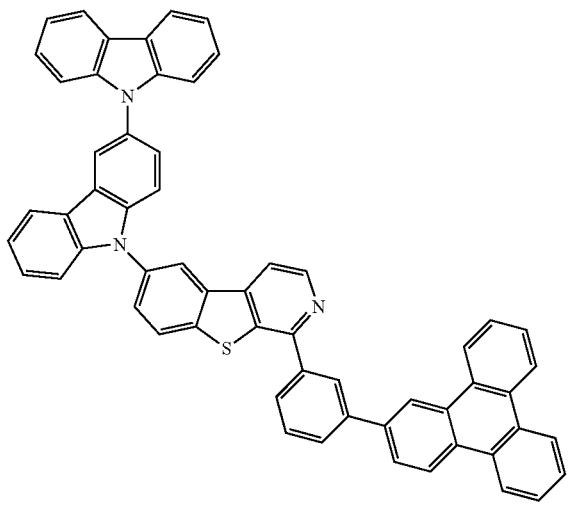

Compound 61
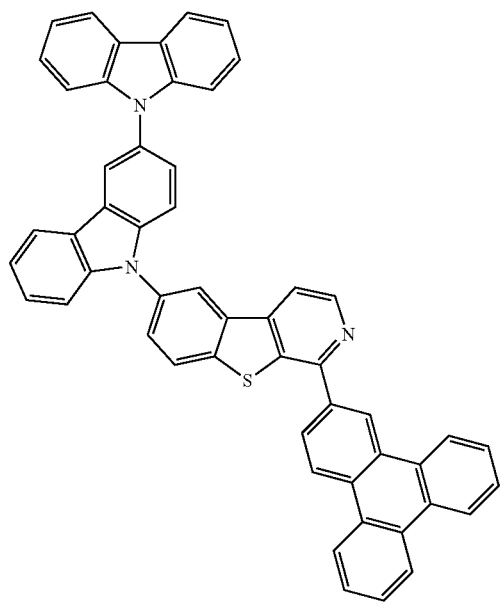
Compound 64
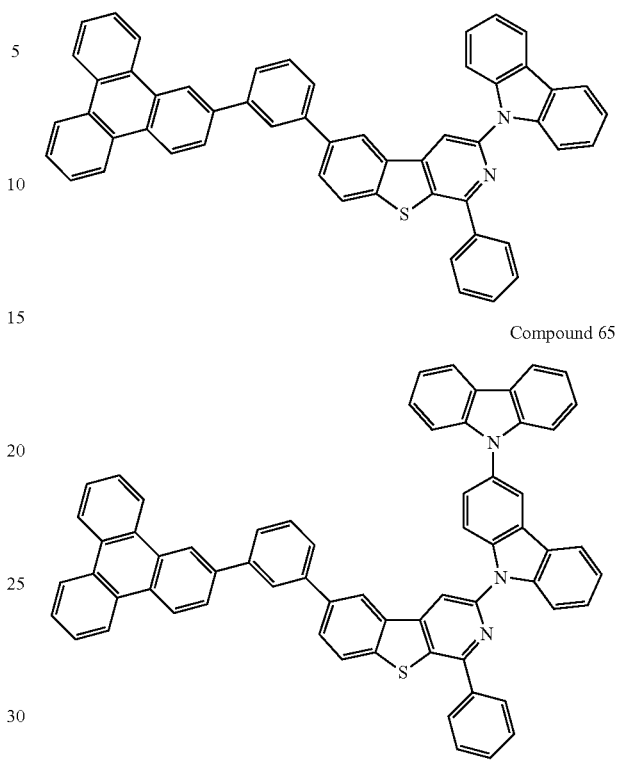
Compound 65
Compound 62
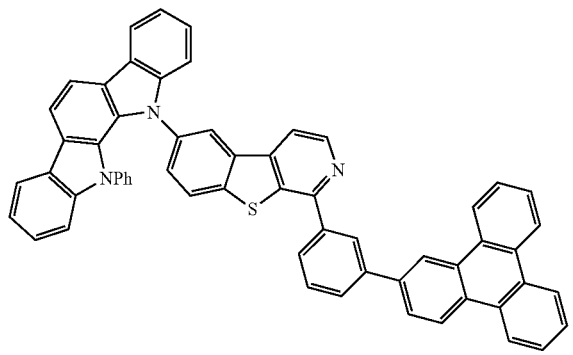
Compound 63
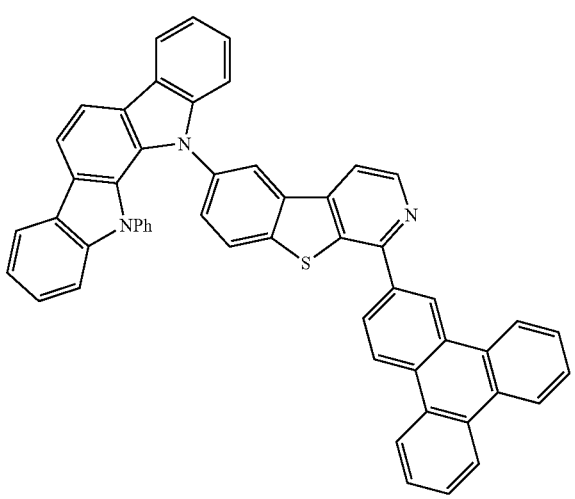
Compound 66
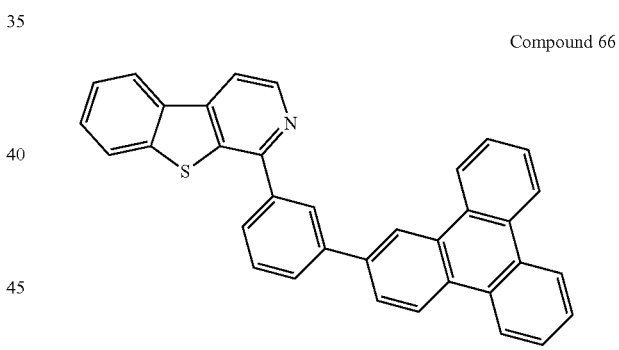
Compound 67
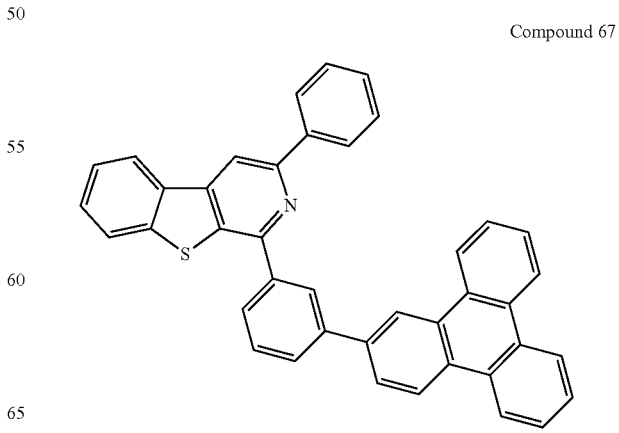

-continued
Compound 68
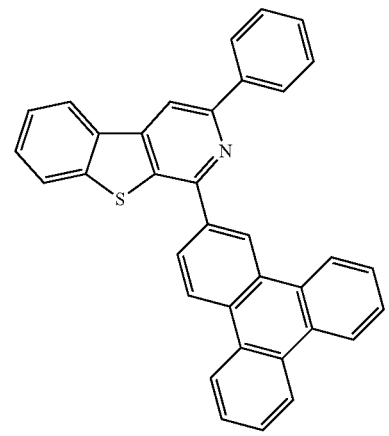
Compound 69
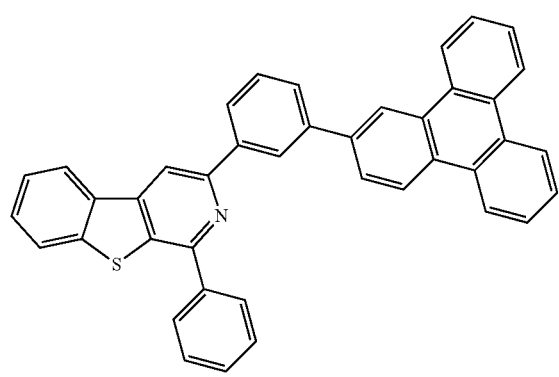
Compound 70
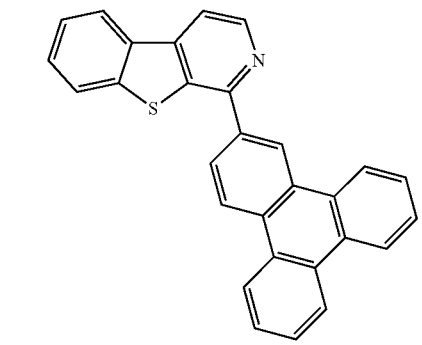
Compound 71
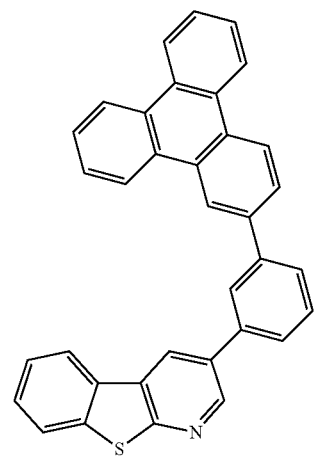
-continued
Compound 72
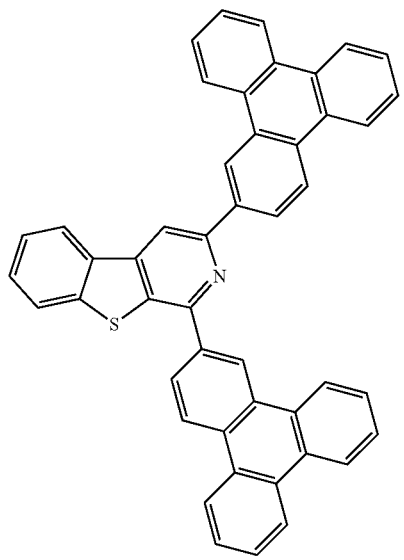
Compound 73
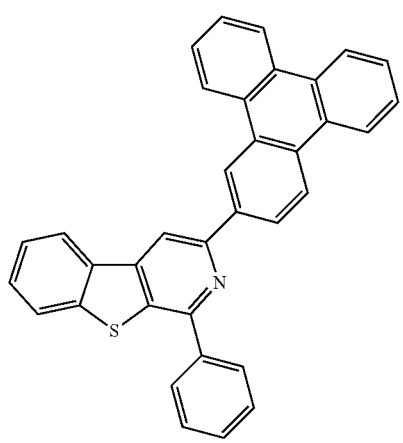
Compound 74
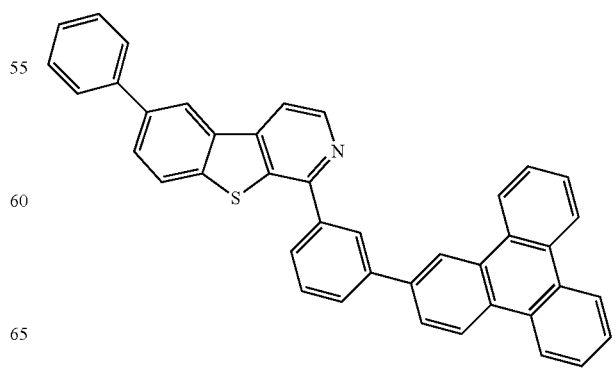

Compound 75

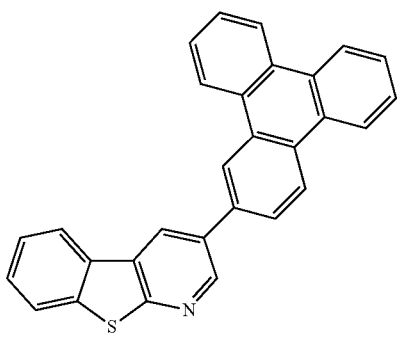

Compound 76

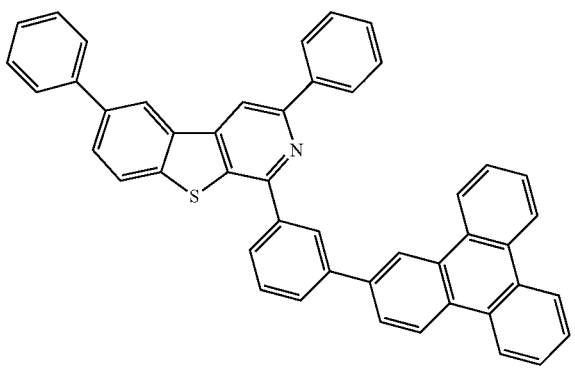

Compound 77

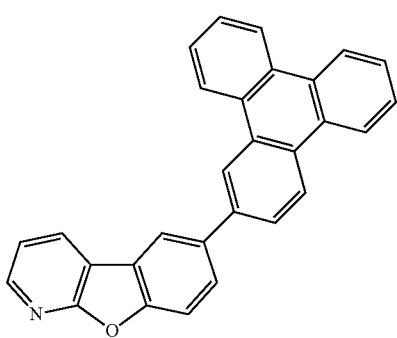

Compound 78

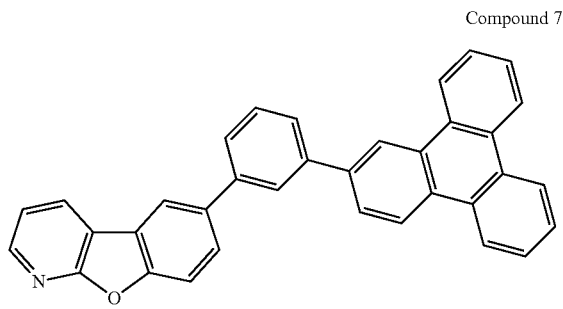

Compound 79

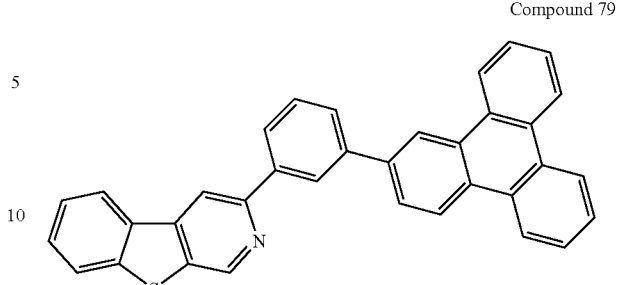

A first device comprising an organic light emitting device is also provided. The device further comprises an anode, a cathode, and an organic layer disposed between the anode and the cathode. The organic layer further comprising a compound having the formula:

FORMULA I

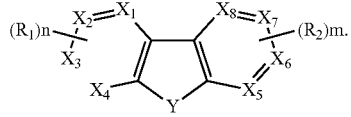

$X_1$, $X_2$, $X_3$, $X_4$, $X_5$, $X_6$, $X_7$, and $X_8$ are independently selected from the group consisting of a carbon atom and a nitrogen atom. At least one of $X_1$, $X_2$, $X_3$, $X_4$, $X_5$, $X_6$, $X_7$, and $X_8$ is a nitrogen atom. Y is S or O. R1 and R2 may represent mono, di, tri, or tetra substitutions. R1 and R2 are independently selected from the group consisting of hydrogen, alkyl, aryl and halide. At least one of R1 and R2 is selected from the group consisting of:

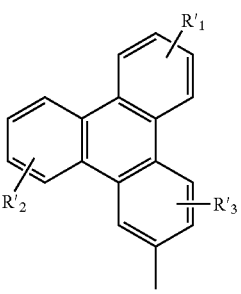 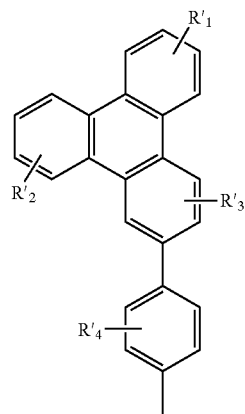

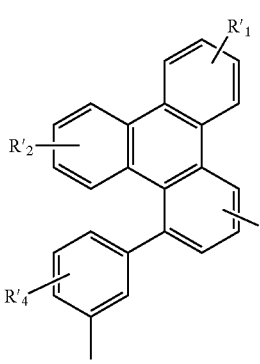 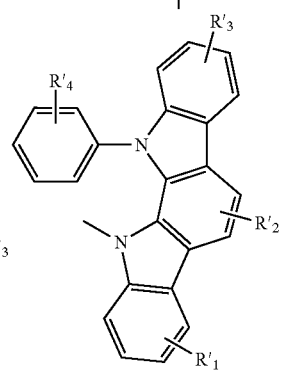

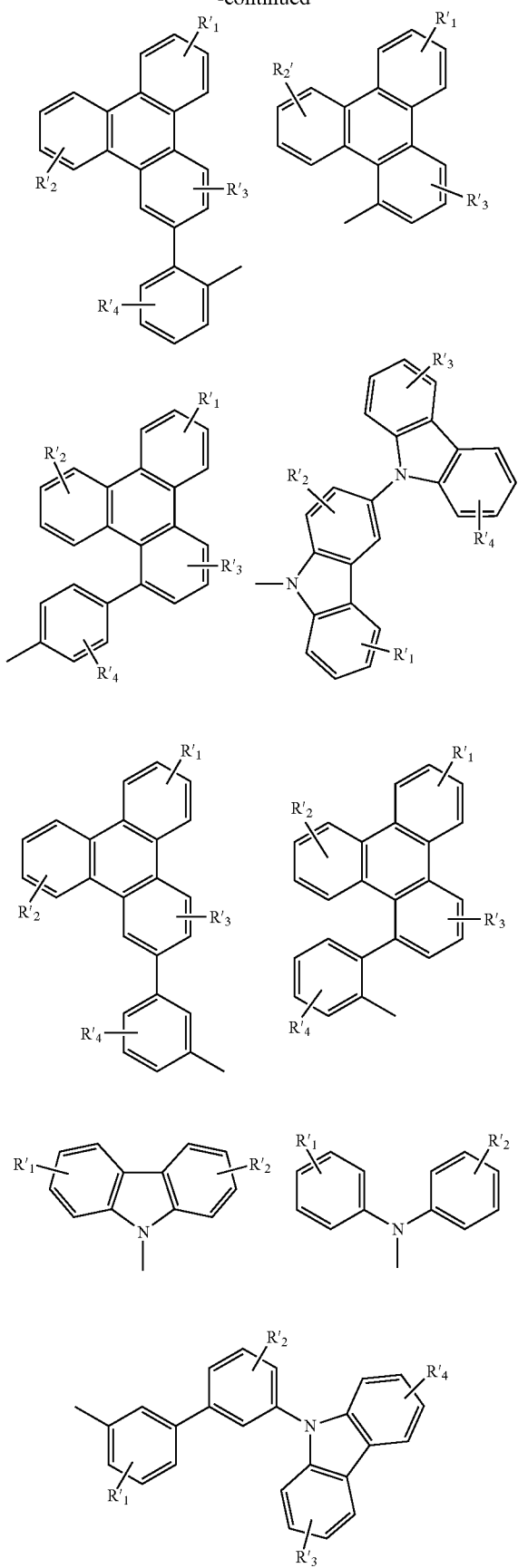
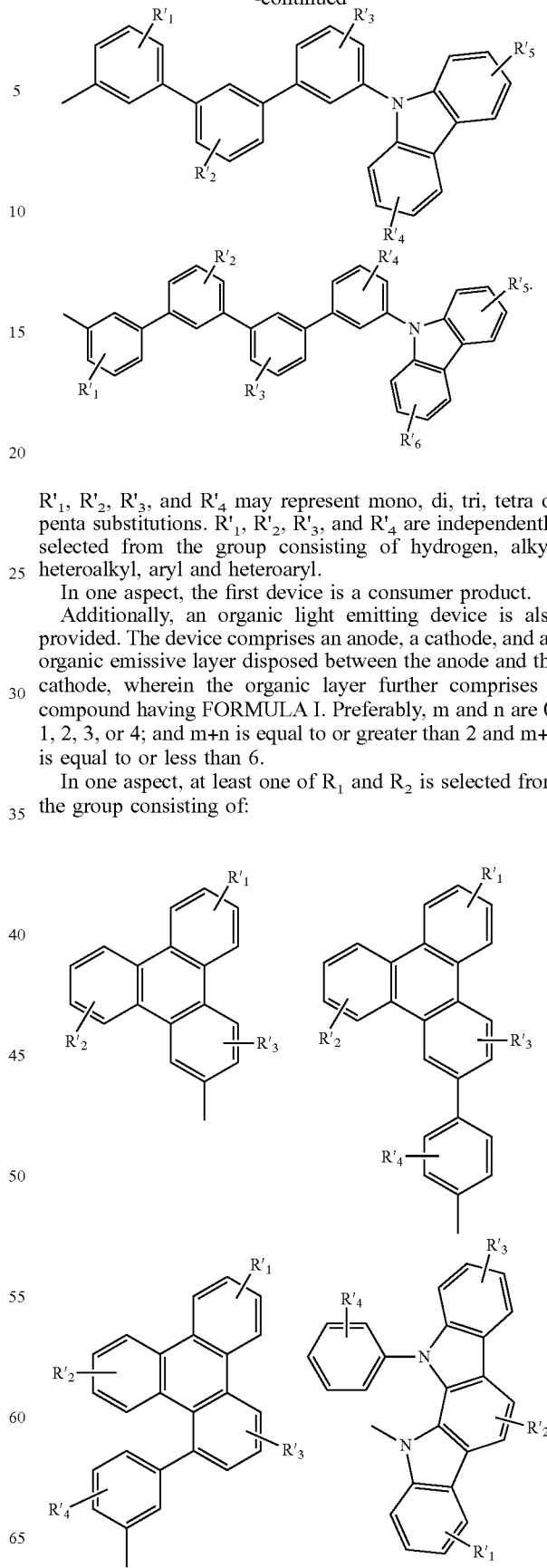

R'₁, R'₂, R'₃, and R'₄ may represent mono, di, tri, tetra or penta substitutions. R'₁, R'₂, R'₃, and R'₄ are independently selected from the group consisting of hydrogen, alkyl, heteroalkyl, aryl and heteroaryl.

In one aspect, the first device is a consumer product.

Additionally, an organic light emitting device is also provided. The device comprises an anode, a cathode, and an organic emissive layer disposed between the anode and the cathode, wherein the organic layer further comprises a compound having FORMULA I. Preferably, m and n are 0, 1, 2, 3, or 4; and m+n is equal to or greater than 2 and m+n is equal to or less than 6.

In one aspect, at least one of $R_1$ and $R_2$ is selected from the group consisting of:

-continued
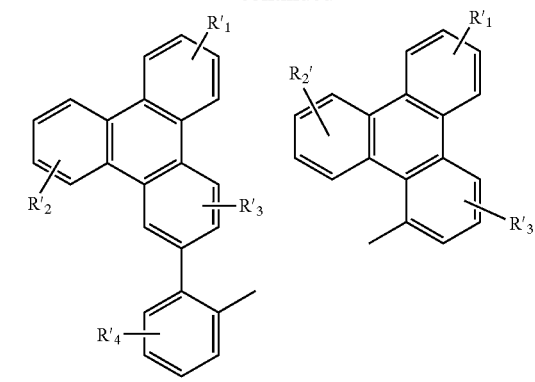
R'₁, R'₂, R'₃, and R'₄ are independently selected from the group consisting of hydrogen, alkyl, heteroalkyl, aryl and heteroaryl.
In another aspect, R₁ and R₂ are each independently selected from the group consisting of hydrogen and
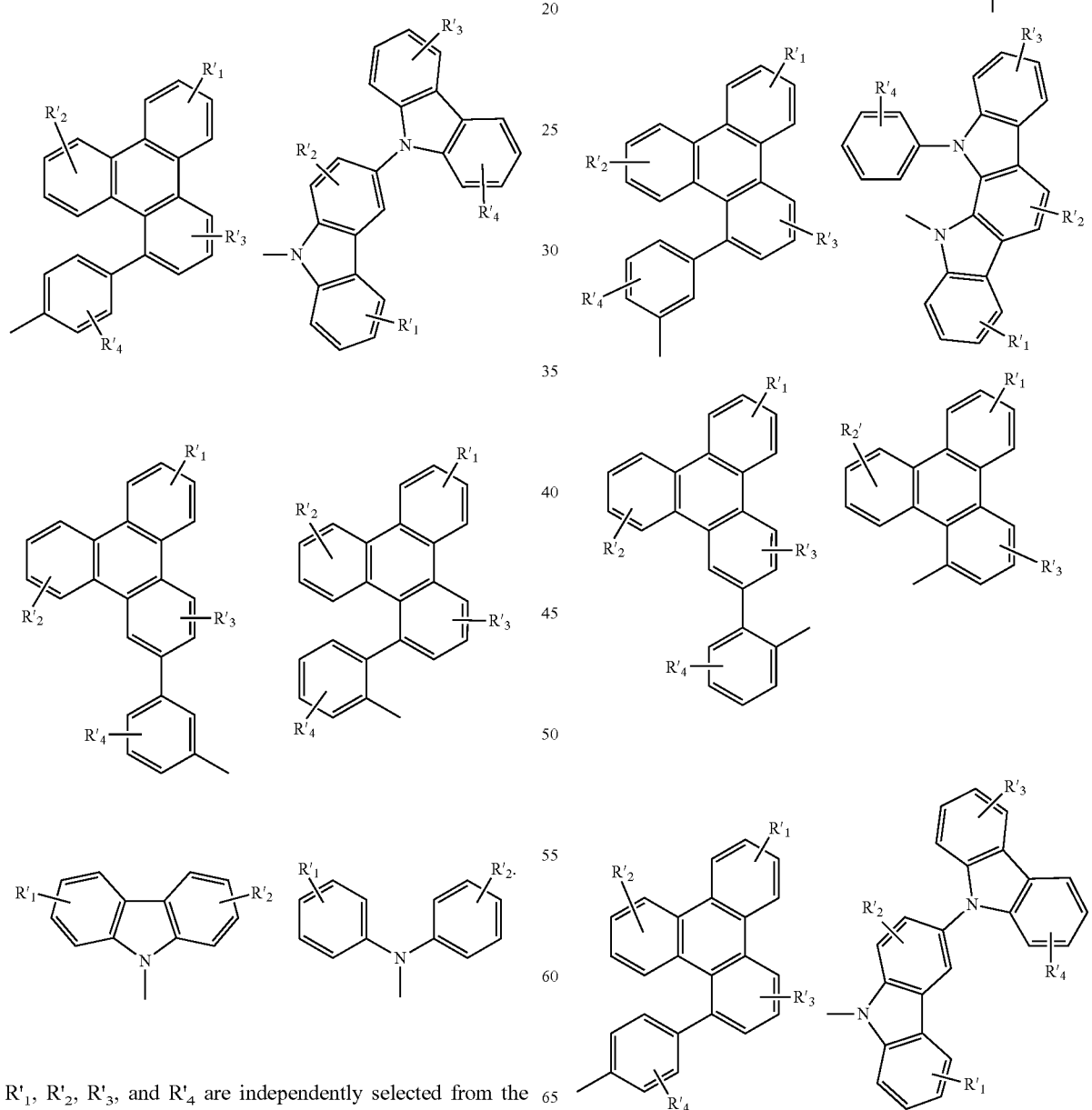

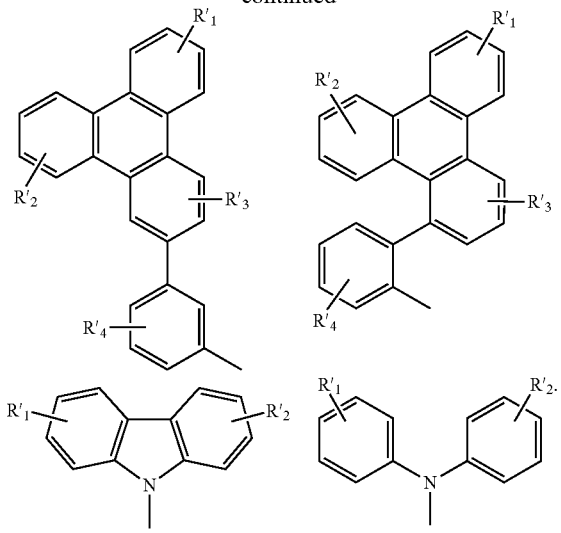

In one aspect, devices are provided that contain a compound selected from the group consisting of Compounds 1-93.

In particular, devices are provided wherein the compound is selected from the group consisting of Compounds 1-79.

In one aspect, the organic layer is an emissive layer and the aza-dibenzothiophene and aza-dibenzofuran having FORMULA I is a host in the organic layer. The organic layer may further comprise an emissive dopant. Preferably, the emissive dopant has the formula

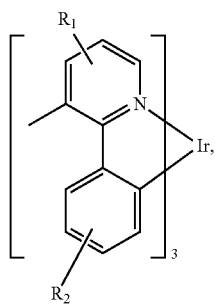

P1 wherein $R_1$ and $R_2$ are each independently selected from the group consisting of hydrogen, alkyl, and aryl.

As discussed above, the aza-dibenzothiophene and aza-dibenzofuran compounds having FORMULA I may be advantageously used as a host material in an emissive layer. However, these compounds may also be used as materials in an enhancement layer. In particular, the compounds described herein may be used the material in a blocking layer.

A consumer device is also provided, wherein the device further comprises an anode, a cathode and an organic layer. The organic layer further comprises an aza-dibenzothiophene or aza-dibenzofuran compound having FORMULA I.

Figure 4:
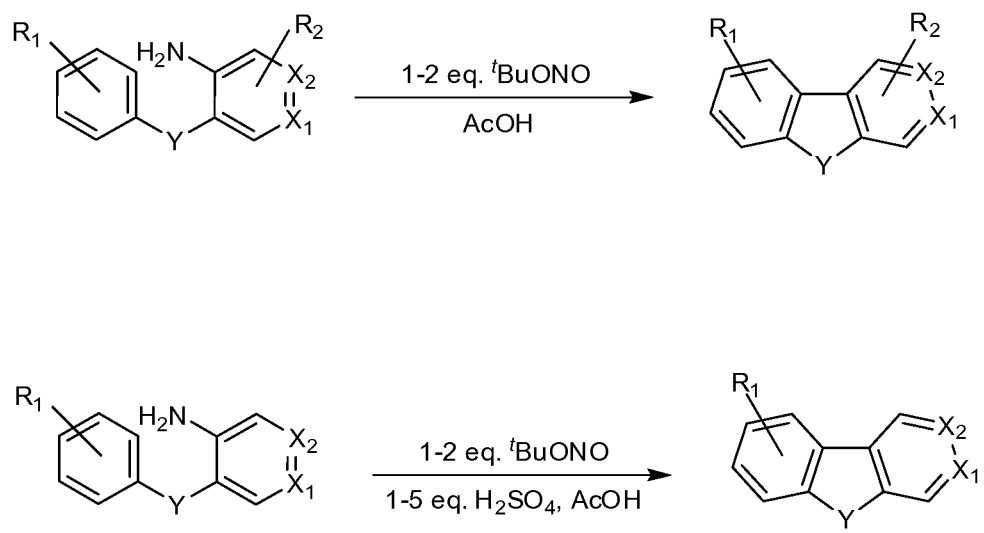
FIG. 4 shows reactions in synthetic pathways.

Additionally, a process for making an aza-dibenzothiophene compound or an aza-dibenzofuran compound is provided (illustrated in FIG. 4, top). The process comprises treating an acetic acid solution of an amino-arylthio pyridine intermediate having the formula:

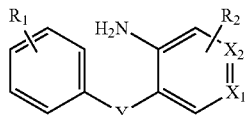

with $^tBuONO$ to produce an aza complex having the formula

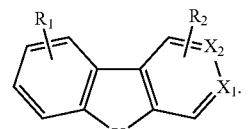

Y is S or O. $X_1$ or $X_2$ is nitrogen. $R_1$ and $R_2$ may be a mono, di, tri, or tetra substitution. $R_1$ is selected from the group consisting of hydrogen, alkyl, aryl and heteroaryl; and $R_2$ is selected from the group consisting of hydrogen, alkyl, aryl and halide. For example, an acetic acid solution of the intermediate 3-amino-4-arylthio pyridine with halide substituents on the pyridine ring or an acetic acid solution of the intermediate 3-arylthio-4-amino pyridine with halide substituents on the pyridine ring may be treated with 1-2 eq. of $^tBuONO$ at room temperature until no gas evolved, usually around 1-3 hours.

Particular examples of the process include intermediates and aza-complexes where Y is S (i.e., dibenzothiophene intermediates and aza-dibenzothiophene complexes). Alternatively, the process may preferably include intermediates and aza-complexes where Y is O (i.e., dibenzofuran intermediates and aza-dibenzofuran complexes). The process provided herein may yield greater than 50% or greater than 70% of the aza-complexes. In particular, the yield of

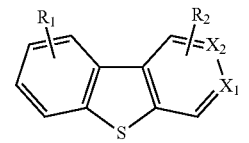

may be greater than 50%.

Examples of the process to make aza-dibenzothiophene or aza-dibenzofuran compounds include intermediates where one of $X_1$ and $X_2$ is carbon and the other is nitrogen. In a particular example of the process, $X_1$ is nitrogen and $X_2$ is carbon. In another particular example, $X_1$ is carbon and $X_2$ is nitrogen.

Examples of the process to make aza-dibenzothiophene or aza-dibenzofuran compounds include compounds where $R_2$ includes at least one halide. In a particular example of the process, $R_2$ includes only halide substituents. Moreover, $R_1$ is preferably halide. Halide substituents may include, but are not limited to, bromide, chloride, fluoride, and iodide.

The process may also be used to make aza-dibenzothiophene or aza-dibenzofuran compounds where $R_2$ is not a halide (i.e. there are no further substituents on the pyridine ring). For these aza-compounds lacking a halide substituent on the pyridine ring, the amino-arylthio pyridine intermediate is treated with $H_2SO_4$ prior to treatment with $^tBuONO$ (illustrated in FIG. 4, bottom). For example, an acetic acid solution of the intermediate 3-amino-4-arylthio pyridine or an acetic acid solution of the intermediate 3-arylthio-4- amino pyridine may be treated with 1-5 eq. of $H_2SO_4$, followed by 1-2 eq. of $^tBuONO$ until no gas evolved, usually around 1-5 hours.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| Hole injection materials | | |
| Phthalocyanine and porphyrin compounds | 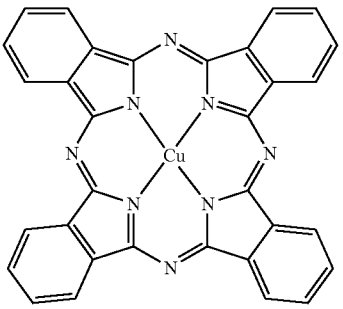 | Appl. Phys. Lett. 69, 2160 (1996) |
| Starburst triarylamines | 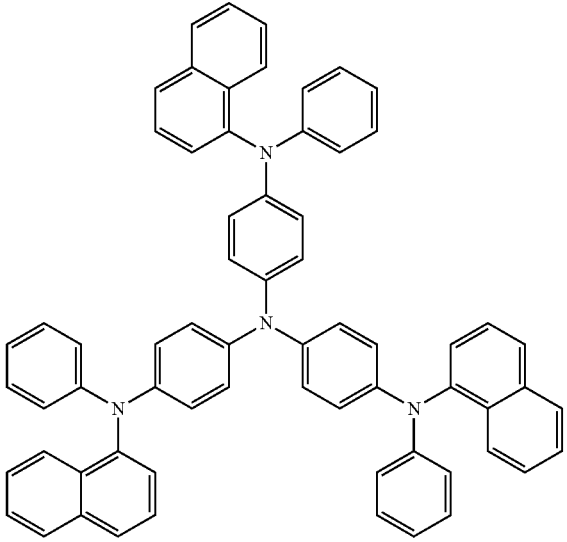 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-(CH_xF_y)_n-$ | Appl. Phys. Lett. 78, 673 (2001) |
| Conducting polymers (e.g., PEDOT:PSS, polyaniline, polythiophene) | 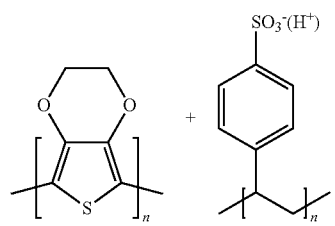 | Synth. Met. 87, 171 (1997) WO2007002683 |

TABLE 1-continued
| MATERIAL | EXAMPLES OF MATERIAL | PUBLICATIONS |
|---|---|---|
| Phosphonic acid and slíane SAMs | 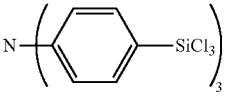 | US20030162053 |
| Triarylamine or polythiophene polymers with conductivity dopants | 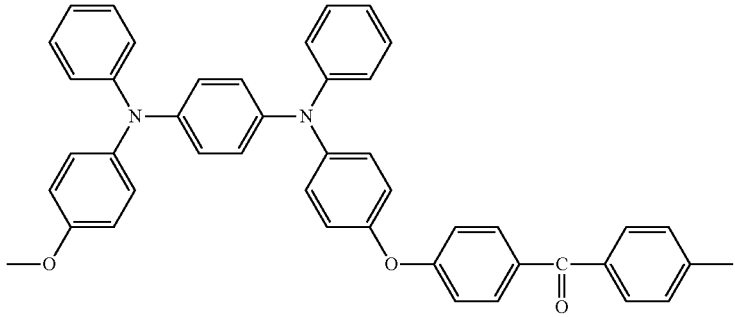 and 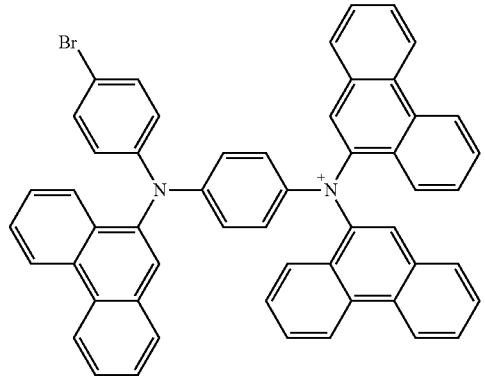 [SMILES: Brc1ccc(N(c2ccc(N(c3cc4ccccc4c4ccccc34)c3cc4ccccc4c4ccccc34)cc2)c2cc3ccccc3c3ccccc23)cc1] 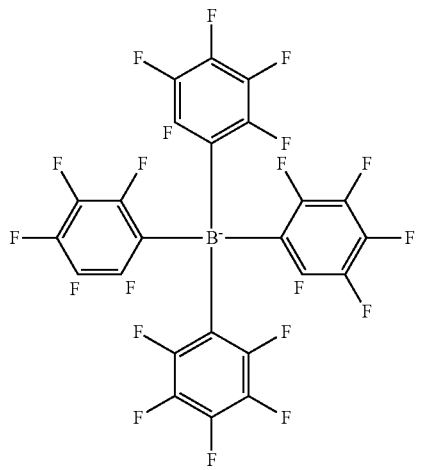 | EA1725079A1 |
| Arylamines complexed with metal oxides such as molybdenum and tungsten oxides | 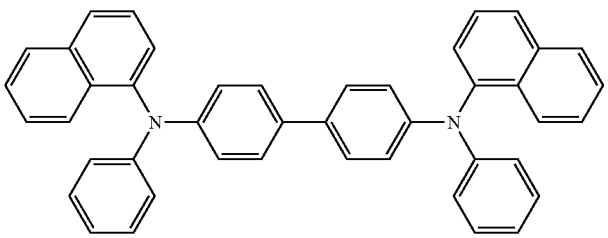 + MoO$_x$ | SID Symposium Digest, 37, 923 (2006) WO2009018009 |

TABLE 1-continued
| MATERIAL | EXAMPLES OF MATERIAL | PUBLICATIONS |
|---|---|---|
| p-type semiconducting organic complexes | 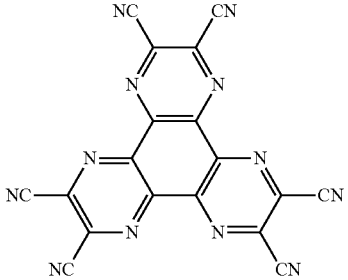 [SMILES: N#Cc1nc2c3nc(C#N)c(C#N)nc3c3nc(C#N)c(C#N)nc3c2nc1C#N] | US20020158242 |
| Metal organometallic complexes | 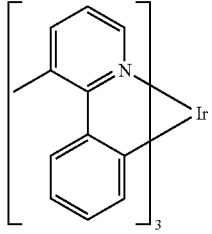 | US20060240279 |
| Cross-linkable compounds | 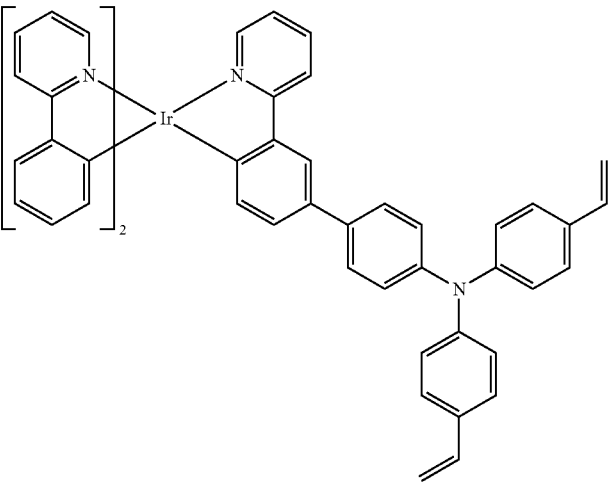 | US20080220265 |
Hole transporting materials
| | | |
|---|---|---|
| Triarylamines (e.g., TPD, α-NPD) | 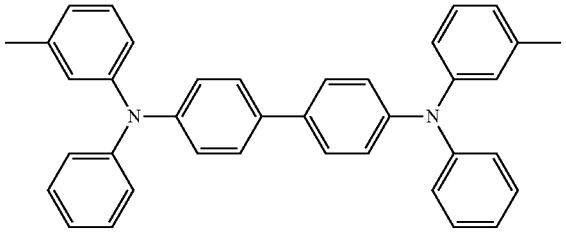 | Appl. Phys. Lett. 51, 913 (1987) |
| | 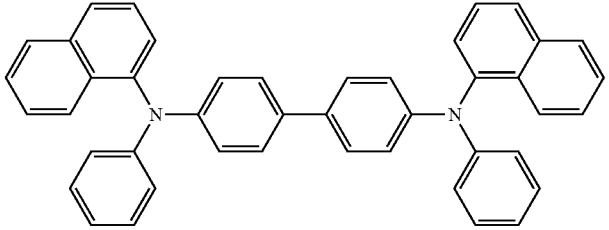 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |

TABLE 1-continued
| MATERIAL | EXAMPLES OF MATERIAL | PUBLICATIONS |
|---|---|---|
| | 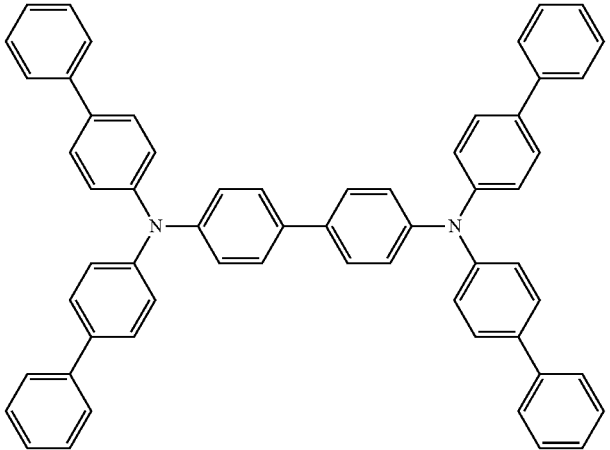 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 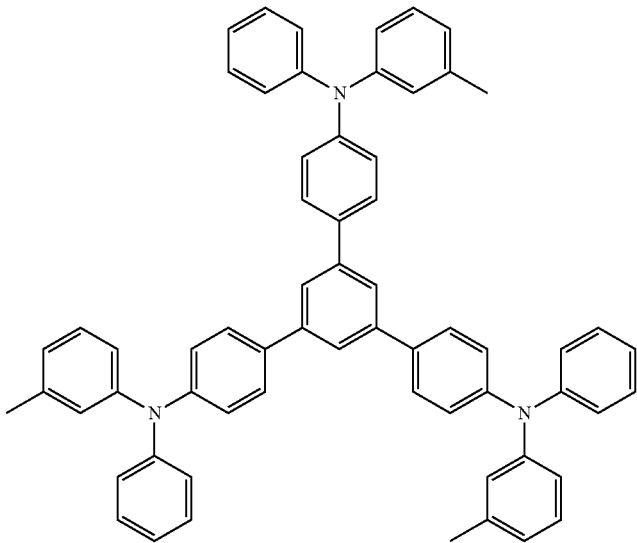 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 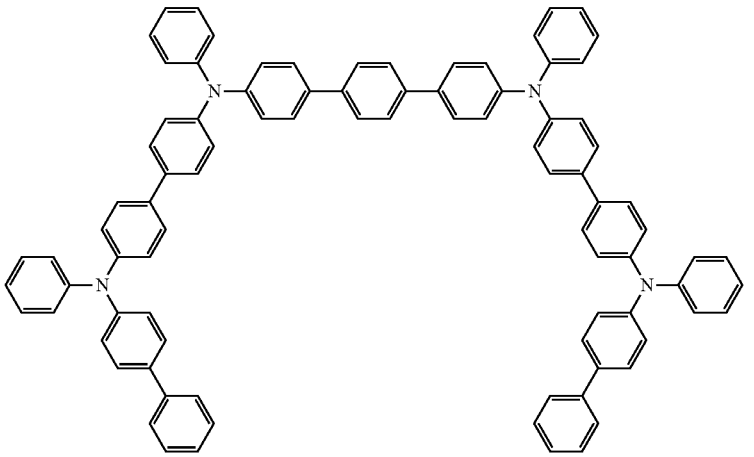 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 |

TABLE 1-continued
| MATERIAL | EXAMPLES OF MATERIAL | PUBLICATIONS |
|---|---|---|
| Indolocarbazoles | 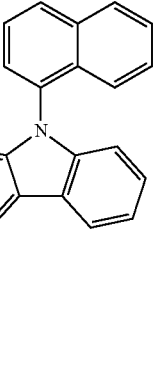 | Synth. Met. 111, 421 (2000) |
| Isoindole compounds | 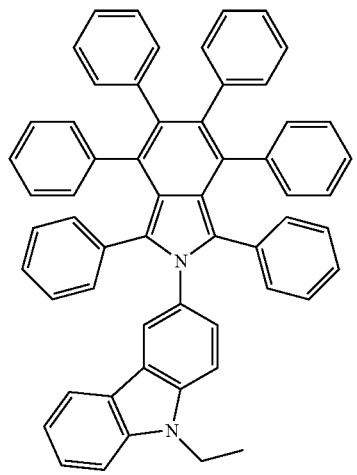 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 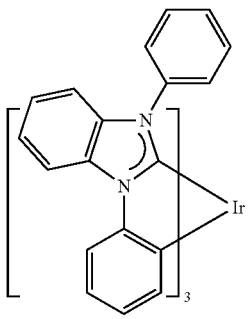 | US20080018221 |
Phosphorescent OLED
host materials
Red hosts
| | | |
|---|---|---|
| Arylcarbazoles | 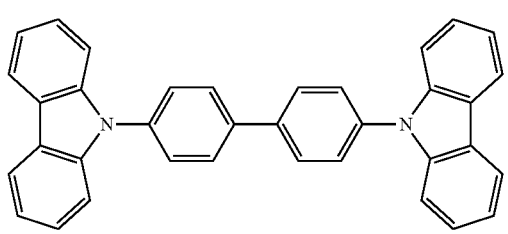 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 1-continued

| MATERIAL | EXAMPLES OF MATERIAL | PUBLICATIONS |
| --- | --- | --- |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxy-benzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 1-continued

| MATERIAL | EXAMPLES OF MATERIAL | PUBLICATIONS |
|---|---|---|
| Zinc complexes | | WO2009062578 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 1-continued

| MATERIAL | EXAMPLES OF MATERIAL | PUBLICATIONS |
|---|---|---|
| | | US20060280965 |
| | | WO2009021126 |
| Donor acceptor type molecules | | WO2008056746 |
| Aza-carbazole/ DBT/DBF | | JP2008074939 |
| Polymers (e.g., PVK) | | Appl. Phys. Lett. 77, 2280 (2000) |

TABLE 1-continued

| MATERIAL | EXAMPLES OF MATERIAL | PUBLICATIONS |
|---|---|---|
| Spirofluorene compounds | | WO2004093207 |
| Metal phenoxy-benzooxazole compounds | | WO2005089025 |
| | | WO2006132173 |
| | | JP200511610 |
| Spirofluorene-carbazole compounds | | JP2007254297 |

TABLE 1-continued
| MATERIAL | EXAMPLES OF MATERIAL | PUBLICATIONS |
|---|---|---|
| | 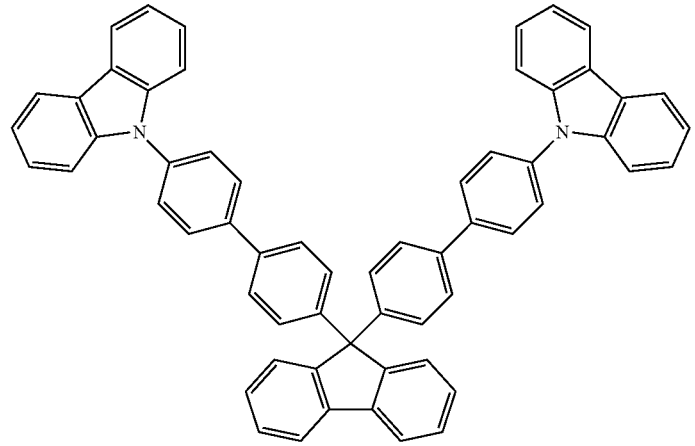 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 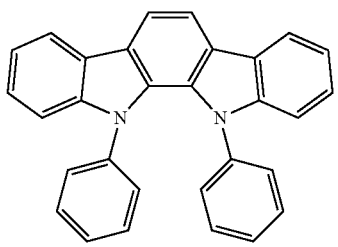 [SMILES: c1ccc(-n2c3ccccc3c3ccc4c5ccccc5n(-c5ccccc5)c4c32)cc1] | WO2007063796 |
| | 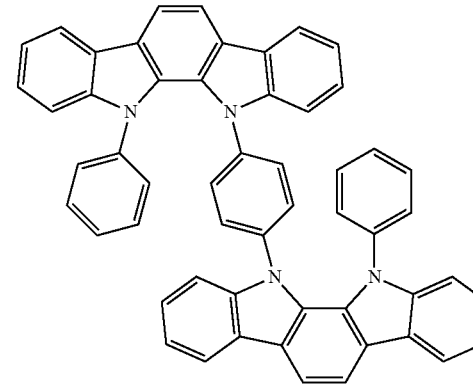 | WO2007063754 |
| 5-member ring electron deficient heterocycles (e.g., triazole, oxadiazole) | 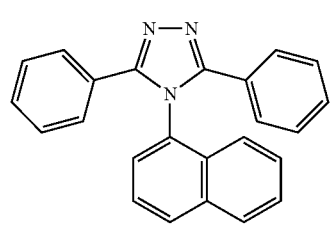 [SMILES: c1ccc(-c2nnc(-c3ccccc3)n2-c2cccc3ccccc23)cc1] | J. Appl. Phys. 90, 5048 (2001) |
| | 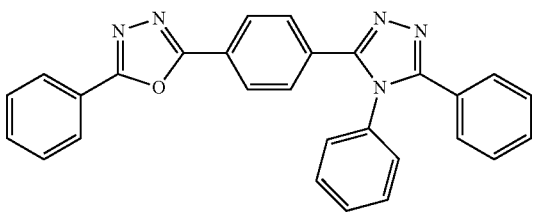 [SMILES: c1ccc(-c2nnc(-c3ccc(-c4nnc(-c5ccccc5)n4-c4ccccc4)cc3)o2)cc1] | WO2004107822 |

TABLE 1-continued

| MATERIAL | EXAMPLES OF MATERIAL | PUBLICATIONS |
|---|---|---|
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |

TABLE 1-continued
| MATERIAL | EXAMPLES OF MATERIAL | PUBLICATIONS |
|---|---|---|
| Dibenzothiophene/ Dibenzofuran-carbazole compounds | 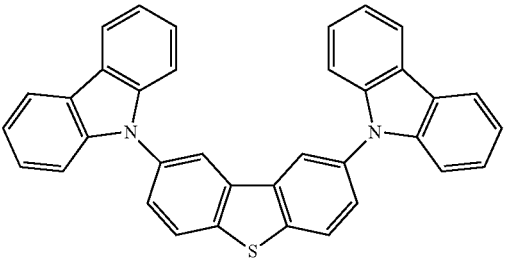 [SMILES: c1ccc2c(c1)c1ccccc1n2-c1ccc2sc3ccc(-n4c5ccccc5c5ccccc54)cc3c2c1] | WO2006114966, US20090167162 |
| | 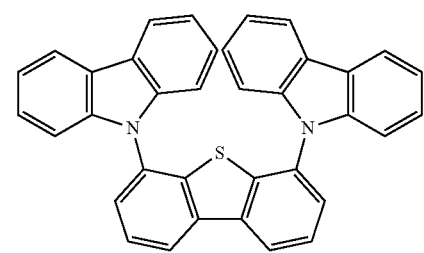 [SMILES: c1cc(-n2c3ccccc3c3ccccc32)c2sc3c(-n4c5ccccc5c5ccccc54)cccc3c2c1] | US20090167162 |
| | 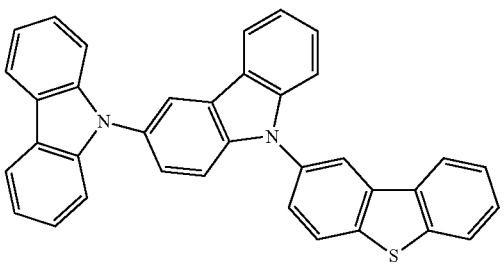 [SMILES: c1ccc2c(c1)sc1ccc(-n3c4ccccc4c4cc(-n5c6ccccc6c6ccccc65)ccc43)cc12] | WO2009086028 |
| | 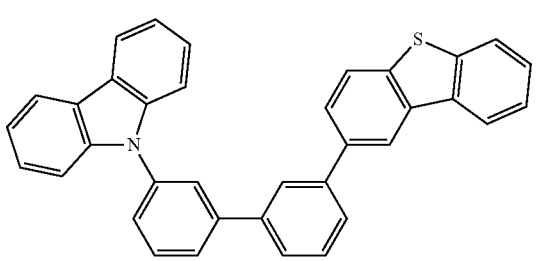 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 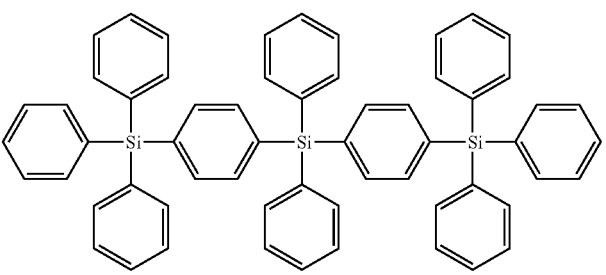 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 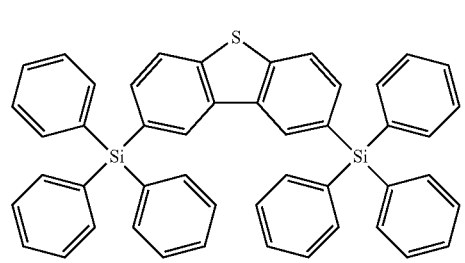 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | U.S. Pat. No. 7,154,114 |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |

TABLE 1-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 1-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum(II) organometallic complexes | | WO2003040257 |

TABLE 1-continued

| MATERIAL | EXAMPLES OF MATERIAL | PUBLICATIONS |
| --- | --- | --- |
| Osmium(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |
| Green dopants | | |
| Iridium(III) organometallic complexes | and its derivatives | Inorg. Chem. 40, 1704 (2001) |
| | | US20020034656 |

TABLE 1-continued

| MATERIAL | EXAMPLES OF MATERIAL | PUBLICATIONS |
|---|---|---|
| | | U.S. Pat. No. 7,332,232 |
| | | US20090108737 |
| | | US20090039776 |
| | | U.S. Pat. No. 6,921,915 |

TABLE 1-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670<br>JP2007123392 |
| | | Adv. Mater. 16, 2003 (2004) |

TABLE 1-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| Monomer for polymeric metal organometallic compounds | | U.S. Pat. No. 7,250,226, U.S. Pat. No. 7,396,598 |

TABLE 1-continued

| MATERIAL | EXAMPLES OF MATERIAL | PUBLICATIONS |
| --- | --- | --- |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 1-continued

| MATERIAL | EXAMPLES OF MATERIAL | PUBLICATIONS |
| --- | --- | --- |
| Cu complexes | | WO2009000673 |
| Gold complexes | | Chem. Commun. 2906 (2005) |
| Rhenium(III) complexes | | Inorg. Chem. 42, 1248 (2003) |
| Deuterated organometallic complexes | | US20030138657 |

TABLE 1-continued

| MATERIAL | EXAMPLES OF MATERIAL | PUBLICATIONS |
|---|---|---|
| Organometallic complexes with two or more metal centers | | US20030152802 |
| | | U.S. Pat. No. 7,090,928 |
| Blue dopants | | |
| Iridium(III) organometallic complexes | | WO2002002714 |
| | | WO2006009024 |
| | | US20060251923 |

TABLE 1-continued
| MATERIAL | EXAMPLES OF MATERIAL | PUBLICATIONS |
|---|---|---|
| | 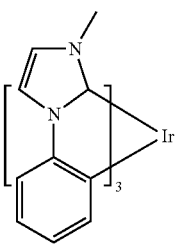 | U.S. Pat. No. 7,393,599, WO2006056418, US20050260441, WO2005019373 |
| | 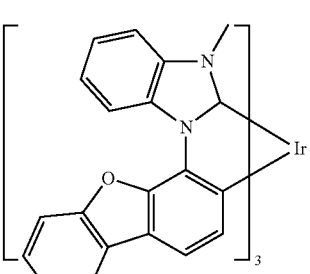 | U.S. Pat. No. 7,534,505 |
| | 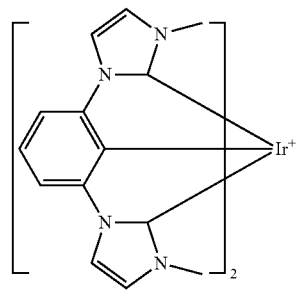 | U.S. Pat. No. 7,445,855 |
| | 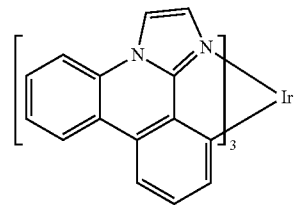 | US20070190359, US20080297033 |
| | 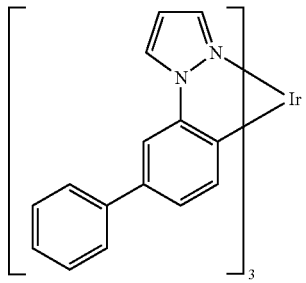 | U.S. Pat. No. 7,338,722 |
| | 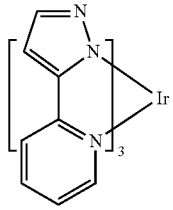 | US20020134984 |

TABLE 1-continued

| MATERIAL | EXAMPLES OF MATERIAL | PUBLICATIONS |
|---|---|---|
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 1-continued
| MATERIAL | EXAMPLES OF MATERIAL | PUBLICATIONS |
|---|---|---|
| | 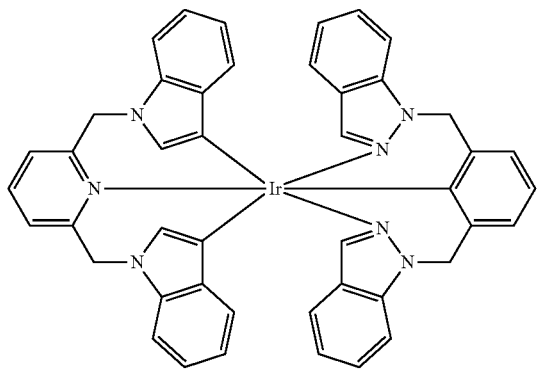 | WO2006082742 |
| Osmium(II) complexes | 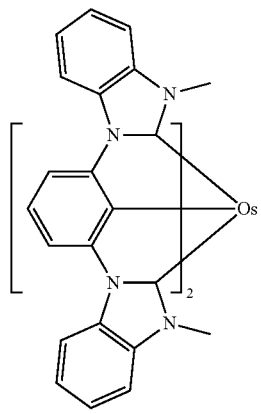 | U.S. Pat. No. 7,279,704 |
| | 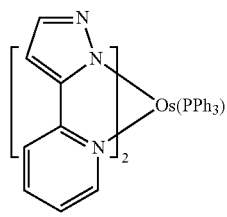 | Organometallics 23, 3745 (2004) |
| Gold complexes | 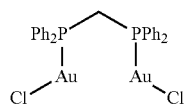 | Appl. Phys. Lett. 74, 1361 (1999) |
| Platinum(II) complexes | 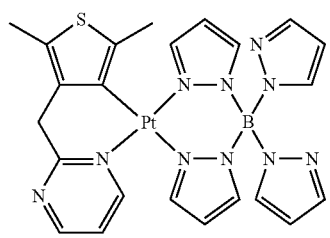 | WO2006098120, WO2006103874 |

TABLE 1-continued
| MATERIAL | EXAMPLES OF MATERIAL | PUBLICATIONS |
|---|---|---|
| Exciton/hole blocking layer materials | | |
| Bathocuprine compounds (e.g., BCP, BPhen) | 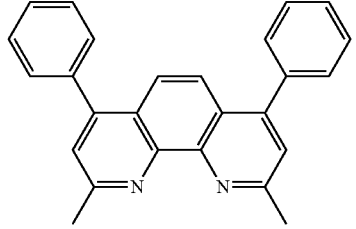 [SMILES: Cc1cc(-c2ccccc2)c2ccc3c(-c4ccccc4)cc(C)nc3c2n1] | Appl. Phys. Lett. 75, 4 (1999) |
| | 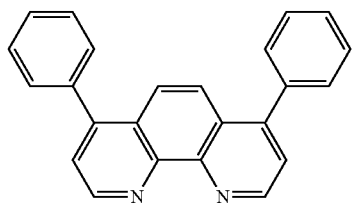 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 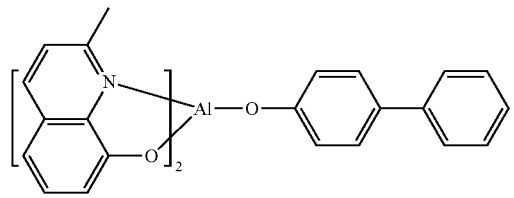 | Appl. Phys. Lett. 81, 162 (2002) |
| 5-member ring electron deficient heterocycles such as triazole, oxadiazole, imidazole, benzoimidazole | 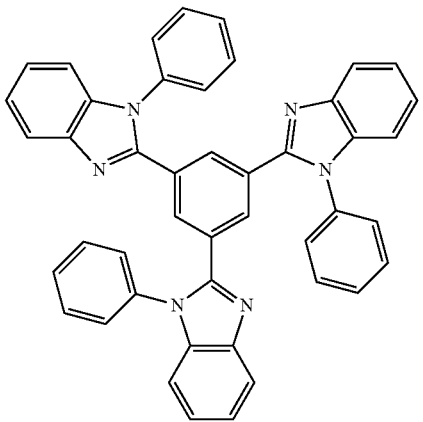 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 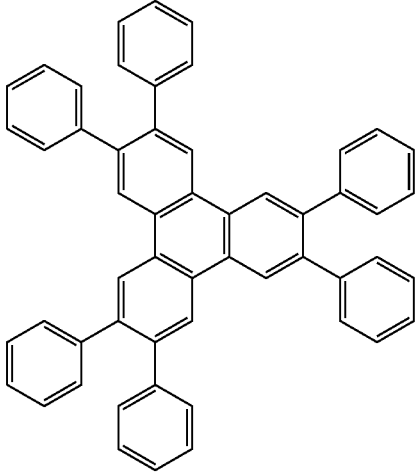 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 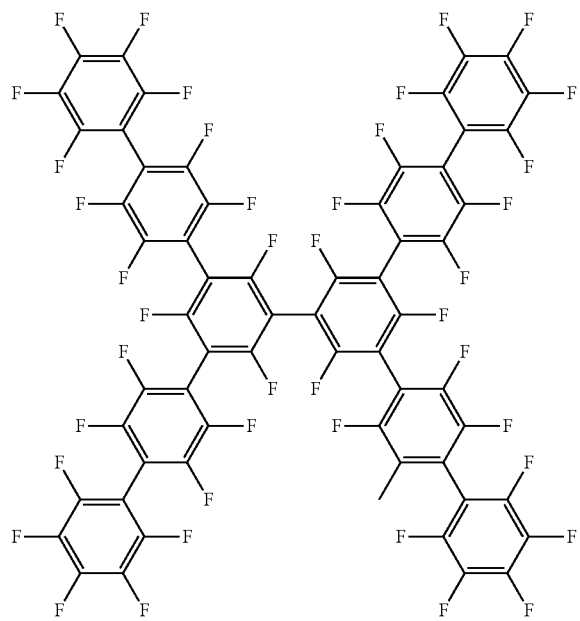 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 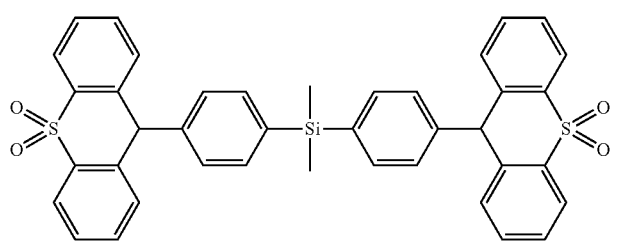 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 1-continued

| MATERIAL | EXAMPLES OF MATERIAL | PUBLICATIONS |
|---|---|---|
| Electron transporting materials | | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987) U.S. Pat. No. 7,230,107 |

TABLE 1-continued

| MATERIAL | EXAMPLES OF MATERIAL | PUBLICATIONS |
| --- | --- | --- |
| Metal hydroxy-benzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued
| MATERIAL | EXAMPLES OF MATERIAL | PUBLICATIONS |
|---|---|---|
| Silole compounds | 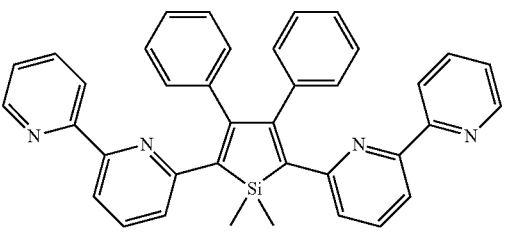 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 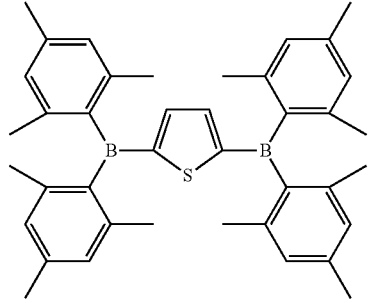 | J. Am. Chem. Soc. 120, 9714 (1998) |
| Fluorinated aromatic compounds | 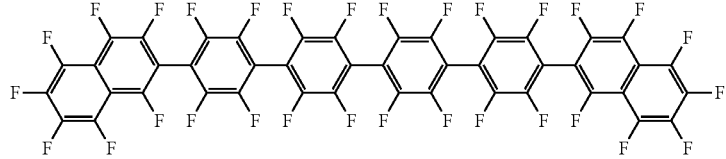 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 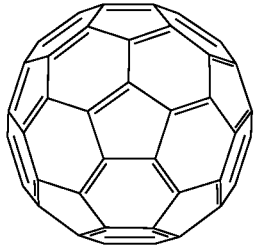 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 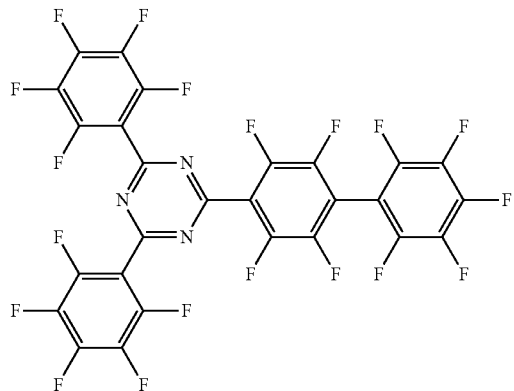 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

| MATERIAL | EXAMPLES OF MATERIAL | PUBLICATIONS |
|---|---|---|
| Zn (N^N) complexes |  | U.S. Pat. No. 6,528,187 |

EXPERIMENTAL

Compound Examples

Example 1

Synthesis of Compound 1

Compound 1

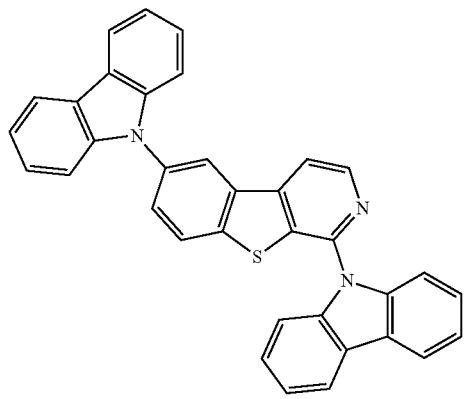

Step 1.

To a 500 mL round flask was added 2-chloro-3-iodo-4-aminopyridine (10 g, 39 mmol), 4-bromothiophenol (7.0 g, 34 mmol), CuI (0.4 g, 2.0 mmol), ethylene glycol (4.9 g, 78 mmol), potassium carbonate (10.8 g, 74 mmol), and 200 mL of isopropanol. The reaction was heated to reflux and stirred under a nitrogen atmosphere for 24 h. After cooling, the mixture was purified by a silica gel column. Yield of 2-chloro-3-(4-bromophenylthio)-4-aminopyridine was 7.4 g.

Step 2.

To a 500 mL round flask was added 2-chloro-3-(4-bromophenylthio)-4-aminopyridine (7.0 g, 22 mmol), and 400 mL of AcOH. To this clear solution, Bu$^t$ONO (2.3 g, 22 mmol) was added drop by drop. After stirring at room temperature for 1 h, another 10 mmol of Bu$^t$ONO was added. The mixture was continued to stir for another 2 h. The reaction was quenched by water, and the product was purified by a silica gel column. Yield of 1-chloro-6-bromo-[1]Benzothieno[2,3-c]pyridine was 6.5 g.

Step 3.

To a 500 mL round flask was added 1-chloro-6-bromo-[1]Benzothieno[2,3-c]pyridine (3.6 g, 12 mmol), carbazole (6.0 g, 36 mmol), Pd$_2$(dba)$_3$ (1.1 g, 1.2 mmol), 2-dicyclohexylphosphino-2',6'-dimethoxybiphenyl (S-Phos, 2.0 g, 4.8 mmol), sodium t-butoxide (6.9 g, 72 mmol), and 250 mL of xylene. The reaction was heated to reflux and stirred under a nitrogen atmosphere for 24 h. After cooling, the mixture was purified by a silica gel column. Yield was 4.0 g. The product was further purified by vacuum sublimation. $^1$H NMR results confirmed the desired compound.

Example 2

Synthesis of Compound 2

Compound 2

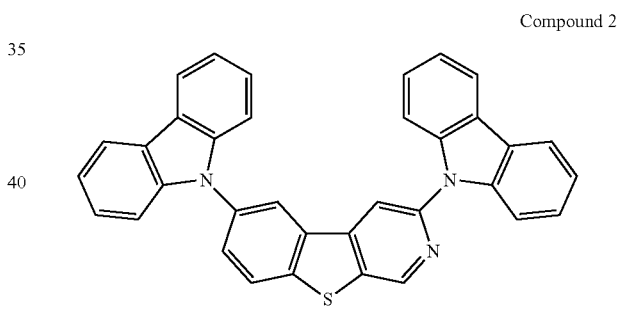

Step 1.

To a 500 mL round flask was added 2-chloro-4-amino-5-iodo-pyridine (11.5 g, 45 mmol), 4-bromothiophenol (8.1 g, 42.8 mmol), CuI (0.4 g, 2.3 mmol), ethylene glycol (5.6 g, 90.4 mmol), potassium carbonate (12.4 g, 90.4 mmol), and 200 mL of isopropanol. The reaction was heated to reflux and stirred under a nitrogen atmosphere for 24 h. After cooling, the mixture was purified by a silica gel column. Yield of 2-chloro-5-(4-bromophenylthio)-4-aminopyridine was 9.2 g.

Step 2.

To a 500 mL round flask was added 2-chloro-5-(4-bromophenylthio)-4-aminopyridine (11 g, 35 mmol), and 600 mL of AcOH. To this clear solution, Bu$^t$ONO (3.6 g, 35 mmol) was added drop by drop. After stirring at room temperature for 1 hr, another 15 mmol of Bu$^t$ONO was added. The mixture was continued to stir for another 2 h. The reaction was quenched by water, and the product was purified by a silica gel column. Yield of 3-chloro-6-bromo-[1]Benzothieno[2,3-c]pyridine was 10 g.

Step 3.

To a 500 mL round flask was added 3-chloro-6-bromo-[1]Benzothieno[2,3-c]pyridine (3.0 g, 10 mmol), carbazole (4.2 g, 25 mmol), Pd(OAc)$_2$ (0.1 g, 0.5 mmol), P(Bu$^t$)$_3$ (1M in toluene, 1.5 mL, 1.5 mmol), sodium t-butoxide (6.3 g, 66 mmol), and 250 mL of xylene. The reaction was heated to reflux and stirred under a nitrogen atmosphere for 24 h. After cooling, the mixture was purified by a silica gel column. Yield was 4.2 g. The product was further purified by vacuum sublimation. $^1$H NMR results confirmed the desired compound.

Example 3

Synthesis of Compound 3

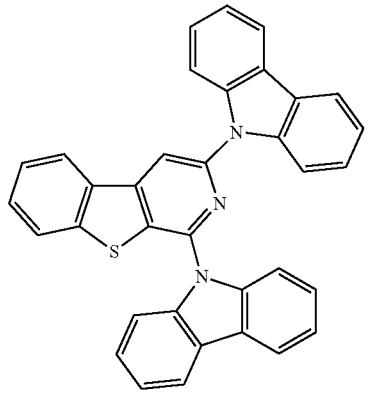

Compound 3

Step 1.

To a 500 mL round flask was added 2,6-dichloro-3-iodo-4-aminopyridine (7.0 g, 28.8 mmol), thiophenol (3.2 g, 34.8 mmol), CuI (0.2 g, 1.2 mmol), ethylene glycol (3.0 g, 57.6 mmol), potassium carbonate (6.6 g, 57.6 mmol), and 200 mL of isopropanol. The reaction was heated to reflux and stirred under a nitrogen atmosphere for 24 h. After cooling, the mixture was purified by a silica gel column. Yield of 2,6-dichloro-3-phenylthio-4-aminopyridine was 4.0 g.

Step 2.

To a 500 mL round flask was added 2,6-dichloro-3-phenylthio-4-aminopyridine (4.0 g, 14.7 mmol), and 200 mL of AcOH. To this clear solution, Bu$^t$ONO (1.5 g, 15 mmol) was added drop by drop. After stirring at room temperature for 1 h, another 8 mmol of Bu$^t$ONO was added. The mixture was continued to stir for another 2 h. The reaction was quenched by water, and the product was purified by a silica gel column. Yield of 1,3-dichloro-[1]Benzothieno[2,3-c]pyridine was 3.2 g.

Step 3.

To a 500 mL round flask was added 1,3-dichloro-[1]Benzothieno[2,3-c]pyridine (2.5 g, 10 mmol), carbazole (4.2 g, 25 mmol), Pd$_2$(dba)$_3$ (0.9 g, 1.0 mmol), 2-dicyclohexylphosphino-2',6'-dimethoxybiphenyl (S-Phos, 1.6 g, 4.0 mmol), sodium t-butoxide (4.8 g, 50 mmol), and 200 mL of xylene. The reaction was heated to reflux and stirred under a nitrogen atmosphere for 24 h. After cooling, the mixture was purified by a silica gel column. Yield was 4.2 g. The product was further purified by vacuum sublimation. $^1$H NMR results confirmed the desired compound.

Example 4

Synthesis of Compound 4

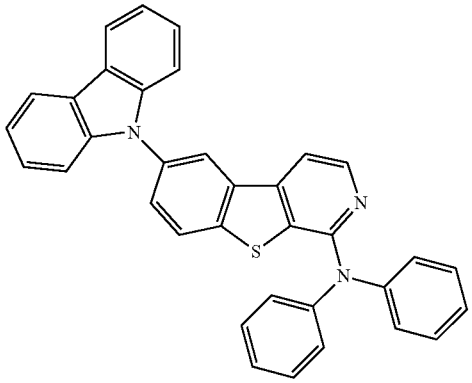

Compound 4

Step 1.

To a 500 mL round flask was added 1-chloro-6-bromo-[1]Benzothieno[2,3-c]pyridine (5.0 g, 16.7 mmol), carbazole (2.8 g, 16.7 mmol), Pd(OAc)$_2$ (0.1 g, 0.4 mmol), PBu$^t_3$ (1.0 M solution in toluene, 1.2 mL, 1.2 mmol), sodium t-butoxide (4.8 g, 50.1 mmol), and 400 mL of xylene. The reaction was heated to reflux and stirred under a nitrogen atmosphere for 24 h. After cooling, the mixture was purified by a silica gel column. Yield of 1-chloro-6-(9-carbazole)-[1]Benzothieno[2,3-c]pyridine was 1.9 g.

Step 2.

To a 500 mL round flask was added 1-chloro-6-(9-carbazole)-[1]Benzothieno[2,3-c]pyridine (1.3 g, 3.4 mmol), diphenylamine (0.7 g, 4.0 mmol), Pd$_2$(dba)$_3$ (0.09 g, 0.1 mmol), 2-dicyclohexylphosphino-2',4',6'-triisopropylbiphenyl (0.2 g, 0.4 mmol), sodium t-butoxide (0.8 g, 8.0 mmol), and 100 mL of toluene. The reaction was heated to reflux and stirred under a nitrogen atmosphere for 24 h. After cooling, the mixture was purified by a silica gel column. Yield of compound 4 was 1.1 g.

Example 5

Synthesis of Compound 21

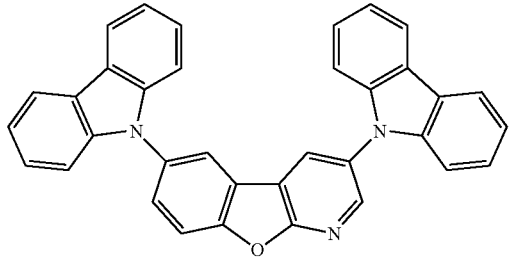

Compound 21

Step 1.

The solution of 2-amino-5-chloropyridine (10.0 g, 77.8 mmol) potassium acetate (7.63 g, 77.8 mmol) in 100 mL of acetic acid was heated to 85° C. and ClI (12.6 g, 77.8 mmol)

in 50 mL of acetic acid was added dropwise. Reaction mixture was kept 2 h at this temperature, diluted with 1 L of water, neutralized with NaOH 1N solution to pH 7 and extracted with ethyl acetate (4×75 mL). Organic fraction were combined, washed with NaHCO$_3$, filtered through celite and evaporated. The residue was subjected to column chromatography on silica (eluent-hexane/ethyl acetate 1/1) providing 5-chloro-3-iodopyridin-2-amine as yellow solid (11.9 g, 60%).

Step 2.

Mixture of 5-chloro-2-methoxyphenylboronic acid (5.0 g, 26.8 mmol), 5-chloro-3-iodopyridin-2-amine (6.83 g, 26.8 mmol), sodium carbonate (8.53 g, 80.5 mmol in 50 mL of water), Pd(PPh$_3$)$_4$ (621 mg, 2 mol. %) and 100 mL of toluene was refluxed overnight under N$_2$, reaction mixture was cooled down to room temperature, organic layer was separated and concentrated in vacuum. The residue was subjected to column chromatography on silica gel with hexane/ethyl acetate gradient mixture as eluent, providing 3.3 g (46% yield) of 5-chloro-3-(5-chloro-2-methoxyphenyl)pyridin-2-amine.

Step 3.

Solution of 5-chloro-3-(5-chloro-2-methoxyphenyl)pyridin-2-amine (5.2 g, 19.3 mmol) in 50 mL of glacial acetic acid and 20 mL of THF was cooled down to −10° C., and tert-butyl nitrite (4.6 mL) was added dropwise. The reaction mixture was stirred overnight at 0° C., warmed to room temperature, diluted with 100 mL of water. Solid material was filtered and dried, providing 2.9 g of pure 3,6-dichlorobenzofuro[2,3-b]pyridine.

Step 4.

The mixture of 3,6-dichlorobenzofuro[2,3-b]pyridine (2.86 g, 12.01 mmol), carbazole (5.02 g, 30.003 mmol), sodium tert-butoxide (4.62 g, 48.05 mmol), 2-dicyclohexylphosphino-2',6'-dimethoxybiphenyl (S-Phos, 430 mg), Pd$_2$(dba)$_3$ (910 mg) in 150 mL of dry xylenes was refluxed under N$_2$ for 48 h. Then reaction mixture was cooled down to room temperature, diluted with 100 mL H$_2$O and extracted with ethyl acetate (4×50 mL). Organic fractions were combined, dried over Na$_2$SO$_4$ anhydr., filtered and evaporated. The residual material was purified by column chromatography on silica gel (eluent-gradient mixture hexane-dichloromethane), then crystallized from hexane/dichloromethane mixture, providing target material as white tiny needles. Additional purification by sublimation (288° C. at 10$^{-5}$ mm Hg) resulted 1.86 g of pure target compound.

Example 6

Synthesis of Compound 39

Compound 39

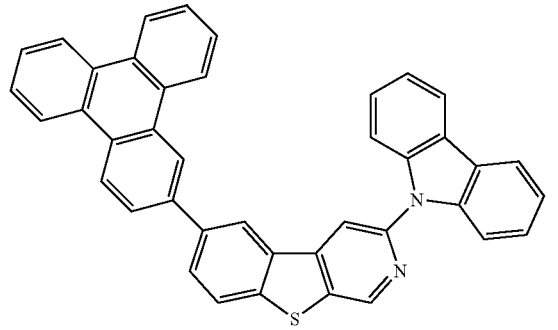

Step 1.

The mixture of 3-chloro-6-bromo-[1]benzothieno[2,3-c]pyridine (1.7 g, 5.8 mmol), triphenylene-2-ylboronic acid (1.6 g, 5.8 mmol), potassium phosphate tribasic (3.7 g, 17 mmol), 200 mL toluene and 10 mL water was prepared and bubbled with nitrogen for twenty minutes. Then the tris(dibenzylideneacetone)dipalladium (53 mg, 0.060 mmol) and 2-dicyclohexylphosphino-2',6'-dimethoxybiphenyl (96 mg, 0.23 mmol) were added. The mixture was bubbled with nitrogen for another twenty minutes. After refluxed overnight under nitrogen, then reaction mixture was cooled to room temperature and filtered through a silica plug and washed with dichloromethane. The first several portions were discarded since they only contained impurities. The combined filtrate was concentrated to give crude product, which was recrystallized from hot dichloromethane and hexanes to give 1.8 g 3-chloro-6-(2-triphenylenyl)-[1]Benzothieno[2,3-c]pyridine as yellow solid (4.0 mmol, 70% yield).

Step 2.

The mixture of 3-chloro-6-(2-triphenylenyl)-[1]Benzothieno[2,3-c]pyridine (1.6 g, 3.6 mmol), carbazole (0.72 g, 4.3 mmol), Pd(OAc)$_2$ (20 mg, 0.090 mmol), sodium t-butoxide (1.0 g, 11 mmol), and 300 mL of xylene was prepared and bubbled with nitrogen for 15 minutes. Then PBu$^t_3$ (1.0 M solution in toluene, 0.27 mL, 0.27 mmol) was added and the mixture was bubbled with nitrogen for another 15 minutes. After refluxed overnight, the reaction mixture was cooled to room temperature and filtered through a silica gel plug, which was then washed with dichloromethane. The xylene portion was discarded. The combined dichloromethane filtrate was concentrated and the crude product was stirred in 100 mL mixture of 20% dichloromethane in hexanes overnight. The residue was collected by filtration to give 1.7 g light yellow solid (2.9 mmol, 80% yield).

Example 7

Synthesis of Compound 59

Compound 59

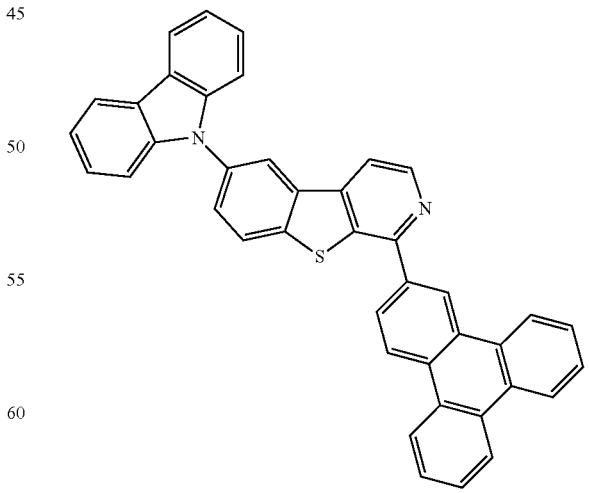

Step 1.

The mixture of 1-chloro-6-(9-carbazole)-[1]benzothieno[2,3-c]pyridine (1.0 g, 1.6 mmol), triphenylene-2-ylboronic acid (0.85 g, 3.1 mmol), potassium phosphate tribasic (1.7 g, 7.8 mmol), 100 mL toluene and 5 mL water was prepared and bubbled with nitrogen for twenty minutes. Then the tris(dibenzylideneacetone)dipalladium (24 mg, 0.030 mmol) and 2-dicyclohexylphosphino-2',6'-dimethoxybiphenyl (43 mg, 0.10 mmol) were added. The mixture was bubble with nitrogen for another twenty minutes. After refluxed overnight under nitrogen, the reaction was cooled to room temperature and concentrated. The obtained solid was redissolved in 800 mL refluxing toluene and filtered through a thin celite plug. The collected filtrate was concentrated to about 100 mL and then refluxed under nitrogen for one hour. After slowly cooled to room temperature, the precipitation was collected by filtration. The residue was stirred in 100 mL hot mixture of 20% dichloromethane in methanol and stirred overnight after it cooled to room temperature. The residue was collected by filtration and dried under vacuum to provide 1.2 g white solid (2.1 mmol, 81% yield).

Example 8

Synthesis of Compound 66

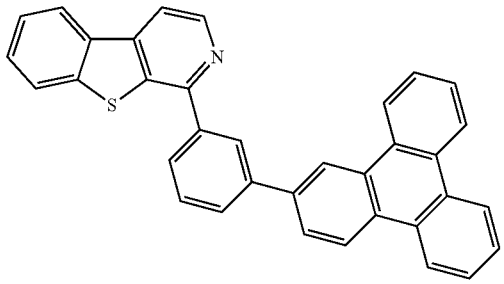

Compound 66

Step 1.

To a 250 mL round flask was added 2-chloro-3-iodo-4-aminopyridine (5.0 g, 19.6 mmol), thiophenol (2.16 g, 19.6 mmol), CuI (0.187 g, 0.98 mmol), ethylene glycol (2.5 g, 39 mmol), potassium carbonate (5.4 g, 39 mmol), and 150 mL of isopropanol. The reaction was heated to reflux and stirred under a nitrogen atmosphere for 24 h. After cooling, the mixture was purified by a silica gel column. Yield (91%) of 2-chloro-3-phenylthio-4-aminopyridine was 4.2 g.

Step 2.

To a 250 mL round flask was added 2-chloro-3-phenylthio-4-aminopyridine (2.7 g, 11.4 mmol), and 60 mL of glacial AcOH. To this clear solution, Bu$^t$ONO (1.36 g, 11.45 mmol) was added drop by drop. After stirring at room temperature for 1 h, another (1.36 g 11.45) mmol of Bu$^t$ONO was added. The mixture was continued to stir at room temperature for 18 h. The reaction was quenched by water, and the product was purified by a silica gel column. Yield (88%) of 1-chloro-benzothieno[2,3-c]pyridine was 2.2 g.

Step 3.

The mixture of 1-chloro-benzothieno[2,3-c]pyridine (1.5 g, 6.8 mmol), 3-(triphenylene-2-yl)phenylboronic acid (2.5 g, 7.2 mmol), synthesized according to U.S. Provisional Application Ser. No. 60/963,944, potassium phosphate tribasic (4.4 g, 20.4 mmol), 100 mL toluene and 10 mL water was prepared and bubbled with nitrogen for fifteen minutes. Then the tris(dibenzylideneacetone)dipalladium (63 mg, 0.068 mmol) and 2-dicyclohexylphosphino-2',6'-dimethoxybiphenyl (116 mg, 0.28 mmol) were added. The mixture was bubbled with nitrogen for another twenty minutes. After refluxed overnight under nitrogen, the reaction mixture was cooled to room temperature. The product was purified by silica gel chromatography column. ~2.7 g (81%) Compound 66 was obtained.

Example 9

Synthesis of Compound 70

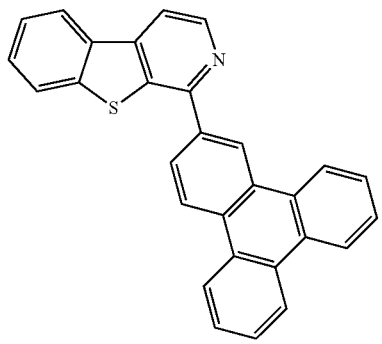

Compound 70

Step 1.

The mixture of 1-chloro-benzothieno[2,3-c]pyridine (1.0 g, 4.5 mmol), 2-triphenylene-boronic acid (1.25 g, 4.5 mmol), synthesized according to U.S. Provisional Application Ser. No. 60/963,944, potassium phosphate tribasic (3.0 g, 18.0 mmol), 100 mL toluene and 10 mL water was prepared and bubbled with nitrogen for fifteen minutes. Then the tris(dibenzylideneacetone)dipalladium (42 mg, 0.045 mmol) and 2-dicyclohexylphosphino-2',6'-dimethoxybiphenyl (77 mg, 0.18 mmol) were added. The mixture was bubbled with nitrogen for another twenty minutes. After refluxed overnight under nitrogen, the reaction mixture was cooled to room temperature. The product was purified by silical gel chromatography column. ~1.5 g (84%) Compound 70 was obtained.

Example 10

Synthesis of Compound 71

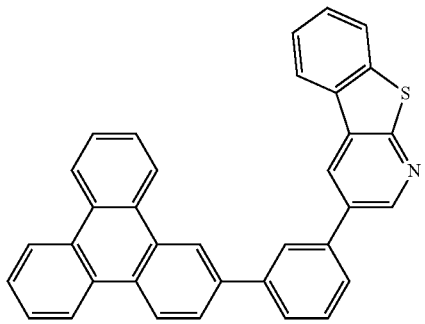

Compound 71

Step 1.

The solution of 2-amino-5-chloropyridine (10.0 g, 77.8 mmol) potassium acetate (7.63 g, 77.8 mmol) in 100 mL of acetic acid was heated to 85° C., and CII (12.6 g, 77.8 mmol) in 50 mL of acetic acid was added dropwise. Reaction mixture was kept 2 h at this temperature, diluted with 1 L of water, neutralized with NaOH 1N solution to pH 7 and extracted with ethyl acetate (4×75 mL). Organic fraction were combined, washed with NaHCO₃, filtered through celite and evaporated. The residue was subjected to column chromatography on silica (eluent-hexane/ethyl acetate 1/1) providing 5-chloro-3-iodopyridin-2-amine as yellow solid (11.9 g, 60%).

Step 2.

Mixture of 2-(methylthio)phenylboronic acid (5.0 g, 29.8 mmol), 5-chloro-3-iodopyridin-2-amine (7.56 g, 29.8 mmol), sodium carbonate (9.0 g, in 50 mL of water), Pd(PPh₃)₄ (621 mg) and 100 mL of toluene was refluxed overnight under N₂, reaction mixture was cooled down to room temperature, organic layer was separated and concentrated in vacuum. The residue was subjected to column chromatography on silica gel with hexane/ethyl acetate gradient mixture as eluent, providing 3.5 g of 5-chloro-3-(2-(methylthio)phenyl)pyridin-2-amine.

Step 3.

Solution of 5-chloro-3-(2-(methylthio)phenyl)pyridin-2-amine (5.2 g, 19.3 mmol) in 50 mL of glacial acetic acid and 20 mL of THF was cooled down to −10° C., and tert-butyl nitrite (4.6 mL) was added dropwise. The reaction mixture was stirred overnight at 0° C., warmed to room temperature, diluted with 100 mL of water. Solid material was filtered and dried, providing 2.5 g of pure 3-chlorobenzothieno[2,3-b]pyridine.

Step 4.

The mixture of 3-chloro-[1]Benzothieno[2,3-b]pyridine (1.3 g, 5.9 mmol), 4,4,5,5-tetramethyl-2-(3-(triphenylene-2-yl)phenyl)-1,3,2-dioxaborolane (3.1 g, 7.1 mmol), potassium phosphate tribasic (3.8 g, 18 mmol), 100 mL toluene and 10 mL water was prepared and bubbled with nitrogen for fifteen minutes. Then the tris(dibenzylideneacetone)dipalladium (54 mg, 0.060 mmol) and 2-dicyclohexylphosphino-2',6'-dimethoxybiphenyl (97 mg, 0.24 mmol) were added. The mixture was bubbled with nitrogen for another twenty minutes. After refluxed overnight under nitrogen, the reaction mixture was cooled to room temperature and filtered to collect the precipitation. The residue was washed by methanol and then redissolved in hot toluene. The solution was filtered through a magnesium sulfate plug, which was washed with dichloromethane. The combined filtrate was concentrated to provide 700 mg white solid (1.4 mmol, 24% yield).

Example 11

Synthesis of Compound 79

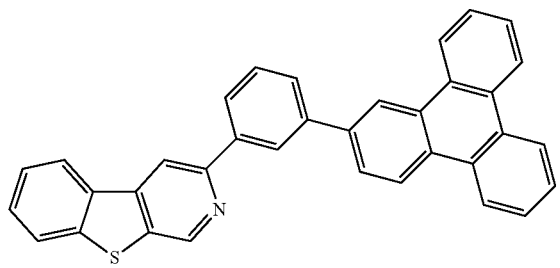

Compound 79

Step 1.

To a 250 mL round flask was added 2-chloro-5-iodo-4-aminopyridine (5.0 g, 19.6 mmol), thiophenol (2.16 g, 19.6 mmol), CuI (0.187 g, 0.98 mmol), ethylene glycol (2.5 g, 39 mmol), potassium carbonate (5.4 g, 39 mmol), and 150 mL of isopropanol. The reaction was heated to reflux and stirred under a nitrogen atmosphere for 24 h. After cooling, the mixture was purified by a silica gel column. Yield (97%) of 2-chloro-3-phenylthio-4-aminopyridine was 4.5 g.

Step 2.

To a 250 mL round flask was added 2-chloro-3-phenylthio-4-aminopyridine (3.7 g, 16.8 mmol), and 60 mL of glacial AcOH. To this clear solution, Bu'ONO (1.8 g, 16.8 mmol) was added drop by drop. After stirring at room temperature for 1 h, another (1.8 g 16.8) mmol of Bu'ONO was added. The mixture was continued to stir at room temperature for 18 h. The reaction was quenched by water, and the product was purified by a silica gel column. Yield (33%) of 3-chloro-benzothieno[2,3-c]pyridine was 1.2 g.

Step 3.

The mixture of 3-chloro-benzothieno[2,3-c]pyridine (1.0 g, 4.5 mmol), 3-(triphenylene-2-yl)phenylboronic acid (2.1 g, 4.8 mmol), synthesized according to U.S. Provisional Application Ser. No. 60/963,944, potassium phosphate tribasic (2.9 g, 13.5 mmol), 100 mL toluene and 10 mL water was prepared and bubbled with nitrogen for fifteen minutes. Then the tris(dibenzylideneacetone)dipalladium (63 mg, 0.068 mmol) and 2-dicyclohexylphosphino-2',6'-dimethoxybiphenyl (116 mg, 0.28 mmol) were added. The mixture was bubbled with nitrogen for another twenty minutes. After refluxed overnight under nitrogen, the reaction mixture was cooled to room temperature. The product was purified by silica gel chromatography column. ~1.2 g (55%) Compound 79 was obtained.

Example 12

Synthesis of Compound 80

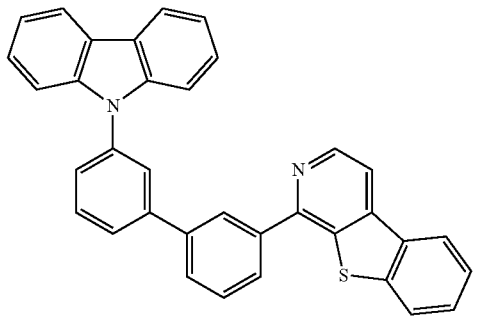

Compound 80

Step 1.

Carbazole (7.3 g, 43.7 mmol), 3-bromoiodobenzene (25 g, 87.3 mmol) and sodium t-buthoxide (8.4 g, 87.3 mmol) is suspended in 150 mL of dry xylene under nitrogen atmosphere. Tris(dibenzylideneacetone)dipalladium (200 mg) and 1,1'-bis(diphenylphosphino) ferrocene (400 mg) are added as one portion and the reaction is heated to reflux and stirred under nitrogen atmosphere for 24 h. After cooling the xylene is evaporated and the residue is subjected to column chromatography on silica gel, providing 3-bromophenyl carbazole (9.5 g, yellow solidified oil).

Step 2.

3-Bromophenyl carbazole (9.5 g, 29.5 mmol), bis(pinacolato)diboron (11.2 g, 44.2 mmol), potassium acetate (8.7 g), tris(dibenzylideneacetone)dipalladium (200 mg) and 1,1'-bis(diphenylphosphino)ferrocene (400 mg) are suspended in 200 mL of dioxane and heated to reflux under nitrogen atmosphere overnight. After cooling down and evaporation the residue is subjected to column chromatography on silica gel, providing 9-(3-(4,4,5,5-tetramethyl-1,3,2-dioxaborolan-2-yl)phenyl)-9H-carbazole b (6.0 g, colorless crystals).

Step 3.

1,3-Dibromobenzene (16 g, 64.9 mmol), 9-(3-(4,4,5,5-tetramethyl-1,3,2-dioxaborolan-2-yl)phenyl)-9H-carbazole b (6.0 g, 11.6 mmol), potassium acetate (saturated solution of 6.6 g in water) and tetrakis(triphenylphosphine)palladium (0) (380 mg) are heated to reflux in 150 mL of toluene overnight under nitrogen atmosphere. After cooling down, evaporation and column chromatography 9-(3'-bromo-[1,1'-biphenyl]-3-yl)-9H-carbazole (5.8 g) is obtained.

Step 4.

Reaction of bis(pinacolato)diboron and 9-(3'-bromo-[1,1'-biphenyl]-3-yl)-9H-carbazole in dioxane, catalyzed with tris(dibenzylideneacetone)dipalladium and 1,1'-bis(diphenylphosphino)ferrocene with potassium acetate as base in the same conditions as Step 2 provides 9-(3'-(4,4,5,5-tetramethyl-1,3,2-dioxaborolan-2-yl)-[1,1'-biphenyl]-3-yl)-9H-carbazole which is purified by column chromatography on silica gel.

Step 5.

1-Chlorobenzo[4,5]thieno[2,3-c]pyridine (described as Compound 66, Step 2) and 9-(3'-(4,4,5,5-tetramethyl-1,3,2-dioxaborolan-2-yl)-[1,1'-biphenyl]-3-yl)-9H-carbazole are dissolved in toluene (150 mL). Catalyst (tris(dibenzylideneacetone)dipalladium, 400 mg and 2-dicyclohexylphosphino-2',6'-dimethoxybiphenyl, 200 mg) and base (potassium phosphate tribasic) are added as one portion and reaction is heated to reflux under nitrogen atmosphere overnight. The product is purified by silica gel column, providing Compound 80.

Device Examples

All example devices were fabricated by high vacuum (<10$^{-7}$ Torr) thermal evaporation. The anode electrode is 800 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package.

Particular devices are provided wherein P1 is the emissive dopant and an invention compound, Compound 1, Compound 2 or Compound 3, is the host. The organic stack of Device Examples 1-3 consisted of, sequentially from the ITO surface, 100 Å of P1 as the hole injecting layer (HIL), 300 Å of 4,4'-bis[N-(1-naphthyl)-N-phenylamino]biphenyl (α-NPD) as the hole transport layer (HTL), 300 Å of the invention compound doped with 15% of P1, an Ir phosphorescent compound, as the emissive layer (EML), 100 Å of invention compound as ETL2 and 400 Å of Alq$_3$ (tris-8-hydroxyquinoline aluminum) as the ETL1.

Comparative Example 1 was fabricated similarly to the Device Examples, except that the EML comprised CBP as the host doped with 10% of P1, and P2 was used as the blocking layer material.

As used herein, the following compounds have the following structures:

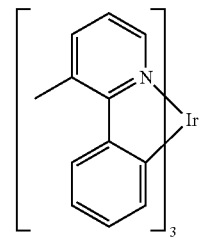

P1

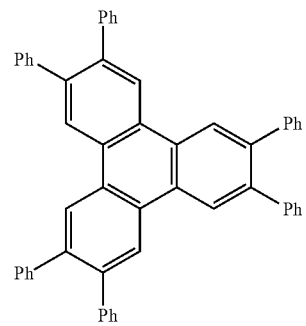

P2

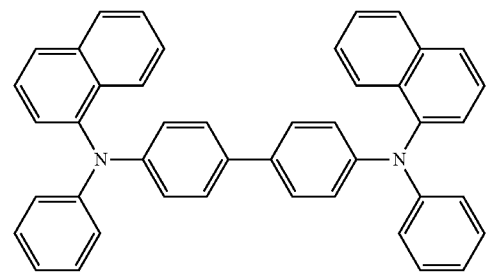

NPD

Particular materials for use in an OLED are provided which may lead to devices having particularly good properties. The materials may be used as the host of an emissive layer or as a material in an enhancement layer. The emissive layer materials and blocking layer materials of Device Examples 1-3 are shown in Table 2. The devices were tested and the results measured are provided in Table 3. Cmpd is an abbreviation for Compound. Devices having an emissive layer and a blocking layer using Compounds 1-3 show high device efficiency, long lifetime, and reduced operating voltage.

TABLE 2

| Device example | Cmpd | Dopant % | BL |
|---|---|---|---|
| 1 | 1 | P1 15% | 1 |
| 2 | 2 | P1 15% | 2 |
| 3 | 3 | P1 15% | 3 |
| Comparative 1 | CBP | P1 10% | P2 |

TABLE 3

| Device example | CIE X | CIE Y | λ max (nm) | FWHM (nm) | At L = 1000 cd/m² V (V) | At L = 1000 cd/m² LE (cd/A) | At L = 1000 cd/m² EQE (%) | At L = 1000 cd/m² PE lm/W | At L = 1000 cd/m² LE per EQE | At RT 40 mA/cm² Lo (cd/m²) | At RT 40 mA/cm² $LT_{80\%}$ (hr) | At RT 40 mA/cm² Gnits² (hr) |
|---|---|---|---|---|---|---|---|---|---|---|---|---|
| 1 | 0.366 | 0.602 | 530 | 79 | 5 | 60.9 | 16.9 | 38.4 | 3.6 | 17,697 | 113 | 35.37 |
| 2 | 0.362 | 0.605 | 530 | 76 | 5.2 | 64.3 | 17.6 | 38.7 | 3.7 | 18,976 | 85 | 30.61 |
| 3 | 0.359 | 0.604 | 528 | 76 | 6 | 47.6 | 13.1 | 24.9 | 3.6 | 15582 | 106 | 25.81 |
| Comparative 1 | 0.345 | 0.615 | 524 | 75 | 5.8 | 61 | 16.7 | 33 | 3.7 | 16148 | 83 | 21.64 |

From Device Examples 1-3, it can be seen that the Invention Compounds as hosts in green phosphorescent OLEDs give high device efficiency (i.e., LE>60 cd/A at 1000 cd/m²), indicating aza-dibenzothiophene as a chromophore has triplet energy high enough for efficient green electrophosphorescence. Also notable is the high stability of the device incorporating Compounds 1 and 2 as the host. The lifetime, $T_{80\%}$ (defined as the time required for the initial luminance, $L_0$, to decay to 80% of its value, at a constant current density of 40 mA/cm² at room temperature) are 113 hrs and 85 hrs for Compounds 1 and 2, respectively, with higher $L_0$ than the comparative example 1. This translates to a 1.5 fold improvement in the device stability. Thus, the invention compounds may function well as the enhancement layer.

Another notable feature is that Compounds 1 and 2 both gave lower device voltage, 5 V at 1000 cd/m² and 5.2 V at 1000 cd/m², respectively, compared to CBP which has 5.8 V at 1000 cd/m².

The data suggests that aza-dibenzothiophenes can be excellent hosts and enhancement layer materials for phosphorescent OLEDs, providing higher efficiency, lower voltage and an improvement in device stability multiple times better than the commonly used host, CBP.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A process comprising:
   treating an acetic acid solution of an intermediate having the formula

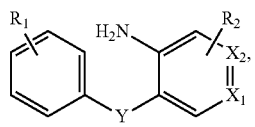

wherein one of $X_1$ and $X_2$ is nitrogen and the other of $X_1$ and $X_2$ is carbon and wherein Y is S or O, with ᵗBuONO to produce an aza complex having the formula

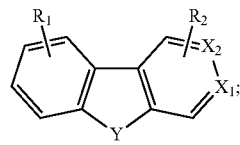

wherein $R_1$ and $R_2$ may represent mono, di, tri, or tetra substitutions;
   wherein $R_1$ is selected from the group consisting of hydrogen, alkyl, aryl, heteroaryl and halide; and
   wherein $R_2$ is selected from the group consisting of hydrogen, alkyl, aryl and halide.

2. The process of claim 1, wherein Y is S.

3. The process of claim 1, wherein Y is O.

4. The process of claim 1, wherein $X_1$ is nitrogen and $X_2$ is carbon.

5. The process of claim 1, wherein $X_1$ is carbon and $X_2$ is nitrogen.

6. The process of claim 1, wherein $R_1$ is halide.

7. The process of claim 1, wherein $R_2$ includes at least one halide.

8. The process of claim 1, wherein $R_2$ includes only halide substituents.

9. The process of claim 1, wherein $R_2$ is not halide, Y is S, and the amino-arylthio pyridine intermediate is treated with $H_2SO_4$ prior to treatment with ᵗBuONO.

10. The process of claim 1, wherein Y is S and the yield of

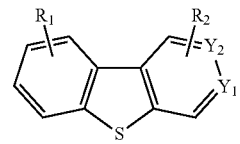

is greater than 50%.

* * * * *